US008232278B2

(12) United States Patent
De Jonghe et al.

(10) Patent No.: US 8,232,278 B2
(45) Date of Patent: Jul. 31, 2012

(54) PYRIDO(3,2-D)PYRIMIDINES AND PHARMACEUTICAL COMPOSITIONS USEFUL FOR TREATING HEPATITIS C

(75) Inventors: Steven Cesar Alfons De Jonghe, Brussels (BE); Piet André Maurits Maria Herdewijn, Rotselaar/Wezemaal (BE); William A. Lee, Los Altos, CA (US); William John Watkins, Saratoga, CA (US)

(73) Assignee: Gilead Sciences, Inc., Foster City, CA (US)

( * ) Notice: Subject to any disclaimer, the term of this patent is extended or adjusted under 35 U.S.C. 154(b) by 1057 days.

(21) Appl. No.: 11/993,832

(22) PCT Filed: Jun. 26, 2006

(86) PCT No.: PCT/BE2006/000072
§ 371 (c)(1),
(2), (4) Date: Apr. 8, 2008

(87) PCT Pub. No.: WO2006/135993
PCT Pub. Date: Dec. 28, 2006

(65) Prior Publication Data
US 2009/0131414 A1 May 21, 2009

Related U.S. Application Data

(60) Provisional application No. 60/809,329, filed on May 30, 2006, provisional application No. 60/693,899, filed on Jun. 24, 2005.

(30) Foreign Application Priority Data

May 4, 2006 (GB) .................................. 0608766.2

(51) Int. Cl.
*A01N 43/90* (2006.01)
*A61K 31/519* (2006.01)
*C07D 475/00* (2006.01)
(52) U.S. Cl. ..................... 514/262.1; 514/247; 544/236; 544/256; 544/258
(58) Field of Classification Search .................. 544/256, 544/236, 258; 514/262.1, 247
See application file for complete search history.

(56) References Cited

U.S. PATENT DOCUMENTS

| 2,512,572 | A | 6/1950 | Smith, Jr. et al. |
| 2,924,599 | A | 2/1960 | Oaks et al. |
| 3,843,638 | A | 10/1974 | Nicki et al. |
| 3,939,268 | A | 2/1976 | Nickl et al. |
| 3,952,001 | A | 4/1976 | Brookes et al. |
| 3,969,268 | A | 7/1976 | Fukuda et al. |
| 4,460,591 | A | 7/1984 | DeGraw et al. |
| 4,492,597 | A | 1/1985 | Aoki et al. |
| 4,818,819 | A | 4/1989 | Taylor et al. |
| 5,167,963 | A | 12/1992 | DeGraw et al. |
| 5,223,503 | A | 6/1993 | Gossett et al. |
| 5,508,281 | A | 4/1996 | Gangjee |
| 5,521,190 | A | 5/1996 | Henrie, II et al. |
| 5,547,954 | A | 8/1996 | Henrie, II et al. |
| 5,654,307 | A | 8/1997 | Bridges et al. |
| 5,780,462 | A | 7/1998 | Lee et al. |
| 6,331,547 | B1 | 12/2001 | Zhu et al. |
| 6,440,991 | B1 | 8/2002 | Zhu et al. |
| 6,476,031 | B1 | 11/2002 | Chakravarty et al. |
| 6,521,620 | B1 * | 2/2003 | Bridges et al. ............. 514/247 |
| 6,562,818 | B1 | 5/2003 | Bridges |
| 6,713,484 | B2 | 3/2004 | Bridges et al. |
| 6,723,726 | B1 | 4/2004 | Cockerill et al. |
| 6,730,682 | B2 | 5/2004 | Schnute et al. |
| 6,946,465 | B2 | 9/2005 | Waer et al. |
| 6,962,920 | B2 | 11/2005 | Gangjee |
| 6,974,808 | B2 | 12/2005 | McCarthy |
| 7,074,799 | B2 | 7/2006 | Bakthavatchalam et al. |
| 7,276,506 | B2 | 10/2007 | Waer et al. |
| 7,501,513 | B2 | 3/2009 | Waer et al. |
| 2002/0049207 | A1 | 4/2002 | McCarthy |
| 2003/0186987 | A1 | 10/2003 | Bridges et al. |
| 2003/0199526 | A1 | 10/2003 | Choquette et al. |
| 2003/0236255 | A1 | 12/2003 | Waer et al. |
| 2004/0039000 | A1 | 2/2004 | Gangjee |
| 2004/0077859 | A1 | 4/2004 | Waer et al. |
| 2004/0106616 | A1 | 6/2004 | Bakthavatchalam et al. |
| 2005/0014771 | A1 | 1/2005 | Hayakawa et al. |
| 2006/0189620 | A1 | 8/2006 | Waer et al. |
| 2006/0287314 | A1 | 12/2006 | Waer et al. |
| 2007/0004721 | A1 | 1/2007 | Waer et al. |
| 2007/0032477 | A1 | 2/2007 | Waer et al. |
| 2007/0043000 | A1 | 2/2007 | Waer et al. |
| 2008/0004285 | A1 | 1/2008 | De Jonghe et al. |
| 2008/0182870 | A1 | 7/2008 | Bondy et al. |
| 2008/0312227 | A1 | 12/2008 | De Jonghe et al. |
| 2009/0036430 | A1 | 2/2009 | De Jonghe et al. |
| 2009/0253696 | A1 | 10/2009 | Herdewijn et al. |
| 2009/0285782 | A1 | 11/2009 | Gao et al. |
| 2009/0318456 | A1 | 12/2009 | Herdewijn et al. |
| 2010/0143299 | A1 | 6/2010 | Gao et al. |
| 2010/0168416 | A1 | 7/2010 | Goff et al. |
| 2010/0305117 | A1 | 12/2010 | Herdewijn et al. |

FOREIGN PATENT DOCUMENTS

DE     2 117 657     10/1972
(Continued)

OTHER PUBLICATIONS

Vippagunta et al., "Crystalline Solids", Adv. Drug Del. Rev., 48 (2001) 3-26.* Vema et al, "Design of EGFR . . . ", B&MC, vol. 22, pp. 4643-4653, (2003).*
International Search Report for PCT/BE2006/000072 Mailed Nov. 7, 2006.
Written Opinion of the International Searching Authority for PCT/BE2006/000072 Mailed Nov. 7, 2006.
International Preliminary Report on Patentability for PCT/BE2006/000072 Mailed Dec. 5, 2007.

(Continued)

*Primary Examiner* — Paul V. Ward
(74) *Attorney, Agent, or Firm* — Clark & Elbing LLP

(57) ABSTRACT

Specifically substituted pyrido(3,2-d)pyrimidine derivatives having the structural formula (I) are useful for the treatment of hepatitis C.

17 Claims, 6 Drawing Sheets

FOREIGN PATENT DOCUMENTS

| | | |
|---|---|---|
| DE | 2 202 367 A1 | 8/1973 |
| DE | 2 208 535 A1 | 8/1973 |
| EP | 0 265 126 | 4/1988 |
| EP | 1 277 738 | 1/2003 |
| GB | 2 120 665 A | 12/1983 |
| WO | WO 94/27439 | 12/1994 |
| WO | WO 99/43681 | 9/1999 |
| WO | WO 99/43682 | 9/1999 |
| WO | WO 00/12497 | 3/2000 |
| WO | WO 01/83456 | 11/2001 |
| WO | WO 02/00623 | 1/2002 |
| WO | WO 02/22602 | 3/2002 |
| WO | WO 02/22607 | 3/2002 |
| WO | WO 03/062209 | 7/2003 |
| WO | WO 03/097615 | 11/2003 |
| WO | WO 2004/010929 | 2/2004 |
| WO | WO 2004/055004 | 7/2004 |
| WO | WO 2005/065691 | 7/2005 |
| WO | WO 2006/039718 | 4/2006 |
| WO | WO 2006/069805 | 7/2006 |
| WO | WO 2006/087229 | 8/2006 |
| WO | WO 2006/090169 | 8/2006 |
| WO | WO 2007/076092 | 7/2007 |
| WO | WO 2007/117394 | 10/2007 |
| WO | WO 2008/009076 | 1/2008 |
| WO | WO 2008/009079 | 1/2008 |
| WO | WO 2008/077651 | 7/2008 |
| WO | WO 2009/003669 | 1/2009 |

OTHER PUBLICATIONS

Written Opinion of the International Searching Authority for PCT/BE2006/000072 Mailed Sep. 4, 2007.
Vema et al., "Design of EGFR Kinase Inhibitors : A Ligand-Based Approach and its Confirmation with Structure-Based Studies," *Bioog. Med. Chem.* 11:4653-4653 (2003).
U.S. Appl. No. 13/176,627, filed Jul. 5, 2011, Herdewijn et al.
Colbry et al., "Synthesis and Antimalarial Properties of 2,4-Diamino-6-[(aryl)thio, sulfinyl, and sulfonyl]pyrido[3,2-d]pyrimidines," *J. Heterocyclic Chem.* 21:1521-1525, 1984.
Di Giacomo et al., "Synthesis and Biological Activity of New Melatonin Dimeric Derivatives," *Bioorg. Med. Chem.* 15:4643-4650, 2007.
Durucasu, "Investigation of Different Synthetic Ways for Protection of 6-Bromo-5-Deazapterin," *Doğe Tu J. Chem.* 13:280-292, 1989.
Griesser, "The Importance of Solvates," in *Polymorphism: In the Pharmaceutical Industry*, Ed. R. Hilfiker, Weinheim: Wiley-VCH Verlag GmbH & Co. KGaA, Ch. 8, pp. 211-233, 2006.
Hayakawa et al., "Synthesis and Biological Evaluation of 4-Morpholino-2-Phenylquinazolines and Related Derivatives as Novel PI3 Kinase p110α Inhibitors," *Bioorg. Med. Chem.* 14: 6847-6858, 2006.
Kuwada et al., "A New Synthesis of 6-Substituted Pyrido[2,3-d]Pyrimidines," *Heterocycles* 57:2081-2090, 2002.
Patani et al., "Bioisosterism: A Rational Approach in Drug Design," *Chem. Rev.* 96: 3147-3176, 1996.
Taylor et al., "A Convenient Synthesis of 6-Formyl-5-Deazapterin," *Synth. Commun.* 18:1187-1191, 1988.
Taylor et al., "Convergent and Efficient Palladium-Effected Synthesis of 5,10-Dideaza-5,6,7,8-tetrahydrofolic Acid (DDATHF)," *J. Org. Chem.* 54:3618-3624, 1989.
Taylor et al., "Protection and Deprotection of Fused 2-Amino-4(3H)-Pyrimidinones: Conversion of Pterins and 5-Deazapterins to 2,4-Diamino Derivatives," *Heterocycles* 36:1883-1895, 1993.
Temple et al., "Synthesis of Potential Antimalarial Agents. VIII. Azaquinolines. II. Preparation of Some 1, 5-Naphthyridines and Pyrido [3, 2-d] pyrimidines," *J. Heterocyclic Chem.* 7:1219-1222, 1970.

* cited by examiner

PYRIDO(3,2-D)PYRIMIDINES AND PHARMACEUTICAL COMPOSITIONS USEFUL FOR TREATING HEPATITIS C

CROSS-REFERENCE TO RELATED APPLICATIONS

This application is the U.S. National Stage of International Application No. PCT/BE2006/000072, filed Jun. 26, 2006, which claims the benefit of U.S. Provisional Application Ser. No. 60/693,899, filed Jun. 24, 2005, Great Britain Application Serial No. GB 0608766.2, filed May 4, 2006, and U.S. Provisional Application Ser. No. 60/809,329, filed May 30, 2006.

The present invention relates to a class of novel pyrido(3, 2-d)pyrimidine derivatives, as well as to pharmaceutical compositions comprising one or more of said pyrido(3,2-d)pyrimidine derivatives and one or more pharmaceutically acceptable excipients. The present invention further relates to the use of pyrido(3,2-d)pyrimidine derivatives as biologically active ingredients for manufacturing medicaments for the prevention or treatment of infection by a virus of the Flaviridae family, more specifically for inhibiting replication of hepatitis C virus.

BACKGROUND OF THE INVENTION

A huge number of pyrido(3,2-d)pyrimidine derivatives is already known in the art. For instance pyrido(3,2-d)pyrimidine derivatives with various substituents on positions 2, 4 and 6 (using the standard atom numbering for the pyrido(3, 2-d)pyrimidine moiety) are known with biological activities such as competitive inhibition of pteroylglutamic acid, inhibition of thrombocyte aggregation and adhesiveness, antineoplastic activity, inhibition of dihydrofolate reductase and thymidylate synthase, e.g. from U.S. Pat. No. 2,924,599, U.S. Pat. No. 3,939,268, U.S. Pat. No. 4,460,591, U.S. Pat. No. 5,167,963 and U.S. Pat. No. 5,508,281.

Pyrido(3,2-d)pyrimidine derivatives with various substituents on positions 2, 4, 6 and 7 (using the standard atom numbering for the pyrido(3,2-d)pyrimidine moiety), some of them with biological activities, are also known e.g. from U.S. Pat. No. 5,521,190, U.S. patent application publication No. 2002/0049207, U.S. patent application publication No. 2003/0186987, U.S. patent application publication No. 2003/0199526, U.S. patent application publication No. 2004/0039000, U.S. patent application publication No. 2004/0106616, U.S. Pat. No. 6,713,484, U.S. Pat. No. 6,730,682 and U.S. Pat. No. 6,723,726.

U.S. Pat. No. 5,654,307 discloses pyrido(3,2-d)pyrimidine derivatives substituted on position 4 with monoarylamino or monobenzylamino, and on positions 6 and 7 with substituents each independently selected from the group consisting of lower alkyl, amino, lower alkoxy, mono- or dialkylamino, halogen and hydroxy. WO 01/083456 discloses pyrido(3,2-d)pyrimidine derivatives substituted on position 4 with morpholinyl and on position 2 with hydroxyphenyl or morpholinoethoxyphenyl, having PI3K and cancer inhibiting activity. U.S. Pat. No. 6,476,031 discloses substituted quinazoline derivatives, including (in reaction scheme 5) a series of pyrido (3,2-d)pyrimidine derivatives which are substituted on position 4 with hydroxy, chloro or an aryl, heteroaryl (including pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl), cycloaliphatic or cycloheteroaliphatic group being optionally spaced from the pyrido(3,2-d)pyrimidine ring by a linker such as NH. WO 02/22602 and WO 02/22607 disclose pyrazole and triazole compounds, including 2-(1-trifluoromethylphenyl)-4-fluorobenzopyrazolyl-pyrido(3,2-d)pyrimidine and 2-(1-trifluoromethylphenyl)-4-methyltriazolyl-pyrido (3,2-d)pyrimidine being useful as protein kinase inhibitors. WO 03/062209 discloses pyrido(3,2-d)pyrimidine derivatives substituted on position 7 with aryl or heteoaryl and on position 4 with monoarylamino or monoheteroarylamino and which may further be substituted on positions 2 and/or 6, being useful as capsaicin receptor modulators.

However there is a continuous need in the art for specific and highly therapeutically active compounds for preventing or treating infections due to Flaviridae and pathologic conditions associated therewith, especially hepatitis C. In particular, there is a need in the art to provide drugs which are active against hepatitis C in a minor dose in order to replace existing drugs having significant side effects and to decrease treatment costs.

Hepatitis is an inflammation of the liver that is most often caused by infection with one of three viruses known as hepatitis A, B or C. Hepatitis A virus (HAV) infection is the most common cause of acute hepatitis, and usually resolves spontaneously after several weeks of acute symptoms. Hepatitis B virus (HBV) and hepatitis C virus (HCV) are the most common viral causes of chronic hepatitis, usually defined as liver inflammation persisting for more than six months. HCV is the second most common cause of viral hepatitis in general and most common cause of chronic hepatitis. The World Health Organization estimates that worldwide 170 million people (3% of the world's population) are chronically infected with HCV. These chronic carriers are at risk of developing cirrhosis and/or liver cancer. In studies with a 10 to 20 year follow-up, cirrhosis developed in 20-30% of the patients, 1-5% of whom may develop liver cancer during the next then years. The 15% to 45% of persons with acute hepatitis C who do recover are not subject to long-term complications and do not need treatment. Since HCV and pestiviruses belong to the same virus family and share many similarities (such as, but not limited to, organisation of the genome, analogous gene products and replication cycle), pestiviruses may be adopted as a model virus and surrogate for HCV. For example the Bovine Viral Diarrhea Virus (BVDV) is closely related to hepatitis C virus (HCV) and may be used as a surrogate virus in drug development for HCV infection.

HCV is a representative and highly significant member of the Flaviviridae family, a family of positive-strand RNA viruses. This family includes the following genera: Genus *Flavivirus* (type species Yellow fever virus, others include West Nile virus and Dengue Fever), Genus *Hepacivirus* (type species Hepatitis C virus), and Genus Pestivirus (type species Bovine viral diarrhea virus (BVDV), others include classical swine fever or hog cholera). Contrary to other families of positive strand RNA viruses such as human immunodeficiency virus (HIV), HCV seems incapable of integrating into the host's genome. The primary immune response to HCV is mounted by cytotoxic T lymphocytes. Unfortunately, this process fails to eradicate infection in most people; in fact, it may contribute to liver inflammation and, ultimately, tissue necrosis. The ability of HCV to escape immune surveillance is the subject of much speculation. One likely means of viral persistence relies on the presence of closely related but heterogeneous populations of viral genomes. Further studies of these quasi-species enable classification of several genotypes and subtypes, which have clinical implications.

The diagnosis of hepatitis C is rarely made during the acute phase of the disease because the majority of people infected experience no symptoms during this phase of the disease.

Those who do experience acute phase symptoms are rarely ill enough to seek medical attention. The diagnosis of chronic phase hepatitis C is also challenging due to the absence or lack of specificity of symptoms until advanced liver disease develops, which may not occur until decades into the disease.

Hepatitis C testing begins with serological blood tests used to detect antibodies to HCV. Anti-HCV antibodies can be detected in about 80% of patients within 15 weeks after exposure, in more than 90% of patients within 5 months after exposure, and in more than 97% of patients by 6 months after exposure. Overall, HCV antibody tests have a strong positive predictive value for exposure to the hepatitis C virus, but may miss patients who have not yet developed antibodies (seroconversion), or have an insufficient level of antibodies to detect. Anti-HCV antibodies indicate exposure to the virus, but cannot determine if ongoing infection is present. All persons with positive anti-HCV antibody tests must undergo additional testing for the presence of the hepatitis C virus itself to determine whether current infection is present. The presence of HCV may be tested by using molecular nucleic acid testing methods such as, but not limited to, polymerase chain reaction (PCR), transcription mediated amplification (TMA), or branched DNA amplification. All HCV nucleic acid molecular tests have the capacity to detect not only whether the virus is present, but also to measure the amount of virus present in the blood (the HCV viral load). The HCV viral load is an important factor in determining the probability of response to interferon-base therapy, but does not indicate disease severity nor the likelihood of disease progression.

The goal of treatment is to prevent complications of HCV infection. This is principally achieved by eradication of infection. Accordingly, treatment responses are frequently characterized by the results of HCV RNA testing. Infection is considered eradicated when there is a sustained virologic response (SVR), defined as the absence of HCV RNA in serum by a sensitive test at the end of treatment and 6 months later. Persons who achieve an SVR almost always have a dramatic earlier reduction in the HCV RNA level, referred to as an early virologic response (EVR). Continued absence of detectable virus at termination of treatment is referred to as end of treatment response (ETR). A patient is considered relapsed when HCV RNA becomes undetectable on treatment but is detected again after discontinuation of treatment. Persons in whom HCV RNA levels remain stable on treatment are considered as non-responders, while those whose HCV RNA levels decline but remain detectable are referred to as partial responders.

Current standard of care for HCV treatment is a combination of (pegylated) interferon alpha and the antiviral drug ribavirin for a period of 24 or 48 weeks, depending upon the viral genotype. Should treatment with pegylated ribavirin-interferon not return a viral load reduction after 12 weeks, the chance of treatment success is less than 1%. Current indication for treatment includes patients with proven hepatitis C virus infection and persistent abnormal liver function tests. SVR of 75% or better occur in people with genotypes HCV 2 and 3 within 24 weeks of treatment, about 50% in those with genotype 1 within 48 weeks of treatment and 65% for those with genotype 4 within 48 weeks of treatment. About 80% of hepatitis C patients in the United States exhibit genotype 1, whereas genotype 4 is more common in the Middle East and Africa.

Best results have been achieved with the combination of weekly subcutaneous injections of long-acting peginterferon alpha and oral ribavirin daily. Interferons are substances naturally released by cells in the body after viral invasion. Interferon alfa-2b and peginterferon alfa-2b are synthetic versions of these substances. The protein product is manufactured by recombinant DNA-technology. Second generation interferons are further derivatized by binding to inert polyethylene glycol, thereby altering the pharmacokinetic properties. Ribavirin is a nucleoside analogue, which disrupts viral replication of hepatitis C virus (HCV).

The most common side effects of HCV treatment with (pegylated) interferon include: a decrease in white blood cells and platelets, anemia, nausea, diarrhea, fever, chills, muscle and joint pain, difficulty in concentrating, thyroid dysfunction, hair loss, sleeplessness, irritability, mild to serious depression, and rarely, suicidal thoughts. Other serious adverse events include bone marrow toxicity, cardiovascular disorders, hypersensitivity, endocrine disorders, pulmonary disorders, colitis, pancreatitis, and opthalmologic disorders (eye and vision problems). (Pegylated) interferon may also cause or make worse fatal or life-threatening neuropsychiatric, autoimmune, ischemic, and infectious disorders. Patients with persistently severe or worsening signs or symptoms of these conditions are advised to stop therapy.

The most common side effect of HCV treatment with ribavirin is anaemia, which can be treated with erythropoietin. Other side effects include mood swings, irritability, anxiety, insomnia, abdominal pain, nervousness, breathlessness, rash, hair loss, dry skin, nausea, diarrhea, loss of appetite, dizziness and weight loss. Ribavirin can also cause birth defects. Ribavirin should not be taken in combination with certain HIV drugs such as, but not limited to, didanosine, since lactic acidosis with fatal hepatic steatosis (fatty liver) may occur. Special attention should be taken for treatment with HIV co-infection.

Although the liver is the primary target of infection, studies to better define the steps of HCV infection are greatly hampered by the lack of a suitable animal model for such studies. The recent development of sub-genomic HCV RNA replicons capable of autonomous replication in the human hepatoma cell line, Huh-7, has been a significant advance in the study of HCV biology. The sub-genomic HCV RNA replicon system provides a cell-based assay to evaluate inhibitors of HCV enzymes like the protease, helicase, and RNA-dependant RNA polymerase or to evaluate nucleic acid targeting strategies like antisense RNA and ribozymes.

Targets for HCV Drug development include HCV-encoded enzymes, namely, NS2-3 and NS3-4A proteases, NS3 helicase, and NS5B RNA dependant RNA polymerase. Alternatively, HCV replication can be inhibited by blocking the conserved RNA elements employing a nucleic acid based approach including antisense oligonucleotides, ribozymes, RNA aptamers, RNA decoys, and RNA interference. A major drawback for such nucleic acid based approach is the size and charge of the nucleic acids, and their usually low physiological stability that do not allow for oral administration. Another target option for therapy is by blocking viral entry into the cell by obstruction of binding to HCV receptors such as, but not limited to, CD 209L and L-SIGN.

There is a strong need in the art to improve, or to provide alternatives to, the existing prophylactic or therapeutic solutions to infections by a virus of the Flaviridae family, more specifically HCV infection. In particular there is still a need in the art for providing alternative synthetic molecules having significant HCV replication inhibiting activity. There is also a need in the art for providing effective inhibiting molecules which are free from the significant drawbacks of the current drugs like pegylated interferon and ribavirin. Meeting these various needs in the art constitutes the main goal of the present invention.

SUMMARY OF THE INVENTION

The present invention is based on the unexpected finding that certain combinations of substituents on positions 2, 4, 6 and/or 7 of the pyrido(3,2-d)pyrimidine moiety (using the standard atom numbering thereof) which are not suggested by the available prior art are however able to meet one or more of the needs recited herein above, in particular to achieve derivatives having desirable pharmacological properties such as an activity against infection by a virus of the Flaviridae family, more particularly a significant HCV replication inhibiting activity.

Based on this finding the present invention relates, in a first embodiment, to a class of pyrido(3,2-d)pyrimidine derivatives having the structural formula (I):

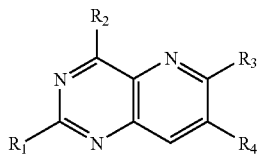

wherein:
  $R_1$ is selected from the group consisting of hydrogen, halogen, cyano, carboxylic acid, acyl, thioacyl, alkoxycarbonyl, acyloxy, carbonate, carbamate, $C_{1-7}$ alkyl, aryl, amino, acetamido, N-protected amino, (mono- or di) $C_{1-7}$ alkylamino, (mono- or di) arylamino, (mono- or di) $C_{3-10}$ cycloalkylamino, (mono- or di) hydroxy $C_{1-7}$ alkylamino, (mono- or di) $C_{1-4}$ alkyl-arylamino, mercapto $C_{1-7}$ alkyl, $C_{1-7}$ alkyloxy, and groups of the formula $R_6$—$NR_7R_{12}$, wherein $R_6$ is a bond or $C_{1-3}$ alkylene, wherein $R_7$ and $R_{12}$ are independently selected from the group consisting of hydrogen, $C_{1-7}$ alkyl, $C_{2-7}$ alkenyl, $C_{2-7}$ alkynyl, aryl, arylalkyl, $C_{3-10}$ cycloalkyl and heteroaryl, or wherein $R_7$ and $R_{12}$ together form a heterocycle,
  $R_2$ is selected from the group consisting of (mono- or di-) $C_{1-12}$ alkylamino; monoarylamino; diarylamino; (mono- or di-) $C_{3-10}$ cycloalkylamino; (mono- or di-) hydroxy$C_{1-7}$ alkylamino; (mono- or di-) $C_{1-4}$ alkylarylamino; (mono- or di-) aryl$C_{1-4}$ alkylamino; N-morpholinyl; mercapto $C_{1-7}$ alkyl; $C_{1-7}$ alkoxy; N-containing heterocyclic; $C_{1-7}$ alkoxy-$C_{1-7}$ alkoxy; heterocyclic-substituted $C_{1-7}$ alkoxy; $C_{3-10}$ cycloalkoxy; $C_{3-10}$ cycloalkyl-$C_{1-7}$ alkoxy; halo $C_{1-7}$ alkyloxy; aryloxy; arylalkyloxy; oxyheterocyclic; heterocyclic-substituted alkoxy; thio $C_{1-7}$ alkyl-thio $C_{1-7}$ alkyl; heterocyclic-substituted thio $C_{1-7}$ alkyl; thio $C_{3-10}$ cycloalkyl; thio $C_{3-10}$ cycloalkyl-$C_{1-7}$ alkyl; halo thio-$C_{1-7}$ alkyl; arylthio; arylalkylthio; thioheterocyclic; heterocyclic-substituted thio $C_{1-7}$ alkyl; homo-piperazinyl and piperazinyl, wherein said homopiperazinyl or piperazinyl is optionally N-substituted with a substituent $R_5$ selected from the group consisting of formyl, acyl, thioacyl, amide, thioamide, sulfonyl, sulfinyl, carboxylate, thiocarboxylate, amino-substituted acyl, alkoxyalkyl, $C_{1-7}$ alkyl, $C_{3-10}$ cycloalkyl-alkyl, $C_{3-10}$ cycloalkyl, dialkylaminoalkyl, heterocyclic-substituted alkyl, acyl-substituted alkyl, thioacyl-substituted alkyl, amido-substituted alkyl, thioamido-substituted alkyl, carboxylato-substituted alkyl, thiocarboxylato-substituted alkyl, (amino-substituted acyl)alkyl, heterocyclic, carboxylic acid ester, ω-cyanoalkyl, ω-carboxylic ester-alkyl, halo $C_{1-7}$ alkyl, $C_{2-7}$ alkenyl, $C_{2-7}$ alkynyl, arylalkenyl, aryloxyalkyl, arylalkyl and aryl, wherein the aryl moiety of each of said arylalkenyl, aryloxyalkyl, arylalkyl and aryl radicals is optionally substituted with one or more substituents independently selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino, hydrazino, alkylhydrazino and phenylhydrazino;
  $R_3$ and $R_4$ are independently selected from the group consisting of hydrogen, halogen, heteroaryl and aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino, hydrazino, alkylhydrazino and phenylhydrazino, provided that $R_3$ and $R_4$ are not both hydrogen, and further provided that $R_4$ is hydrogen when $R_2$ is monoarylamino, or a pharmaceutical acceptable addition salt thereof or a stereoisomer thereof or a N-oxide thereof or a solvate thereof.

Within the above defined class of compounds, a preferred group is one wherein $R_1$ is not hydrogen, i.e. position 2 of the pyrido(3,2-d)pyrimidine moiety is substituted. Another preferred group of compounds is one wherein $R_1$ is amino or N-protected amino such as, but not limited to, amido and in particular acetamido. Another preferred group of compounds is one wherein $R_1$ is amino or N-protected amino, and further wherein $R_3$ is a substituted aryl group. Another preferred group of compounds is one wherein $R_1$ is amino or N-protected amino, wherein $R_3$ is a substituted aryl group and further wherein $R_4$ is hydrogen.

In a second embodiment, the present invention relates to certain groups of tri-substituted pyrido(3,2-d)pyrimidines which are useful as intermediates for making some of the pyrido(3,2-d)pyrimidine derivatives having the structural formula (I), in particular:
  a group of 2-amino-4-hydroxy-6-$R_3$-substituted pyrido(3,2-d)pyrimidines and 2,4-diamino-6-$R_3$-substituted pyrido(3,2-d)pyrimidines wherein $R_3$ is as defined in the general formula (I) but $R_3$ is not hydrogen;

a group of 2-N-protected-amino-4-hydroxy-6-$R_3$-substituted pyrido(3,2-d)pyrimidines, 2-N-protected-amino-4-chloro-6-$R_3$-substituted pyrido(3,2-d)pyrimidines and 2-N-protected-amino-4-triazolyl-6-$R_3$-substituted pyrido(3,2-d)pyrimidines wherein $R_3$ is as defined in the general formula (I) but $R_3$ is not hydrogen, and wherein N-protected-amino may be, but is not limited to, acetamido and pivalamido;

a group of 2-$R_1$-substituted-4-hydroxy-6-$R_3$-substituted pyrido(3,2-d)pyrimidines, 2-$R_1$-substituted-4-chloro-6-$R_3$-substituted pyrido(3,2-d)pyrimidines and 2-$R_1$-substituted-4-triazolyl-6-$R_3$-substituted pyrido(3,2-d)pyrimidines wherein $R_1$ and $R_3$ are as defined in the general formula (I) but are not hydrogen;

a group of 2,4-dihydroxy-6-$R_3$-substituted pyrido(3,2-d)pyrimidines and 2,4-dichloro-6-$R_3$-substituted pyrido(3,2-d)pyrimidines wherein $R_3$ is as defined in the general formula (I) but $R_3$ is not hydrogen;

a group of 2-chloro-4-$R_2$-substituted-6-$R_3$-substituted pyrido(3,2-d)pyrimidines wherein $R_2$ and $R_3$ are as defined in the general formula (I) but are not hydrogen;

a group of 2-amino-4-hydroxy-7-$R_4$-substituted pyrido(3,2-d)pyrimidines and 2,4-diamino-7-$R_4$-substituted pyrido(3,2-d)pyrimidines wherein $R_4$ is as defined in the general formula (I) but $R_4$ is not hydrogen;

a group of 2-N-protected-amino-4-hydroxy-7-$R_4$-substituted pyrido(3,2-d)pyrimidines, 2-N-protected-amino-4-chloro-7-$R_4$-substituted pyrido(3,2-d)pyrimidines and 2-N-protected-amino-4-triazolyl-7-$R_4$-substituted pyrido(3,2-d)pyrimidines wherein $R_4$ is as defined in the general formula (I) but $R_4$ is not hydrogen, and wherein N-protected-amino may be, but is not limited to, acetamido and pivalamido;

a group of 2-$R_1$-substituted-4-hydroxy-7-$R_4$-substituted pyrido(3,2-d)pyrimidines, 2-$R_1$-substituted-4-chloro-7-$R_4$-substituted pyrido(3,2-d)pyrimidines and 2-$R_1$-substituted-4-triazolyl-7-$R_4$-substituted pyrido(3,2-d)pyrimidines wherein $R_1$ and $R_4$ are as defined in the general formula (I) but are not hydrogen;

a group of 2,4-dihydroxy-7-$R_4$-substituted pyrido(3,2-d)pyrimidines and 2,4-dichloro-7-$R_4$-substituted pyrido(3,2-d)pyrimidines wherein $R_4$ is as defined in the general formula (I) but $R_4$ is not hydrogen; and a group of 2-chloro-4-$R_2$-substituted-7-$R_4$-substituted pyrido(3,2-d)pyrimidines wherein $R_2$ and $R_4$ are as defined in the general formula (I) but are not hydrogen.

In a third embodiment, the present invention relates to the unexpected finding that desirable pharmacological properties such as an activity against infection by a virus of the Flaviridae family, more specifically the ability to inhibit hepatitis C virus (HCV) replication is present in one or more of the groups of compounds described herein.

As a consequence, the invention relates to the manufacture of pharmaceutical compositions comprising one or more pharmaceutically acceptable carriers and, as a biologically active principle, a therapeutically effective amount of at least one pyrido(3,2-d)pyrimidine derivative having the structural formula (I) and/or a pharmaceutically acceptable addition salt thereof and/or a stereoisomer thereof and/or a N-oxide thereof and/or a solvate thereof.

As a result of their biological properties mentioned hereinabove, compounds having the structural formula (I) are highly active anti-flaviridae agents, especially anti-HCV agents which, together with one or more pharmaceutically acceptable carriers, may be formulated into pharmaceutical compositions for the prevention or treatment of pathologic conditions such as, but not limited to, hepatitis C infection. It has been surprisingly found that their activity is virus-specific, especially since they do not exhibit activity against other families of positive strand RNA viruses such as human immunodeficiency virus (HIV-1 or HIV-2).

In a further embodiment, the present invention relates to combined preparations containing at least one compound of the structural formula (I) and one or more antiviral agents, especially one or more other anti-flaviridae agents. In a further embodiment, the present invention relates to the prevention or treatment of the above-cited pathologic conditions or infections by administering to the patient in need thereof a therapeutically effective amount of a compound having the structural formula (I), optionally in the form of a pharmaceutical composition or a combined preparation with one or more other suitable drugs, in particular antiviral agents.

In another embodiment, the present invention relates to various processes and methods for making the novel pyrido(3,2-d)pyrimidine derivatives defined by the structural formula (I) as well as their pharmaceutically acceptable salts, N-oxides, solvates and/or stereoisomers, e.g. via one or more groups of tri-substituted pyrido(3,2-d)pyrimidine intermediates such as specified herein before.

DEFINITIONS

Figure 1:
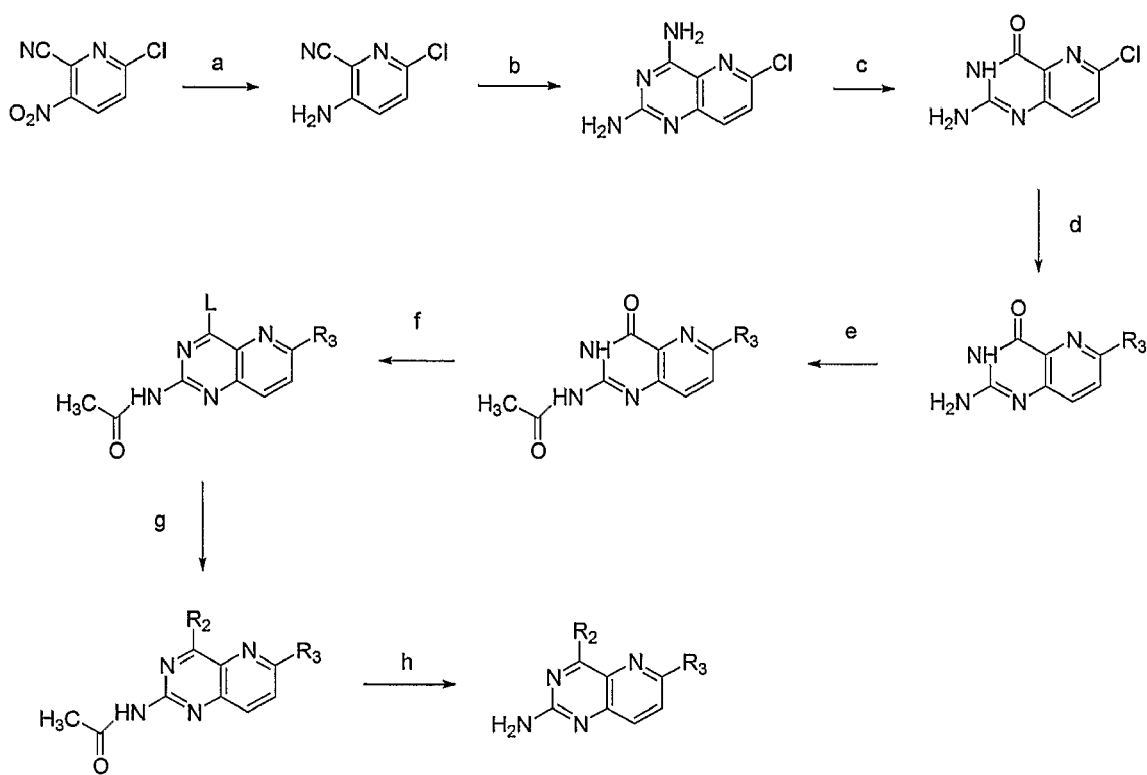
FIG. 1 schematically shows a first method for making 2,4,6-tri-substituted pyrido(3,2-d)pyrimidine derivatives having the formula (I) wherein the substituent in position 2 is amino, as well as intermediates therefor wherein the substituent in position 2 is a N-protected amino such as acetamido and/or wherein the substituent in position 4 is hydroxy, chloro or triazolyl.

Unless otherwise stated herein, the term "tri-substituted" means that three of the carbon atoms being in positions 2, 4 and 6 or, alternatively, in positions 2, 4 and 7 of the pyrido(3, 2-d)pyrimidine moiety (according to standard atom numbering for the pyrido(3,2-d)pyrimidine moiety) are substituted with an atom or group of atoms other than hydrogen. The term "tetra-substituted" means that all four carbon atoms being in positions 2, 4, 6 and 7 of the pyrido(3,2-d)pyrimidine moiety are substituted with an atom or group of atoms other than hydrogen.

As used herein with respect to a substituting radical, and unless otherwise stated, the term "$C_{1-7}$ alkyl" means straight and branched chain saturated acyclic hydrocarbon monovalent radicals having from 1 to 7 carbon atoms such as, for example, methyl, ethyl, propyl, n-butyl, 1-methylethyl (isopropyl), 2-methylpropyl (isobutyl), 1,1-dimethylethyl (terbutyl), 2-methylbutyl, n-pentyl, dimethylpropyl, n-hexyl, 2-methylpentyl, 3-methylpentyl, n-heptyl and the like. By analogy, the term "$C_{1-12}$ alkyl" refers to such radicals having from 1 to 12 carbon atoms, i.e. up to and including dodecyl.

As used herein with respect to a substituting radical, and unless otherwise stated, the term "acyl" broadly refers to a substituent derived from an acid such as an organic monocarboxylic acid, a carbonic acid, a carbamic acid (resulting into a carbamoyl substituent) or the thioacid or imidic acid (resulting into a carbamidoyl substituent) corresponding to said acids, and the term "sulfonyl" refers to a substituent derived from an organic sulfonic acid, wherein said acids comprise an aliphatic, aromatic or heterocyclic group in the molecule. A more specific kind of "acyl" group within the scope of the above definition refers to a carbonyl (oxo) group adjacent to a $C_{1-7}$ alkyl, a $C_{3-10}$ cycloalkyl, an aryl, an arylalkyl or a heterocyclic group, all of them being such as herein defined. Suitable examples of acyl groups are to be found below.

Acyl and sulfonyl groups originating from aliphatic or cycloaliphatic monocarboxylic acids are designated herein as aliphatic or cycloaliphatic acyl and sulfonyl groups and include, but are not limited to, the following:
 alkanoyl (for example formyl, acetyl, propionyl, butyryl, isobutyryl, valeryl, isovaleryl, pivaloyl and the like);
 cycloalkanoyl (for example cyclobutanecarbonyl, cyclopentanecarbonyl, cyclohexanecarbonyl, 1-adamantanecarbonyl and the like);
 cycloalkyl-alkanoyl (for example cyclohexylacetyl, cyclopentylacetyl and the like);
 alkenoyl (for example acryloyl, methacryloyl, crotonoyl and the like);
 alkylthioalkanoyl (for example methylthioacetyl, ethylthioacetyl and the like);
 alkanesulfonyl (for example mesyl, ethanesulfonyl, propanesulfonyl and the like);
 alkoxycarbonyl (for example methoxycarbonyl, ethoxycarbonyl, propoxycarbonyl, isopropoxycarbonyl, butoxycarbonyl, isobutoxycarbonyl and the like);
 alkylcarbamoyl (for example methylcarbamoyl and the like);
 (N-alkyl)-thiocarbamoyl (for example (N-methyl)-thiocarbamoyl and the like);
 alkylcarbamidoyl (for example methylcarbamidoyl and the like); and
 alkoxyalkyl (for example methoxyalkyl, ethoxyalkyl, propoxyalkyl and the like);

Acyl and sulfonyl groups may also originate from aromatic monocarboxylic acids and include, but are not limited to, the following:
 aroyl (for example benzoyl, toluoyl, xyloyl, 1-naphthoyl, 2-naphthoyl and the like);
 arylalkanoyl (for example phenylacetyl and the like);
 arylalkenoyl (for example cinnamoyl and the like);
 aryloxyalkanoyl (for example phenoxyacetyl and the like);
 arylthioalkanoyl (for example phenylthioacetyl and the like);
 arylaminoalkanoyl (for example N-phenylglycyl, and the like);
 arylsulfonyl (for example benzenesulfonyl, toluenesulfonyl, naphthalene sulfonyl and the like);
 aryloxycarbonyl (for example phenoxycarbonyl, naphthyloxycarbonyl and the like);
 arylalkoxycarbonyl (for example benzyloxycarbonyl and the like);
 arylcarbamoyl (for example phenylcarbamoyl, naphthylcarbamoyl and the like);
 arylglyoxyloyl (for example phenylglyoxyloyl and the like).
 arylthiocarbamoyl (for example phenylthiocarbamoyl and the like); and
 arylcarbamidoyl (for example phenylcarbamidoyl and the like).

Acyl groups may also originate from an heterocyclic monocarboxylic acids and include, but are not limited to, the following:
 heterocyclic-carbonyl, in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiophenoyl, furoyl, pyrrolecarbonyl, nicotinoyl and the like); and
 heterocyclic-alkanoyl in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiopheneneacetyl, furylacetyl, imidazolylpropionyl, tetrazolylacetyl, 2-(2-amino-4-thiazolyl)-2-methoxyiminoacetyl and the like).

As used herein with respect to a substituting radical, and unless otherwise stated, the term "$C_{1-7}$ alkylene" means the divalent hydrocarbon, radical corresponding to the above defined $C_{1-7}$ alkyl, such as methylene, bis(methylene), tris (methylene), tetramethylene, hexamethylene and the like.

As used herein with respect to a substituting radical, and unless otherwise stated, the term "$C_{3-10}$ cycloalkyl" means a mono- or polycyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein with respect to a substituting radical, and unless otherwise stated, the term "$C_{3-10}$ cycloalkyl-alkyl" refers to an aliphatic saturated hydrocarbon monovalent radical (preferably a $C_{1-7}$ alkyl such as defined above) to which a $C_{3-10}$ cycloalkyl (such as defined above) is already linked such as, but not limited to, cyclohexylmethyl, cyclopentylmethyl and the like.

As used herein with respect to a substituting radical, and unless otherwise stated, the term "$C_{3-10}$ cycloalkylene"

means the divalent hydrocarbon radical corresponding to the above defined $C_{3-10}$ cycloalkyl.

As used herein with respect to a substituting radical, and unless otherwise stated, the term "aryl" designate any mono- or polycyclic aromatic monovalent hydrocarbon radical having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_{4-8}$ cycloalkyl radicals (the latter being as defined above) such as, for instance, indanyl, tetrahydronaphtyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein, e.g. with respect to a substituting radical such as the combination of substituents in certain positions of the pyrido(3,2-d)pyrimidine ring together with the carbon atoms in the same positions of said ring, and unless otherwise stated, the term "homocyclic" means a mono- or polycyclic, saturated or mono-unsaturated or polyunsaturated hydrocarbon radical having from 4 up to 15 carbon atoms but including no heteroatom in the said ring; for instance said combination of substituents may form a $C_{2-6}$ alkylene radical, such as tetramethylene, which cyclizes with the carbon atoms in certain positions of the pyrido(3,2-d)pyrimidine ring.

As used herein with respect to a substituting radical (including the combination of substituents in certain positions of the pyrido(3,2-d)pyrimidine ring together with the carbon atoms in the same positions of said ring), and unless otherwise stated, the term "heterocyclic" means a mono- or polycyclic, saturated or mono-unsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphto-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxathiinyl, benzodioxinyl, benzodithiinyl, benzoxazepinyl, benzothiazepinyl, benzodiazepinyl, benzodioxepinyl, benzodithiepinyl, benzoxazocinyl, benzothiazocinyl, benzodiazocinyl, benzoxathiocinyl, benzodioxocinyl, benzotrioxepinyl, benzoxathiazepinyl, benzoxadiazepinyl, benzothiadiazepinyl, benzotriazepinyl, benzoxathiepinyl, benzotriazinonyl, benzoxazolinonyi, azetidinonyl, azaspiroundecyl, dithiaspirodecyl, selenazinyl, selenazolyl, selenophenyl, hypoxanthinyl, azahypoxanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzocarbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphtindazolyl, naphtindolyl, naphtothiazolyl, naphtothioxolyl, naphtoxindolyl, naphtotriazolyl, naphtopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydro-pyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, phenometoxazinyl, phenoparoxazinyl, phentriazinyl, thiodiazinyl, thiodiazolyl, indoxyl, thioindoxyl, benzodiazinyl (e.g. phtalazinyl), phtalidyl, phtalimidinyl, phtalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of said heterocyclic ring may furthermore be independently substituted with a substituent selected from the group consisting of halogen, nitro, $C_{1-7}$ alkyl (optionally containing one or more functions or radicals selected from the group consisting of carbonyl (oxo), alcohol (hydroxyl), ether (alkoxy), acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxylalkylamino, mercaptoalkylamino, heterocyclic-substituted alkylamino, heterocyclic amino, heterocyclic-substituted arylamino, hydrazino, alkylhydrazino, phenylhydrazino, sulfonyl, sulfonamido and halogen), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic-substituted alkylamino, heterocyclic amino, heterocyclic-substituted arylamino, hydrazino, alkylhydrazino, phenylhydrazino, sulfhydryl, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof; depending upon the number of unsaturations in the 3 to 10 atoms ring, heterocyclic radicals may be sub-divided into heteroaromatic (or "heteroaryl") radicals and non-aromatic heterocyclic radicals; when a heteroatom of said non-aromatic heterocyclic radical is nitrogen, the latter may be substituted with a substituent selected from the group consisting of $C_{1-7}$ alkyl, $C_{3-10}$ cycloalkyl, aryl, arylalkyl and alkylaryl.

As used herein with respect to a substituting radical, and unless otherwise stated, the terms "$C_{1-7}$ alkoxy", "$C_{3-10}$ cycloalkoxy", "aryloxy", "arylalkoxy", "oxyheterocyclic", "heterocyclic-substituted alkoxy", "thio $C_{1-7}$ alkyl", "thio $C_{3-10}$ cycloalkyl", "arylthio", "arylalkylthio" and "thioheterocyclic" refer to substituents wherein a carbon atom of a $C_{1-7}$ alkyl, respectively a $C_{3-10}$ cycloalkyl, aryl, arylalkyl, heterocyclic radical or heterocyclic-substituted alkyl (each of them such as defined herein), is attached to an oxygen atom or a divalent sulfur atom through a single bond such as, but not limited to, methoxy, ethoxy, propoxy, butoxy, pentoxy, isopropoxy, sec-butoxy, tert-butoxy, isopentoxy, cyclopropyloxy, cyclobutyloxy, cyclopentyloxy, thiomethyl, thioethyl, thiopropyl, thiobutyl, thiopentyl, thiocyclopropyl, thiocyclobutyl, thiocyclopentyl, thiophenyl, phenyloxy, benzyloxy, mercaptobenzyl and cresoxy, and various isomers of piperidinoxy, 1-methylpiperidinoxy, pyrrolidinoxy, pyridinoxy, tetrahydrofuranyloxy, morpholinoethoxy, piperazinoethoxy, piperi-dinoethoxy, pyridinoethoxy, pyrrolidinoethoxy, piperidinomethoxy, methylpyridinoxy, methylquinolinoxy, pyridinopropoxy and the like.

As used herein with respect to a substituting atom, and unless otherwise stated, the term halogen means any atom selected from the group consisting of fluorine, chlorine, bromine and iodine.

As used herein with respect to a substituting radical, and unless otherwise stated, the term "halo $C_{1-7}$ alkyl" means a $C_{1-7}$ alkyl radical (such as above defined) in which one or more hydrogen atoms are independently replaced by one or more halogens (preferably fluorine, chlorine or bromine), such as but not limited to difluoromethyl, trifluoromethyl, trifluoroethyl, octafluoropentyl, dodecafluoroheptyl, dichloromethyl and the like.

As used herein with respect to a substituting radical, and unless otherwise stated, the terms "$C_{2-7}$ alkenyl" designate a straight and branched acyclic hydrocarbon monovalent radical having one or more ethylenic unsaturations and having from 2 to 7 carbon atoms such as, for example, vinyl, 1-propenyl, 2-propenyl (allyl), 1-butenyl, 2-butenyl, 2-pentenyl, 3-pentenyl, 3-methyl-2-butenyl, 3-hexenyl, 2-hexenyl, 2-heptenyl, 1,3-butadienyl, pentadienyl, hexadienyl, heptadienyl, heptatrienyl and the like, including all possible isomers thereof.

As used herein with respect to a substituting radical, and unless otherwise stated, the term "$C_{3-10}$ cycloalkenyl" means a monocyclic mono- or polyunsaturated hydrocarbon monovalent radical having from 3 to 8 carbon atoms, such as for instance cyclopropenyl, cyclobutenyl, cyclopentenyl, cyclopentadienyl, cyclohexenyl, cyclohexadienyl, cycloheptenyl, cyclohepta-dienyl, cycloheptatrienyl, cyclooctenyl, cyclooctadienyl and the like, or a $C_{7-10}$ polycyclic mono- or polyunsaturated hydrocarbon mono-valent radical having from 7 to 10 carbon atoms such as dicyclopentadienyl, fenchenyl (including all isomers thereof, such as α-pinolenyl), bicyclo[2.2.1]hept-2-enyl, bicyclo[2.2.1]hepta-2,5-dienyl, cyclo-fenchenyl and the like.

As used herein with respect to a substituting radical, and unless otherwise stated, the term "$C_{2-7}$ alkynyl" defines straight and branched chain hydrocarbon radicals containing one or more triple bonds and optionally at least one double bond and having from 2 to 7 carbon atoms such as, for example, acetylenyl, 1-propynyl, 2-propynyl, 1-butynyl, 2-butynyl, 2-pentynyl, 1-pentynyl, 3-methyl-2-butynyl, 3-hexynyl, 2-hexynyl, 1-penten-4-ynyl, 3-penten-1-ynyl, 1,3-hexadien-1-ynyl and the like.

As used herein with respect to a substituting radical, and unless otherwise stated, the terms "arylalkyl", "arylalkenyl" and "heterocyclic-substituted alkyl" refer to an aliphatic saturated or ethylenically unsaturated hydrocarbon monovalent radical (preferably a $C_{1-7}$ alkyl or $C_{2-7}$ alkenyl radical such as defined above) onto which an aryl or heterocyclic radical (such as defined above) is already bonded via a carbon atom, and wherein the said aliphatic radical and/or the said aryl or heterocyclic radical may be optionally substituted with one or more substituents independently selected from the group consisting of halogen, amino, hydroxyl, sulfhydryl, $C_{1-7}$ alkyl, $C_{1-7}$ alkoxy, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-ter-butylbenzyl, phenylpropyl, 1-naphthylmethyl, phenylethyl, 1-amino-2-phenylethyl, 1-amino-2-[4-hydroxyphenyl]ethyl, 1-amino-2-[indol-2-yl]ethyl, styryl, pyridylmethyl (including all isomers thereof), pyridylethyl, 2-(2-pyridyl)isopropyl, oxazolylbutyl, 2-thienylmethyl, pyrrolylethyl, morpholinylethyl, imidazol-1-yl-ethyl, benzodioxolylmethyl and 2-furylmethyl.

As used herein with respect to a substituting radical, and unless otherwise stated, the terms "alkylaryl" and "alkyl-substituted heterocyclic" refer to an aryl or, respectively, heterocyclic radical (such as defined above) onto which are bonded one or more aliphatic saturated or unsaturated hydrocarbon monovalent radicals, preferably one or more $C_{1-7}$ alkyl, $C_{2-7}$ alkenyl or $C_{3-10}$ cycloalkyl radicals as defined above such as, but not limited to, o-toluoyl, m-toluoyl, p-toluoyl, 2,3-xylyl, 2,4-xylyl, 3,4-xylyl, o-cumenyl, m-cumenyl, p-cumenyl, o-cymenyl, m-cymenyl, p-cymenyl, mesityl, ter-butylphenyl, lutidinyl (i.e. dimethylpyridyl), 2-methylaziridinyl, methylbenzimidazolyl, methylbenzofuranyl, methylbenzothiazolyl, methylbenzotriazolyl, methylbenzoxazolyl and methylbenzselenazolyl.

As used herein with respect to a substituting radical, and unless otherwise stated, the term "alkoxyaryl" refers to an aryl radical (such as defined above) onto which is (are) bonded one or more $C_{1-7}$ alkoxy radicals as defined above, preferably one or more methoxy radicals, such as, but not limited to, 2-methoxyphenyl, 3-methoxyphenyl, 4-methoxyphenyl, 3,4-dimethoxyphenyl, 2,4,6-trimethoxyphenyl, methoxynaphtyl and the like.

As used herein with respect to a substituting radical, and unless otherwise stated, the terms "alkylamino", "cycloalkylamino", "alkenylamino", "cyclo-alkenylamino", "arylamino", "arylalkylamino", "heterocyclic-substituted alkylamino", "heterocyclic-substituted arylamino", "heterocyclic amino", "hydroxyalkylamino", "mercaptoalkylamino" and "alkynylamino" mean that respectively one (thus monosubstituted amino) or even two (thus disubstituted amino) $C_{1-7}$ alkyl, $C_{3-10}$ cycloalkyl, $C_{2-7}$ alkenyl, $C_{3-10}$ cycloalkenyl, aryl, arylalkyl, heterocyclic-substituted alkyl, heterocyclic-substituted aryl, heterocyclic (provided in this case the nitrogen atom is attached to a carbon atom of the heterocyclic ring), mono- or polyhydroxy $C_{1-7}$ alkyl, mono- or polymercapto $C_{1-7}$ alkyl, or $C_{2-7}$ alkynyl radical(s) (each of them as defined herein, respectively, and including the presence of optional substituents independently selected from the group consisting of halogen, amino, hydroxyl, sulfhydryl, $C_{1-7}$ alkyl, $C_{1-7}$ alkoxy, trifluoromethyl and nitro) is/are attached to a nitrogen atom through a single bond such as, but not limited to, anilino, 2-bromoanilino, 4-bromoanilino, 2-chloroanilino, 3-chloroanilino, 4-chloroanilino, 3-chloro-4-methoxyanilino, 5-chloro-2-methoxyanilino, 2,3-dimethylanilino, 2,4-dimethylanilino, 2,5-dimethylanilino, 2,6-dimethylanilino, 3,4-dimethylanilino, 2-fluoroanilino, 3-fluoroanilino, 4-fluoroanilino, 3-fluoro-2-methoxyanilino, 3-fluoro-4-methoxyanilino, 2-fluoro-4-methylanilino, 2-fluoro-5-methylanilino, 3-fluoro-2-methylanilino, 3-fluoro-4-methylanilino, 4-fluoro-2-methylanilino, 5-fluoro-2-methylanilino, 2-iodoanilino, 3-iodoanilino, 4-iodoanilino, 2-methoxy-5-methylanilino, 4-methoxy-2-methylanilino, 5-methoxy-2-methylanilino, 2-ethoxyanilino, 3-ethoxyanilino, 4-ethoxyanilino, benzylamino, 2-methoxybenzylamino, 3-methoxybenzylamino, 4-methoxybenzylamino, 2-fluorobenzylamino, 3-fluorobenzylamino, 4-fluorobenzylamino, 2-chlorobenzylamino, 3-chlorobenzylamino, 4-chlorobenzylamino, 2-aminobenzylamino, diphenylmethylamino, α-naphthylamino, methylamino, dimethylamino, ethylamino, diethylamino, isopropylamino, propenylamino, n-butylamino, ter-butylamino, dibutylamino, 1,2-diaminopropyl, 1,3-diaminopropyl, 1,4-diaminobutyl, 1,5-diaminopentyl, 1,6-diaminohexyl, morpholinomethylamino, 4-morpholinoanilino, hydroxymethylamino, β-hydroxyethylamino and ethynylamino; this definition also includes mixed disubstituted amino radicals wherein the nitrogen atom is attached to two such radicals belonging to two different sub-sets of radicals, e.g. an alkyl radical and an alkenyl radical, or to two different radicals within the same sub-set of radicals, e.g. methylethylamino; among di-substituted amino radicals, symmetrically-substituted amino radicals are more easily accessible and thus usually preferred from a standpoint of ease of preparation.

As used herein with respect to a substituting radical, and unless otherwise stated, the terms "(thio)carboxylic acid ester", "(thio)carboxylic acid thioester" and "(thio)carboxylic acid amide" refer to radicals wherein the carboxyl or thiocarboxyl group is bonded to the hydrocarbonyl residue of an alcohol, a thiol, a polyol, a phenol, a thiophenol, a primary or secondary amine, a polyamine, an amino-alcohol or ammonia, the said hydrocarbonyl residue being selected from the group consisting of alkyl, alkenyl, alkynyl, cycloalkyl, cycloalkenyl, aryl, arylalkyl, alkylaryl, alkylamino, cycloalkylamino, alkenylamino, cycloalkenylamino, arylamino, arylalkylamino, heterocyclic-substituted alkylamino, heterocyclic amino, heterocyclic-substituted arylamino, hydroxyalkylamino, mercapto-alkylamino or alkynylamino (such as above defined, respectively).

As used herein with respect to a substituting radical, and unless otherwise stated, the term "amino-acid" refers to a radical derived from a molecule having the chemical formula $H_2N$—CHR—COOH, wherein R is the side group of atoms characterising the amino-acid type; said molecule may be one of the 20 naturally-occurring amino-acids or any similar non naturally-occurring amino-acid.

As used herein and unless otherwise stated, the term "stereoisomer" refers to all possible different isomeric as well as conformational forms which the compounds of formula (I) may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a pyrido(3,2-d)pyrimidine derivative of this invention with a suitable inorganic solvent (e.g. hydrates) or organic solvent, such as but not limited to alcohols, ketones, esters, ethers, nitriles and the like.

DETAILED DESCRIPTION OF THE INVENTION

In the first embodiment of the invention, the novel pyrido (3,2-d)pyrimidine derivatives are as defined in the structural formula (I), wherein each of the substituents $R_1$, $R_2$, $R_3$ and/or $R_4$ may independently correspond to any of the definitions given above, in particular with any of the individual meanings (such as illustrated above) of generic terms used for substituting radicals such as, but not limited to, "$C_{1-7}$ alkyl", "$C_{3-10}$ cycloalkyl", "$C_{2-7}$ alkenyl", "$C_{2-7}$ alkynyl", "aryl", "homocyclic", "heterocyclic", "halogen", "$C_{3-10}$ cycloalkenyl", "alkylaryl", "arylalkyl", "alkylamino", "cycloalkylamino", "alkenylamino", "alkynylamino", "arylamino", "arylalkylamino", "heterocyclic-substituted alkylamino", "heterocyclic amino", "heterocyclic-substituted arylamino", "hydroxyalkylamino", "mercaptoalkylamino", "alkynylamino", "$C_{1-7}$ alkoxy", "$C_{3-10}$ cycloalkoxy", "aryloxy", "arylalkoxy", "oxyheterocyclic", "thioheterocyclic", "heterocyclic-substituted alkoxy", "thio $C_{1-7}$ alkyl", "thio $C_{3-10}$ cycloalkyl", "halo $C_{1-7}$ alkyl", "amino-acid" and the like.

In the second embodiment of the invention, the novel pyrido(3,2-d)pyrimidine intermediates are as specified herein before, wherein each of the substituents $R_1$, $R_2$, $R_3$ and/or $R_4$ may independently correspond to any of the definitions given with respect to the structural formula (I), in particular with any of the individual meanings (such as illustrated above) of generic terms used for substituting radicals such as, but not limited to, "$C_{1-7}$ alkyl", "$C_{3-10}$ cycloalkyl", "$C_{2-7}$ alkenyl", "$C_{2-7}$ alkynyl", "aryl", "homocyclic", "heterocyclic", "halogen", "$C_{3-10}$ cycloalkenyl", "alkylaryl", "aryl-alkyl", "alkylamino", "cycloalkylamino", "alkenylamino", "alkynylamino", "aryl-amino", "arylalkylamino", "heterocyclic-substituted alkylamino", "heterocyclic amino", "heterocyclic-substituted arylamino", "hydroxyalkylamino", "mercaptoalkylamino", "alkynylamino", "$C_{1-7}$ alkoxy", "$C_{3-10}$ cycloalkoxy", "aryloxy", "arylalkoxy", "oxyheterocyclic", "thioheterocyclic", "heterocyclic-substituted alkoxy", "thio $C_{1-7}$ alkyl", "thio $C_{3-10}$ cycloalkyl", "halo $C_{1-7}$ alkyl", "amino-acid" and the like.

Within the broad class of compounds having the structural formula (I), a useful group of compounds is one wherein $R_2$ is a homopiperazinyl or piperazinyl group optionally N-substituted with a substituent $R_5$ such as defined herein above. Said homopiperazinyl or piperazinyl group may be further suitably substituted, at one or more carbon atoms, by a number n of substituents $R_0$ wherein n is an integer from 0 to 6 and wherein, when n is at least 2, each $R_0$ may be defined independently from the others. The presence of one or more such substituents $R_0$ at one or more carbon atoms is a suitable way for introducing chirality into the pyrido(2,3-d)pyrimidine derivatives having the structural formula (I) as well as into the corresponding intermediates. In practice, the choice of such substituents $R_0$ may be restricted by the commercial availability of the substituted piperazine. More preferably $R_2$ is a piperazin-1-yl group, n is 0, 1 or 2, and a representative example of the substituent $R_0$ is methyl or phenyl such as for instance in 2-methylpiperazin-1-yl, 2-phenylpiperazin-1-yl and 2,5-dimethyl-piperazin-1-yl. Within this group of compounds, a more specific embodiment of the invention is one wherein one of the two nitrogen atoms of the piperazinyl group bears a substituent $R_5$ which has a carbonyl (oxo) or thiocarbonyl (thioxo) or sulfonyl function preferably immediately adjacent to the said nitrogen atom. In other words, this specific embodiment means that when $R_5$ is selected from, respectively, acyl, thioacyl, amide, thioamide, sulfonyl, sulfinyl, carboxylate and thiocarboxylate, then $R_5$ together with the nitrogen atom to which it is attached respectively forms an amide, thioamide, urea, thiourea, sulfonamido, sulfinamido, carbamato or thiocarbamato group.

Especially useful species of pyrido(3,2-d)pyrimidine derivatives having the structural formula (I) are those wherein the substituent $R_2$ is a piperazin-1-yl group, said group being substituted in the 4 position with a substituent $R_5$, wherein $R_5$ is selected from the group consisting of:

$COR_8$ wherein $R_8$ is selected from the group consisting of hydrogen; $C_{1-7}$ alkyl; $C_{3-10}$ cycloalkyl; aryl optionally substituted with one or more substituents selected from the group consisting of halogen, $C_{1-7}$ alkyl, cyano and $C_{1-7}$ alkoxy; heterocyclic optionally substituted with one or more halogen atoms; arylalkyl; aryloxyalkyl; arylalkoxyalkyl; alkoxyalkyl; arylalkoxy; aryloxy; arylalkenyl; heterocyclic-substituted alkyl; alkylamino and arylamino; representative but non limiting examples of $R_8$ include methyl, ethyl, pentyl, cyclohexyl, phenyl, 4-fluorophenyl, 4-chlorophenyl, 3,4-dichlorophenyl, 4-butylphenyl, 4-cyanophenyl, 2-methoxyphenyl, 3-methoxyphenyl, 4-pentoxyphenyl, naphthyl, 2-thienyl, 4-pyridinyl, 1-tetrahydropyrrolyl, 2-tetrahydropyrrolyl, 2-furanyl, 3-furanyl, 2,4-dichloro-5-fluoro-3-pyridinyl, diethylamino, diisopropylamino, dimethylamino, dibutylamino, ethylamino, isopropylamino, methylamino, butylamino, phenylamino, diphenylamino, phenylethyl, 4-chlorobenzyl, phenoxymethyl, benzyloxymethyl, methoxymethyl, ethoxymethyl, methoxyethyl, ethoxyethyl, 2-thienylmethyl, styryl, benzyloxy, phenoxy, 1-amino-2-phenylethyl, 1-amino-2-[4-hydroxyphenyl]ethyl and 1-amino-2-[indol-2-yl]ethyl;

$CSR_9$, wherein $R_9$ is selected from the group consisting of alkylamino and aryloxy, such as, but not limited to, dimethylamino, methylamino, diethylamino, ethylamino, naphthoxy and phenoxy;

$SO_2R_{10}$, wherein $R_{10}$ is selected from the group consisting of aryl and arylalkyl, such as, but not limited to, phenyl, naphthyl and benzyl; and $R_{11}$, wherein $R_{11}$ is selected from the group consisting of $C_{1-7}$ alkyl, aryl, arylalkyl, arylalkenyl, alkoxyalkyl, heterocyclic-substituted alkyl, cycloalkylalkyl, heterocyclic, $C_{3-10}$ cycloalkyl, alkylaminoalkyl, aryloxyalkyl, alkoxyaryl, $\omega$-cyanoalkyl, $\omega$-carboxylatoalkyl and carboxamidoalkyl.

Especially useful species of pyrido(3,2-d)pyrimidine derivatives having the structural formula (I) are those wherein the substituent $R_1$ is a group of the structural formula $R_6NR_7R_{12}$, wherein $R_6$ is a bond or a $C_{1-3}$ alkylene group, and wherein $R_7$ and $R_{12}$ are independently selected from the group consisting of hydrogen, $C_{1-7}$ alkyl, $C_{2-7}$ alkenyl, $C_{2-7}$ alkynyl, aryl, arylalkyl, $C_{3-10}$ cycloalkyl and heteroaryl, or wherein N, $R_7$ and $R_{12}$ together form a heterocycle. Within this sub-class of derivatives of the invention, it is preferred when $R_6$ is a bond or methylene, and/or $R_7$ is methyl, ethyl, propyl or cyclopropylmethyl, and/or N, $R_7$ and $R_{12}$ together form a heterocyclic group selected from the group consisting of morpholinyl, 2,6-dimethylmorpholinyl, pyrrolidinyl, azepanyl, 3,3,5-trimethylazepanyl, piperidinyl, 2-methylpiperidinyl, 2-ethylpiperidinyl and the like. Methods for introducing such substituents in position 2 of the pyrido(3,2-d) pyrimidine ring are well known in the art and, for instance, extensively described in WO 03/062209.

The present invention further provides various processes and methods for making the novel pyrido(3,2-d)pyrimidine derivatives having the structural formula (I). As a general rule, the preparation of these compounds is based on the principle that, starting from a suitable pyrido(3,2-d)pyrimidine precursor (usually a 2,3,6-trisubstituted pyridine), each of the substituents $R_2$, $R_3$, $R_4$ and $R_1$ may be introduced separately without adversely influencing the presence of one or more substituents already introduced at other positions on the pyrido(3,2-d)pyrimidine moiety or the capacity to introduce further substituents later on.

Methods of manufacture have been developed by the present inventors which may be used alternatively to, or may be combined with, the methods of synthesis already known in the art of pyrido(3,2-d)pyrimidine derivatives (depending upon the targeted final compound). For instance, the synthesis of mono- and di-N-oxides of the pyrido(3,2-d)pyrimidine derivatives of this invention can easily be achieved by treating the said derivatives with an oxidizing agent such as, but not limited to, hydrogen peroxide (e.g. in the presence of acetic acid) or a peracid such as chloroperbenzoic acid. The methods for making the pyrido(3,2-d)pyrimidine derivatives of the present invention will now be explained in more details by reference to the appended FIGS. 1 to 8 wherein, unless otherwise stated hereinafter, each of the substituting groups or atoms $R_2$, $R_3$, $R_4$ and $R_1$ is as defined in formula (I) of the summary of the invention and, more specifically, may correspond to any of the individual meanings disclosed above.

In the description of the reaction steps involved in each figure, reference is made to the use of certain catalysts and/or certain types of solvents. It should be understood that each catalyst mentioned should be used in a catalytic amount well known to the skilled person with respect to the type of reaction involved. Solvents that may be used in the following reaction steps include various kinds of organic solvents such as protic solvents, polar aprotic solvents and non-polar solvents as well as aqueous solvents which are inert under the relevant reaction conditions. More specific examples include aromatic hydrocarbons, chlorinated hydrocarbons, ethers, aliphatic hydrocarbons, alcohols, esters, ketones, amides, water or mixtures thereof, as well as supercritical solvents such as carbon dioxide (while performing the reaction under supercritical conditions). The suitable reaction temperature and pressure conditions applicable to each kind of reaction step will not be detailed herein but do not depart from the relevant conditions already known to the skilled person with respect to the type of reaction involved and the type of solvent used (in particular its boiling point).

FIG. 1 schematically shows a first method for making 2,4,6-tri-substituted pyrido(3,2-d)pyrimidine derivatives having the formula (I) wherein the substituent in position 2 is amino, as well as intermediates therefor wherein the substituent in position 2 is a N-protected amino such as acetamido and/or wherein the substituent in position 4 is hydroxy, chloro or triazolyl. The nitro group of 6-chloro-2-cyano-3-nitropyridine is reduced in step (a) either catalytically (e.g. by using platinum or palladium under an atmosphere of hydrogen) or chemically (e.g. by using iron or tin under acidic conditions). A ring closure reaction leading to the formation of the pyrido[3,2-d]pyrimidine scaffold occurs in step (b) by treatment of 6-chloro-2-cyano-3-aminopyridine with a ring closure reagent such as, but not limited to, chloroformamidine or guanidine. Aqueous hydrolysis under aqueous acidic conditions then yields 2-amino-6-chloro-pyrido[3,2-d]pyrimidin-4(3H)one in step (c). In step (d), the chlorine atom at position 6 can be used as a leaving group for a variety of palladium-catalyzed reactions such as, but not limited to, a Suzuki reaction (by treatment of 2-amino-6-chloro-pyrido[3,2-d]pyrimidin-4(3H)one with an aryl boronic acid leading to the formation of a biaryl derivative) and a Heck reaction (by treatment of 2-amino-6-chloro-pyrido[3,2-d]pyrimidin-4(3H)one with a wide variety of terminal alkenes or alkynes, thus yielding alkenyl or alkynyl compounds). In step (e), the amino group at position 2 is protected, for example by a pivaloyl (not shown in FIG. 1) or acetyl group, by reaction with acetic anhydride or pivaloyl anhydride in pyridine as a solvent, thus resulting into the introduction of a N-protected amino group at position 2 such as, but not limited to, acetamido or pivalamido. Activation of the tautomeric hydroxyl group at position 4 of the pyrido[3,2-d]pyrimidine scaffold for the subsequent nucleophilic displacement reaction occurs in step (f) by preparing the corresponding 4-(1,2,4-triazolyl)-pyrido[3,2-d]pyrimidine derivative or 4-chloro-pyrido[3,2-d]pyrimidine derivative. The 4-triazolyl derivative can be obtained by treating the 4-oxo-pyrido[3,2-d]pyrimidine derivative with POCl$_3$ or 4-chlorophenyl phosphorodichloridate and 1,2,4-triazole in an appropriate solvent such as, but not limited to, pyridine or acetonitrile. The 4-chloro derivative can be obtained by treating the 4-oxo-pyrido[3,2-d]pyrimidine derivative with thionyl chloride or POCl$_3$. The chlorine atom or triazolyl group is designated as L in FIG. 1. Nucleophilic displacement of the triazolyl group or chlorine atom occurs in step (g) by reaction with an appropriate nucleophile having the general formula R$_2$H, wherein R$_2$ is as defined in the general formula (I), in a polar aprotic solvent. When piperazine is introduced in step (g) of this method, as well as in the corresponding step of some of the further methods described herein, the second nitrogen atom of this piperazin-1-yl substituent may, if desired, be coupled with a suitable carboxylic acid or thio-carboxylic acid chloride or sulfonyl chloride R$_5$Cl at room temperature in a solvent such as pyridine. Representative but non limiting examples of commercially available N-alkylpiperazines, N-arylpiperazines and N-alkylarylpiperazines that can suitably be used in step (g) of this method, as well as in the corresponding step of some of the further methods described herein, include 1-cyclohexylpiperazine, 1-cyclopentylpiperazine, 1-(2,6-dichlorobenzyl)piperazine, 1-(3,4-dichlorophenyl)piperazine, 1-[2-(dimethylamino)-ethyl]piperazine, 1-[3-(dimethylamino)propyl]piperazine, 1-(3,4-dimethylphenyl)piperazine, 1-(2-ethoxyethyl)piperazine, 1-isobutylpiperazine, 1-(1-methylpiperidin-4-yl-methyl)piperazine, 1-(2-nitro-4-trifluoromethylphenyl)piperazine, 1-(2-phenoxyethyl)piperazine, 1-(1-phenylethyl)piperazine, 2-(piperazin-1-yl)acetic acid ethyl ester, 2-(piperazin-1-yl)acetic acid N-methyl-N-phenyl amide, 2-(piperazin-1-yl)acetic acid N-(2-thiazolyl)amide, 2-[2-(piperazin-1-yl)ethyl]-1,3-dioxolan-3-(1-piperazinyl)propionitrile, 1-[(2-pyridyl)-methyl]piperazine and 1-thiazol-2-yl-piperazine. In the final step (h), the amino protecting group is cleaved off by using standard cleavage conditions such as acidic or basic hydrolysis.

Figure 2:
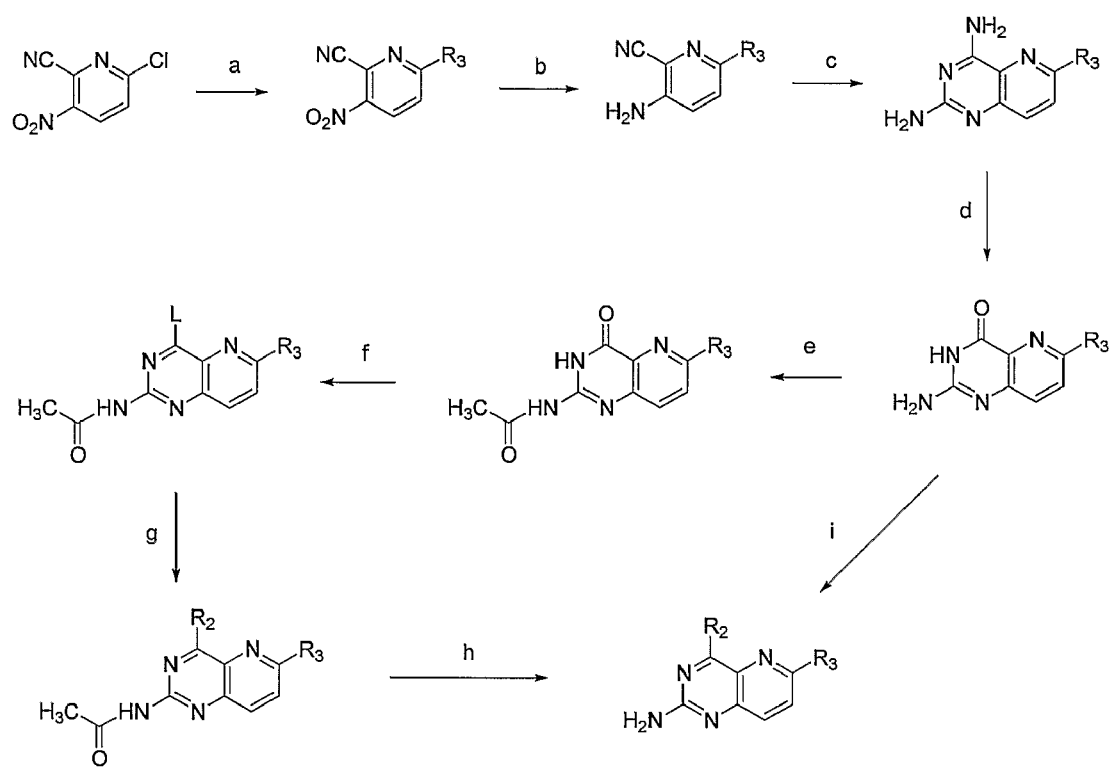
FIG. 2 schematically shows a second method for making 2,4,6-tri-substituted pyrido(3,2-d)pyrimidine derivatives having the formula (I) wherein the substituent in position 2 is amino, as well as intermediates therefor wherein the substituent in position 2 is a N-protected amino such as acetamido and/or wherein the substituent in position 4 is hydroxy, chloro or triazolyl.

FIG. 2 schematically shows a second method for making 2,4,6-tri-substituted pyrido(3,2-d)pyrimidine derivatives having the formula (I) wherein the substituent in position 2 is amino, as well as intermediates therefor wherein the substituent in position 2 is a N-protected amino such as acetamido and/or wherein the substituent in position 4 is hydroxy, chloro or triazolyl. In step (a), 6-chloro-2-cyano-3-nitropyridine is subjected to a palladium-catalyzed reaction such as, but not limited to, a Suzuki reaction with an aryl boronic acid to yield the corresponding biaryl derivative or a Heck reaction with a terminal alkene or alkyne leading to the formation of an alkenyl or alkynyl derivative. The 3-nitro group is reduced in step (b), either catalytically (e.g. by using platinum or palladium under an atmosphere of hydrogen) or chemically (e.g. by using iron or tin under acidic conditions). A ring closure reaction leading to the formation of the pyrido[3,4-d]pyrimidine scaffold occurs in step (c) by treatment of the 6-R$_3$-substituted-2-cyano-3-aminopyridine intermediate with a ring closure reagent such as, but not limited to, chloroformamidine or guanidine. Aqueous hydrolysis of the 4-amino group, either under acidic or alcaline conditions, yields the 2-amino-6-R$_3$-pyrido[3,2-d]pyrimidin-4(3H)one. In step (e), the amino group at position 2 is protected, for example by a pivaloyl (not shown in FIG. 2) or acetyl group, by reaction with acetic anhydride or pivaloyl anhydride respectively, in pyridine as a solvent, thus resulting into the introduction of a N-protected amino group at position 2 such as, but not limited to, acetamido or pivalamido. Activation of the tautomeric hydroxyl group at position 4 of the pyrido[3,2-d]pyrimidine scaffold for the subsequent nucleophilic displacement reaction occurs in step (f) by preparing the corresponding 4-(1,2,4-triazolyl)-pyrido[3,2-d]pyrimidine derivative or 4-chloro-pyrido[3,2-d]pyrimidine derivative. The 4-triazolyl derivative can be obtained by treating the 4-oxo-pyrido[3,2-d]pyrimidine derivative with POCl$_3$ or 4-chlorophenyl phosphorodichloridate and 1,2,4-triazole in an appropriate solvent such as, but not limited to, pyridine or acetonitrile. The 4-chloro derivative can be obtained by treating the 4-oxo-pyrido[3,2-d]pyrimidine derivative with thionyl chloride or POCl$_3$. The triazolyl group or chlorine atom is designated as L in FIG. 2. Nucleophilic displacement of the triazolyl group or chlorine atom occurs in step (g) by reaction with an appropriate nucleophile having the general formula R$_2$H, wherein R$_2$ is as defined in the general formula (I), in a polar aprotic solvent. In the final step (h), the amino protecting group is cleaved off by using standard cleavage conditions such as acidic or basic hydrolysis. Alternatively, an alkylamino, arylamino or alkylarylamino group R$_2$ can also be directly introduced, in step (i), at position 4 of the pyrido[3,2-d]pyrimidine scaffold by treatment of the 2-amino-6-R$_3$-substituted-pyrido[3,2-d]pyrimidine with an appropriate alkylamine, arylamine or alkylarylamine in the presence of a suitable amount of 1,1,1,3,3,3-hexamethyldisilazane as a reagent.

Figure 3:
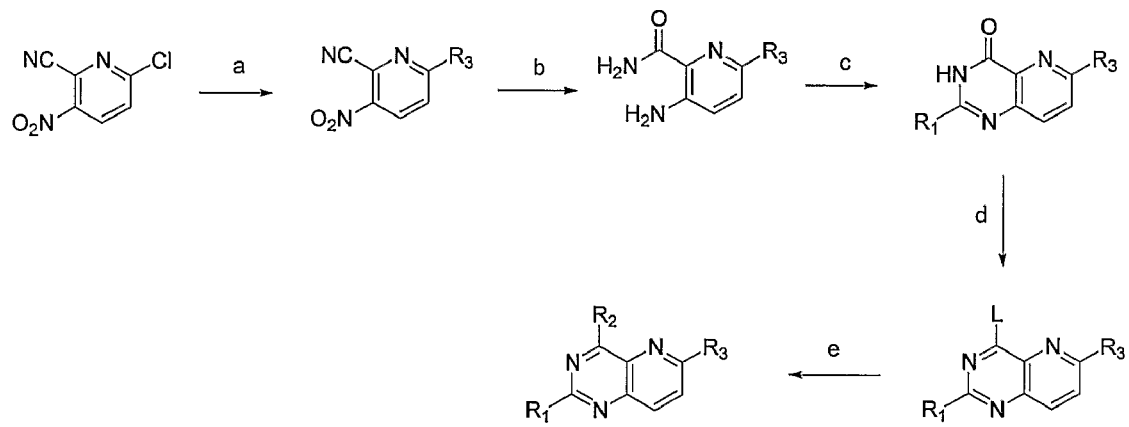
FIG. 3 schematically shows a method for making 2,4,6-tri-substituted pyrido(3,2-d)pyrimidine intermediates having the formula (I), as well as intermediates wherein the substituent in position 4 is hydroxy, chloro or triazolyl.

FIG. 3 schematically shows a method for making 2,4,6-tri-substituted pyrido(3,2-d)pyrimidine intermediates having the formula (I), as well as intermediates wherein the substituent in position 4 is hydroxy, chloro or triazolyl. In step (a), 6-chloro-2-cyano-3-nitropyridine is subjected to a palladium-catalyzed reaction such as, but not limited to, a Suzuki reaction with an aryl boronic acid to yield the corresponding biaryl derivative or, alternatively, a Heck reaction with a terminal alkene or alkyne leading to the formation of alkenyl or alkynyl derivatives. In step (b), the 3-nitro group is reduced, either catalytically (e.g. by using platinum or palladium under an atmosphere of hydrogen) or chemically (e.g. by using iron or tin under acidic conditions) and at the same time the cyano group is hydrolyzed into a carboxamide function. Formation of the 2-$R_1$-substituted-pyrido[3,2-d]pyrimidine scaffold occurs in step (c) by treatment of a 6-$R_3$-substituted-2-carboxamido-3-aminopyridine derivative either with an orthoester (such as, but not limited to, triethyl orthoformate) or with an acid chloride followed by treatment with a base such as sodium hydroxide. Activation of the tautomeric hydroxyl group at position 4 of the pyrido[3,2-d]pyrimidine scaffold for the subsequent nucleophilic displacement reaction occurs in step (d) by preparing the corresponding 4-chloro-pyrido[3,2-d]pyrimidine derivative or the corresponding 4-(1,2,4-triazolyl)-pyrido[3,2-d]pyrimidine derivative. The triazolyl derivative can be obtained by treating the 4-oxo-pyrido[3,2-d]pyrimidine derivative with $POCl_3$ or 4-chlorophenyl phosphorodichloridate and 1,2,4-triazole in an appropriate solvent such as, but not limited to, pyridine or acetonitrile. The 4-chloro derivative can be obtained by treating the 4-oxo-pyrido[3,2-d]pyrimidine derivative with thionyl chloride or $POCl_3$. The triazolyl group or chlorine atom at position 4 are indicated as L in FIG. 3. Nucleophilic displacement of the chlorine atom or 1,2,4-triazolyl moiety occurs in step (e) by reaction with an appropriate nucleophile having the general formula $R_2H$, wherein $R_2$ is as defined in the general formula (I), in a polar protic or aprotic solvent.

Figure 4:
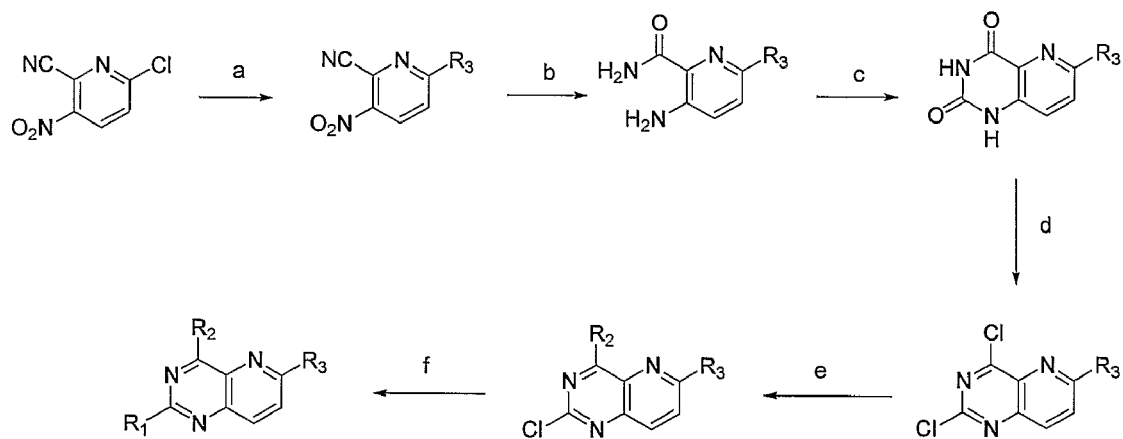
FIG. 4 schematically shows another method for making 2,4,6-tri-substituted pyrido(3,2-d)pyrimidine intermediates having the formula (I), as well as intermediates wherein the substituent in positions 2 and 4 are hydroxy or chloro.

FIG. 4 schematically shows another method for making 2,4,6-tri-substituted pyrido(3,2-d)pyrimidine intermediates having the formula (I), as well as intermediates wherein the substituent in positions 2 and 4 are hydroxy or chloro. In step (a), 6-chloro-2-cyano-3-nitropyridine is subjected to a palladium-catalyzed reaction such as, but not limited to, a Suzuki reaction with an aryl boronic acid to yield the corresponding biaryl derivative or, alternatively, a Heck reaction with a terminal alkene or alkyne leading to the formation of an alkenyl or alkynyl derivative. In step (b), the 3-nitro group is reduced, either catalytically (e.g. by using platinum or palladium under an atmosphere of hydrogen) or chemically (e.g. by using iron or tin under acidic conditions) and at the same time the cyano group is hydrolyzed into a carboxamide function. Ring closure reaction leading to the formation of the pyrido[3,2-d]pyrimidine scaffold occurs in step (c) by treatment of a 6-$R_3$-substituted-2-carboxamido-3-aminopyridine derivative either with a phosgene derivative in an aprotic solvent or with a carbonate (such as, but not limited to, dimethylcarbonate or diethylcarbonate) in a protic or aprotic solvent. Activation of the tautomeric hydroxyl groups at positions 2 and 4 of the pyrido[3,2-d]pyrimidine scaffold for the subsequent nucleophilic displacement reaction occurs in step (d) by preparing the corresponding 2,4-dichloro-pyrido[3,2-d]pyrimidine derivative, e.g. by treating the 4-oxo-pyrido[3,2-d]pyrimidine derivative with thionyl chloride or $POCl_3$. Selective nucleophilic displacement of the chlorine at position 4 occurs in step (e) by reaction with an appropriate nucleophile having the general formula $R_2H$ in a polar protic or aprotic solvent at an appropriate temperature. In step (f), the 2-chloro derivative is then treated with an appropriate nucleophile having the general formula $R_1H$ in a polar protic or aprotic solvent at an appropriate temperature in order to afford the desired 2,4,6-trisubstituted derivative.

Figure 5:
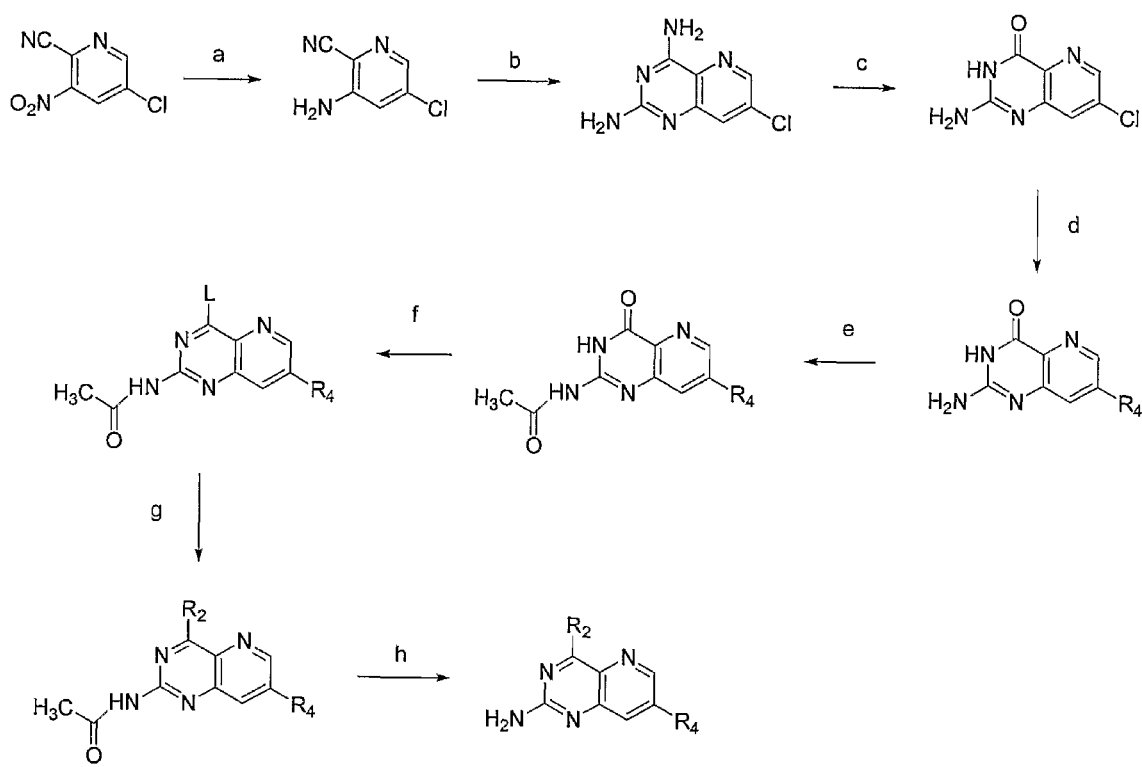
FIG. 5 schematically shows a first method for making 2,4,7-tri-substituted pyrido(3,2-d)pyrimidine derivatives having the formula (I) wherein the substituent in position 2 is amino, as well as intermediates therefor wherein the substituent in position 2 is a N-protected amino such as acetamido and/or wherein the substituent in position 4 is hydroxy, chloro or triazolyl.

FIG. 5 schematically shows a first method for making 2,4,7-tri-substituted pyrido(3,2-d)pyrimidine derivatives having the formula (I) wherein the substituent in position 2 is amino, as well as intermediates therefor wherein the substituent in position 2 is a N-protected amino such as acetamido and/or wherein the substituent in position 4 is hydroxy, chloro or triazolyl. The nitro group of 5-chloro-2-cyano-3-nitropyridine is first reduced in step (a) either catalytically (e.g. by using platinum or palladium under an atmosphere of hydrogen) or chemically (e.g. by using iron or tin under acidic conditions). A ring closure reaction leading to the formation of the pyrido[3,2-d]pyrimidine scaffold occurs in step (b) by treatment of 5-chloro-2-cyano-3-aminopyridine with a ring closure reagent such as, but not limited to, chloroformamidine or guanidine. Aqueous hydrolysis under aqueous acidic conditions then yields 2-amino-7-chloro-pyrido[3,2-d]pyrimidin-4(3H)one in step (c). In step (d), the chlorine atom at position 7 can be used as a leaving group for a variety of palladium-catalyzed reactions such as, but not limited to, a Suzuki reaction (by treatment of 2-amino-7-chloro-pyrido[3,2-d]pyrimidin-4(3H)one with an aryl boronic acid leading to the formation of a biaryl derivative) and a Heck reaction (by treatment of 2-amino-7-chloro-pyrido[3,2-d]pyrimidin-4 (3H)one with a wide variety of terminal alkenes or alkynes, thus yielding alkenyl or alkynyl compounds). In step (e), the amino group at position 2 is protected, for example by a pivaloyl (not shown in FIG. 1) or acetyl group, by reaction with acetic anhydride or pivaloyl anhydride in pyridine as a solvent, thus resulting into the introduction of a N-protected amino group at position 2 such as, but not limited to, acetamido or pivalamido. Activation of the tautomeric hydroxyl group at position 4 of the pyrido[3,2-d]pyrimidine scaffold for the subsequent nucleophilic displacement reaction occurs in step (f) by preparing the corresponding 4-(1,2,4-triazolyl)-pyrido[3,2-d]pyrimidine derivative or 4-chloro-pyrido[3,2-d] pyrimidine derivative. The 4-triazolyl derivative can be obtained by treating the 4-oxo-pyrido[3,2-d]pyrimidine derivative with $POCl_3$ or 4-chlorophenyl phosphorodichloridate and 1,2,4-triazole in an appropriate solvent such as, but not limited to, pyridine or acetonitrile. The 4-chloro derivative can be obtained by treating the 4-oxo-pyrido[3,2-d]pyrimidine derivative with thionyl chloride or $POCl_3$. The chlorine atom or triazolyl group is designated as L in FIG. 5. Nucleophilic displacement of the triazolyl group or chlorine atom occurs in step (g) by reaction with an appropriate nucleophile having the general formula $R_2H$, wherein $R_2$ is as defined in the general formula (I), in a polar aprotic solvent. In the final step (h), the amino protecting group is cleaved off by using standard cleavage conditions such as acidic or basic hydrolysis.

Figure 6:
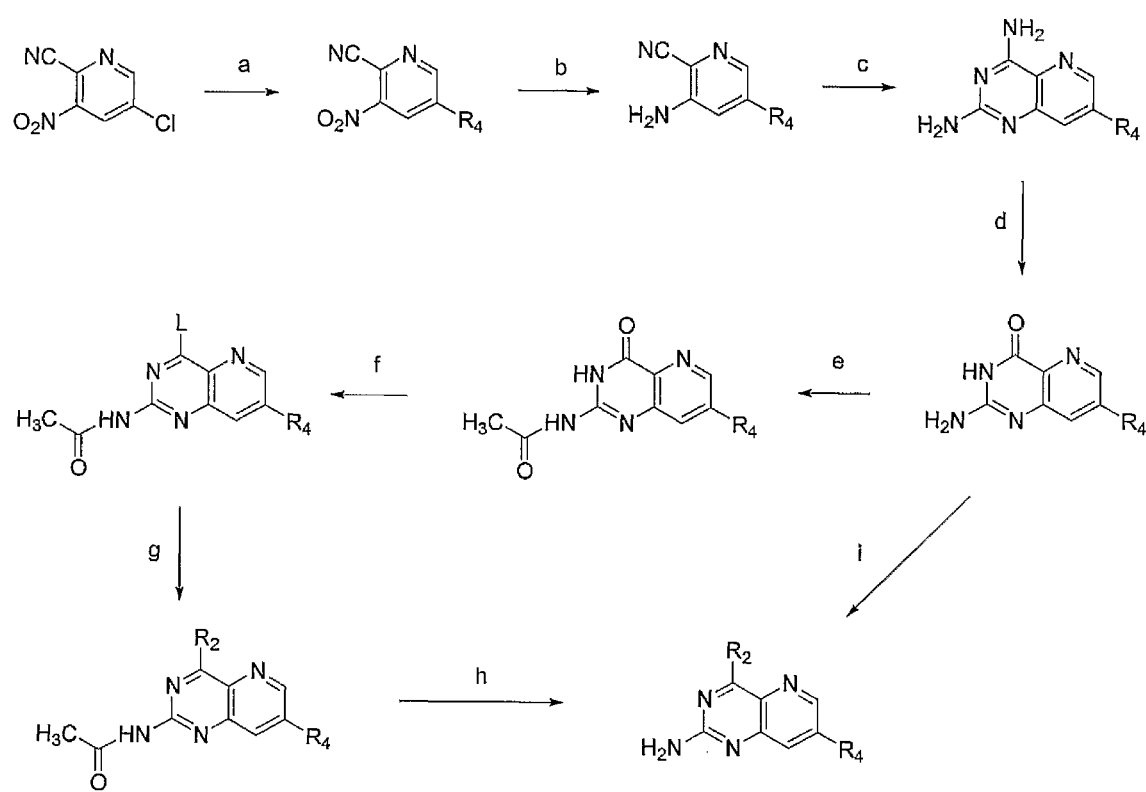
FIG. 6 schematically shows a second method for making 2,4,7-tri-substituted pyrido(3,2-d)pyrimidine derivatives having the formula (I) wherein the substituent in position 2 is amino, as well as intermediates therefor wherein the substituent in position 2 is a N-protected amino such as acetamido and/or wherein the substituent in position 4 is hydroxy, chloro or triazolyl.

FIG. 6 schematically shows a second method for making 2,4,7-tri-substituted pyrido(3,2-d)pyrimidine derivatives having the formula (I) wherein the substituent in position 2 is amino, as well as intermediates therefor wherein the substituent in position 2 is a N-protected amino such as acetamido and/or wherein the substituent in position 4 is hydroxy, chloro or triazolyl. In step (a), 5-chloro-2-cyano-3-nitropyridine is subjected to a palladium-catalyzed reaction such as, but not limited to, a Suzuki reaction with an aryl boronic acid to yield the corresponding biaryl derivative or a Heck reaction with a terminal alkene or alkyne leading to the formation of an alkenyl or alkynyl derivative. The 3-nitro group is reduced in step (b), either catalytically (e.g. by using platinum or palladium under an atmosphere of hydrogen) or chemically (e.g. by using iron or tin under acidic conditions). A ring closure reaction leading to the formation of the pyrido[3,4-d]pyrimidine scaffold occurs in step (c) by treatment of the 5-$R_4$-substituted-2-cyano-3-aminopyridine intermediate with a ring closure reagent such as, but not limited to, chloroformamidine or guanidine. Aqueous hydrolysis of the 4-amino group, either under acidic or alcaline conditions, yields the 2-amino-7-$R_4$-pyrido[3,2-d]pyrimidin-4(3H)one. In step (e), the amino group at position 2 is protected, for example by a pivaloyl (not shown in FIG. 2) or acetyl group, by reaction with acetic anhydride or pivaloyl anhydride respectively, in pyridine as a solvent, thus resulting into the introduction of a N-protected amino group at position 2 such as, but not limited to, acetamido or pivalamido. Activation of the tautomeric hydroxyl group at position 4 of the pyrido[3,2-d]pyrimidine scaffold for the subsequent nucleophilic displacement reaction occurs in step (f) by preparing the corresponding 4-(1,2, 4-triazolyl)-pyrido[3,2-d]pyrimidine derivative or 4-chloropyrido[3,2-d]pyrimidine derivative. The 4-triazolyl derivative can be obtained by treating the 4-oxo-pyrido[3,2-d]pyrimidine derivative with $POCl_3$ or 4-chlorophenyl phosphorodichloridate and 1,2,4-triazole in an appropriate solvent such as, but not limited to, pyridine or acetonitrile. The 4-chloro derivative can be obtained by treating the 4-oxo-pyrido[3,2-d]pyrimidine derivative with thionyl chloride or $POCl_3$. The triazolyl group or chlorine atom is designated as L in FIG. 6. Nucleophilic displacement of the triazolyl group or chlorine atom occurs in step (g) by reaction with an appropriate nucleophile having the general formula $R_2H$, wherein $R_2$ is as defined in the general formula (I), in a polar aprotic solvent. In the final step (h), the amino protecting group is cleaved off by using standard cleavage conditions such as acidic or basic hydrolysis. Alternatively, an alkylamino, arylamino or alkylarylamino group $R_2$ can also be directly introduced, in step (i), at position 4 of the pyrido[3,2-d]pyrimidine scaffold by treatment of the 2-amino-7-$R_4$-substituted-pyrido [3,2-d]pyrimidine with an appropriate alkylamine, arylamine or alkylarylamine in the presence of a suitable amount of 1,1,1,3,3,3-hexamethyldisilazane as a reagent.

Figure 7:
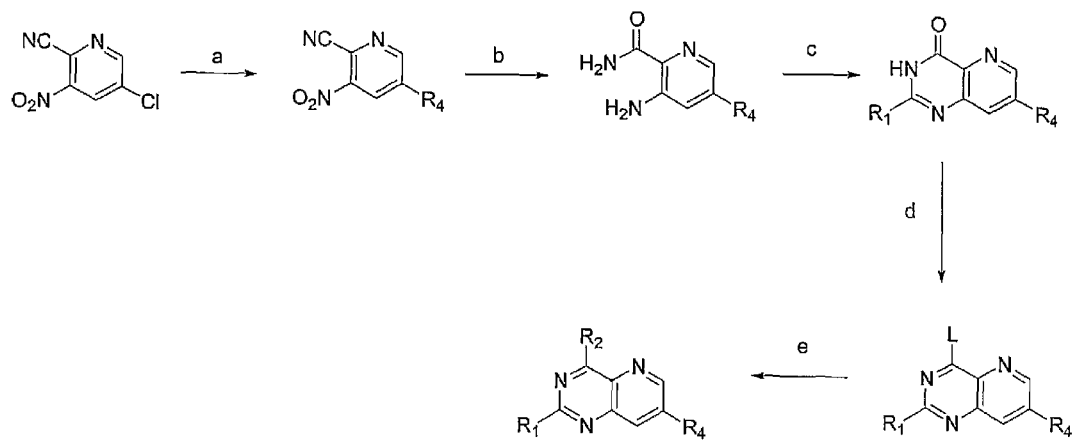
FIG. 7 schematically shows a method for making 2,4,7-tri-substituted pyrido(3,2-d)pyrimidine intermediates having the formula (I), as well as intermediates wherein the substituent in position 4 is hydroxy, chloro or triazolyl.

FIG. 7 schematically shows a method for making 2,4,7-trisubstituted pyrido(3,2-d)pyrimidine intermediates having the formula (I), as well as intermediates wherein the substituent in position 4 is hydroxy, chloro or triazolyl. In step (a), 5-chloro-2-cyano-3-nitropyridine is subjected to a palladium-catalyzed reaction such as, but not limited to, a Suzuki reaction with an aryl boronic acid to yield the corresponding biaryl derivative or, alternatively, a Heck reaction with a terminal alkene or alkyne leading to the formation of alkenyl or alkynyl derivatives. In step (b), the 3-nitro group is reduced, either catalytically (e.g. by using platinum or palladium under an atmosphere of hydrogen) or chemically (e.g. by using iron or tin under acidic conditions) and at the same time the cyano group is hydrolyzed into a carboxamide function. Formation of the 2-$R_1$-substituted-pyrido[3,2-d]pyrimidine scaffold occurs in step (c) by treatment of a 5-$R_4$-substituted-2-carboxamido-3-aminopyridine derivative either with an orthoester (such as, but not limited to, triethyl orthoformate) or with an acid chloride followed by treatment with a base such as sodium hydroxide. Activation of the tautomeric hydroxyl group at position 4 of the pyrido[3,2-d]pyrimidine scaffold for the subsequent nucleophilic displacement reaction occurs in step (d) by preparing the corresponding 4-chloro-pyrido[3,2-d]pyrimidine derivative or the corresponding 4-(1,2,4-triazolyl)-pyrido[3,2-d]pyrimidine derivative. The triazolyl derivative can be obtained by treating the 4-oxo-pyrido[3,2-d]pyrimidine derivative with $POCl_3$ or 4-chlorophenyl phosphorodichloridate and 1,2,4-triazole in an appropriate solvent such as, but not limited to, pyridine or acetonitrile. The 4-chloro derivative can be obtained by treating the 4-oxo-pyrido[3,2-d]pyrimidine derivative with thionyl chloride or $POCl_3$. The triazolyl group or chlorine atom at position 4 are indicated as L in FIG. 7. Nucleophilic displacement of the chlorine atom or 1,2,4-triazolyl moiety occurs in step (e) by reaction with an appropriate nucleophile having the general formula $R_2H$, wherein $R_2$ is as defined in the general formula (I), in a polar protic or aprotic solvent.

Figure 8:
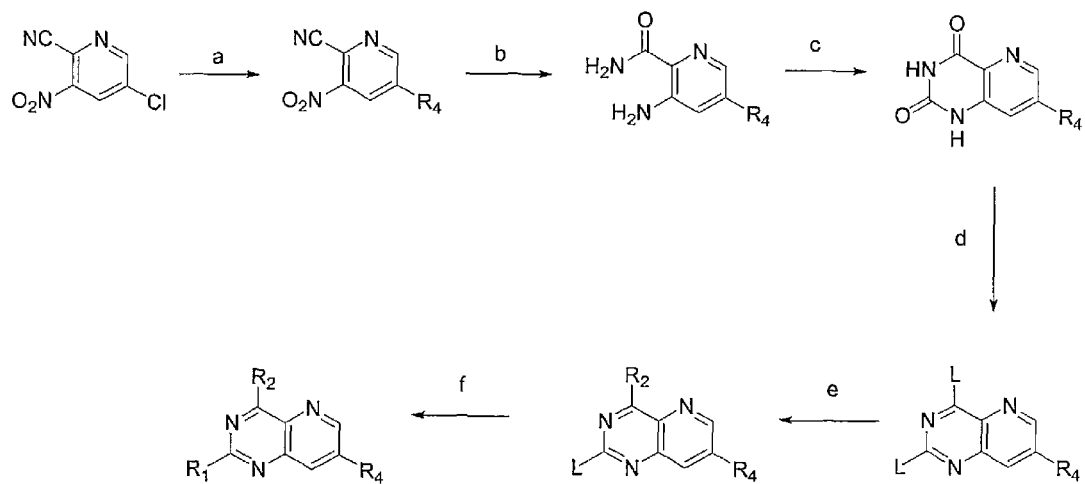
FIG. 8 schematically shows another method for making 2,4,7-tri-substituted pyrido(3,2-d)pyrimidine intermediates having the formula (I), as well as intermediates wherein the substituent in positions 2 and 4 are hydroxy or chloro.

FIG. 8 schematically shows another method for making 2,4,7-tri-substituted pyrido(3,2-d)pyrimidine intermediates having the formula (I), as well as intermediates wherein the substituent in positions 2 and 4 are hydroxy or chloro. In step (a), 5-chloro-2-cyano-3-nitropyridine is subjected to a palladium-catalyzed reaction such as, but not limited to, a Suzuki reaction with an aryl boronic acid to yield the corresponding biaryl derivative or, alternatively, a Heck reaction with a terminal alkene or alkyne leading to the formation of an alkenyl or alkynyl derivative. In step (b), the 3-nitro group is reduced, either catalytically (e.g. by using platinum or palladium under an atmosphere of hydrogen) or chemically (e.g. by using iron or tin under acidic conditions) and at the same time the cyano group is hydrolyzed into a carboxamide function. Ring closure reaction leading to the formation of the pyrido[3,2-d]pyrimidine scaffold occurs in step (c) by treatment of a 5-$R_4$-substituted-2-carboxamido-3-aminopyridine derivative either with a phosgene derivative in an aprotic solvent or with a carbonate (such as, but not limited to, dimethylcarbonate or diethylcarbonate) in a protic or aprotic solvent. Activation of the tautomeric hydroxyl groups at positions 2 and 4 of the pyrido[3,2-d]pyrimidine scaffold for the subsequent nucleophilic displacement reaction occurs in step (d) by preparing the corresponding 2,4-dichloro-pyrido[3,2-d]pyrimidine derivative, e.g. by treating the 4-oxo-pyrido[3, 2-d]pyrimidine derivative with thionyl chloride or $POCl_3$. Selective nucleophilic displacement of the chlorine at position 4 occurs in step (e) by reaction with an appropriate nucleophile having the general formula $R_2H$ in a polar protic or aprotic solvent at an appropriate temperature. In step (f), the 2-chloro derivative is then treated with an appropriate nucleophile having the general formula $R_1H$ in a polar protic or aprotic solvent at an appropriate temperature in order to afford the desired 2,4,7-trisubstituted derivative.

In another particular embodiment, the invention relates to a group of pyrido(3,2-d)pyrimidine derivatives, as well as pharmaceutical compositions comprising such pyrido(3,2-d)pyrimidine derivatives as active principle, having the above general formula (I) and being in the form of a pharmaceutically acceptable salt. The latter include any therapeutically active non-toxic addition salt which compounds having the general formula (I) are able to form with a salt-forming agent. Such addition salts may conveniently be obtained by treating the pyrido(3,2-d)pyrimidine derivatives of the invention with an appropriate salt-forming acid or base. For instance, pyrido(3, 2-d)pyrimidine derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as but not limited to hydrohalides (e.g. hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzene-sulfonate, p-toluenesulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphtoate, hydroxyethanesulfonate, mandelate, methylsulfate, pantothenate, stearate, as well as salts derived from ethanedioic, propanedioic, butanedioic, (Z)-2-butenedioic, (E)2-butenedioic, 2-hydroxybutanedloic, 2,3-dihydroxybutane-dioic, 2-hydroxy-1,2,3-propanetricarboxylic and cyclohexanesulfamic acids and the like.

Pyrido(3,2-d)pyrimidine derivatives of the general formula (I) having acidic properties may be converted in a similar manner into the corresponding therapeutically active, non-toxic base addition salt form. Examples of appropriate salt-forming bases include, for instance, inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylenediamine, chloroprocaine, choline, diethanolamine, ethylene-diamine, N-methylglucamine, procaine and the like.

Reaction conditions for treating the pyrido(3,2-d)pyrimidine derivatives having the general formula (I) of this invention with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water-solubility, lower toxicity, greater stability and/or slower dissolution rate to the pyrido(3,2-d)pyrimidine derivative of this invention.

The present invention further provides the use of a pyrido (3,2-d)pyrimidine derivative represented by the structural formula (I), or a pharmaceutically acceptable salt or a solvate thereof, as a biologically-active ingredient, i.e. active principle, especially as a medicine or for the manufacture of a medicament for the treatment of hepatitis C.

The invention further relates to a pharmaceutical composition comprising:
(a) one or more pyrido(3,2-d)pyrimidine derivatives represented by the structural formula (I), and
(b) one or more pharmaceutically acceptable carriers.

In another embodiment, this invention provides combinations, preferably synergistic combinations, of one or more pyrido(3,2-d)pyrimidine derivatives represented by the general formula (I) with one or more antiviral agents. As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively. As will be explained in more detail herein below, this principle may be applied to a number of desirable effects such as, but not limited to, anti-viral activity against HCV.

The invention further relates to a pharmaceutical composition or combined preparation having synergistic effects against a hepatitis C infection and containing:
(a) one or more anti-viral agents, and
(b) at least one pyrido(3,2-d)pyrimidine derivative represented by the general formula (I), and
(c) optionally one or more pharmaceutical excipients or pharmaceutically acceptable carriers,
for simultaneous, separate or sequential use in the treatment of HCV infection.

Suitable anti-viral agents for inclusion into the synergistic antiviral compositions or combined preparations of this invention include, for instance, retroviral enzyme inhibitors belonging to categories well known in the art, such as HIV-1 IN inhibitors, nucleoside reverse transcriptase inhibitors (e.g. zidovudine, lamivudine, didanosine, stavudine, zalcitabine and the like), non-nucleoside reverse transcriptase inhibitors (e.g. nevirapine, delavirdine and the like), other reverse transcriptase inhibitors (e.g. foscarnet sodium and the like), and HIV-1 protease inhibitors (e.g. saquinavir, ritonavir, indinavir, nelfinavir and the like). Other suitable antiviral agents include for instance acemannan, acyclovir, adefovir, alovudine, alvircept, amantadine, aranotin, arildone, atevirdine, pyridine, cidofovir, cipamfylline, cytarabine, desciclovir, disoxaril, edoxudine, enviradene, enviroxime, famciclovir, famotine, fiacitabine, fialuridine, floxuridine, fosarilate, fosfonet, ganciclovir, idoxuridine, kethoxal, lobucavir, memotine, methisazone, penciclovir, pirodavir, somantadine, sorivudine, tilorone, trifluridine, valaciclovir, vidarabine, viroxime, zinviroxime, moroxydine, podophyllotoxin, ribavirine, rimantadine, stallimycine, statolon, tromantadine and xenazoic acid, and their pharmaceutically acceptable salts.

Especially relevant to this aspect of the invention is the inhibition of the replication of viruses selected from the group consisting of picorna-, toga-, bunya, orthomyxo-, paramyxo-, rhabdo-, retro-, arena-, hepatitis B-, hepatitis C-, hepatitis D-, adeno-, vaccinia-, papilloma-, herpes-, corona-, varicella- and zoster-virus, in particular human immunodeficiency virus (HIV). Synergistic activity of the pharmaceutical compositions or combined preparations of this invention against viral infection may be readily determined by means of one or more tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration (hereinafter referred as FIC). When the minimum FIC index corresponding to the FIC of combined compounds (e.g., $FIC_x+FIC_y$) is equal to 1.0, the combination is said to be additive; when it is between 1.0 and 0.5, the combination is defined as subsynergistic, and when it is lower than 0.5, the combination is by defined as synergistic. When the minimum FIC index is between 1.0 and 2.0, the combination is defined as subantagonistic and, when it is higher than 2.0, the combination is defined as antagonistic.

The pharmaceutical composition or combined preparation with synergistic activity against viral infection according to this invention may contain the pyrido(3,2-d)pyrimidine derivative of the general formula (I) over a broad content range depending on the contemplated use and the expected effect of the preparation. Generally, the pyrido(3,2-d)pyrimidine derivative content of the combined preparation is within the range of from 0.1 to 99.9% by weight, preferably from 1 to 99% by weight, more preferably from about 5 to 95% by weight.

The pharmaceutical compositions and combined preparations according to this invention may be administered orally or in any other suitable fashion. Oral administration is preferred and the preparation may have the form of a tablet, aqueous dispersion, dispersable powder or granule, emulsion, hard or soft capsule, syrup, elixir or gel. The dosing forms may be prepared using any method known in the art for manufacturing these pharmaceutical compositions and may comprise as additives sweeteners, flavoring agents, coloring agents, preservatives and the like. Carrier materials and excipients are detailed hereinbelow and may include, inter alia, calcium carbonate, sodium carbonate, lactose, calcium phosphate or sodium phosphate; granulating and disintegrating agents, binding agents and the like. The pharmaceutical composition or combined preparation of this invention may be included in a gelatin capsule mixed with any inert solid diluent or carrier material, or has the form of a soft gelatin capsule, in which the ingredient is mixed with a water or oil medium. Aqueous dispersions may comprise the biologically active composition or combined preparation in combination with a suspending agent, dispersing agent or wetting agent. Oil dispersions may comprise suspending agents such as a vegetable oil. Rectal administration is also applicable, for instance in the form of suppositories or gels. Injection (e.g. intramuscularly or intraperiteneously) is also applicable as a mode of administration, for instance in the form of injectable solutions or dispersions, depending upon the disorder to be treated and the condition of the patient.

The term "pharmaceutically acceptable carrier or excipient" as used herein in relation to pharmaceutical compositions and combined preparations means any material or substance with which the active principle, i.e. the pyrido(3,2-d) pyrimidine derivative of the general formula (I), and optionally the antiviral agent, may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the pyrido(3,2-d)pyrimidine derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. may also be prepared by micronisation, for instance in view to obtain them in the form of microspheres usually having a diameter of about 1 to 10 μm, namely for the manufacture of microcapsules for controlled or sustained release of the biologically active ingredient(s).

Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidylcholine, dipalmitoylphoshatidylcholine and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylpropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further sub-stituents, unsubstituted or halogenated lower alkyl, benzyl and/or hydroxy-$C_{1-4}$ alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions and combined preparations of the invention. Control release compositions may thus be achieved by selecting appropriate polymer carriers such as for example polyesters, polyamino-acids, polyvinyl-pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethyl-cellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

Other modes of local drug administration can also be used. For example, the selected active agent may be administered topically, in an ointment, gel or the like, or transdermally, using a conventional transdermal drug delivery system.

Since, in the case of combined preparations including the pyrido(3,2-d)pyrimidine derivative of this invention and antiviral agent, both ingredients do not necessarily bring out their synergistic therapeutic effect directly at the same time in the patient to be treated, the said combined preparation may be in the form of a medical kit or package containing the two ingredients in separate but adjacent form. In the latter context, each ingredient may therefore be formulated in a way suitable for an administration route different from that of the other ingredient, e.g. one of them may be in the form of an oral or parenteral formulation whereas the other is in the form of an ampoule for intravenous injection or an aerosol.

The present invention further relates to a method for treating hepatitis C in a patient, preferably a mammal, more preferably a human being. The method of this invention consists of administering to the patient in need thereof an effective amount of a pyrido(3,2-d)pyrimidine derivative having the general formula (I), optionally together with an effective amount of an antiviral agent, or a pharmaceutical composition comprising the same, such as disclosed above in extensive details. The effective amount is usually in the range of about 0.01 mg to 20 mg, preferably about 0.1 mg to 5 mg, per day per kg bodyweight for humans. Depending upon the pathologic condition to be treated and the patient's condition, the said effective amount may be divided into several subunits per day or may be administered at more than one day intervals. The patient to be treated may be any warm-blooded animal, preferably a mammal, more preferably a human being, suffering from said pathologic condition.

The preferred compounds of the present invention are non-sedating. In other words, a dose of such compounds that is twice the minimum dose sufficient to provide analgesia in an animal model for determining pain relief causes only transient (i.e. lasting for no more than half the time that pain relief lasts) or preferably no statistically significant sedation in an animal model assay of sedation (using the method described by Fitzgerald et al. in *Toxicology* (1988) 49:433-9). Preferably, a dose that is five times the minimum dose sufficient to provide analgesia does not produce statistically significant sedation. More preferably, a compound provided herein does not produce sedation at intravenous doses of less than 10 mg/kg per day or at oral doses of less than 30 mg/kg per day. If desired, compounds provided herein may be evaluated for toxicity (a preferred compound is non-toxic when an immunomodulating amount or a cell anti-proliferative amount is administered to a subject) and/or side effects (a preferred compound produces side effects comparable to placebo when a therapeutically effective amount of the compound is administered to a subject). Toxicity and side effects may be assessed using any standard method. In general, the term "non-toxic" as used herein shall be understood as referring to any substance that, in keeping with established criteria, is susceptible to approval by the United States Federal Drug Administration for administration to mammals, preferably humans. Toxicity may be also evaluated using assays including bacterial reverse mutation assays, such as an Ames test, as well as standard teratogenicity and tumorogenicity assays. Preferably, administration of compounds provided herein within the therapeutic dose ranges disclosed hereinabove does not result in prolongation of heart QT intervals (e.g. as determined by electrocardiography in guinea pigs, minipigs or dogs). When administered daily, such doses also do not cause liver enlargement resulting in an increase of liver to body weight ratio of more than 50% over matched controls in laboratory rodents (e.g. mice or rats). Such doses also preferably do not cause liver enlargement resulting in an increase of liver to body weight ratio of more than 10% over matched untreated controls in dogs or other non-rodent mammals. The preferred compounds of the present invention also do not promote substantial release of liver enzymes from hepatocytes in vivo, i.e. the therapeutic doses do not elevate serum levels of such enzymes by more than 50% over matched untreated controls in vivo in laboratory rodents.

Another embodiment of this invention includes the various precursor or "pro-drug" forms of the compounds of the present invention. It may be desirable to formulate the compounds of the present invention in the form of a chemical species which itself is not significantly biologically-active, but which when delivered to the body of a human being or higher mammal will undergo a chemical reaction catalyzed by the normal function of the body, inter alia, enzymes present in the stomach or in blood serum, said chemical reaction having the effect of releasing a compound as defined herein. The term "pro-drug" thus relates to these species which are converted in vivo into the active pharmaceutical ingredient.

The pro-drugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used.

For the purposes of the present invention the term "therapeutically suitable pro-drug" is defined herein as "a compound modified in such a way as to be transformed in vivo to the therapeutically active form, whether by way of a single or by multiple biological transformations, when in contact with the tissues of humans or mammals to which the pro-drug has been administered, and without undue toxicity, irritation, or allergic response, and achieving the intended therapeutic outcome".

The present invention will be further described with reference to certain more specific embodiments and examples, but the present invention is not limited thereto but only by the attached claims. The following examples are given by way of illustration only.

Example 1

Synthesis of
6-chloro-2-carboxamido-3-amino-pyridine

Method A: To a solution of 6-chloro-2-cyano-3-nitro-pyridine (3.03 g, 16.5 mmol) in ethanol (166 ml) and $H_2O$ (16 ml) was added iron (165 mmol, 9.2 g) and calcium chloride (2.75 g, 24.8 mmol). The reaction mixture was refluxed for 4 hours and then cooled down to room temperature. The precipitate was filtered off over Celite and the filtrate was evaporated to dryness. The residue was redissolved in ethyl acetate and extracted with brine. The aqueous layer was extracted back with ethyl acetate. The combined organic layers were evaporated in vacuo. The residue was adsorbed on silica and purified by silica gel column chromatography, the mobile phase being a ethyl acetate/hexane mixture in a ratio of 3:7, resulting in the pure title compound (1.89 g, yield 67%) which was characterised by its mass spectrum as follows: MS (m/z): 172, 174 ([M+H]$^+$, 100).

Method B: To a suspension of 6-chloro-3-nitro-pyridine-2-carbonitrile (9.2 g, 50 mmol) in water (100 ml), was added 20 ml of a 25% ammonia aqueous solution. The mixture was stirred at room temperature for 20 minutes. Then, $Na_2S_2O_4$ (50 g, 86%, 150 mmol) was added portion wise, and the mixture was stirred at room temperature for another 2 hours. The precipitate formed was collected by filtration, washed two times with cold water (10 ml) and then dried over $P_2O_5$, resulting in the title compound (7.0 g, yield 81%) as a yellowish solid which was characterized by its mass spectrum as follows: MS (m/z): 172.1 ([M+H]$^+$, 100).

Example 2

Synthesis of
3-amino-5-chloro-pyridine-2-carboxamide

This compound was synthesized, by using the procedure of example 1, method B but from 5-chloro-3-nitro-pyridine-2-carbonitrile as a starting material, in 80% yield as a yellowish solid which was characterized by its mass spectrum as follows: MS (m/z): 172.1 ([M+H]$^+$, 100).

Example 3

Synthesis of
6-chloro-pyrido[3,2-d]pyrimidin-4(3H)-one

A suspension of 6-chloro-2-carboxamido-3-amino-pyridine (1.34 mmol, 230 mg) in triethyl orthoformate (10 ml) was refluxed for 3 hours. A white suspension was formed which was cooled down to room temperature. The precipitate was filtered off and dried under vacuum resulting in the pure title compound (174 mg, yield 72%) which was characterised by its mass spectrum as follows: MS (m/z): 182, 184 ([M+H]$^+$, 100).

Example 4

Preparation of 6-(3,4-dimethoxyphenyl)-pyrido[3,2-d]pyrimidin-4(3H)-one

Method A: To a solution of 6-chloro-pyrido[3,2-d]pyrimidin-4(3H)-one (200 mg, 1.1 mmol) in 1,4-dioxane (20 ml) and water (10 ml) was added 3,4-dimethoxyphenyl boronic acid (240 mg, 1.32 mmol), potassium carbonate (380 mg, 2.75 mmol) and tetrakis(triphenylphosphine)palladium(0) (63 mg, 0.055 mmol). The reaction mixture was refluxed for 3 hours, cooled down to room temperature and the solvents were evaporated in vacuo. The residue was adsorbed on silica, purified by silica gel column chromatography (the mobile phase being a acetone/dichloromethane mixture, in a ratio gradually ranging from 30:70 to 40:60) and characterised by its mass spectrum as follows: MS (m/z): 284 ([M+H]$^+$, 100).

Method B: A suspension of 2-carboxamido-3-amino-6-(3,4-dimethoxyphenyl)-pyridine (770 mg, 2.8 mmol) in triethyl orthoformate (28 ml) was refluxed for 12 hours. Then, the reaction mixture was cooled down and evaporated to dryness. The residue was purified by silica gel column chromatography (the mobile phase being an ethyl acetate/hexane mixture in a ratio gradually ranging from 2:8 to 3:7), resulting in the pure title compound (530 mg, yield 67%) which was characterised by its mass spectrum as follows: MS (m/z): 284 ([M+H)$^+$, 100].

Example 5

Preparation of 4-chloro-6-(3,4-dimethoxyphenyl)-pyrido[3,2-d]pyrimidine

To a suspension of 6-(3,4-dimethoxyphenyl)-pyrido[3,2-d]pyrimidin-4(3H)-one (150 mg, 0.53 mmol) in toluene (30 ml) was added phosphorus oxychloride (148 µl, 1.59 mmol) and 2,6-lutidine (185 µl, 1.59 mmol). The reaction mixture was refluxed overnight until a black solution was obtained. After evaporation to dryness, the residue was redissolved in ethyl acetate and extracted with a saturated sodium bicarbonate solution. The combined organic layers were evaporated in vacuo. The residue was purified by silica gel column chromatography, the mobile phase being an ethyl acetate/hexane mixture, in a ratio gradually ranging from 2:8 to 3:7, resulting in the pure title compound (123 mg, yield 77%) which was characterised by its mass spectrum as follows: MS (m/z): 302, 304 ([M+H]$^+$, 100).

Example 6

Synthesis of 4-[(2-phenoxyethyl)-piperazin-1-yl]-6-(3,4-dimethoxyphenyl)-pyrido[3,2-d]pyrimidine To a suspension of 4-chloro-6-(3,4-dimethoxyphenyl)-pyrido[3,2-d]pyrimidine (120 mg, 0.398 mmol) in isopropanol (15 ml) was added 1-(2-phenoxyethyl)-piperazine (0.795 mmol, 164 mg). The suspension was stirred at 80° C., after which the suspension became a clear colourless solution. The solvents were evaporated in vacuo. The residue was redissolved in ethyl acetate and extracted with a NaOH solution (1 N). The combined organic layers were evaporated in vacuo and purified by silica gel column chromatography (the mobile phase being a mixture of methanol and dichloromethane in a ratio gradually ranging from 1:99 to 2:98), resulting in the title compound (157 mg, yield 84%) which was characterised by its mass spectrum as follows: MS (m/z): 472 ([M+H]$^+$, 100).

Example 7

Synthesis of 2-carboxamido-3-amino-6-(3,4-dimethoxyphenyl)-pyridine

To a solution of 6-(3,4-dimethoxyphenyl)-3-nitropyridine-2-carbonitrile (1.42 g, 5 mmol) in ethanol (50 ml) and water (5 ml) was added iron (1.39 g, 25 mmol) and calcium chloride (6 mmol, 666 mg). The reaction mixture was refluxed for 1 hour. An additional amount of iron (1.39 g, 25 mmol) was added and the reaction was refluxed for another 3 hours. The reaction was cooled down and filtered over a paper filter, followed by washings with boiling ethyl acetate. The filtrate was evaporated in vacuo and the residue was partitioned between ethyl acetate and water. The organic layers were evaporated to dryness and the residue was purified by silica gel column chromatography (the mobile phase being a mixture of ethyl acetate and hexane in a ratio of 1:1), resulting in the pure title compound (770 mg, yield 56%) which was characterised by its mass spectrum as follows: MS (m/z): 273 [(M+H)$^+$, 100).

Example 8

Synthesis of 4-(4-[3-methylphenyl)amino]carbonyl] piperazin-1-yl]-6-(3,4-dimethoxyphenyl)-pyrido[3,2-d]pyrimidine To a suspension of 4-chloro-6-(3,4-dimethoxyphenyl)-pyrido[3,2-d]pyrimidine (227 mg, 0.8 mmol) in isopropanol (20 ml) was added piperazine-1-carboxylic acid m-tolylamide (351 mg, 1.6 mmol). The reaction mixture was stirred for 3 hours at 80° C. Then, the reaction was cooled down and evaporated to dryness. The residue was redissolved in ethyl acetate and extracted with a saturated sodium bicarbonate solution. The combined organic layers were evaporated in vacuo. The crude residue was purified by silica gel column chromatography (the mobile phase being a mixture of methanol and dichloromethane in a ratio gradually ranging from 1:99 to 2:98), resulting in the pure title compound (217 mg, yield 56%) which was characterised by its mass spectrum as follows: MZ (m/z): 485 ([M+H)$^+$, 100).

Example 9

Preparation of 2-methyl-6-(3,4-dimethoxyphenyl)-pyrido[3,2-d]pyrimidin-4(3H)-one A suspension of 2-carboxamido-3-amino-6-(3,4-dimethoxyphenyl)-pyridine (546 mg, 2 mmol) in triethyl orthoacetate (25 ml) was refluxed for 12 hours. Then, the reaction mixture was cooled down and evaporated to dryness. The residue was purified by silica gel column chromatography (the mobile phase being an ethyl acetate/hexane mixture in a ratio gradually ranging from 2:8 to 3:7), resulting in the pure title compound (437 mg, yield 73%) which was characterised by its mass spectrum as follows: MS (m/z): 297 ([M+H]$^+$, 100).

Example 10

Preparation of 2-methyl-4-chloro-6-(3,4-dimethoxyphenyl)-pyrido[3,2-d]pyrimidine To a solution of 2-methyl-6-(3,4-dimethoxyphenyl)-pyrido[3,2-d]pyrimidin-4(3H)-one (416 mg, 1.4 mmol) in toluene (28 ml) was added 2,6-lutidine (490 µl, 4.2 mmol) and POCl$_3$ (4.2 mmol, 385 µl). The mixture was refluxed under nitrogen atmosphere for 5 hours. The reaction mixture was cooled down, diluted with ethyl acetate (50 ml) and extracted with a saturated sodium bicarbonate solution. The combined organic layers were evaporated in vacuo and the residue was purified by silica gel column chromatography (the mobile phase being an ethyl acetate/hexane mixture in a ratio of 15:85), resulting in the pure title compound (330 mg, yield 75%) which was characterised by its mass spectrum as follows: MS (m/z): 316, 318 ([M+H]$^+$, 100).

Example 11

Synthesis of 2-methyl-4-(4-[3-methylphenyl)amino] carbonyl]piperazin-1-yl)-6-(3,4-dimethoxyphenyl)-pyrido[3,2-d]pyrimidine To a suspension of 2-methyl-4-chloro-6-(3,4-dimethoxyphenyl)-pyrido[3,2-d]pyrimidine (330 mg, 1.04 mmol) in acetonitrile (20 ml) was added piperazine-1-carboxylic acid m-tolylamide (479 mg, 2.2 mmol). The reaction mixture was refluxed for 2 hours. The mixture was cooled down and ethyl acetate was added (100 ml). The reaction mixture was extracted with a saturated sodium bicarbonate solution. The combined organic layers were evaporated to dryness. The residue was purified by a first silica gel column chromatography (the mobile phase being a methanol/dichloromethane mixture in a ratio gradually ranging from 1:99 to 2:98) and then a second silica gel column purification was performed with a mobile phase consisting of a 95:5 ethyl acetate/hexane mixture, resulting in the pure title compound (319 mg, yield 62%) which was characterised by its mass spectrum as follows: MS (m/z): 499 ([M+H]$^+$, 100).

Example 12

Synthesis of 6-(3,4-dimethoxyphenyl)pyrido[3,2-d]pyrimidin-2(1H)-4(3H)-dione

To a solution of 2-carboxamido-3-amino-6-(3,4-dimethoxyphenyl)-pyridine (4.10 g, 15 mmol) in 1,4-dioxane (150 ml) was added triphosgene (2.22 g, 7.5 mmol). The solution was refluxed for 25 minutes and then evaporated to dryness. The crude compound was crystallized from acetic acid (150 ml) and washed with ethyl acetate, diethyl ether and dried under vacuum over $P_2O_5$, resulting in the pure title compound (3.60 g, yield 80%) which was characterised by its mass spectrum as follows: MS (m/z): 300 ([M+H]$^+$, 100).

Example 13

Synthesis of 2,4-dichloro-6-(3,4-dimethoxyphenyl)pyrido[3,2-d]pyrimidine

To a suspension of 6-(3,4-dimethoxyphenyl)pyrido[3,2-d]pyrimidin-2(1H)-4(3H)-dione (2.69 g, 9 mmol) in POCl$_3$ (60 ml) was added triethylamine (3.47 ml). The reaction mixture was refluxed under nitrogen until completion. The reaction was cooled down to room temperature and evaporated to dryness. The residue was partitioned between water and dichloromethane. The organic layer was washed with brine. The combined organic layers were evaporated and the residue was purified by silica gel column chromatography (the mobile phase being a hexane/ethyl acetate mixture in a ratio 6:4), resulting in the pure title compound (yield 83%) which was characterised by its mass spectrum as follows: MS (m/z): 336, 338 ([M+H]$^+$, 100).

Example 14

Synthesis of 2-chloro-4-(4-[3-methylphenyl)amino]carbonyl]piperazin-1-yl)-6-(3,4-dimethoxyphenyl)pyrido[3,2-d]pyrimidine To a suspension of 2,4-dichloro-6-(3,4-dimethoxyphenyl)pyrido[3,2-d]pyrimidine (672 mg, 2 mmol) in THF (10 ml) was added piperazine-1-carboxylic acid m-tolylamide (484 mg, 2.2 mmol) and triethylamine (10 mmol, 1.40 ml). The reaction mixture was stirred at room temperature for 10 minutes. The mixture was evaporated to dryness. The residue was redissolved in dichloromethane and extracted with brine. The combined organic layers were evaporated in vacuo and the crude residue was purified by silica gel column chromatography (the mobile phase being a hexane/ethyl acetate mixture in a ratio 1:1), resulting in the pure title compound (760 mg, yield 73%) which was characterised by its mass spectrum as follows: MS (m/z): 519, 521 ([M+H]$^+$, 100).

Example 15

Synthesis of 2-dimethylamino-4-(4-[3-methylphenyl)amino]carbonyl]piperazin-1-yl)-6-(3,4-dimethoxyphenyl)pyrido[3,2-d]pyrimidine To a suspension of 2-chloro-4-(4-[3-methylphenyl)amino]carbonyl]piperazin-1-yl)-6-(3,4-dimethoxyphenyl)pyrido[3,2-d]pyrimidine (0.35 mmol, 181 mg) in dioxane (5 ml) was added dimethylamine (100 µl of a 40% solution in water). The reaction was stirred at 80° C. for 1.5 hours, after which an additional amount (100 µl) of the dimethylamine solution was added. The reaction was stirred for another 18 hours and then, cooled down, and diluted with dichloromethane (50 ml). The reaction mixture was extracted with a saturated sodium bicarbonate solution. The combined organic layers were evaporated in vacuo. The residue was purified by preparative thin layer chromatography on silica (the mobile phase being a hexane/ethyl acetate mixture in a ratio 1:9), resulting in the pure title compound (57 mg, yield 31%) which was characterised by its mass spectrum as follows: MS (m/z): 528 ([M+H]$^+$, 100).

Example 16

Synthesis of 2-acetamido-4-[(N-3-methyl-phenylcarbamoyl)-piperazin-1-yl]-6-(3,4-dimethoxyphenyl)-pyrido[3,2-d]pyrimidine 2-acetamido-4-[(N-3-methyl-phenylcarbamoyl)-piperazin-1-yl]-6-(3,4-dimethoxyphenyl)-pyrido[3,2-d]pyrimidine was synthesized from 2-chloro-4-(4-[3-methylphenyl)amino]carbonyl]piperazin-1-yl)-6-(3,4-dimethoxyphenyl)pyrido[3,2-d]pyrimidine. In a first step, 2-amino-4-[(N-3-methyl-phenylcarbamoyl)-piperazin-1-yl]-6-(3,4-dimethoxyphenyl)-pyrido[3,2-d]pyrimidine was synthesized according to the procedure mentioned for examples 15, using ammonia (instead of dimethylamine). Subsequent acetylation yielded the title compound.

Example 17

Synthesis of 2-[(N-hydroxyethyl)morpholino]-4-(4-[3-methylphenyl)amino]carbonyl]piperazin-1-yl)-6-(3,4-dimethoxyphenyl)pyrido[3,2-d]pyrimidine N-(2-hydroxyethyl)morpholine (55 µl, 0.45 mmol) was dissolved in dry tetrahydrofuran (5 ml) and sodium hydride 60% (20 mg, 0.495 mmol) was added. The solution was stirred at 60° C. under nitrogen for 20 minutes and then, 2-chloro-4-(4-[3-methylphenyl)amino]carbonyl]piperazin-1-yl)-6-(3,4-dimethoxyphenyl)pyrido[3,2-d]pyrimidine (156 mg, 0.3 mmol) was added. The reaction mixture was stirred for 1 hour at 60° C. The mixture was cooled down to room temperature, diluted with brine and extracted with ethyl acetate. The combined organic layers were evaporated in vacuo and purified by preparative thin layer chromatography on silica (the mobile phase being a methanol/dichloromethane mixture in a ratio 7.5:92.5), resulting in the pure title compound (166 mg, yield 90%) which was characterised by its mass spectrum as follows: MS (m/z): 614 ([M+H]$^+$, 100).

Example 18

Synthesis of 2-(1-methyl-2-pyrrolidino-ethoxy)-4-(4-[3-methylphenyl)amino]carbonyl]piperazin-1-yl)-6-(3,4-dimethoxyphenyl)pyrido[3,2-d]pyrimidine Sodium hydride 60% (20 mg, 0.495 mmol) was dissolved in dry tetrahydrofuran (5 ml) and 1-methyl-2-pyrrolidine-ethanol (62 μl, 0.45 mmol) was added. The mixture was refluxed under an $N_2$-atmosphere for 15 minutes. Then, 2-chloro-4-(4-[3-methylphenyl)amino]carbonyl]piperazin-1-yl)-6-(3,4-dimethoxyphenyl)pyrido[3,2-d]pyrimidine (156 mg, 0.30 mmol) was added and the reaction mixture was refluxed under nitrogen for 16 hours. The reaction mixture was diluted with distilled water and extracted three times with ethyl acetate. The combined organic extracts were washed with brine and dried over $Na_2SO_4$. Upon filtration and evaporation in vacuo, the crude product was purified by preparative thin layer chromatography on silica with a dichloromethane/methanol mixture (ratio 9:1) as the mobile phase to afford 79 mg (yield 43%) of the title compound which was characterised by its mass spectrum as follows: MS (m/z): 612 ([M+H]$^+$, 100).

Example 19

Synthesis of 2-(2-phenoxyethoxy)-4-(4-[3-methylphenyl)amino]carbonyl]piperazin-1-yl)-6-(3,4-dimethoxyphenyl)pyrido[3,2-d]pyrimidine Sodium hydride 60% (25 mg, 0.62 mmol) and 2-phenoxyethanol (63 mg, 0.45 mmol) were dissolved in dry tetrahydrofuran (5 ml). The reaction mixture was refluxed under a nitrogen atmosphere for 15 minutes. Then, 2-chloro-4-(4-[3-methylphenyl)amino]carbonyl]piperazin-1-yl)-6-(3,4-dimethoxyphenyl)pyrido[3,2-d]pyrimidine (156 mg, 0.30 mmol) was added and the reaction was refluxed under nitrogen for 3 hours. The reaction mixture was diluted with distilled water and extracted with dichloromethane. Combined organic extracts were dried over $Na_2SO_4$. Upon filtration and evaporation in vacuo, the crude product was purified by preparative thin layer chromatography on silica with a n-hexane/ethyl acetate mixture (ratio 1.5:1) as the mobile phase. Recrystallization from ethyl acetate afforded 124 mg (yield 67%) of the title compound which was characterised by its mass spectrum as follows: MS (m/z): 621 ([M+H]$^+$, 100).

Example 20

Synthesis of 2-phenyl-4-(4-[3-methylphenyl)amino]carbonyl]piperazin-1-yl)-6-(3,4-dimethoxyphenyl)pyrido[3,2-d]pyrimidine A suspension of 2-chloro-4-(4-[3-methylphenyl)amino]carbonyl]piperazin-1-yl)-6-(3,4-dimethoxyphenyl)pyrido[3,2-d]pyrimidine (156 mg, 0.30 mmol), potassium carbonate (181 mg, 1.31 mmol) and phenylboronic acid (49 mg, 0.39 mmol) in 1,4-dioxane (4.5 ml) and water (1.5 ml) was purged with a stream of nitrogen gas for 10 minutes. Tetrakis(triphenylphosphine)palladium(0) (18 mg, 15.6 μmol) was added and the reaction mixture was refluxed under a nitrogen atmosphere for 30 minutes. Upon cooling, the mixture was diluted with ethyl acetate and washed twice with brine. The organic layer was dried over $Na_2SO_4$ and subsequently filtered and evaporated in vacuo. Recrystallization from ethyl acetate afforded 74 mg (yield 44%) of the title compound which was characterised by its mass spectrum as follows: MS (m/z): 561 ([M+H]$^+$, 100).

Example 21

Synthesis of 2-amino-6-chloro-pyrido[3,2-d]pyrimidin-4(3H)-one

Method A: 2,4-diamino-6-chloropyrido[3,2-c]pyrimidine (7.5 g, 38 mmole), e.g. prepared according to Colbry et al. *J. Heterocycl. Chem.* (1984) 21:1521, was suspended in 6 N HCl (300 ml) and the mixture was refluxed for 5 hours. After cooling, the pH was made alkaline (pH about 9-10) by means of 10 N NaOH. The precipitate obtained was filtered, washed with $H_2O$ and dried at 100° C., resulting in the pure title compound (7.0 g, yield 95%) which was characterized by its mass spectrum as follows: MS (m/z): 197 ([M+H]$^+$, 100).

Method B: A mixture of 3-amino-6-chloro-pyridine-2-carboxamide (5.1 g, 30 mmol), chloroform-amidine hydrochloride (6.99 g, 60 mmol), dimethylsulfone (24 g) and sulfolane (2.4 ml) was heated at 165° C. for 30 min. To the hot mixture was added water (50 ml). After cooling to room temperature, a diluted ammonium hydroxide solution was slowly added drop wise till pH 7. The resulting precipitate was filtered off, washed with water and dried overnight at 100° C. to give the pure title compound (5.8 g, 98%). The obtained compound was used as such for further reactions without additional purification. M.p. >330° C.; elemental analysis calc. for $C_7H_5ClN_4O$ (196.6): C, 42.77; H, 2.56; N, 28.50. Found: C, 41.61; H, 2.74; N, 28.76.

Example 22

Synthesis of 2-amino-7-chloro-pyrido[3,2-d]pyrimidin-4(3H)one

This compound was synthesized from 3-amino-5-chloro-pyridine-2-carboxamide, using method B of example 21. MS (m/z): 197, 199 ([M+H]+, 100)

Example 23

Synthesis of 2-amino-6-(3,4-dimethoxyphenyl)-pyrido[3,2-d]pyrimidin-4(3H)-one (and its hydrochloride acid (HCl) salt)

Method A: To a degassed suspension of 2-amino-6-chloro-pyrido[3,2-d]pyrimidin-4(3H)-one (7.30 g, 37 mmol), 3,4-dimethoxyphenyl boronic acid (7.50 g, 40 mmol) and potassium carbonate (20.70 g, 152 mmol) in a mixture of dioxane (540 ml) and $H_2O$ (120 ml), was added a catalytic amount of tetrakis(triphenylphosphine)palladium(0) (2.16 g, 18.5 mmol). The mixture was refluxed for 24 hours and, after cooling at room temperature, was filtered. The filtrate was acidified with 5 N HCl to pH 4 and the resulting precipitate was filtered and then washed successively with $H_2O$, ethanol and diethyl ether, and dried under vacuum resulting in the pure title compound (8.0 g, yield 73%).

Method B: 2,4-diamino-6-(3,4-dimethoxyphenyl)pyrido[3,2-o]pyrimidine (1.27 g, 4.27 mmol) was suspended in 6 N HCl (85 ml) and the mixture was refluxed for 8 hours. After cooling, the precipitate was filtered off, washed with $H_2O$ and dried over $P_2O_5$ and KOH, resulting in the pure title compound as its HCl salt (1.29 g; yield 90%).

The title compound was characterized by its mass spectrum: MS (m/z): 299 ([M+H]⁺, 100).

Example 24

Synthesis of 2-amino-7-(3,4-dimethoxyphenyl)-pyrido[3,2-d]pyrimidin-4(3H)one

This compound was synthesized from 2-amino-7-chloro-pyrido[3,2-d]pyrimidin-4(3H)one using the procedure described for example 23. MS (m/z): 299 ([M+H]+, 100)

Example 25

Synthesis of 2-acetamido-6-(3,4-dimethoxyphenyl) pyrido[3,2-d]pyrimidin-4(3H)-one 2-amino-6-(3,4-dimethoxyphenyl)-pyrido[3,2-d]pyrimidin-4(3H)-one (2.0 g, 6.70 mmol) was suspended in acetic anhydride (180 ml) and acetic acid (20 ml) and the mixture was refluxed for 16 hours. The hot suspension was filtered and the filtrate was concentrated under reduced pressure until crystallization started. The precipitate was filtered off to give the pure title compound (1.76 g, yield 77%) which was characterized by its mass spectrum as follows: MS (m/z): 341 ([M+H]⁺, 100).

Example 26

Synthesis of 2-acetamido-7-(3,4-dimethoxyphenyl)-pyrido[3,2-d]pyrimidin-4(3H)one This compound was synthesized from 2-amino-7-(3,4-dimethoxyphenyl)-pyrido[3,2-d]pyrimidin-4(3H)one using the procedure described for example 25. MS (m/z): 341 ([M+H]+, 100)

Example 27

Synthesis of 2-acetamido-4-(1,2,4-triazolyl)-6-(3,4-dimethoxyphenyl)-pyrido[3,2-d]pyrimidine A suspension of 1,2,4-triazole (8.28 g, 120 mmol) and phosphorus oxychloride (3.2 ml, 36 mmol) in dry acetonitrile (150 ml) was added to a stirred suspension of 2-acetamido-6-(3,4-dimethoxyphenyl)pyrido[3,2-d]pyrimidin-4(3H)-one (4.08 g, 12 mmol) and triethylamine (5.2 ml, 36 mmol) in dry acetonitrile (150 ml). The mixture was stirred at room temperature under nitrogen for 3 days and the yellow precipitate was filtered off, then successively washed with ethanol and ether, and dried over P₂O₅ in a vacuum dessicator resulting in the pure title compound (4.3 g, yield 90%) which was characterized by its mass spectrum as follows: MS (m/z): 392 ([M+H]⁺, 100), 414 ([M+Na]⁺; 804 [2M+Na]⁺

Example 28

Synthesis of 2-acetamido-4-(1,2,4-triazolyl)-7-(3,4-dimethoxyphenyl)-pyrido[3,2-d]pyrimidine This compound was synthesized from 2-acetamido-7-(3,4-dimethoxyphenyl)-pyrido[3,2-d]pyrimidin-4(3H)one, using the procedure described for example 27. MS (m/z): 392 ([M+H]+, 100)

Examples 29 and 30

Synthesis of 2-amino-6-(3,4-dimethoxyphenyl)-4-alkoxy-pyrido[3,2-d]pyrimidines

Sodium (44 mg, 2 mmol) was suspended in a suitable alcohol (10 ml) and the solution was warmed up to 50° C. until the sodium dissolved completely. Then, 2-acetamido-4-(1,2,4-triazolyl)-6-(3,4-dimethoxyphenyl)-pyrido[3,2-d]pyrimidine (160 mg, 0.4 mmol) was added and the mixture was stirred at room temperature for 16 hours. The mixture was then neutralized with a solution of 1 N HCl and the volatiles were removed under reduced pressure. The crude mixture was purified by silica gel column chromatography, the mobile phase consisting of CH₃OH/CH₂Cl₂ mixtures (in a ratio gradually ranging from 2:98 to 10:90), thus providing the desired compound with yields ranging from 40 to 60%, depending upon the alcohol used. The following compounds were made according to this procedure:

2-amino-4-isopropoxy-6-(3,4-dimethoxyphenyl)pyrido[3,2-d]pyrimidine (example 29) was obtained from isopropyl alcohol and characterized by its mass spectrum as follows: MS (m/z): 341 ([M+H]⁺, 100), and 2-amino-4-(2-phenoxyethoxy)-6-(3,4-dimethoxyphenyl)-pyrido[3,2-d]pyrimidine (example 30) was obtained from 2-phenoxyethanol and characterized by its mass spectrum as follows: MS (m/z): 419 ([M+H]⁺, 100).

Examples 31 to 41

Synthesis of 2-acetylamino-4-alkylamino-6-(3,4-dimethoxyphenyl)pyrido[3,2-d]pyrimidines, 2-acetylamino-4-cycloalkylamino-6-(3,4-dimethoxyphenyl) pyrido[3,2-d]pyrimidines, 2-acetylamino-4-heteroarylalkylamino-6-(3,4-dimethoxyphenyl) pyrido[3,2-d]pyrimidines, 2-acetylamino-4-arylamino-6-(3,4-dimethoxyphenyl)pyrido[3,2-d] pyrimidines and 2-acetylamino-4-heterocyclic amino-6-(3,4-dimethoxyphenyl)pyrido[3,2-d]pyrimidines and the corresponding 2-amino-4-alkylamino-6-(3,4-dimethoxyphenyl)pyrido[3,2-d]pyrimidines, 2-amino-4-cycloalkylamino-6-(3,4-dimethoxyphenyl)pyrido[3,2-d]pyrimidines, 2-amino-4-heteroarylalkylamino-6-(3,4-dimethoxyphenyl)pyrido[3,2-d] pyrimidines, 2-amino-4-arylamino-6-(3,4-dimethoxyphenyl)pyrido[3,2-d]pyrimidines and 2-amino-4-heterocyclic amino-6-(3,4-dimethoxyphenyl)pyrido[3,2-d]pyrimidines A suitable alkylamine, cycloalkylamine, arylamine, heterocyclic amine or heteroarylalkylamine (2 equivalents, 0.8 mmol) was added to a stirred suspension of 2-acetamido-4-(1,2,4-triazolyl)-6-(3,4-dimethoxyphenyl)pyrido[3,2-d]pyrimidine (160 mg, 0.4 mmol) in dioxane. The mixture was heated at 50° C. for 24 hours and the volatiles were removed under reduced pressure, yielding a crude 2-acetylamino-4-alkylamino-6-(3,4-dimethoxyphenyl)pyrido[3,2-d]pyrimidine, 2-acetylamino-4-cycloalkylamino-6-(3,4-dimethoxyphenyl)pyrido[3,2-d]pyrimidine, 2-acetylamino-4-heteroarylalkylamino-6-(3,4-dimethoxyphenyl)pyrido[3,2-d]pyrimidine, 2-acetylamino-4-arylamino-6-(3,4-dimethoxyphenyl)pyrido[3,2-d]pyrimidine or 2-acetylamino-4-heterocyclic amino-6-(3,4-dimethoxyphenyl)pyrido[3,2-d]pyrimidine as an intermediate. This crude residue was resuspended in a 0.2 N sodium ethoxide (20 ml) and the mixture was stirred at room temperature for 24 hours and neutralized with 5-6 N HCl in isopropyl alcohol, yielding the crude corresponding 2-amino-4-alkylamino-6-(3,4-dimethoxyphenyl)pyrido[3,2-d]pyrimidine, 2-amino-4-cycloalkylamino-6-(3,4-dimethoxyphenyl)pyrido[3,2-d]pyrimidine, 2-amino-4-heteroarylalkylamino-6-(3,4-dimethoxyphenyl)pyrido[3,2-d]pyrimidine, 2-amino-4-arylamino-6-(3,4-dimethoxyphenyl)pyrido[3,2-d] pyrimidine or 2-amino-4-heterocyclic amino-6-(3,4-dimethoxyphenyl)pyrido[3,2-d]pyrimidine as the final compound. This crude residue was purified by silica gel column chromatography, the mobile phase consisting of $CH_3OH/CH_2Cl_2$ mixtures (in a ratio gradually ranging from 2:98 to 10:90) with 0.5% concentrated ammonia if needed. This procedure provided the desired final compounds with yields ranging from 40 to 80%. The following final compounds were synthesized according to this procedure (each time through the corresponding intermediate having the 2-amino group protected in the form of acetamido):

2-amino-4-[4-(ethoxycarbonyl)piperidin-1-yl]-6-(3,4-dimethoxyphenyl)pyrido[3,2-d]pyrimidine (example 31) was obtained from ethyl isonipecotate and characterized by its mass spectrum as follows: MS (m/z): 438 ([M+H]$^+$, 100), 2-amino-4-(3-methyl-anilino)-6-(3,4-dimethoxyphenyl)-pyrido[3,2-d]pyrimidine (example 32) was obtained from 3-methyl-aniline and characterized by its mass spectrum as follows: MS (m/z): 388 ([M+H]$^+$, 100), 2-amino-4-[3,4-(methylenedioxy)aniline]-6-(3,4-dimethoxyphenyl)pyrido[3,2-d]pyrimidine (example 33) was obtained from 3,4-(methylenedioxy)aniline and characterized by its mass spectrum as follows: MS (m/z): 418 ([M+H]$^+$, 100), 2-amino-4-(3-bromo-anilino)-6-(3,4-dimethoxyphenyl)pyrido[3,2-d]-pyrimidine (example 34) was obtained from 3-bromo-aniline and characterized by its mass spectrum as follows: MS (m/z): 452 ([M+H]$^+$, 100), 2-amino-4-(2-chloro-5-methoxy-anilino)-6-(3,4-dimethoxyphenyl)pyrido[3,2-d]pyrimidine (example 35) was obtained from 2-chloro-5-methoxy-aniline and characterized by its mass spectrum as follows: MS (m/z): 438 ([M+H]$^+$, 100), 2-amino-4-(N-methyl-piperazino)-6-(3,4-dimethoxyphenyl)-pyrido[3,2-d]pyrimidine (example 36) was obtained from N-methyl-piperazine and characterized by its mass spectrum as follows: MS (m/z): 381 ([M+H]$^+$, 100), 2-amino-4-(thienyl-2-methylamino)-6-(3,4-dimethoxyphenyl)-pyrido[3,2-d]pyrimidine-2,4-diamine (example 37) was obtained from 2-thiophenylmethylamine and characterized by its mass spectrum as follows: MS (m/z): 394 ([M+H]$^+$, 100), 2-amino-4-[4-(2-aminoethyl)morpholino]-6-(3,4-dimethoxyphenyl)-pyrido[3,2-d]pyrimidine (example 38) was obtained from 4-(2-aminoethyl)morpholine and characterized by its mass spectrum as follows: MS (m/z) 411 ([M+H]$^+$, 100), 2-amino-4-(2,2-dimethoxyethylamino)-6-(3,4-dimethoxyphenyl)pyrido[3,2-d]-pyrimidine (example 39) was obtained from 2,2-dimethoxyethylamine and characterized by its mass spectrum as follows: MS (m/z): 386 ([M+H]$^+$, 100), 2-amino-4-[2-(aminomethyl)pyridino]-6-(3,4-dimethoxyphenyl)-pyrido[3,2-d]pyrimidine (example 40) was obtained from 2-(aminomethyl)pyridine and characterized by its mass spectrum as follows: MS (m/z): 389 ([M+H]$^+$, 100), and 2-amino-4-(1,4-diaminocyclohexyl)-6-(3,4-dimethoxyphenyl)pyrido[3,2-d]pyrimidine (example 41) was obtained from trans-1,4-diaminocyclohexane and characterized by its mass spectrum as follows: MS (m/z): 395 ([M+H]$^+$, 100).

Example 42

Synthesis of 6-(3,4-dimethoxyphenyl)-3-nitropyridine-2-carbonitrile

To a degassed suspension of 6-chloro-2-cyano-3-nitropyridine (5.51 g, 30 mmol), 3,4-dimethoxyphenyl boronic acid (6.55 g, 36 mmole) and potassium carbonate (16.59 g, 120 mmol) in dry toluene (300 ml), was added a catalytic amount of tetrakis(triphenylphosphine)palladium (3.47 g, 3 mmol). The mixture was refluxed for 24 hours and after cooling, the volatiles were evaporated to dryness. The crude mixture was purified by silica gel column chromatography, the mobile phase consisting of hexane/$CH_2Cl_2$ mixtures (in a ratio gradually ranging from 15:85 to 0:100). The appropriated fractions were collected, evaporated to dryness and the residue was suspended in ether. The orange precipitate was filtered off, washed with ether and dried, resulting in the pure title compound (6.79 g, yield 79%).

Example 43

Synthesis of 3-amino-6-(3,4-dimethoxyphenyl)pyridine-2-carbonitrile

Iron (7.14 g, 128 mmol) was added portion wise to a stirred suspension of 6-(3,4-dimethoxyphenyl)-3-nitropyridine-2-carbonitrile (4.56 g; 16 mmol) in methanol (80 ml) and 37% HCl (25 ml). The mixture was refluxed for 5 hours and, after cooling, the pH was adjusted to 9-10 by means of concentrated ammonium hydroxide (30 ml). The mixture was filtered over Celite and washed with MeOH and EtOAc. The filtrate was evaporated to dryness and the residue was purified on silica gel column chromatography, using a mixture of $CH_2Cl_2$/EtOAc (in a ratio of 95:5) as eluent, to obtain the pure title compound (2.62 g, yield 64%) which was characterized by its mass spectrum as follows: MS (m/z): 256 ([M+H]$^+$, 100).

Example 44

Synthesis of 2,4-diamino-6-(3,4-dimethoxyphenyl)pyrido[3,2-d]pyrimidine

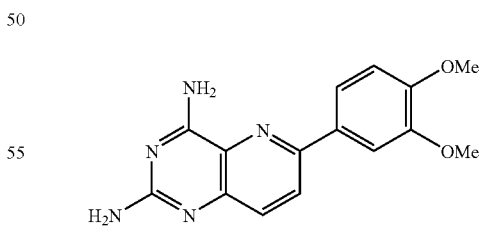

Method A: A solution of sodium (423 mg, 18.4 mmole) in n-butanol (180 ml) was added to 3-amino-6-(3,4-dimethoxyphenyl)pyridine-2-carbonitrile (2.36 g; 9.20 mmole) and guanidine hydrochloride (1.76 g; 18.4 mmole). The mixture was refluxed for 4 hours and, after cooling, the solvent was evaporated under reduced pressure. The residue was purified on silica gel column chromatography, using a mixture of $CH_2Cl_2$/MeOH (in a ratio of 95:5) as eluent, resulting in the pure title compound (1.88 g; yield 69%) which was characterized by its mass spectrum as follows: MS (m/z): 298 ([M+H]⁺, 100).

Method B: A suspension of 2-amino-6-(3,4-dimethoxyphenyl)-pyrido[3,2-d]pyrimidin-4(3H)one (298 mg, 1.0 mmol), 1,1,1,3,3,3-hexamethyldisilazane (1 ml, 4.7 mmol), ammonium chloride (4.0 mmol), p-toluenesulfonic acid (20 mg, 0.1 mmol) and ammonium sulfate (20 mg, 0.15 mmol) in pyridine (5 ml) was refluxed for 12 to 48 hours. The solvents were evaporated in vacuo and the residue was purified by silica gel flash chromatography, the mobile phase being a MeOH/dichloromethane mixture (in a volume ratio of 1:20 to 1:30), resulting into the title compounds as yellow solids (56%) which characterised as follows:
Rf=0.23 (MeOH/CH₂Cl₂ 1:4);
UV (MeOH/H₂O, nm): 245, 585; and
MS (m/z): 298 ([M+H]⁺, 100).

Example 45

Synthesis of 2-amino-4-morpholino-6-(3,4-dimethoxyphenyl)-pyrido[3,2-d]pyrimidine 2-amino-6-(3,4-dimethoxyphenyl)pyrido[3,2-d]pyrimidin-4(3H)-one hydrochloride (332 mg; 1 mmole) was suspended in toluene (10 ml) with a catalytic amount of p-toluenesulfonic acid and ammonium sulfate. Then, 1,1,1,3,3,3-hexamethyldisilazane (3.2 ml; 15 mmole) and morpholine (0.53 ml; 6 mmole) were added. The mixture was refluxed for 24 hours and evaporated to dryness. The residue was purified by silica gel column chromatography, using a mixture of CH₂Cl₂/MeOH: 96:4 as eluent, resulting in the pure title compound (120 mg; yield 32%) which was characterized by its mass spectrum as follows: MS (m/z): 368 ([M+H]⁺, 100).

Example 46

Synthesis of 2-amino-4-(4-{[(3-methylphenyl)amino]carbonyl}piperazin-1-yl)-6-(3,4-dimethoxyphenyl)-pyrido[3,2-d]pyrimidine Piperazine (258 mg; 3 mmole) was added to a stirred suspension of 2-acetamido-6-(3,4-dimethoxyphenyl)-4-(1,2,4-triazolyl)pyrido[3,2-d]pyrimidine (586 mg; 1.5 mmole) in dioxane (50 ml). The mixture was stirred at room temperature for 24 hours and the volatiles were removed under reduced pressure, yielding 2-acetamido-4-(N-piperazinyl)-6-(3,4-dimethoxyphenyl)-pyrido[3,2-d]pyrimidine as a crude residue. The latter was dissolved in DMF and m-tolyl isocyanate (0.66 ml, 5 mmole) was added. After 18 hours at room temperature, the solvent was removed and the residue was suspended in a mixture of CH₂Cl₂ (20 ml) and sodium ethoxide 0.2 N (20 ml). The suspension was stirred during 16 hours and neutralized with 5-6 N HCl in isopropyl alcohol. The crude residue was purified by silica gel column chromatography, the mobile phase consisting of a CH₃OH/CH₂Cl₂ mixture in a ratio gradually ranging from 2:98 to 5:95, thus resulting in the pure title compound (350 mg, yield 43%) which was characterized by its mass spectrum as follows: MS (m/z): 542 ([M+H]⁺, 100).

Example 47

Synthesis of 2-amino-4-(N-3-methyl-phenyl-carbamoyl)-piperazin-1-yl])-7-(3,4-dimethoxyphenyl)-pyrido[3,2-d]pyrimidine This compound was synthesized from 2-acetamido-4-(1,2,4-triazolyl)-7-(3,4-dimethoxyphenyl)-pyrido[3,2-d]pyrimidin-4(3H)one, using the procedure described for example 46. MS (m/z): 500 ([M+H]⁺, 100)

Example 48

Synthesis of 2-amino-4-(4-fluorophenyl-piperazin-1-yl)-6-(3,4-dimethoxyphenyl)-pyrido[3,2-d]pyrimidine 1-(4-fluorophenyl)-piperazine (90 mg, 0.5 mmole) was added to a stirred suspension of 2-acetamido-6-(3,4-dimethoxyphenyl)-4-(1,2,4-triazolyl)pyrido[3,2-d]pyrimidine (120 mg, 0.3 mmole) in dioxane (10 ml). The mixture was stirred at 60° C. for 48 hours and the volatiles were removed under reduced pressure, yielding the crude 2-acetamido-4-(4-fluorophenyl-piperazin-1-yl-)-6-(3,4-dimethoxyphenyl)-pyrido[3,2-d]pyrimidine. The latter was dissolved in a mixture of CH₂Cl₂ (20 ml) and sodium ethoxide 0.2 N (20 ml). The suspension was stirred during 16 hours and neutralized with 5-6 N HCl in isopropyl alcohol. The crude residue was purified by preparative thin layer chromatography, the mobile phase consisting of a CH₃OH/CH₂Cl₂ mixture in a ratio of 5:95, resulting in the pure title compound (40 mg, yield 29%) which was characterized by its mass spectrum as follows: MS (m/z): 461 ([M+H]⁺, 100).

Example 49

Synthesis of 2-amino-4-(4-methylphenyl-piperazin-1-yl)-6-(3,4-dimethoxyphenyl)-pyrido[3,2-d]pyrimidine A similar procedure as in example 48 was used but starting from 1-(4-methylphenyl)-piperazine and resulted, through the corresponding 2-acetamido intermediate, in the pure title compound (49% yield) which was characterized by its mass spectrum as follows: MS (m/z): 457 ([M+H]⁺, 100).

Example 50

Synthesis of 2-amino-4-(phenoxy-ethyl-piperazin-1-yl)-6-(3,4-dimethoxyphenyl)-pyrido[3,2-d]pyrimidine A similar procedure as in example 48 was used but starting from 1-(2-phenoxy-ethyl)-piperazine and resulted, through the corresponding 2-acetamido intermediate, in the pure title compound (56% yield) which was characterized by its mass spectrum as follows: MS (m/z): 488 ([M+H]⁺, 100).

Example 51

Synthesis of 2-amino-4-(3-chlorophenyl-piperazin-1-yl)-6-(3,4-dimethoxyphenyl)-pyrido[3,2-d]pyrimidine A similar procedure as in example 48 was used but starting from 1-(3-chlorophenyl)-piperazine and resulted, through the corresponding 2-acetamido intermediate, in the pure title compound (42% yield) which was characterized by its mass spectrum as follows: MS (m/z): 478 ([M+H]⁺, 100)

Example 52

Synthesis of 2-amino-4-(2-pyridyl-piperazin-1-yl)-6-(3,4-dimethoxyphenyl)-pyrido[3,2-d]pyrimidine A similar procedure as in example 48 was used but starting from 1-(2-pyridyl)piperazine and resulted, through the corresponding 2-acetamido intermediate, in the pure title compound (37% yield) which was characterized by its mass spectrum as follows: MS (m/z): 444 ([M+H]$^+$, 100).

Example 53

Synthesis of 2-amino-4-[2-(piperazin-1-yl)-acetic acid N-(2-thiazolyl)-amide]-6-(3,4-dimethoxyphenyl)-pyrido[3,2-d]pyrimidine A similar procedure as in example 48 was used but starting from 2-(piperazin-1-yl)-acetic acid N-(2-thiazolyl)-amide and resulted, through the corresponding 2-acetamido intermediate, in the pure title compound (52% yield) which was characterized by its mass spectrum as follows: MS (m/z): 507 ([M+H]$^+$, 100).

Example 54

Synthesis of 2-amino-4-(N-acetyl-piperazinyl)-6-(3,4-dimethoxyphenyl)-pyrido[3,2-d]pyrimidine A similar procedure as in example 48 was used but starting from N-acetylpiperazine and resulted, through the corresponding 2-acetamido intermediate, in the pure title compound (33% yield) which was characterized by its mass spectrum as follows: MS (m/z): 409 ([M+H]$^+$, 100).

Example 55

Synthesis of 2-amino-4-(1-piperonyl-piperazin-1-yl)-6-(3,4-dimethoxyphenyl)-pyrido[3,2-d]pyrimidine A similar procedure as in example 48 was used but starting from 1-piperonylpiperazine and resulted, through the corresponding 2-acetamido intermediate, in the pure title compound (38% yield) which was characterized by its mass spectrum as follows: MS (m/z): 501 ([M+H]$^+$, 100).

Example 56

Synthesis of 2-amino-4-[1-(2-furoyl)-piperazin-1-yl]-6-(3,4-dimethoxyphenyl)-pyrido[3,2-d]pyrimidine A similar procedure as in example 48 was used but starting from 1-(2-furoyl)-piperazine instead of 1-(4-fluorophenyl)-piperazine and resulted, through the corresponding 2-acetamido intermediate, in the pure title compound which was characterized by its mass spectrum as follows: MS (m/z): 461 ([M+H]$^+$, 100).

Example 57

Synthesis of 2-amino-4-(1-benzylpiperazin-1-yl)-6-(3,4-dimethoxyphenyl)-pyrido[3,2-d]pyrimidine A similar procedure as in example 48 was used but starting from 1-benzylpiperazine and resulted, through the corresponding 2-acetamido intermediate, in the pure title compound (39% yield) which was characterized by its mass spectrum as follows: MS (m/z): 457 ([M+H]$^+$, 100).

Example 58

Synthesis of 2-acetamido-4-(piperazin-1-yl)-6-(3,4-dimethoxyphenyl)-pyrido[3,2-d]pyrimidine Piperazine (430 mg, 5 mmole) was added to a stirred suspension of 2-acetamido-6-(3,4-dimethoxyphenyl)-4-(1,2,4-triazolyl)pyrido[3,2-d]pyrimidine (977 mg, 2.5 mmole) in dioxane (70 ml). The reaction mixture was refluxed for 16 hours. The precipitate was filtered off and washed with a small amount of dioxane. The filtrate was evaporated to dryness and the residue washed with diethyl ether. Both fractions (the precipitate and the washed filtrate) were combined, resulting in the pure title compound (805 mg, yield 79%) which was characterized by its mass spectrum as follows: MS (m/z): 409 ([M+H]$^+$, 100).

Examples 59 to 63

Synthesis of 2-amino-4-(N-carbamoyl-piperazin-1-yl)-6-(3,4-dimethoxy-phenyl)-pyrido[3,2-d]pyrimidines To a solution of 2-acetamido-4-(piperazin-1-yl)-6-(3,4-dimethoxyphenyl)-pyrido[3,2-d]pyrimidine (200 mg, 0.5 mmole) in DMF (5 ml) was added a suitable isocyanate (0.75 mmole). The reaction mixture was stirred for 16 hours at room temperature. The solvents were evaporated in vacuo yielding a crude 2-acetamido-4-(N-carbamoyl-piperazin-1-yl)-6-(3,4-dimethoxyphenyl)-pyrido[3,2-d]pyrimidine as an intermediate. This crude residue was dissolved in a mixture of $CH_2Cl_2$ (10 ml) and sodium ethoxide 0.2 N (10 ml), the resulting suspension was stirred for 16 hours and neutralized with 5-6 N HCl in isopropyl alcohol, yielding a crude 2-amino-4-(N-carbamoyl-piperazin-1-yl)-6-(3,4-dimethoxyphenyl)-pyrido[3,2-d]pyrimidine as the final compound. This crude product was purified by preparative thin layer chromatography on silica, the mobile phase consisting of a $CH_3OH/CH_2Cl_2$ mixture in a ratio of 10:90, resulting in the pure desired compounds in yields varying from 20 to 40%, depending upon the isocyanate used. The following final compounds were synthesized according to this procedure (each time through the corresponding intermediate having the 2-amino group protected in the form of acetamido):

2-amino-4(N-3-thienylcarbamoyl-piperazin-1-yl)-6-(3,4-dimethoxyphenyl)-pyrido[3,2-d]pyrimidine (example 59) was obtained from 3-thienyl isocyanate and characterized by its mass spectrum as follows: MS (m/z): 492 ([M+H]$^+$, 100), 2-amino-4(N-2,6-dichloro-pyridinyl-carbamoyl-piperazin-1-yl)-6-(3,4-dimethoxyphenyl)-pyrido[3,2-d]pyrimidine (example 60) was obtained from 2,6-dichloro-4-isocyanate-pyridine and was characterized by its mass spectrum as follows: MS (m/z): 555, 557 ([M+H]$^+$, 100), 2-amino-4(N-4-fluoro-phenyl-carbamoyl-piperazin-1-yl)-6-(3,4-dimethoxyphenyl)-pyrido[3,2-d]pyrimidine (example 61) was obtained from 4-fluoro-phenyl isocyanate and was characterized by its mass spectrum as follows: MS (m/z): 504 ([M+H]$^+$, 100), 2-amino-4(N-3-chloro-4-fluoro-phenyl-carbamoyl-piperazin-1-yl)-6-(3,4-dimethoxyphenyl)-pyrido[3,2-d]pyrimidine (example 62) was obtained from 3-chloro-4-fluoro-phenyl isocyanate and was characterized by its mass spectrum as follows: MS (m/z): 539 ([M+H]$^+$, 100), and 2-amino-4(N-3-chloro-phenyl-carbamoyl-piperazin-1-yl)-6-(3,4-dimethoxyphenyl)-pyrido[3,2-d]pyrimidine (example 63) was obtained from 3-chlorophenyl isocyanate and was characterized by its mass spectrum as follows: MS (m/z): 521 ([M+H]$^+$, 100).

Example 64

Synthesis of 2-amino-4[(N-4-chloro-phenoxyacetyl)-piperazin-1-yl]-6-(3,4-dimethoxyphenyl)-pyrido[3,2-d]pyrimidine To a solution of 2-acetamido-4-(piperazin-1-yl)-6-(3,4-dimethoxyphenyl)-pyrido[3,2-d]pyrimidine (200 mg, 0.5 mmole) in dioxane (15 ml) was added p-chloro-phenoxy acetyl chloride (0.75 mmol). The reaction mixture was stirred for 16 hours at 50° C. overnight. The solvents were evaporated in vacuo yielding crude 2-acetamido-4-[(N-4-chloro-phenoxy-acetyl)-piperazin-1-yl]-6-(3,4-dimethoxyphenyl)-pyrido[3,2-d]pyrimidine as an intermediate. This crude residue was dissolved in a mixture of $CH_2Cl_2$ (10 ml) and sodium ethoxide 0.2 N (10 ml). The suspension was stirred for 16 hours and neutralized with 5-6 N HCl in isopropyl alcohol, yielding crude 2-amino-4-[(N-4-chloro-phenoxy-acetyl)-piperazin-1-yl]-6-(3,4-dimethoxyphenyl)-pyrido[3,2-d]pyrimidine as the final compound. This crude product was purified by preparative thin layer chromatography on silica, the mobile phase consisting of a $CH_3OH/CH_2Cl_2$ mixture in a ratio of 10:90, resulting in the pure title compound (98 mg, yield 37%) which was characterized by its mass spectrum as follows: MS (m/z): 536 ($[M+H]^+$, 100).

Example 65

Synthesis of 2-amino-4[(N-phenoxy-acetyl)-piperazin-1-yl]-6-(3,4-dimethoxyphenyl)-pyrido[3,2-d]pyrimidine A similar procedure as described in example 64 was performed, but using phenoxy acetyl chloride instead of p-chloro-phenoxy acetyl chloride and resulted, through the corresponding 2-acetamido intermediate, in the pure title compound which was characterized by its mass spectrum as follows: MS (m/z): 501 ($[M+H]^+$, 100).

Example 66

Synthesis of 7-chloro-pyrido[3,2-d]pyrimidin-4(3H)one

A suspension of 3-amino-5-chloro-pyridine-2-carboxamide (3.43 g, 20 mmole) in triethyl orthoformate (50 ml) was refluxed for 3 hours. After cooling to room temperature, the precipitate was collected by filtration and washed with hexane. The title compound was obtained as a white solid (3.4 g, yield 94%) which was characterized by its mass spectrum as follows: MS (m/z): 182.1 ($[M+H]^+$, 100).

Example 67

Synthesis of 4,6-dichloro-pyrido[3,2-d]pyrimidine

To a mixture of 6-chloro-pyrido[3,2-d]pyrimidin-4(3H)one (3.0 g, 16.5 mmole) and N,N-diisopropylethylamine (9 ml, 50 mmole) in toluene (150 ml), was added $POCl_3$ (4.7 ml, 50 mmol). The resulting reaction mixture was refluxed for 1.5 hour. After cooling to room temperature, the solvent was removed under reduced pressure. The residue was dissolved in dichloromethane (200 ml) and washed with cold water till pH=6-7. The organic phase was dried over $MgSO_4$, filtrated and concentrated under reduced pressure to yield crude 4,6-dichloro-pyrido[3,2-d]pyrimidine which was not purified but used as such for further reactions.

Example 68

Synthesis of 4-(piperazin-1-yl)-6-chloro-pyrido[3,2-d]pyrimidine

To a solution of piperazine (7.0 g) in 1,4-dioxane (100 ml) was added a solution of crude 4,6-dichloro-pyrido[3,2-d]pyrimidine in 1,4-dioxane (50 ml). The resulting mixture was stirred at room temperature for 1 hour. After concentration under reduced pressure, the residue was purified by silica gel flash chromatography, the mobile phase being a methanol/dichloromethane mixture (in a ratio gradually ranging from 1:10 to 1:5), resulting in the pure title compound as a yellowish solid (3.1 g, yield 76%) which was characterized by its mass spectrum as follows: MS (m/z): 250.1 ($[M+H]^+$, 100).

Example 69

Synthesis of 4,7-dichloro-pyrido[3,2-d]pyrimidine

This compound was synthesized from 7-chloro-pyrido[3,2-d]pyrimidin-4(3H)one using the procedure mentioned in example 64.

Example 70

Synthesis of 7-chloro-4-(piperazin-1-yl)-pyrido[3,2-d]pyrimidine

The title compound was synthesized in 72% yield from 4,7-dichloro-pyrido[3,2-d]pyrimidine by the procedure of example 65 and was characterized by its mass spectrum as follows: MS (m/z): 250.1 ($[M+H]^+$, 100).

Example 71

Synthesis of 4-morpholino-6-chloro-pyrido[3,2-d]pyrimidine

The title compound was synthesized in 71% yield from 4,6-dichloro-pyrido[3,2-d]pyrimidine and morpholine by the procedure of example 65, and was characterized by its mass spectrum as follows: MS (m/z): 251.1 ($[M+H]^+$, 100).

Example 72

Synthesis of 4-[(N-3-chlorophenylcarbamoyl)-piperazin-1-yl]-7-chloro-pyrido[3,2-d]pyrimidine To a solution of 4-(piperazin-1-yl)-7-chloro-pyrido[3,2-d]pyrimidine (1.0 g, 4 mmole) in dichloromethane (40 ml), was added 3-chlorophenyl isocyanate (615 mg, 4 mmole). The reaction mixture was stirred at room temperature for 1 hour. The solvent was removed under reduced pressure, resulting in the pure title compound (1.6 g, yield 99%) as a white solid which was characterized by its mass spectrum as follows: MS (m/z): 403.1 ($[M+H]^+$, 100).

Example 73

Synthesis of 4-[(N-3-chlorophenylcarbamoyl)-piperazin-1-yl]-6-chloro-pyrido[3,2-d]pyrimidine This compound was synthesized from 4-(piperazin-1-yl)-6-chloro-pyrido[3,2-d]pyrimidine (2.5 g, 10 mmole) and 3-chlorophenyl isocyanate (1.54 g, 10 mmole) using the procedure of example 69, resulting in the pure title compound (4.0 g, 99%) as a white solid which was characterized by its mass spectrum as follows: MS (m/z): 403.1 ($[M+H]^+$, 100).

Examples 74 to 81

Synthesis of 4-[(N-3-chlorophenylcarbamoyl)-piperazin-1-yl]-7-aryl-pyrido[3,2-d]pyrimidines To a solution of 4-[(N-3-chlorophenylcarbamoyl)-piperazin-1-yl]-7-chloro-pyrido[3,2-d]pyrimidine (0.5 mmole) in dioxane (20 ml) and water (5 ml) was added an appropriate arylboronic acid (0.5 mmole), $K_2CO_3$ (1.5 mmole), and tetrakis (triphenylphosphine)palladium(0) (0.025 mmole). The mixture was heated at 95° C. until the starting materials disappeared on thin layer chromatography. The reaction mixture was diluted with $CH_2Cl_2$ (50 ml) and washed with a 0.5 M $Na_2CO_3$ solution (10 ml), and the organic phase was concentrated under reduced pressure. The residue was purified by silica gel column chromatography, the mobile phase being an acetone/dichloromethane mixture (in a ratio gradually ranging from 1:3 to 1:2), resulting in the pure following compounds:

4-[(N-3-chlorophenylcarbamoyl)-piperazin-1-yl]-7-(3-chloro-4-methoxyphenyl)-pyrido[3,2-d]pyrimidine (example 74) was obtained from 3-chloro-4-methoxyphenyl boronic acid (yield 81%) as a white solid which was characterized by its mass spectrum as follows: MS (m/z): 509.1 ([M+H]$^+$, 100), 4-[(N-3-chlorophenylcarbamoyl)-piperazin-1-yl]-7-(3,4-dimethylphenyl)-pyrido[3,2-d]pyrimidine (example 75) was obtained from 3,4-dimethylphenyl boronic acid (yield 80%) as a white solid which was characterized by its mass spectrum as follows: MS (m/z): 473.2 ([M+H]$^+$, 100), 4-[(N-3-chlorophenylcarbamoyl)-piperazin-1-yl]-7-(3,4-dichlorophenyl)-pyrido[3,2-d]pyrimidine (example 76) was obtained from 3,4-dichlorophenyl boronic acid (yield 82%) as a white solid which was characterized by its mass spectrum as follows: MS (m/z): 515.1 ([M+H]$^+$, 100), 4-[(N-3-chlorophenylcarbamoyl)-piperazin-1-yl]-7-(3-fluoro-4-methyl-phenyl)-pyrido[3,2-d]pyrimidine (example 77) was obtained from 3-fluoro-4-methylphenyl boronic acid (yield 92%) as a white solid which was characterized by its mass spectrum as follows: MS (m/z): 477.1 ([M+H]$^+$, 100), 4-[(N-3-chlorophenylcarbamoyl)-piperazin-1-yl]-7-(3-chloro-4-fluoro-phenyl)-pyrido[3,2-d]pyrimidine (example 78) was obtained from 3-chloro-4-fluoro-phenyl boronic acid (yield 86%) as a white solid which was characterized by its mass spectrum as follows: MS (m/z): 497.2 ([M+H]$^+$, 100), 4-[(N-3-chlorophenylcarbamoyl)-piperazin-1-yl]-7-(3,4-methylenedioxyphenyl)-pyrido[3,2-d]pyrimidine (example 79) was obtained from 3,4-methylenedioxyphenyl-boronic acid (yield 87%) as a white solid which was characterized by its mass spectrum as follows: MS (m/z): 489.2 ([M+H]$^+$, 100), 4-[(N-3-chlorophenylcarbamoyl)-piperazin-1-yl]-7-(3-chloro-4-ethoxy-phenyl)-pyrido[3,2-d]pyrimidine (example 80) was obtained from 3-chloro-4-ethoxyphenylboronic acid (yield 81%) as a white solid which was characterized by its mass spectrum as follows: MS (m/z): 523.2 ([M+H]$^+$, 100), and 4-[(N-3-chlorophenylcarbamoyl)-piperazin-1-yl]-7-(3-fluoro-4-ethoxy-phenyl)-pyrido[3,2-d]pyrimidine (example 81) was obtained from 3-fluoro-4-ethoxyphenyl boronic acid (yield 88%) as a white solid which was characterized by its mass spectrum as follows: MS (m/z): 507.2.2 ([M+H]$^+$, 100).

Examples 82 to 87

Synthesis of 4-[(N-3-chlorophenylcarbamoyl)-piperazin-1-yl]-6-aryl-pyrido[3,2-d]pyrimidines The procedure of examples 74 to 81 was repeated, using 4-[(N-3-chlorophenylcarbamoyl)-piperazin-1-yl]-6-chloro-pyrido[3,2-d]pyrimidine as the starting material, for preparing the following pure compounds:

4-[(N-3-chlorophenylcarbamoyl)-piperazin-1-yl]-6-(3-chloro-4-methoxyphenyl)-pyrido[3,2-d]pyrimidine (example 82) was obtained from 3-chloro-4-methoxyphenyl boronic acid (yield 86%) as a white solid which was characterized by its mass spectrum as follows: MS (m/z): 509.1 ([M+H]$^+$, 100), 4-[(N-3-chlorophenylcarbamoyl)-piperazin-1-yl]-6-(1,4-benzodioxan-6-yl)-pyrido[3,2-d]pyrimidine (example 83) was obtained from 1,4-benzodioxane-6-boronic acid (yield 93%) as a white solid which was characterized by its mass spectrum as follows: MS (m/z): 503.2 ([M+H]$^+$, 100), 4-[(N-3-chlorophenylcarbamoyl)-piperazin-1-yl]-6-(3,4-dimethylphenyl-pyrido[3,2-d]pyrimidine (example 84) was obtained from 3,4-dimethylphenyl boronic acid (yield 80%) as a white solid which was characterized by its mass spectrum as follows: MS (m/z): 473.2 ([M+H]$^+$, 100), 4-[(N-3-chlorophenylcarbamoyl)-piperazin-1-yl]-6-(3,4-methylenedioxy)phenyl-pyrido[3,2-d]pyrimidine (example 85) was obtained from 3,4-methylenedioxyphenyl boronic acid (yield 92%) as a white solid which was characterized by its mass spectrum as follows: MS (m/z): 489.2 ([M+H]$^+$, 100), 4-[(N-3-chlorophenylcarbamoyl)-piperazin-1-yl]-6-(3-chloro-4-ethoxyphenyl-pyrido[3,2-d]pyrimidine (example 86) was obtained from 3-chloro-4-ethoxyphenylboronic acid (yield 92%) as a white solid which was characterized by its mass spectrum as follows: MS (m/z): 523.1 ([M+H]$^+$, 100), and 4-[(N-3-chlorophenylcarbamoyl)-piperazin-1-yl]-6-(3,4-dichlorophenyl-pyrido[3,2-d]pyrimidine (example 87) was obtained from 3,4-dichlorophenyl boronic acid (yield 76%) as a white solid which was characterized by its mass spectrum as follows: MS (m/z): 515.1 ([M+H]$^+$, 100).

Example 88

Synthesis of 6-chloro-pyrido[3,2-d]pyrimidin-2(1H)-4(3H)-dione

Adding triphosgene (3.05 g, 10.14 mmole) to a solution of 6-chloro-2-carboxamido-3-amino-pyridine (3.48 g, 20.28 mmole) in dry dioxane (125 ml) under a $N_2$ atmosphere resulted in the immediate formation of a precipitate. The dark orange reaction mixture was stirred under reflux under a $N_2$ atmosphere for 30 minutes. Upon cooling, the solvent was removed under reduced pressure and the residue was purified by silica gel flash chromatography, the mobile phase being a $CH_3OH/CH_2Cl_2$ mixture (in a ratio gradually ranging from 5:95 to 15:95), resulting in the pure title compound as a white powder (2.96 g, yield 74%) which was characterized by its mass spectrum as follows: MS (m/z): 198 ([M+H]$^+$, 100).

Example 89

Synthesis of 6-(3,4-dimethoxy-phenyl)-pyrido[3,2-d]pyrimidin-2(1H)-4-(3H)-dione

A suspension of 6-chloro-pyrido[3,2-d]pyrimidin-2(1H)-4(3H)-dione (300 mg, 1.52 mmole), $K_2CO_3$ (840 mg, 6 mmole) and 3,4-dimethoxyphenylboronic acid (360 mg, 1.98 mmole) in 1,4-dioxane (22.5 ml) and water (8 ml) was purged with a nitrogen stream for 15 minutes. Tetrakis(triphenylphosphine)palladium(0) (90 mg, 76 mmole) was added and the mixture was heated to reflux for 24 hours. Upon cooling, the reaction mixture was filtered. The solid residue was recrystallized from hot acetic acid, then washed successively with acetic acid, ethyl acetate and diethyl ether, and finally dried, resulting in the pure title compound (297 mg, yield 65%) which was characterized by its mass spectrum as follows: MS (m/z): 300 ([M+H]$^+$, 100).

Example 90

Synthesis of 2,4-dichloro-6-(3,4-dimethoxyphenyl)-pyrido[3,2-d]pyrimidine 6-(3,4-dimethoxyphenyl)-pyrido[3,2-d]pyrimidin-2(1H)-4(3H)-dione (2.39 g, 7.97 mmole) was suspended in POCl$_3$ (54 ml) and triethylamine (3.1 ml, 21.8 mmole) was added. The dark brown mixture was stirred at reflux for 2.5 hours and allowed to cool down to room temperature. Most of POCl$_3$ was removed under reduced pressure and the rest was poured into ice/water and extracted with dichloromethane. The crude residue was purified by silica gel flash chromatography, the mobile phase being a n-hexane/EtOAc mixture, in a ratio gradually ranging from 1.5:1 to 1:1, to afford the pure title compound (1.69 g, yield 63%) which was characterized by its mass spectrum as follows: MS (m/z): 336 [(M+H)$^+$, 100].

Example 91

Synthesis of 2-morpholino-4-[(N-3-methyl-phenyl-carbamoyl-piperazin-1-yl]-6-(3,4-dimethoxyphenyl)-pyrido[3,2-d]pyrimidine 2-chloro-4-[(N-3-methyl-phenylcarbamoyl)-piperazin-1-yl]-6-(3,4-dimethoxyphenyl)-pyrido[3,2-d]pyrimidine (156 mg, 0.3 mmole) was suspended in 1,4-dioxane (10 ml) and morpholine (0.6 mmole) was added. The reaction mixture was heated at reflux for 4 hours, allowed to cool down to room temperature and partitioned between dichloromethane and a saturated aqueous sodium bicarbonate solution. The solid residue from the organic phase was purified by preparative thin layer chromatography on silica using a mixture of ethyl acetate and n-hexane (in a ratio of 1:4) as the mobile phase, to afford the pure title compound (21 mg, yield 12%) which was characterized by its mass spectrum as follows: MS (m/z): 570 ([M+H]$^+$, 100).

Example 92

Synthesis of 2-butoxy-4-[(N-3-methyl-phenylcar-bamoyl)-piperazin-1-yl]-6-(3,4-dimethoxyphenyl)-pyrido[3,2-d]pyrimidine 28 mg (0.7 mmole) of 60% by weight NaH in mineral oil was suspended in dry tetrahydrofuran (5 ml) under a N$_2$ atmosphere, followed by the addition of n-butanol (0.6 mmole). Then, 2-chloro-[(N-3-methyl-phenylcarbamoyl)-piperazin-1-yl]-6-(3,4-dimethoxyphenyl)-pyrido[3,2-d]pyrimidine (149 mg, 0.29 mmole) was added. The mixture was heated at reflux under N$_2$ for 2.5 hours and then diluted with water. The crude product was extracted four times from the reaction mixture with ethyl acetate. The organic extracts were combined, dried over MgSO$_4$ and evaporated to dryness under reduced pressure. Preparative thin layer chromatography on silica using a n-hexane/ethyl acetate 1:4 mixture as eluent afforded the pure title compound (148 mg, yield 93%) which was characterized by its mass spectrum as follows: MS (m/z): 557 ([M+H]$^+$, 100).

Example 93

Synthesis of 2-methoxy-4-[(N-3-methyl-phenylcar-bamoyl)-piperazin-1-yl]-6-(3,4-dimethoxy-phenyl)-pyrido[3,2-d]pyrimidine 24 mg (0.6 mmole) of 60% by weight NaH in mineral oil was suspended in dry tetrahydrofuran (3 ml) under a N$_2$ atmosphere followed by the addition of methanol (0.4 mmole). The mixture was stirred at room temperature for 15 minutes, and 2-chloro-4-[(N-3-methyl-phenylcarbamoyl)-piperazin-1-yl]-6-(3,4-dimethoxy phenyl)-pyrido[3,2-d]pyrimidine (104 mg, 0.2 mmole) was added. The solution was heated at reflux under N$_2$ for 1 hour and diluted with water. The crude product was extracted from the reaction mixture with ethyl acetate and the organic layer was washed with brine, dried over MgSO$_4$ and evaporated to dryness under reduced pressure. Preparative thin layer chromatography on silica, using a n-hexane/ethyl acetate mixture in a ratio of 1:5 as eluent, afforded the pure title compound (52 mg, yield 51%) which was characterized by its mass spectrum as follows: MS (m/z): 515 ([M+H]$^+$, 100).

Example 94

Synthesis of 2-(p-tolylamino)-4-[(N-3-methylphe-nylcarbamoyl)-piperazin-1-yl]-6-(3,4-dimethoxy-phenyl)-pyrido[3,2-d]pyrimidine A white suspension of 2-chloro-4-[(N-3-methyl-phenyl-carbamoyl)-piperazin-1-yl]-6-(3,4-dimethoxyphenyl)-pyrido[3,2-d]pyrimidine (104 mg, 0.2 mmole), K$_2$CO$_3$ (64 mg, 0.46 mmole), and p-toluidine (46 mg, 0.43 mmole) in a mixture of 1,4-dioxane/t-BuOH 5:1 (2 ml) was stirred at room temperature under nitrogen for 5 minutes. Thereafter, tetrakis (triphenylphosphine)palladium(0) (26 mg, 23 µmole) was added and the reaction mixture was heated at reflux under a N$_2$ atmosphere for 48 hours. Upon cooling, the mixture was diluted with water and extracted three times with ethyl acetate (brine added). The combined organic extracts were dried over Na$_2$SO$_4$, filtered and evaporated under reduced pressure. The crude residue was purified by column chromatography on silica using an ethyl acetate/n-hexane mixture as the mobile phase (in a ratio gradually ranging from 1:1 to 3:1), resulting in the pure title compound (30 mg, yield 25%) which was characterized by its mass spectrum as follows: MS (m/z): 590 ([M+H]$^+$, 100).

Example 95

Synthesis of 2-[(3-chloro-4-fluoro-anilino)-4-[(N-3-methylphenylcarbamoyl)-piperazin-1-yl]-6-(3,4-dimethoxyphenyl)-pyrido[3,2-d]pyrimidine A suspension of 2-chloro-4-[(N-3-methyl-phenylcarbam-oyl)-piperazin-1-yl]-6-(3,4-dimethoxyphenyl)-pyrido[3,2-d]pyrimidine (106 mg, 0.20 mmole), K$_2$CO$_3$ (62 mg, 0.45 mmole) and 3-chloro-4-fluoroaniline (60 mg 0.40 mmole) in a 1,4-dioxane/t-BuOH 5:1 mixture (2 ml) was purged with nitrogen for 15 minutes. Thereafter, tetrakis(triphenylphos-phine)palladium(0) (28 mg, 24 µmol) was added and the reaction mixture was heated at reflux under a N$_2$ atmosphere for 20 hours. Upon cooling, the mixture was partitioned between ethyl acetate and brine. The organic phase was evaporated under reduced pressure and the crude residue was purified by flash chromatography on silica, using an ethyl acetate/n-hexane mixture as the mobile phase (in a ratio

Example 96

Synthesis of 2,4-diamino-6-(4-hydroxy-3-methoxyphenyl)-pyrido[3,2-d]pyrimidine

A suspension of 2,4-diamino-6-chloropyrido[3,2-d]pyrimidine (378 mg, 1.93 mmole), $K_2CO_3$ (1075 mg, 7.78 mmole) and 2-methoxy-4-(4,4,5,5-tetramethyl-[1,3,2]dioxaborolan-2-yl)-phenol (599 mg, 2.32 mmole) in 1,4-dioxane (29 ml) and water (6 ml) was purged with a nitrogen stream for 30 minutes. Then, tetrakis(triphenylphosphine)palladium (0) (240 mg, 0.21 mmole) was added and purging with $N_2$ was continued for 15 minutes. The reaction mixture was then heated at reflux under a $N_2$ atmosphere for 2 hours. Upon cooling, the mixture was partitioned between $CH_2Cl_2$ and brine and the organic phase was dried over $Na_2SO_4$, filtered and evaporated under reduced pressure. Purification of the residue by silica gel flash chromatography with 10% methanol and 1% $Et_3N$ in $CH_2Cl_2$ as mobile phase, afforded the pure title compound (375 mg, yield 69%) which was characterized by its mass spectrum as follows: MS (m/z): 284 ([M+H]$^+$, 100).

Example 97

Synthesis of 2,4-diamino-6-(3-chloro-4-methoxyphenyl)-pyrido[3,2-d]pyrimidine

A suspension of 2,4-diamino-6-chloropyrido[3,2-d]pyrimidine (464 mg, 2.37 mmole), $K_2CO_3$ (1332 mg, 9.64 mmole), 3-chloro-4-methoxyphenyl boronic acid (907 mg, 4.86 mmole) in 1,4-dioxane (35.5 ml) and water (7 ml) was purged with a stream of nitrogen for 15 minutes. Then, tetrakis(triphenylphosphine)palladium(0) (278 mg, 0.24 mmole) was added and the reaction mixture was heated at reflux under a $N_2$ atmosphere for 4 hours. Upon cooling, the mixture was partitioned between $CH_2Cl_2$ and a saturated aqueous sodium bicarbonate solution. The organic phase was dried over $Na_2SO_4$, filtered and evaporated under reduced pressure. The crude residue was purified by silica gel flash chromatography, using methanol and 1% $Et_3N$ in $CH_2Cl_2$ as eluent, gradually increasing the methanol concentrations from 5% to 10%, to afford the pure title compound (277 mg, yield 39%) which was characterized by its mass spectrum as follows: MS (m/z): 302 ([M+H]$^+$, 100).

Example 98

Synthesis of 2-amino-6-(4-hydroxy-3-methoxy-phenyl)-pyrido[3,2-d]pyrimidin-4(3H)-one A suspension of 2,4-diamino-6-(4-hydroxy-3-methoxy)-pyrido[3,2-d]pyrimidine (268 mg, 0.95 mmole) in 6 M aqueous HCl (7.6 ml) was refluxed for 26 hours. The cooled reaction mixture was stored at 4° C. for 16 hours. The yellow precipitate obtained was filtered off, washed with water until neutral pH value of the filtrate and dried to afford 243 mg (yield 90%) of the pure title compound which was characterized by its mass spectrum as follows: MS (m/z): 285 ([M+H]$^+$, 100)

Example 99

Synthesis of 2-amino-4-(N-morpholino)-6-(4-hydroxy-3-methoxy)-pyrido[3,2-d]pyrimidine A suspension of 2-amino-6-(4-hydroxy-3-methoxyphenyl)-pyrido[3,2-d]pyrimidin-4(3H)one (66 mg, 0.23 mmole), p-toluenesulphonic acid monohydrate (10 mg, 53 µmole), $(NH_4)_2SO_4$ (11 mg, 83 µmole), 1,1,1,3,3,3-hexamethyldisilazane (1.15 mmole) and morpholine (1.83 mmole) in toluene (2 ml) was refluxed for 33 hours. The reaction mixture was allowed to cool down and partitioned between ethyl acetate and brine/saturated $NaHCO_3$ aqueous solution. The aqueous layer was extracted two times with ethyl acetate. The combined organic layers were dried over $MgSO_4$, filtered and evaporated under reduced pressure. The crude residue was purified by preparative thin layer chromatography on silica with 5% MeOH and 1% $Et_3N$ in $CH_2Cl_2$ as mobile phase to afford the pure title compound (68 mg, yield 84%) which was characterized by its mass spectrum as follows: MS (m/z): 354 ([M+H]$^+$, 100).

Example 100

Synthesis of 2-amino-4-(N-morpholino)-6-(4-ethoxy-3-methoxyphenyl)-pyrido[3,2-d]pyrimidine A yellow suspension of 2-amino-4-(N-morpholino)-6-(4-hydroxy-3-methoxyphenyl)-pyrido[3,2-d]pyrimidine (32 mg, 90 µmole), anhydrous potassium carbonate (30 mg, 0.22 mmole) and iodoethane (0.36 mmole) in acetone (2 ml) was refluxed under a nitrogen atmosphere. After 24 hours, second aliquots of $K_2CO_3$ and iodoethane were added and the reaction was continued for another 24 hours. Upon cooling, the reaction mixture was partitioned between EtOAc and a 5% aqueous sodium bicarbonate solution. The aqueous layer was extracted with ethyl acetate. The combined organic layers were dried over $MgSO_4$, filtered and evaporated under reduced pressure. Preparative thin layer chromatography of the crude residue on silica, using 5% methanol, 1% $Et_3N$ in $CH_2Cl_2$ as mobile phase, afforded the pure title compound (26 mg, yield 76%) which was characterized by its mass spectrum as follows: MS (m/z): 382 ([M+H]$^+$, 100).

Example 101

Synthesis of 2-amino-4-(N-morpholino)-6-(4-cyclopentyloxy-3-methoxyphenyl)-pyrido[3,2-d]pyrimidine A dark orange solution of 2-amino-4-(N-morpholino)-6-(4-hydroxy-3-methoxyphenyl)-pyrido[3,2-d]pyrimidine (68 mg, 0.19 mmole), anhydrous potassium carbonate (53 mg, 0.38 mmole) and cyclopentyl iodide (0.75 mmole) in dimethylformamide (4 ml) was stirred at 60° C. After 24 hours, a second aliquot of cyclopentyl iodide was added and the reaction was continued for another 24 hours. Upon cooling, the reaction mixture was partitioned between ethyl acetate and brine/5% $NaHCO_3$ aqueous solution. The aqueous layer was extracted two times with ethyl acetate. The combined organic layers were dried over $MgSO_4$, filtered and evaporated under reduced pressure. Preparative thin layer chromatography of the crude residue on silica using 5% methanol in $CH_2Cl_2$ as mobile phase, afforded the pure title compound (6 mg, yield 7%) which was characterized by its mass spectrum as follows: MS (m/z): 422 ([M+H]$^+$, 100).

gradually ranging from 1:1 to 4:1), thus affording the pure title compound (60 mg, yield 47%) which was characterized by its mass spectrum as follows: MS (m/z): 628 ([M+H]$^+$, 100).

Example 102

Synthesis of 2-amino-4-(N-morpholino)-6-(4-isopropoxy-3-methoxyphenyl)-pyrido[3,2-d]pyrimidine To a yellow solution of 2-amino-4-(N-morpholino)-6-(3-methoxy-4-hydroxyphenyl)-pyrido[3,2-d]pyrimidine (107 mg, 0.30 mmole) in dry dimethylformamide (10 ml), was added 60% by weight NaH in mineral oil (0.93 mmole), resulting in an orange suspension. Then, 2-iodopropane (6.02 mmole) was added and the reaction mixture was stirred at room temperature for 40 minutes. The reaction mixture was partitioned between ethyl acetate and brine. The organic phase is dried over MgSO$_4$, filtered and evaporated under reduced pressure. Preparative thin layer chromatography of the crude residue on silica, using 5% methanol, 1% Et$_3$N in CH$_2$Cl$_2$ as mobile phase, afforded the title compound (83 mg, 70%) which was characterized by its mass spectrum as follows: MS (m/z): 396 ([M+H]$^+$, 100).

Example 103

Synthesis of 2-amino-4-(N-piperazin-1-yl)-6-(3-methoxy-4-hydroxyphenyl)-pyrido[3,2-d]pyrimidine A suspension of 2-amino-6-(4-hydroxy-3-methoxyphenyl)-pyrido[3,2-d]pyrimidin-4(3H)-one (227 mg, 0.80 mmole), p-toluenesulphonic acid monohydrate (88 μmole), (NH$_4$)$_2$SO$_4$ (0.12 mmole), 1,1,1,3,3,3-hexamethyldisilazane (3.98 mmole) and piperazine (11.72 mmole) in toluene (3 ml) was refluxed for 24 hours. Upon cooling, the reaction mixture was partitioned between ethyl acetate and 5% NaHCO$_3$ aqueous solution/brine. The aqueous layer was extracted 3 times with ethyl acetate. The combined organic layers were dried over MgSO$_4$, filtered and evaporated under reduced pressure. The crude residue was purified by preparative thin layer chromatography on silica using 15% methanol, 1% Et$_3$N in CH$_2$Cl$_2$ as mobile phase, affording the title compound (74 mg, yield 62%) which was characterized by its mass spectrum as follows: MS (m/z): 353 ([M+H]$^+$, 100).

Example 104

Synthesis of 2-amino-4-[(N-4-fluoro-phenyl-carbamoyl)-piperazin-1-yl]-6-(4-hydroxy-3-methoxy-phenyl)-pyrido[3,2-d]pyrimidine A solution of 4-fluorophenyl isocyanate (0.39 mmole) in dimethylformamide (0.5 ml) was added to a yellow suspension of 2-amino-4-(N-piperazin-1-yl)-6-(4-hydroxy-3-methoxy)-pyrido[3,2-d]pyrimidine (0.31 mmole) in dimethylformamide (2 ml). The mixture was stirred at room temperature for 1 hour. The solvent was evaporated in vacuo. Preparative thin layer chromatography of the crude residue on silica using 5% methanol, 1% Et$_3$N in CH$_2$Cl$_2$ as mobile phase, afforded the pure title compound (100 mg, yield 66%) which was characterized by its mass spectrum as follows: MS (m/z): 490 ([M+H]$^+$, 100).

Example 105

Synthesis of 2-amino-4-[(N-4-fluoro-phenyl-carbamoyl-piperazin-1-yl)-6-(4-ethoxy-3-methoxyphenyl)-pyrido[3,2-d]pyrimidine A suspension of 2-amino-4-[(N-4-fluoro-phenyl-carbamoyl)-piperazin-1-yl]-6-(4-hydroxy-3-methoxyphenyl)-pyrido[3,2-d]pyrimidine (0.13 mmole), anhydrous potassium carbonate (0.80 mmole) and iodoethane (1.23 mmole) in acetone (5 ml) was refluxed for 24 hours. Upon cooling, the reaction mixture was partitioned between ethyl acetate and brine. The aqueous layer was extracted with ethyl acetate. The combined organic layers were dried over MgSO$_4$, filtered and evaporated under reduced pressure. Preparative thin layer chromatography of the residue on silica using 5% methanol in CH$_2$Cl$_2$ as mobile phase, afforded the pure title compound (15 mg, yield 22%) which was characterized by its mass spectrum as follows: MS (m/z): 518 ([M+H]$^+$, 100).

Example 106

Synthesis of 2-amino-4-[(N-4-fluoro-phenyl-carbamoyl)-piperazin-1-yl]-6-(4-isopropoxy-3-methoxyphenyl)-pyrido[3,2-d]pyrimidine A suspension of 2-amino-4-[(N-4-fluoro-phenyl-carbamoyl)-piperazin-1-yl]-6-(4-hydroxy-3-methoxy-phenyl)-pyrido[3,2-d]pyrimidine (96 μmole), anhydrous potassium carbonate (0.22 mmole) and 2-iodopropane (0.96 mmole) in acetone (7 ml) was refluxed under a nitrogen atmosphere for 20 hours. Then, another aliquot of 2-iodopropane was added and the reaction was continued for another 24 hours. Upon cooling, the reaction mixture was partitioned between ethyl acetate and brine and the aqueous layer was extracted several times with ethyl acetate. The combined organic layers were dried over MgSO$_4$, filtered and evaporated under reduced pressure. Purification of the crude residue by silica gel flash chromatography, using 10% methanol in CH$_2$Cl$_2$ as mobile phase, afforded the pure title compound (20 mg, yield 39%) which was characterized by its mass spectrum as follows: MS (m/z): 532 ([M+H]$^+$, 100).

Example 107

Synthesis of 2-amino-4-[(N-3-methyl-phenyl-carbamoyl)-piperazin-1-yl]-6-(4-hydroxy-3-methoxyphenyl)-pyrido[3,2-d]pyrimidine m-toluoyl isocyanate (0.55 mmole) was added to a suspension of 2-amino-4-(N-piperazin-1-yl)-6-(4-hydroxy-3-methoxyphenyl)-pyrido[3,2-d]pyrimidine (0.55 mmole) in dimethylformamide (7 ml). The mixture was stirred at room temperature for 20 minutes, and then partitioned between ethyl acetate and a 5% NaHCO$_3$ aqueous solution. The aqueous layer was extracted two times with ethyl acetate. The combined organic layers were dried over MgSO$_4$, filtered and evaporated under reduced pressure. Purification of the crude residue by preparative thin layer chromatography on silica using 5% methanol, 1% Et$_3$N in CH$_2$Cl$_2$ as eluent, afforded the pure title compound (123 mg, yield 46%) which was characterized by its mass spectrum as follows: MS (m/z): 486 ([M+H]$^+$, 100).

Example 108

Synthesis of 4-(4-methyl-phenyl-piperazin-1-yl)-6-(3,4-dimethoxyphenyl)-pyrido[3,2-d]pyrimidine To a suspension of 4-chloro-6-(3,4-dimethoxyphenyl)-pyrido[3,2-d]pyrimidine (0.597 mmole) in isopropanol (20 ml) was added 1-(4-methyl)phenyl-piperazine (1.2 mmole). The reaction mixture was heated at 80° C. for 2 hours, after which the suspension became a yellow solution. The solvent was evaporated in vacuo. The residue was redissolved in ethyl acetate and extracted with a NaOH solution (1 N). The combined organic layers were evaporated in vacuo and purified by silica gel column chromatography (the mobile phase being a mixture of methanol and dichloromethane in a ratio gradually ranging from 1:99 to 2:98), resulting in the title compound (191 mg, yield 73%) which was characterized by its mass spectrum as follows: MS (m/z): 442 ([M+H]$^+$, 100).

Example 109

Synthesis of 4-(4-fluorophenyl-piperazin-1-yl)-6-(3,4-dimethoxyphenyl)-pyrido[3,2-d]pyrimidine The procedure of example 108 was performed, but using 1-(4-fluoro)phenyl-piperazine as the starting material, thus resulting in the pure title compound which was characterized by its mass spectrum as follows: MS (m/z): 446 ([M+H]$^+$, 100).

Example 110

Synthesis of 4-(N-piperazin-1-yl)-6-(3,4-dimethoxyphenyl)-pyrido[3,2-d]-pyrimidine To a suspension of 4-chloro-6-(3,4-dimethoxyphenyl)-pyrido[3,2-d]pyrimidine (1.47 mmole) in isopropanol (50 ml) was added piperazine (1.2 mmole). The reaction mixture was heated at 80° C. for 2 hours. Volatiles were evaporated in vacuo. The crude residue was purified by silica gel flash chromatography, the mobile phase being a methanol/dichloromethane mixture with an 0.5% aqueous NH$_3$ solution (in a ratio gradually ranging from 2:98 to 3:97), resulting in the pure title compound (351 mg, yield 68%) which was characterized by its mass spectrum as follows: MS (m/z): 352 ([M+H]$^+$, 100).

Examples 111 to 115

Synthesis of 4-(N-carbamoyl-piperazin-1-yl)-6-(3,4-dimethoxyphenyl)-pyrido[3,2-d]pyrimidines To a solution of 4-(N-piperazin-1-yl)-6-(3,4-dimethoxyphenyl)-pyrido[3,2-d]-pyrimidine (0.26 mmole) in dimethylformamide (20 ml) was added an appropriate isocyanate (0.39 mmole). The reaction mixture was stirred at room temperature for 2 hours. The solvents was evaporated in vacuo and the crude residue was purified by silica gel flash chromatography, the mobile phase being a mixture of methanol and dichloromethane in a ratio gradually ranging from 2:98 to 3:97, affording the pure title compounds in yields from 65 to 80% depending upon the relevant isocyanate. The following individual compounds were made according to this procedure:

4-[(N-3-chloro-4-fluorophenylcarbamoyl)-piperazin-1-yl]-6-(3,4-dimethoxyphenyl)-pyrido[3,2-d]pyrimidine (example 111) was obtained from 3-chloro-4-fluorophenyl isocyanate and was characterized by its mass spectrum as follows: MS (m/z): 524 ([M+H]$^+$, 100), 4-[(N-2-thienyl-carbamoyl)-piperazin-1-yl]-6-(3,4-dimethoxyphenyl-pyrido[3,2-d]pyrimidine (example 112) was obtained from 2-thienyl isocyanate and was characterized by its mass spectrum as follows: MS (m/z): 477 ([M+H]$^+$, 100), 4-[(N-2,6-dichloro-pyridyl-carbamoyl)-piperazin-1-yl]-6-(3,4-dimethoxyphenyl)-pyrido[3,2-d]pyrimidine (example 113) was obtained from 2,6-dichloro-4-isocyanato-pyridine and was characterized by its mass spectrum as follows: MS (m/z): 541 ([M+H]$^+$, 100), 4-[(N-4-fluorophenylcarbamoyl)-piperazin-1-yl]-6-(3,4-dimethoxyphenyl)-pyrido[3,2-d]pyrimidine (example 114) was obtained from 4-fluoro-phenyl isocyanate and was characterized by its mass spectrum as follows: MS (m/z): 489 ([M+H]$^+$, 100), and 4-[(N-3-chlorophenylcarbamoyl)-piperazin-1-yl]-6-(3,4-dimethoxyphenyl)-pyrido[3,2-d]pyrimidine (example 115) was obtained from 3-chlorophenyl isocyanate and was characterized by its mass spectrum as follows: MS (m/z): 506 ([M+H]$^+$, 100).

Example 116

Synthesis of 4-[(N-4-chlorophenoxy-acetyl)-piperazin-1-yl]-6-(3,4-dimethoxyphenyl)-pyrido[3,2-d]pyrimidine To a solution of 4-(N-piperazin-1-yl)-6-(3,4-dimethoxyphenyl)-pyrido[3,2-d]-pyrimidine (0.18 mmole) in dimethylformamide (20 ml) was added triethylamine (0.26 mmole) and p-chloro-phenoxy acetyl chloride (0.23 mmole). The reaction mixture was stirred at room temperature for 3 hours, and then quenched with water. The aqueous phase was extracted with dichloromethane. The combined organic layers were evaporated in vacuo. The residue was purified by silica gel flash chromatography, the mobile phase being a methanol/dichloromethane mixture in a ratio of 2:98, affording the pure title compound (66 mg, yield 71%) which was characterized by its mass spectrum as follows: MS (m/z): 521 ([M+H]$^+$, 100).

Example 117

Synthesis of 6-(3-methyl-4-methoxyphenyl)-pyrido[3,2-d]pyrimidin-4(3H)one

To a solution of 6-chloro-pyrido[3,2-d]pyrimidin-4(3H)one (1.94 mmole) in 1,4-dioxane (40 ml) and water (20 ml) was added 4-methoxy-3-methylphenyl boronic acid (2.33 mmole), potassium carbonate (4.85 mmole) and tetrakis(triphenylphosphine)palladium(0) (0.097 mmole). The reaction mixture was refluxed for two hours, cooled to room temperature and the solvents were evaporated in vacuo. The residue was adsorbed on silica and purified by silica gel column chromatography (the mobile phase being a methanol/dichloromethane mixture in a ratio of 3:97), affording the title compound as a pure white powder (398 mg, yield 77%) which was characterized by its mass spectrum as follows: MS (m/z): 268 ([M+H]$^+$, 100).

Example 118

Synthesis of 4-chloro-6-(3-methyl-4-methoxyphenyl)-pyrido[3,2-d]pyrimidine

To a suspension of 6-(3-methyl-4-methoxyphenyl)-pyrido[3,2-d]pyrimidin-4(3H)one (1.41 mmole) in toluene (80 ml) was added phosphorus oxychloride (4.23 mmole) and 2,6-lutidine (4.23 mmole). The reaction mixture was refluxed for 16 hours until a black solution was obtained. After evaporation to dryness, the residue was redissolved in ethyl acetate and extracted with a saturated sodium bicarbonate solution. The combined organic layers were evaporated in vacuo. The residue was purified by silica gel column chromatography (the mobile phase being a ethylacetate/hexane mixture in a ratio gradually ranging from 2:8 to 3:7), resulting in the pure title compound (300 mg, yield 74%) which was characterized by its mass spectrum as follows: MS (m/z): 287 ([M+H]$^+$, 100).

Example 119

Synthesis of 4-(piperazin-1-yl)-6-(3-methyl-4-methoxyphenyl)-pyrido[3,2-d]pyrimidine To a suspension of 4-chloro-6-(3-methyl-4-methoxyphenyl)-pyrido[3,2-d]pyrimidine (0.99 mmole) in isopropanol (40 ml) was added piperazine (1.99 mmole). The reaction mixture was heated at 80° C. for 2 hours. The solvents were evaporated in vacuo. The crude residue was purified by silica gel flash chromatography (the mobile phase being a mixture of methanol and dichloromethane with an 0.5% aqueous NH$_3$ solution (in a ratio gradually ranging from 2:98 to 3:97), resulting in the pure title compound (259 mg, yield 78%) which was characterized by its mass spectrum as follows: MS (m/z): 336 ([M+H]$^+$, 100).

Example 120

Synthesis of 4-[(N-3-chloro-phenylcarbamoyl)-piperazin-1-yl]-6-(3-methyl-4-methoxyphenyl)-pyrido[3,2-d]pyrimidine To a solution of 4-(N-piperazin-1-yl)-6-(3-methyl-4-methoxyphenyl)-pyrido[3,2-d]-pyrimidine (0.25 mmole) in DMF (30 ml) was added 3-chlorophenyl isocyanate (0.38 mmole). The reaction mixture was stirred at room temperature for 2 hours. The solvents were evaporated in vacuo and the crude residue was purified by silica gel flash chromatography, the mobile phase being a mixture of methanol and dichloromethane in a ratio gradually ranging from 2:98 to 3:97, affording the pure title compound (81 mg, yield 66%) which was characterized by its mass spectrum as follows: MS (m/z): 490 ([M+H]$^+$, 100).

Example 121

Synthesis of 4-[(N-4-chloro-phenylcarbamoyl)-piperazin-1-yl]-6-(3-methyl-4-methoxyphenyl)-pyrido[3,2-d]pyrimidine The procedure of example 120 was followed, but using 4-chlorophenyl isocyanate as the starting material. The pure title compound was isolated in a yield of 81% and was characterized by its mass spectrum as follows: MS (m/z): 490 ([M+H]$^+$, 100).

Example 122

Synthesis of 4-[(N-3-chloro-phenylcarbamoyl)-piperazin-1-yl]-6-(3-methoxy-4-hydroxyphenyl)-pyrido[3,2-d]pyrimidine To a solution of 4-[(N-3-chloro-phenylcarbamoyl)-piperazin-1-yl]-6-chloro-pyrido[3,2-d]pyrimidine (0.51 mmole) in 1,4-dioxane (15 ml) and water (5 ml) was added 2-methoxy-4-(4,4,5,5-tetramethyl-[1,3,2]dioxaborolan-2-yl)-phenol (0.51 mmole), potassium carbonate (1.53 mmole) and tetrakis(triphenylphosphine)palladium(0) (0.02 mmole). The reaction mixture was refluxed for two hours, cooled down to room temperature and the solvents were evaporated in vacuo. The residue was purified by silica gel column chromatography (the mobile phase being an acetone/dichloromethane mixture in a ratio of 20:80), affording the title compound as a pure white powder (135 mg, yield 54%) which was characterized by its mass spectrum as follows: MS (m/z): 492 ([M+H]$^+$, 100).

Example 123

Synthesis of 4-[(N-3-chloro-phenylcarbamoyl)-piperazin-1-yl]-6-(3-methoxy-4-ethoxy-phenyl)-pyrido[3,2-d]pyrimidine To a solution of 4-[(N-4-chloro-phenylcarbamoyl)-piperazin-1-yl]-6-(3-methoxy-4-hydroxyphenyl-pyrido[3,2-d]pyrimidine (0.19 mmole) in dry dimethylformamide (15 ml) was added potassium carbonate (0.19 mmole). This mixture was stirred at room temperature for 30 minutes under nitrogen and then, ethyl iodide (0.19 mmole) was added. The reaction mixture was stirred at room temperature for 16 hours. The solvent was evaporated in vacuo and the residue was purified by silica gel flash chromatography (the mobile phase being a methanol/dichloromethane mixture in a ratio of 2:98), affording the pure title compound as a white powder (67 mg, yield 68%) which was characterized by its mass spectrum as follows: MS (m/z): 520 ([M+H]$^+$, 100).

Example 124

Synthesis of 4-[(N-3-chloro-phenylcarbamoyl)-piperazin-1-yl]-6-(3-methoxy-4-isopropoxy-phenyl-pyrido[3,2-d]pyrimidine The procedure of example 120 was followed, but using 2-iodopropane as the starting material. The pure title compound was isolated and characterized by its mass spectrum as follows: MS (m/z): 533 ([M+H]$^+$, 100).

Example 125

Synthesis of 4-[(N-3-chlorophenylacetyl)-piperazin-1-yl]-6-chloro pyrido[3,2-d]pyrimidine A suspension of 3-chlorophenylacetic acid (2 mmole) in thionyl chloride (10 ml) was refluxed for 1 hour. The excess thionyl chloride was removed under reduced pressure to yield crude 3-chlorophenyl acetic acid chloride. This crude residue was redissolved in dichloromethane (10 ml) and this solution was added to a solution of 4-(piperazin-1-yl)-6-chloro-pyrido[3,2-d]pyrimidine (2 mmole) in dichloromethane (10 ml). The resulting mixture was stirred at room temperature for 1 hour. The solvents were removed by evaporation in vacuo. The crude residue was purified by silica gel column chromatography, the mobile phase being a MeOH/dichloromethane mixture in a ratio of 1:40, affording the pure title compound (yield 60%) as a yellowish solid which was characterized by its mass spectrum as follows: MS (m/z): 403.1 ([M+H]$^+$, 100).

Example 126

Synthesis of 4-morpholino-6-(3,4-dichlorophenyl)-pyrido[3,2-d]pyrimidine

The reaction of 4-morpholino-6-chloro-pyrido[3,2-d]pyrimidine and 3,4-dichlorophenylboronic acid afforded the pure title compound (yield 97%) as a yellowish solid which was characterized by its mass spectrum as follows: MS (m/z): 361.2 ([M+H]$^+$, 100).

Example 127

Synthesis of 4-morpholino-6-(4-chlorophenyl)-pyrido[3,2-d]pyrimidine

The reaction of 4-morpholino-6-chloro-pyrido[3,2-d]pyrimidine and 4-chlorophenylboronic acid afforded the pure title compound (yield 92%) as a white solid solid which was characterized by its mass spectrum as follows: MS (m/z): 341.2 ([M+H]$^+$, 100).

Example 128

Synthesis of 4-[(N-3-chlorophenylacetyl)-piperazin-1-yl]-6-(3,4-dichlorophenyl)pyrido[3,2-d]pyrimidine The reaction of 4-[(N-3-chlorophenylacetyl)piperazin-1-yl]-6-chloro-pyrido[3,2-d]pyrimidine and 3,4-dichlorophenyl boronic acid afforded the pure title compound (yield 86%) as a yellowish solid which was characterized by its mass spectrum as follows: MS (m/z): 512.2 ([M+H]$^+$, 100).

Examples 129 to 137

Synthesis of 2-amino-6-aryl-pyrido[3,2-d]pyrimidin-4(3H)-ones

To a degassed suspension of 2-amino-6-chloro-pyrido[3,2-d]pyrimidin-4(3H)-one (6 mmole), an appropriate aryl boronic acid (6.6 mmole) and potassium carbonate (30 mmole) in a mixture of dioxane (120 ml) and H$_2$O (30 ml), was added a catalytic amount of tetrakis(triphenylphosphine)palladium(0) (0.9 g). The mixture was refluxed for 24 hours and after cooling to room temperature, the reaction mixture was filtered. The filtrate was acidified with 5 N HCl to pH 4 and the resulting precipitate was filtered off, washed successively with H$_2$O, ethanol and diethyl ether, and further dried under vacuum to afford the desired compound in a yield higher than 65%, depending upon the relevant aryl boronic acid used. The following compounds were synthesized according to this procedure:
2-amino-6-(3-methoxy-4-methyl-phenyl)pyrido[3,2-d]pyrimidin-4(3H)-one (example 129) was obtained from 3-methoxy-4-methylphenyl boronic acid and was characterized by its mass spectrum as follows: MS (m/z): 317 ([M+H]$^+$, 100),
2-amino-6-(3-chloro-4-ethoxy-phenyl)pyrido[3,2-d]pyrimidin-4(3H)-one (example 130) was obtained from 3-chloro-4-ethoxyphenyl boronic acid and was characterized by its mass spectrum as follows: MS (m/z): 317 ([M+H]$^+$, 100),
2-amino-6-(3-ethoxy-4-fluoro-phenyl)pyrido[3,2-d]pyrimidin-4(3H)-one (example 131) was obtained from 3-ethoxy-4-fluorophenyl boronic acid and was characterized by its mass spectrum as follows: MS (m/z): 301 ([M+H]$^+$, 100),
2-amino-6-(3-methyl-4-fluoro-phenyl)pyrido[3,2-d]pyrimidin-4(3H)-one (example 132) was obtained from 3-methyl-4-fluorophenyl boronic acid and was characterized by its mass spectrum as follows: MS (m/z): 271 ([M+H]$^+$, 100),
2-amino-6-(3,4-dichloro-phenyl)pyrido[3,2-d]pyrimidin-4(3H)-one (example 133) was obtained from 3,4-dichlorophenyl boronic acid was characterized by its mass spectrum as follows: MS (m/z): 307 ([M+H]$^+$, 100),
2-amino-6-(3,4-(methylenedioxy)phenyl)pyrido[3,2-d]pyrimidin-4(3H)-one (example 134) was obtained from 3,4-(methylenedioxy)phenyl boronic acid and was characterized by its mass spectrum as follows: MS (m/z): 283 ([M+H]$^+$, 100), and
2-amino-6-(1,4-benzodioxane-phenyl)pyrido[3,2-d]pyrimidin-4(3H)-one (example 135) was obtained from 1,4-benzodioxane-phenyl boronic acid and was characterized by its mass spectrum as follows: MS (m/z): 297 ([M+H]$^+$, 100).
2-amino-6-(4-fluoro-phenyl)-pyrido[3,2-d]pyrimidin-4(3H)-one (example 136) was obtained from 4-fluoro-phenyl boronic acid in 78% yield and was characterized by its mass spectrum as follows: MS (m/z): 257 ([M+H]$^+$, 100)
2-amino-6-phenyl-pyrido[3,2-d]pyrimidin-4(3H)one (examples 137) was obtained from phenyl boronic acid and characterized by its mass spectrum: MS (m/z): 239 ([M+H]$^+$, 100)

Examples 138 to 146

Synthesis of 2-acetamido-6-aryl-pyrido[3,2-d]pyrimidin-4(3H)-ones

A 2-amino-6-aryl-pyrido[3,2-d]pyrimidin-4(3H)-one (2.0 g) was suspended in acetic anhydride (180 ml) and acetic acid (20 ml) and the mixture was refluxed for 16 hours. The hot suspension was filtered and the filtrate was concentrated under reduced pressure until crystallization started. The precipitate was filtered off to give the pure title compound in a yield varying from 70 to 80%, depending upon the 6-aryl substituent present in the starting material. The following compounds were synthesized according to this procedure:
2-acetamido-6-(3-methoxy-4-methyl-phenyl)pyrido[3,2-d]pyrimidin-4(3H)-one (example 138) was characterized by its mass spectrum as follows: MS (m/z): 325 ([M+H]$^+$, 100),
2-acetamido-6-(3-chloro-4-ethoxy-phenyl)pyrido[3,2-d]pyrimidin-4(3H)-one (example 139) was characterized by its mass spectrum as follows: MS (m/z): 359 ([M+H]$^+$, 100),
2-acetamido-6-(3-ethoxy-4-fluoro-phenyl)pyrido[3,2-d]pyrimidin-4(3H)-one (example 140) was characterized by its mass spectrum as follows: MS (m/z): 343 ([M+H]$^+$, 100),
2-acetamido-6-(3-methyl-4-fluoro-phenyl)pyrido[3,2-d]pyrimidin-4(3H)-one (example 141) was obtained from 2-amino-6-(3-methyl-4-fluoro-phenyl)-pyrido[3,2-d]pyrimidin-4(3H)-one in 90% yield and was characterized by its mass spectrum as follows: MS (m/z): 313 ([M+H]$^+$, 100),
2-acetamido-6-(3,4-dichlorophenyl)pyrido[3,2-d]pyrimidin-4(3H)-one (example 142) was obtained from 2-amino-6-(3,4-dichloro-phenyl)-pyrido[3,2-d]pyrimidin-4(3H)-one in 90% yield and was characterized by its mass spectrum as follows: MS (m/z): 349, 351 ([M+H]$^+$, 100),
2-acetamido-6-(3,4-(methylenedioxy)phenyl)pyrido[3,2-d]pyrimidin-4(3H)-one (example 143) was obtained from 2-amino-6-(3,4-methylenedioxyphenyl)-pyrido[3,2-d]pyrimidin-4(3H)-one in 74% yield and was characterized by its mass spectrum as follows: MS (m/z): 325 ([M+H]$^+$, 100), and
2-acetamido-6-(1,4-benzodioxane-phenyl)pyrido[3,2-d]pyrimidin-4(3H)-one (example 144) was obtained from 2-amino-6-(1,4-benzodioxane)-pyrido[3,2-d]pyrimidin-4(3H)-one in 68% yield and was characterized by its mass spectrum as follows: MS (m/z): 338 ([M+H]$^+$, 100).

2-acetamido-6-(4-fluoro-phenyl)-pyrido[3,2-d]pyrimidin-4 (3H)-one (example 145) was obtained from 2-amino-6-(4-fluoro-phenyl)-pyrido[3,2-d]pyrimidin-4(3H)-one in 78% yield and characterized by its mass spectrum as follows: MS (m/z): 299 ([M+H]$^+$, 100)

synthesis of 2-acetamido-6-phenyl-pyrido[3,2-d]pyrimidin-4(3H)one (example 146), characterized by its mass spectrum as follows: MS (m/z): 281 ([M+H]$^+$, 100)

Examples 147 to 156

Synthesis of 2-acetamido-4-(1,2,4-triazolyl)-6-aryl-pyrido[3,2-d]pyrimidines

A suspension of 1,2,4-triazole (120 mmole) and phosphorus oxychloride (36 mmole) in dry acetonitrile (150 ml) was added to a stirred suspension of a 2-acetamido-6-aryl-pyrido [3,2-d]pyrimidin-4(3H)-one (12 mmole) (obtained in examples 133 to 139) and triethylamine (36 mmole) in dry acetonitrile (150 ml). Ether the mixture was stirred at room temperature under nitrogen for 70 hours and the yellow precipitate formed was filtered off, then successively washed with ethanol and ether, and further dried over P$_2$O$_5$ in a vacuum dessicator to afford the pure title compounds. Alternatively, the resulting mixture was stirred at 50° C. under nitrogen for 24 hours. The solvents were evaporated in vacuo. The crude residue was redissolved in dichloromethane and extracted with a diluted hydrochloric acid solution (HCl 0.01 N). The combined organic layers were dried over anhydrous MgSO$_4$ and evaporated yielding the title compounds, which were used for further reaction without need for any additional purification.

Yields were above 60%, depending upon the 6-aryl substituent present. The following compounds were synthesized according to this procedure:

2-acetamido-4-(1,2,4-triazolyl)-6-(3-methyl-4-methoxyphenyl)pyrido-[3,2-d]pyrimidine (example 147) was characterized by its mass spectrum as follows: MS (m/z): 376 ([M+H]$^+$, 100), 2-acetamido-4-(1,2,4-triazolyl)-6-(3-chloro-4-methoxy-phenyl)pyrido-[3,2-d]pyrimidine (example 148) was characterized by its mass spectrum as follows: MS (m/z): 396 ([M+H]$^+$, 100), 2-acetamido-4-(1,2,4-triazolyl)-6-(3-chloro-4-ethoxy-phenyl)pyrido-[3,2-d]pyrimidine (example 149) was characterized by its mass spectrum as follows: MS (m/z): 411 ([M+H]$^+$, 100), 2-acetamido-4-(1,2,4-triazolyl)-6-(3-fluoro-4-ethoxy-phenyl)pyrido-[3,2-d]pyrimidine (example 150) was characterized by its mass spectrum as follows: MS (m/z): 395 ([M+H]$^+$, 100), 2-acetamido-4-(1,2,4-triazolyl)-6-(3-methyl-4-fluoro-phenyl)pyrido-[3,2-d]pyrimidine (example 151) was characterized by its mass spectrum as follows: MS (m/z): 365 ([M+H]$^+$, 100), 2-acetamido-4-(1,2,4-triazolyl)-6-(3,4-dichloro-phenyl)pyrido-[3,2-d]pyrimidine (example 152) was characterized by its mass spectrum as follows: MS (m/z): 400 ([M+H]$^+$, 100), 2-acetamido-4-(1,2,4-triazolyl)-6-(3,4-(methylenedioxy) phenyl)pyrido[3,2-d]pyrimidine (example 153) was characterized by its mass spectrum as follows: MS (m/z): 377 ([M+H]$^+$, 100), and 2-acetamido-4-(1,2,4-triazolyl)-6-(1,4-benzodioxane-phenyl)pyrido[3,2-d]pyrimidin-4(3H)-one (example 154) was characterized by its mass spectrum as follows: MS (m/z): 381 ([M+H]$^+$, 100).

2-acetamido-4-(1,2,4-triazolyl)-6-(4-fluoro-phenyl)-pyrido [3,2-d]pyrimidine (example 155) was obtained from 2-acetamido-6-(4-fluoro-phenyl)-pyrido[3,2-d]pyrimidin-4 (3H)-one in 72% yield and was characterized by its mass spectrum as follows: MS (m/z): 350 ([M+H]$^+$, 100).

2-acetamido-4-(1,2,4-triazolyl)-6-phenyl-pyrido[3,2-d]pyrimidine (example 156) was obtained from 2-acetamido-6-phenyl-pyrido[3,2-d]pyrimidin-4(3H)-one and characterized by its mass spectrum: MS (m/z): 350 ([M+H]$^+$, 100)

Examples 157 to 167

Synthesis of 2-acetamido-4-(N-piperazin-1-yl)-6-aryl-pyrido[3,2-d]pyrimidines

To a suspension of a 2-acetamido-4-(1,2,4-triazolyl)-6-aryl-pyrido[3,2-d]pyrimidine (1.25 mmole) in dioxane (50 ml) was added piperazine (2.5 mmole). The reaction mixture was stirred for 16 hours at 50° C. The solvent was evaporated and the crude residue was purified by preparative thin layer chromatography on silica, using a methanol/dichloromethane mixture in a ratio of 20:80 as mobile phase, affording the pure title compounds in yields varying between 30 and 40%, depending upon the 6-aryl substituent being present. The following compounds were made according to this procedure:

2-acetamido-4-(N-piperazin-1-yl)-6-(3-methyl-4-methoxy-phenyl)pyrido-[3,2-d]pyrimidine (example 157) was characterized by its mass spectrum as follows: MS (m/z): 394 ([M+H]$^+$, 100), 2-acetamido-4-(N-piperazin-1-yl)-6-(3-chloro-4-methoxy-phenyl)pyrido-[3,2-d]pyrimidine (example 158) was characterized by its mass spectrum as follows: MS (m/z): 414 ([M+H]$^+$, 100), 2-acetamido-4-(N-piperazin-1-yl)-6-(3-chloro-4-ethoxy-phenyl)pyrido-[3,2-d]pyrimidine (example 159) was characterized by its mass spectrum as follows: MS (m/z): 428 ([M+H]$^+$, 100), 2-acetamido-4-(N-piperazin-1-yl)-6-(3-fluoro-4-ethoxy-phenyl)pyrido-[3,2-d]pyrimidine (example 160) was characterized by its mass spectrum as follows: MS (m/z): 412 ([M+H]$^+$, 100), 2-acetamido-4-(N-piperazin-1-yl)-6-(3-methyl-4-fluoro-phenyl)pyrido-[3,2-d]pyrimidine (example 161) was characterized by its mass spectrum as follows: MS (m/z): 382 ([M+H]$^+$, 100), 2-acetamido-4-(N-piperazin-1-yl)-6-(3,4-dichloro-phenyl) pyrido-[3,2-d]pyrimidine (example 162) was characterized by its mass spectrum as follows: MS (m/z): 418 ([M+H]$^+$, 100), 2-acetamido-4-(N-piperazin-1-yl)-6-(3,4-(methylenedioxy) phenyl)pyrido[3,2-d]pyrimidine (example 163) was characterized by its mass spectrum as follows: MS (m/z): 393 ([M+H]$^+$, 100), 2-acetamido-4-(N-piperazin-1-yl)-6-(1,4-benzodioxane-phenyl)pyrido[3,2-d]pyrimidine (example 164) was characterized by its mass spectrum as follows: MS (m/z): 407 ([M+H]$^+$, 100), 2-acetamido-4-(N-piperazin-1-yl)-6-(4-fluorophenyl)-pyrido[3,2-d]pyrimidine (example 165) was obtained from 2-acetamido-4-(1,2,4-triazolyl)-6-(4-fluorophenyl)-pyrido[3,2-d]pyrimidine in 68% yield. MS (m/z): 368 ([M+H]$^+$, 100), 2-acetamido-4-(N-piperazin-1-yl)-6-phenyl-pyrido[3,2-d] pyrimidine (example 166) was obtained from 2-acetamido-4-(1,2,4-triazolyl)-6-phenyl-pyrido[3,2-d]pyrimidine and was characterized by its mass spectrum: MS (m/z): 349 ([M+H]+, 100), 2-acetamido-4-(N-morpholino)-6-(3,4-dimethoxyphenyl)-pyrido[3,2-d]pyrimidine (example 167) was obtained in 41% yield and characterized by its mass spectrum: MS (m/z): 410 ([M+H]+, 100).

Examples 168 to 174

Synthesis of 2-acetamido-4-[(N-3-chloro-phenyl-carbamoyl)-piperazin-1-yl]-6-aryl-pyrido[3,2-d]pyrimidines and 2-amino-4-[(N-3-chloro-phenylcarbamoyl)-piperazin-1-yl]-6-aryl-pyrido[3,2-d]pyrimidines To a solution of a 2-acetamido-4-(piperazin-1-yl)-6-aryl-pyrido[3,2-d]pyrimidine (0.5 mmole) in dimethylformamide (5 ml) was added 3-chlorophenyl isocyanate (0.75 mmole). The reaction mixture was stirred for 16 hours at room temperature. The solvent was evaporated in vacuo, affording a crude 2-acetamido-4-[(N-3-chloro-phenyl-carbamoyl)-piperazin-1-yl]-6-aryl-pyrido[3,2-d]pyrimidine as an intermediate. This crude residue was dissolved in a mixture of $CH_2Cl_2$ (10 ml) and sodium ethoxide 0.2 N (10 ml). The suspension was stirred for 16 hours and neutralized with 5-6 N HCl in isopropyl alcohol, resulting in a crude 2-amino-4-[(N-3-chloro-phenyl-carbamoyl)-piperazin-1-yl]-6-aryl-pyrido[3, 2-d]pyrimidine as the final product. This crude product was purified by preparative thin layer chromatography, the mobile phase consisting of $CH_3OH/CH_2Cl_2$ mixtures in a ratio of 10:90, yielding the pure title compounds, in yields varying from 20 to 40%, depending on the 6-aryl substituent being present. The following compounds were synthesized according to this procedure (each time through the corresponding intermediate having the 2-amino group protected in the form of acetamido):

2-amino-4-[(N-3-chloro-phenyl-carbamoyl)-piperazin-1-yl]-6-(3-methyl-4-methoxy-phenyl)pyrido-[3,2-d]pyrimidine (example 168) was characterized by its mass spectrum as follows: MS (m/z): 505 ([M+H]$^+$, 100), 2-amino-4-[(N-3-chloro-phenyl-carbamoyl)piperazin-1-yl]-6-(3-chloro-4-methoxy-phenyl)pyrido-[3,2-d]pyrimidine (example 169) was characterized by its mass spectrum as follows: MS (m/z): 525 ([M+H]$^+$, 100), 2-amino-4-[(N-3-chloro-phenyl-carbamoyl)piperazin-1-yl]-6-(3-chloro-4-ethoxy-phenyl)pyrido-[3,2-d]pyrimidine (example 170) was characterized by its mass spectrum as follows: MS (m/z): 538 ([M+H]$^+$, 100), 2-amino-4-[(N-3-chloro-phenyl-carbamoyl)-piperazin-1-yl]-6-(3-fluoro-4-ethoxyphenyl)pyrido-[3,2-d]pyrimidine (example 171) was characterized by its mass spectrum as follows: MS (m/z): 523 ([M+H]$^+$, 100), 2-amino-4-[N-3-chloro-phenyl-carbamoyl)-piperazin-1-yl]-6-(3,4-dichlorophenyl)-pyrido-[3,2-d]pyrimidine (example 172) was characterized by its mass spectrum as follows: MS (m/z): 528 ([M+H]$^+$, 100), 2-amino-4-[N-3-chloro-phenyl-carbamoyl)-piperazin-1-yl]-6-(3,4-(methylenedioxy)phenyl)pyrido[3,2-d]pyrimidine (example 173) was characterized by its mass spectrum as follows: MS (m/z): 505 ([M+H]$^+$, 100), and 2-amino-4-[(N-3-chloro-phenyl-carbamoyl)-piperazin-1-yl]-6-(1,4-benzodioxane-phenyl)pyrido[3,2-d]pyrimidine (example 174) was characterized by its mass spectrum as follows: MS (m/z): 519 ([M+H]$^+$, 100).

Examples 175 to 177

Synthesis of 2-amino-4-morpholino-6-aryl-pyrido[3,2-d]pyrimidines

To a suspension of a 2-acetamido-6-aryl-pyrido[3,2-d]pyrimidin-4(3H)-one (1 mmole) in toluene (10 ml) was added morpholine (4 mmole), p-toluene sulfonic acid (0.1 mmole), ammonium sulfate (0.1 mmole) and 1,1,1,3,3,3-hexamethyldisilazane (8 mmole). The reaction mixture was refluxed for 48 hours until a brown solution was formed. The solvent was evaporated in vacuo and the crude resulting residue was redissolved in dichloromethane and extracted successively with a saturated sodium bicarbonate aqueous solution and water. The combined organic layers were dried over sodium sulfate and evaporated in vacuo, resulting in a crude 2-amino-4-morpholino-6-aryl-pyrido[3,2-d]pyrimidine as a final product. This crude residue was purified by preparative thin layer chromatography on silica, using a methanol/dichloromethane mixture in a ratio of 10:90 as mobile phase, affording the pure final compounds in yields between 20 and 30%, depending on the 6-aryl substituent being present. The following final compounds were synthesized according to this procedure (each time through the corresponding intermediate having the 2-amino group protected in the form of acetamido):

2-amino-4-(morpholino)-6-(3-methyl-4-methoxyphenyl)pyrido[3,2-d]pyrimidine (example 175) was characterized by its mass spectrum as follows: MS (m/z): 352 ([M+H]$^+$, 100), 2-amino-4-(morpholino)-6-(3-chloro-4-methoxyphenyl)pyrido[3,2-d]pyrimidine (example 176) was characterized by its mass spectrum as follows: MS (m/z) 372 ([M+H]$^+$, 100), and 2-amino-4-(morpholino)-6-(1,4-benzodioxane-phenyl)pyrido[3,2-d]pyrimidine (example 177) was characterized by its mass spectrum as follows: MS (m/z): 366 ([M+H]$^+$, 100).

Examples 178 to 180

Synthesis of 2-amino-4-morpholino-6-aryl-pyrido[3, 2-d]pyrimidines

To a suspension of a 2-acetamido-4-(1,2,4-triazolyl)-6-aryl-pyrido[3,2-d]pyrimidine (0.5 mmole) in dioxane (5 ml) was added morpholine (1 mmole). The reaction mixture was stirred for 16 hours at 50° C. The solvent was evaporated in vacuo yielding a crude 2-acetamido-4-morpholino-6-aryl-pyrido[3,2-d]pyrimidine as an intermediate product. This crude residue was dissolved in a mixture of $CH_2Cl_2$ (10 ml) and sodium ethoxide 0.2 N (10 ml). The suspension was stirred for 16 hours and neutralized with 5-6 N HCl in isopropyl alcohol, resulting in a crude 2-amino-4-morpholino-6-aryl-pyrido[3,2-d]pyrimidine as a final product. This crude product was purified by preparative thin layer chromatography, the mobile phase consisting of a $CH_3OH/CH_2Cl_2$ mixtures in a ratio of 10:90, affording the pure title compounds, in yields varying from 20 to 40% depending on the 6-aryl substituent being present. The following compounds were synthesized according to this procedure (each time through the corresponding intermediate having the 2-amino group protected in the form of acetamido):

2-amino-4-morpholino-6-(3-fluoro-4-ethoxy-phenyl)-pyrido[3,2-d]pyrimidine (example 178) was characterized by its mass spectrum as follows: MS (m/z): 370 ([M+H]$^+$, 100), 2-amino-4-morpholino-6-(4-chlorophenyl)-pyrido[3,2-d]pyrimidine (example 179) was characterized by its mass spectrum as follows: MS (m/z): 342 ([M+H]$^+$, 100), and 2-amino-4-morpholino-6-(3,4-(methylenedioxy)phenyl)-pyrido[3,2-d]pyrimidine (example 180) was characterized by its mass spectrum as follows: MS (m/z): 352 ([M+H]$^+$, 100).

Example 181

Synthesis of 2-amino-4-(morpholino)-6-(3-methyl-4-fluoro-phenyl)-pyrido[3,2-d]pyrimidine Either of the two following methods may be used:
Method A: to a suspension of 2-acetamido-6-(3-methyl-4-fluorophenyl)-pyrido[3,2-d]pyrimidin-4(3H)-one (312 mg, 1 mmol) in toluene (10 ml) was added morpholine (4 mmol, 0.23 ml), p-toluene sulfonic acid (0.1 mmol, 19 mg), ammonium sulfate (13 mg, 0.1 mmol) and 1,1,1,3,3,3-hexamethyldisilazane (2 ml, 8 mmol). The reaction mixture was refluxed for 48 hours till a brown solution was formed. The solvents were evaporated in vacuo, yielding crude 2-acetamido-4-(morpholino)-6-(4-methyl-3-fluoro-phenyl)-pyrido[3,2-d]pyrimidine. The residue was redissolved in a mixture of dichloromethane and ethanol (in a ratio of 80/20, 10 ml). A sodium ethoxide solution (0.2 N solution) was added till pH 12 and the resulting mixture was stirred overnight at room temperature. The solvents were evaporated in vacuo. The crude residue was purified by preparative TLC on silica, using a methanol/dichloromethane mixture in a ratio of 10:90 as mobile phase, yielding pure 2-amino-4-(morpholino)-6-(3-methyl-4-fluoro-phenyl)-pyrido[3,2-d]pyrimidine (80 mg, yield: 25%).

Method B: to a solution of 2-amino-4-morpholino-6-chloro-pyrido[3,2-d]pyrimidine (53 mg, 0.2 mmol) in 1,4-dioxane (15 ml) and water (5 ml) was added an appropriate aryl or heteroaryl boronic acid (0.2 mmol), potassium carbonate (280 mg, 2 mmol) and tetrakis(triphenylphosphine)palladium(0) (30 mg, 0.026 mmol). The reaction mixture was refluxed for three hours, cooled down to room temperature and the solvents were evaporated in vacuo. The residue was purified by silica gel column chromatography, the mobile phase being a CH$_3$OH/dichloromethane mixture, thus resulting in the pure desired compound (81% yield) which was characterized as follows:
MS (m/z): 340 ([M+H]$^+$, 100);
UV (MeOH, nm): 211, 278, 361; and
Rf=0.60 (MeOH/CH$_2$Cl$_2$ 1:9).

Example 182

Synthesis of 2-amino-4-(morpholino)-6-(3,4-dichlorophenyl)-pyrido[3,2-d]pyrimidine Either of the two following methods may be used:
Method A: to a suspension of 2-acetamido-4-(1,2,4-triazolyl)-6-(3,4-dichlorophenyl)-pyrido[3,2-d]pyrimidine (400 mg, 1 mmol) in dioxane (10 ml) was added morpholine (174 mg, 2 mmol). The reaction mixture was stirred overnight at 50° C. The solvents were evaporated in vacuo yielding crude 2-acetamido-4-(morpholino)-6-(3,4-dichlorophenyl)-pyrido[3,2-d]pyrimidine. The residue was redissolved in a mixture of dichloromethane and ethanol (in a ratio of 80/20, 10 ml). A sodium ethoxide solution (0.2 N solution) was added till pH 12 and the resulting mixture was stirred overnight at room temperature. The solvents were evaporated in vacuo. The crude residue was purified by preparative TLC on silica, using a methanol/dichloromethane mixture in a ratio of 10:90 as mobile phase, yielding the pure title compound (220 mg, yield: 60%) which was characterised as follows:
MS (m/z): 376, 378 ([M+H]$^+$, 100); and
UV (MeOH, nm): 282, 365.

Method B: to a solution of 2-amino-4-morpholino-6-chloro-pyrido[3,2-d]pyrimidine (53 mg, 0.2 mmol) in 1,4-dioxane (15 ml) and water (5 ml) was added 3,4-dichlorophenylboronic acid (0.2 mmol), potassium carbonate (280 mg, 2 mmol) and tetrakis(triphenylphosphine)palladium(0) (30 mg, 0.026 mmol). The reaction mixture was refluxed for three hours, cooled down to room temperature and the solvents were evaporated in vacuo. The residue was purified by silica gel column chromatography, the mobile phase being a CH$_3$OH/dichloromethane mixture, thus resulting in the pure desired compound as a yellowish solid (yield: 79%) and was characterised as follows:
Rf=0.55 (MeOH/CH$_2$Cl$_2$ 1:9);
UV (MeOH/H$_2$O, nm): 283.8, 365.9; and
MS (m/z): 376, 378 ([M+H]$^+$, 100).

Example 183

Synthesis of 2-amino-4-[(N-4-chloro-benzylcarbamoyl)-piperazin-1-yl]-6-(4-fluorophenyl)-pyrido[3,2-d]pyrimidine

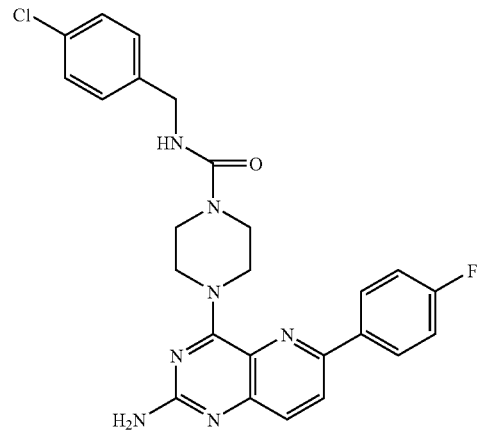

To a solution of 2-acetamido-4-(N-piperazin-1-yl)-6-(4-fluorophenyl)-pyrido[3,2-d]pyrimidine (367 mg, 1 mmol) in DMF (10 ml) was added 4-chloro-benzyl isocyanate (201 mg, 1.2 mmol). The solution was stirred overnight at room temperature. The solvents were evaporated in vacuo yielding crude 2-acetamido-4-[(N-4-chloro-benzylcarbamoyl)-piperazin-1-yl]-6-(4-fluoro-phenyl)-pyrido[3,2-c]pyrimidine. The residue was redissolved in a mixture of dichloromethane and ethanol (in a ratio of 80/20, 10 ml). A sodium ethoxide solution (0.2 N solution) was added till pH 12 and the resulting mixture was stirred overnight at room temperature. The solvents were evaporated in vacuo. The crude residue was purified by preparative TLC on silica, using a methanol/dichloromethane mixture in a ratio of 10:90 as mobile phase, yielding the pure title compound (280 mg, yield: 58%) which was characterised as follows:
MS (m/z): 492, 494 ([M+H]$^+$, 100); and
UV (MeOH, nm): 245, 350, 460, 560.

Example 184

Synthesis of 2-amino-4-[N-acetyl-piperazin-1-yl]-6-(3,4-methylenedioxyphenyl)-pyrido[3,2-d]pyrimidine

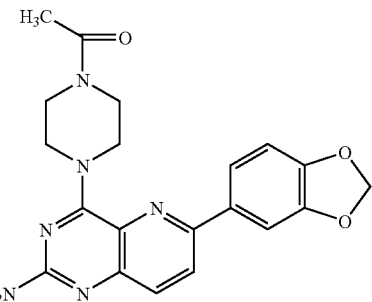

This compound was synthesized according to method A of example 182, starting from N-acetyl-piperazine and 2-acetamido-4-(1,2,4-triazolyl)-6-(3,4-methylenedioxy-phenyl)-pyrido[3,2-d]pyrimidine, and was characterised as follows: MS (m/z): 393 ([M+H]+, 100).

Example 185

Synthesis of 2-amino-4-[2-(Piperazin-1-yl acetic acid N-(2-thiazolyl)-amide)]-6-3,4-methylenedioxyphenyl)-pyrido[3,2-d]pyrimidine

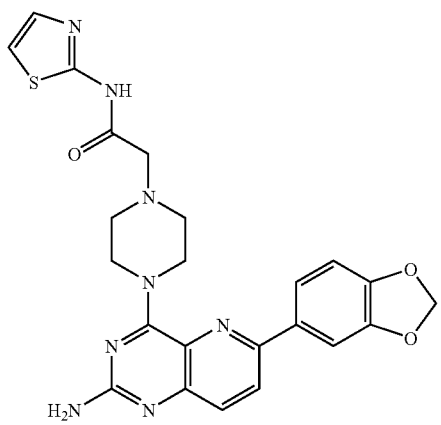

This compound was prepared according to method A of example 182, starting from 4-[2-(piperazin-1-yl acetic acid N-(2-thiazolyl)-amide) and 2-acetamido-4-(1,2,4-triazolyl)-6-(3,4-methylenedioxyphenyl)-pyrido[3,2-d]pyrimidine, and was characterised as follows: MS (m/z): 491 ([M+H]+, 100).

Example 186

Synthesis of 2-amino-4-[N-(2-furoyl)-piperazin-1-yl]-6-(3,4-methylenedioxyphenyl)-pyrido[3,2-d]pyrimidine

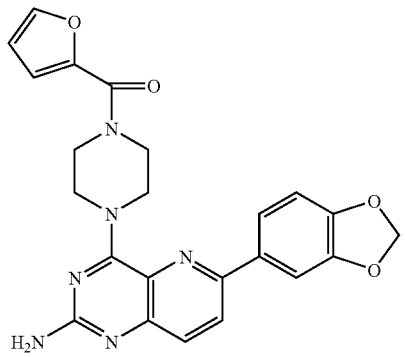

This compound was obtained using the method A of example 182, starting from 2-furoyl-piperazine and 2-acetamido-4-(1,2,4-triazolyl)-6-(3,4-methylenedioxyphenyl)-pyrido[3,2-d]pyrimidine, and was characterised as follows: MS (m/z): 445 ([M+H]+, 100).

Example 187

Synthesis of 2-amino-4-[N-(4-chlorophenoxy-acetyl)-piperazin-1-yl]-6-(3,4-methylenedioxyphenyl)-pyrido[3,2-d]pyrimidine

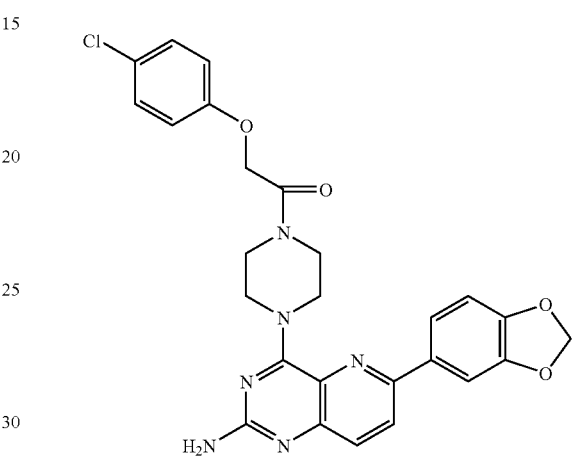

To a solution of 2-acetamido-4-(N-piperazin-1-yl)-6-(3,4-methylenedioxyphenyl)-pyrido[3,2-d]pyrimidine (60 mg, 0.16 mmol) in pyridine (5 ml) was added was added 4-chlorophenoxy acetyl chloride (80 mg, 0.4 mmol). The solution was stirred overnight at 50° C. The solvents were evaporated in vacuo, thus yielding crude 2-acetamido-4-[N-(4-chlorophenoxy-acetyl)-piperazin-1-yl]-6-(3,4-methylenedioxyphenyl)-pyrido[3,2-d]pyrimidine. The residue was redissolved in 5 ml of a dichloromethane/ethanol mixture (in a volume ratio 80/20). A sodium ethoxide solution (0.2 N solution) was added till pH 12 and the resulting mixture was stirred overnight at room temperature. The solvents were evaporated in vacuo. The crude residue was purified by preparative TLC on silica, using a methanol/dichloromethane mixture in a volume ratio 10:90 as a mobile phase, yielding the pure title compound (48 mg, yield: 47%) which was characterised as follows: MS (m/z): 519, 521 ([M+H]+, 100).

Example 188

Synthesis of 2-amino-4-[N-(4-chlorophenoxy-acetyl)-piperazin-1-yl]-6-(3,4-dichlorophenyl)-pyrido[3,2-d]pyrimidine This compound was obtained using method A of example 182, starting from 2-acetamido-4-(N-piperazin-1-yl)-6-(3,4-dichlorophenyl)-pyrido[3,2-d]pyrimidine, and was characterised as follows: MS (m/z): 542, 544 ([M+H]+, 100).

Example 189

Synthesis of 2-amino-4-[N-(4-chlorophenoxy-acetyl)-piperazin-1-yl]-6-(1,4-benzodioxane)-pyrido[3,2-d]pyrimidine This compound was obtained using method A of example 182, starting from 2-acetamido-4-(N-piperazin-1-yl)-6-(1,4-benzodioxane)-pyrido[3,2-d]pyrimidine and was characterised as follows: MS (m/z): 532, 534 ([M+H]$^+$, 100).

Example 190

Synthesis of 2-amino-4-[N-(3-methyl-phenyl-carbamoyl)-piperazin-1-yl]-6-(3,4-methylenedioxyphenyl)-pyrido[3,2-d]pyrimidine

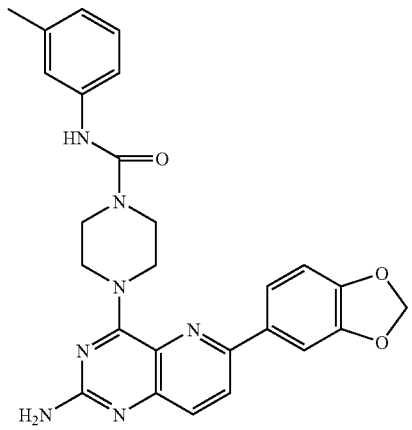

To a solution of 2-acetamido-4-(N-piperazin-1-yl)-6-(3,4-methylenedioxyphenyl)-pyrido[3,2-d]pyrimidine (60 mg, 0.16 mmol) in DMF (5 ml) was added m-tolyl isocyanate (31 µl, 0.24 mmol). The solution was stirred overnight at room temperature. The solvents were evaporated in vacuo yielding crude 2-acetamido-4-[N-(3-methyl-phenyl-carbamoyl)-piperazin-1-yl]-6-(3,4-methylenedioxyphenyl)-pyrido[3,2-d]pyrimidine. The residue was redissolved in a mixture of dichloromethane and ethanol (in a ratio of 80/20, 5 ml). A sodium ethoxide solution (0.2 N solution) was added till pH 12 and the resulting mixture was stirred overnight at room temperature. The solvents were evaporated in vacuo. The crude residue was purified by preparative TLC on silica, using a methanol/dichloromethane mixture in a ratio of 10:90 as mobile phase, yielding the pure title compound (32 mg, yield: 43%) which was characterised as follows: MS (m/z): 484 ([M+H]$^+$, 100).

Example 191

Synthesis of 2-amino-4-[N-(3-methyl-phenyl-carbamoyl)-piperazin-1-yl]-6-(3,4-dichlorophenyl)-pyrido[3,2-d]pyrimidine This compound was synthesized according to the procedure of example 190, starting from 2-acetamido-4-(N-piperazin-1-yl)-6-(3,4-dichlorophenyl)-pyrido[3,2-d]pyrimidine, and was characterised as follows: MS (m/z): 507, 509 ([M+H]$^+$, 100).

Example 192

Synthesis of 2-amino-4-[N-(3-methyl-phenyl-carbamoyl)-piperazin-1-yl]-6-(1,4-benzodioxane)-pyrido[3,2-d]pyrimidine This compound was synthesized according to the procedure of example 190, starting from 2-acetamido-4-(N-piperazin-1-yl)-6-(1,4-benzodioxane)-pyrido[3,2-d]pyrimidine and was characterised as follows: MS (m/z): 498 ([M+H]$^+$, 100).

Example 193

Synthesis of 2-amino-4-[N-acetyl-piperazin-1-yl]-6-(1,4-benzodioxane)-pyrido[3,2-d]pyrimidine

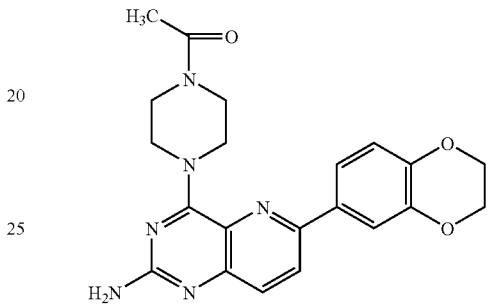

This compound was synthesized according to method A of example 182, starting from N-acetyl-piperazine and 2-acetamido-4-(1,2,4-triazolyl)-6-(1,4-benzodioxane)-pyrido[3,2-d]pyrimidine and was characterised as follows: MS (m/z): 407 ([M+H]$^+$, 100).

Example 194

Synthesis of 2-amino-4-[N-acetyl-piperazin-1-yl]-6-(3,4-dichlorophenyl)-pyrido[3,2-d]pyrimidine This compound was synthesized according to the method A of example 182, starting from N-acetyl-piperazine and 2-acetamido-4-(1,2,4-triazolyl)-6-(3,4-dichlorophenyl)-pyrido[3,2-d]pyrimidine, and was characterised as follows: MS (m/z): 416, 418 ([M+H]$^+$, 100).

Example 195

Synthesis of 2-amino-4-[2-(piperazin-1-yl acetic acid N-(2-thiazolyl)-amide]-6-(1,4-benzodioxane)-pyrido[3,2-d]pyrimidine

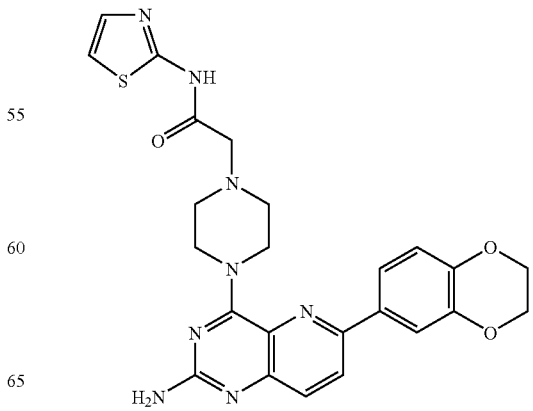

This compound was prepared according to the method A of example 182, starting from 2-(piperazin-1-yl acetic acid)-N-(2-thiazolyl)-amide and 2-acetamido-4-(1,2,4-triazolyl)-6-(3,4-methylenedioxyphenyl)-pyrido[3,2-a]pyrimidine and was characterised as follows: MS (m/z): 505 ([M+H]$^+$, 100).

Example 196

Synthesis of 2-amino-4-[2-(piperazin-1-yl acetic acid N-(2-thiazolyl)-amide]-6-(3,4-dichlorophenyl)-pyrido[3,2-d]pyrimidine

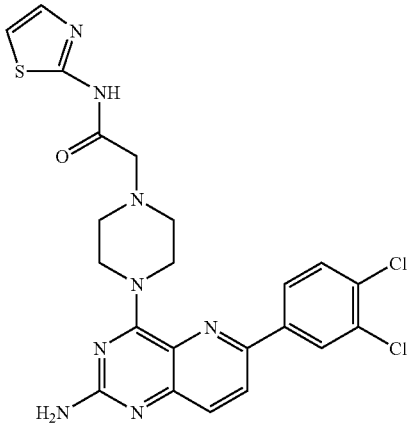

This compound was prepared according to the method A of example 182, starting from 2-(piperazin-1-yl acetic acid)-N-(2-thiazolyl)-amide and 2-acetamido-4-(1,2,4-triazolyl)-6-(3,4-dichlorophenyl)-pyrido[3,2-d]pyrimidine and was characterised as follows: MS (m/z): 514, 516 ([M+H]$^+$, 100).

Example 197

Synthesis of 2-amino-4-[N-(2-furoyl)-piperazin-1-yl]-6-(1,4-benzodioxane)-pyrido[3,2-d]pyrimidine

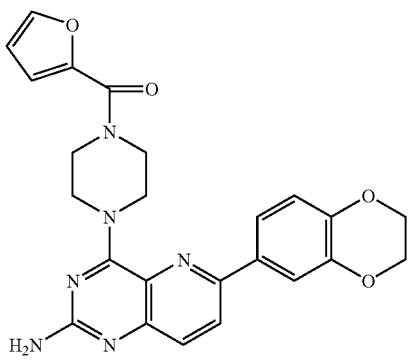

This compound was obtained using method A of example 182, starting from 2-furoyl-piperazine and 2-acetamido-4-(1, 2,4-triazolyl)-6-(1,4-benzodioxane)-pyrido[3,2-d]pyrimidine, and was characterised as follows: MS (m/z): 459 ([M+H]$^+$, 100).

Example 198

Synthesis of 2-amino-4-[N-(4-fluoro-phenyl)-piperazin-1-yl]-6-(4-fluorophenyl)-pyrido[3,2-d]pyrimidine

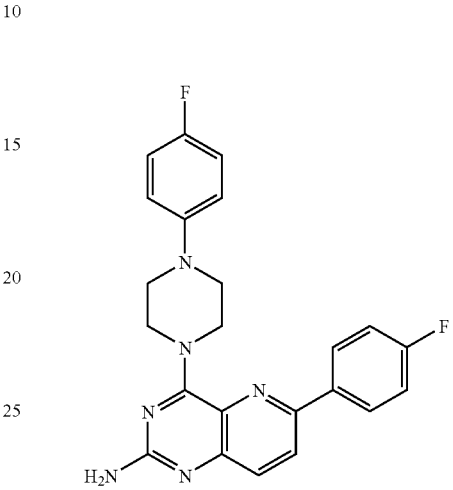

To a solution of 2-acetamido-4-(1,2,4-triazolyl)-6-(4-fluorophenyl)-pyrido[3,2-d]pyrimidine (367 mg, 1 mmol) in dioxane (10 ml) was added 1-(4-fluorophenyl)piperazine (360 mg, 2 mmol). The solution was stirred for 16 hours at 60° C. The solvents were evaporated in vacuo, yielding crude 2-acetamido-4-[N-(4-fluorophenyl)-piperazin-1-yl]-6-(4-fluoro-phenyl)-pyrido[3,2-d]pyrimidine. The residue was redissolved in 10 ml of a dichloromethane/ethanol mixture (in a volume ratio 80/20). A sodium ethoxide solution (0.2 N solution) was added till pH 12 and the resulting mixture was stirred for 16 hours at room temperature. The solvents were evaporated in vacuo. The crude residue was purified by preparative TLC on silica, using a methanol/dichloromethane mixture (volume ratio 10:90) as a mobile phase, yielding the pure title compound (280 mg, yield: 69%) which was characterised as follows:
MS (m/z): 419 ([M+H]$^+$, 100); and
UV (MeOH, nm): 250, 345, 560.

Example 199

Synthesis of 2-amino-4-[N-(phenoxy-ethyl)-piperazin-1-yl)]-6-(4-fluorophenyl)-pyrido[3,2-d]pyrimidine To a suspension of 2-acetamido-4-(1,2,4-triazolyl)-6-(4-fluorophenyl)-pyrido[3,2-d]pyrimidine (367 mg, 1 mmol) in dioxane (10 ml) was added 1-(2-phenoxy-ethyl)-piperazine (412 mg, 2 mmol). The solution was stirred overnight at 60° C. The solvents were evaporated in vacuo yielding crude 2-acetamido-4-[N-(phenoxy-ethyl-piperazin-1-yl)]-6-(4-fluoro-phenyl)-pyrido[3,2-d]pyrimidine. The residue was redissolved in a mixture of dichloromethane and ethanol (in a ratio of 80/20, 10 ml). A sodium ethoxide solution (0.2 N solution) was added till pH 12 and the resulting mixture was stirred overnight at room temperature. The solvents were evaporated in vacuo. The crude residue was purified by preparative TLC on silica, using a methanol/dichloromethane mixture in a ratio of 10:90 as mobile phase, yielding the pure title compound (200 mg, yield: 45%) which was characterised as follows:
MS (m/z): 445 ([M+H]$^+$, 100)
UV (MeOH, nm): 250, 345, 495, 580

Example 200

Synthesis of 2-amino-4-(anilino)-6-(4-fluorophenyl)-pyrido[3,2-d]pyrimidine

To a suspension of 2-acetamido-4-(1,2,4-triazolyl)-6-(4-fluorophenyl)-pyrido[3,2-d]pyrimidine (367 mg, 1 mmol) in dioxane (20 ml) was added aniline (186 mg, 2 mmol). The solution was stirred overnight at 60° C. The solvents were evaporated in vacuo yielding crude 2-acetamido-4-anilino-6-(4-fluoro-phenyl)-pyrido[3,2-d]pyrimidine. The residue was redissolved in a mixture of dichloromethane and ethanol (in a ratio of 80/20, 10 ml). A sodium ethoxide solution (0.2 N solution) was added till pH 12 and the resulting mixture was stirred overnight at room temperature. The solvents were evaporated in vacuo. The crude residue was purified by preparative TLC on silica, using a methanol/dichloromethane mixture in a ratio of 10:90 as mobile phase, yielding the pure title compound (160 mg, 50%) which was characterised as follows:
MS (m/z): 332 ([M+H]$^+$, 100);
UV (MeOH, nm): 250, 350 and 565 nm; and
Rf=0.75 (MeOH/CH$_2$Cl$_2$ 1:4).

Example 201

Synthesis of 2-amino-4-[(N-4-chloro-phenoxy-acetyl)-piperazin-1-yl]-6-(4-fluorophenyl)-pyrido[3,2-d]pyrimidine To a solution of 2-acetamido-4-(N-piperazin-1-yl)-6-(4-fluorophenyl)-pyrido[3,2-d]pyrimidine (367 mg, 1 mmol) in pyridine (10 ml) was added 4-chloro-phenoxy acetyl chloride (410 mg, 2 mmol). The solution was stirred overnight at 50° C. The solvents were evaporated in vacuo yielding crude 2-acetamido-4-[(N-4-chloro-phenoxyacetyl)-piperazin-1-yl]-6-(4-fluoro-phenyl)-pyrido[3,2-d]pyrimidine. The residue was redissolved in a mixture of dichloromethane and ethanol (in a ratio of 80/20, 10 ml). A sodium ethoxide solution (0.2 N solution) was added till pH 12 and the resulting mixture was stirred overnight at room temperature. The solvents were evaporated in vacuo. The crude residue was purified by preparative TLC on silica, using a methanol/dichloromethane mixture in a ratio of 10:90 as mobile phase, yielding the pure title compound (250 mg, yield: 50%) which was characterised as follows:
MS (m/z): 493, 495 ([M+H]$^+$, 100); and
UV (CH$_3$OH): 245, 345, 465 and 560 nm.

Example 202

Synthesis of 2-acetamido-6-chloro-pyrido[3,2-d]pyrimidin-4(3H)-one

A suspension of 2-amino-6-chloro-pyrido[3,2-d]pyrimidin-4 (3H)-one (1.96 g, 10 mmol) in acetic anhydride (200 ml) was refluxed for 2 hours till a clear solution was obtained. The solvents were evaporated in vacuo till crystallization started. The precipitate was filtered off and dried under vacuum yielding the pure title compound (2 g, 80%) which was characterised as follows:
MS (m/z): 239, 241 ([M+H]$^+$, 100);
m.p. 317-319° C.;
UV (MeOH): 208 (4.13), 216 (sh 4.17), 280 (4.13), 310 (sh 3.44); and
elemental analysis: calculated for C$_9$H$_7$ClN$_4$O$_2$ (238.6): C, 45.30; H, 2.96; N, 23.48. found: C, 45.61; H, 3.53; N, 23.28.

Example 203

Synthesis of 2-amino-4-morpholino-6-chloro-pyrido[3,2-d]pyrimidine

Either of the two following methods may be used:
Method A: to a suspension of 2-acetamido-6-chloro-pyrido [3,2-d]pyrimidin-4(3H)-one (2.38 g, 10 mmol) in dioxane (100 ml) was added diisopropylethylamine (5.3 ml, 30 mmol). The mixture was stirred for 10 minutes at 80° C., after which phosphorus oxychloride (1.4 ml, 15 mmol) was added. This reaction mixture was stirred for 90 minutes at 80° C. The solvents were evaporated in vacuo. The residue was redissolved in dichloromethane and extracted with water. The combined organic layers were evaporated till a volume of 50 ml. Then, morpholine (870 mg, 10 mmol) was added and the reaction was stirred overnight at room temperature. The solvents were evaporated in vacuo. The residue was redissolved in a mixture of dichloromethane and ethanol (80/20, 100 ml). A sodium ethoxide solution (0.2 N solution) was added till pH=11. The mixture was stirred overnight at room temperature. The solvents were evaporated in vacuo. The residue was redissolved in dichloromethane and washed with water. The combined organic layers were combined and evaporated in vacuo, yielding the title compound (1 g, yield: 40%) which was characterised as follows: MS (m/z): 266, 268 ([M+H]$^+$, 100).

Method B: a suspension of 2-acetamido-4-morpholino-6-chloro-pyrido[3,2-d]pyrimidine (500 mg, 1.6 mmol) and K$_2$CO$_3$ (660 mg, 4.8 mmol) in MeOH (30 ml) and water (10 ml) was refluxed for 2 hours. After cooling to room temperature, the mixture was extracted with dichloromethane (100 ml), washed with water and dried over MgSO$_4$. After filtration and concentration, the residue was purified by silica gel flash chromatography, the mobile phase being a MeOH/CH$_2$Cl$_2$ mixture (in a ratio of 1:35) yielding the title compound as yellowish solid (425 mg, yield: 98%) which was characterised as follows:
Rf=0.64 (MeOH/CH$_2$Cl$_2$ 1:9);
UV (MeOH/H$_2$O): 245, 330, and 455 nm; and
MS (m/z): 266, 268 ([M+H]$^+$, 100).

Example 204

Synthesis of 2-amino-4-morpholino-6-(2-bromo-phenyl)-pyrido[3,2-d]pyrimidine

A solution of 2-amino-4-morpholino-6-chloro-pyrido[3,2-d] pyrimidine (265 mg, 1 mmol), potassium carbonate (690 mg, 5 mmol), tetrakis(triphenylphosphine)palladium(0) (100 mg) in dioxane (10 ml) and water (3 ml) was refluxed. To this refluxing solution was added dropwise (with a speed of 0.25 ml/min) a solution of 2-bromo-phenyl boronic acid (220 mg, 1.1 mmol) in dioxane (2 ml). Once the addition was complete, the reaction mixture was refluxed for another 2 hours. The reaction mixture was cooled down and the solvents were evaporated in vacuo. The residue was redissolved in dichloromethane and extracted with water. The combined organic layers were dried over Na$_2$SO$_4$ and the crude residue was purified by preparative TLC on silica, using a methanol/ dichloromethane mixture in a ratio of 10:90 as mobile phase, yielding the pure title compound (100 mg, yield: 30%) which was characterised as follows: MS (m/z): 386, 388 ([M+H]$^+$, 100).

Example 205

Synthesis of 4-[N-(3-chloro-phenylcarbamoyl)-piperazin-1-yl]-6-(3-methoxy-4-cyclopropylmethoxyphenyl)-pyrido[3,2-d]pyrimidine The procedure of example 123 was followed, but using cyclopropylmethyl bromide as a starting material. The pure title compound was isolated and characterized by its mass spectrum as follows: MS (m/z): 560, 562 ([M+H]$^+$, 100).

Example 206

Synthesis of 4-[N-(3-chloro-phenylcarbamoyl)-piperazin-1-yl]-6-(3-hydroxy-4-methoxy-phenyl)-pyrido[3,2-d]pyrimidine To a solution of 4-[N-(3-chloro-phenylcarbamoyl)-piperazin-1-yl]-6-chloro-pyrido[3,2-d]pyrimidine (650 mg, 1.61 mmol) in 1,4-dioxane (40 ml) and water (13 ml) was added 2-methoxy-5-(4,4,5,5-tetramethyl-1,3,2-dioxaborolan-2-yl) phenyl acetate (470 mg, 1.61 mmol), potassium carbonate (667 mg, 4.83 mmol) and tetrakis(triphenylphosphine)palladium(0) (93 mg, 0.0805 mmol). The reaction mixture was refluxed for 3 hours, then cooled down to room temperature and the solvents were evaporated in vacuo. The residue was purified by silica gel column chromatography, the mobile phase being an acetone/dichloromethane mixture (in a ratio ranging from 20:80 to 30:70), yielding the title compound as a pure white powder (513 mg, yield: 63%) which was characterised as follows: MS (m/z): 506, 508 ([M+H]$^+$, 100).

Examples 207 to 209

Synthesis of 4-[(N-3-chloro-phenylcarbamoyl)-piperazin-1-yl]-6-(3-alkoxy-4-methoxy-phenyl)-pyrido[3,2-d]pyrimidine analogues To a solution of 4-[N-(3-chloro-phenylcarbamoyl)-piperazin-1-yl]-6-(3-hydroxy-4-methoxy-phenyl)-pyrido[3,2-d] pyrimidine (100 mg, 0.20 mmol) in dry DMF (10 ml) was added potassium carbonate (42 mg, 0.3 mmol). This mixture was stirred at room temperature for 30 minutes under nitrogen and then, the appropriate alkyl halide (0.3 mmol) was added. After stirring for 5 hours, there was still starting material left and therefore an additional amount of the alkyl halide (0.3 mmol) and potassium carbonate (0.3 mmol) was added. The reaction mixture was further stirred at room temperature overnight. The solvents were evaporated in vacuo and purified by silica gel flash chromatography, the mobile phase being a mixture of methanol/dichloromethane (in a ratio ranging from 2:98 to 3:97), yielding the title compound as white powders, in yields varying from 60% to 70%, depending on the alkyl halide used.

Example 207

(4-[N-(3-chloro-phenylcarbamoyl)-piperazin-1-yl]-6-(3-ethoxy-4-methoxy-phenyl)-pyrido[3,2-d]pyrimidine)

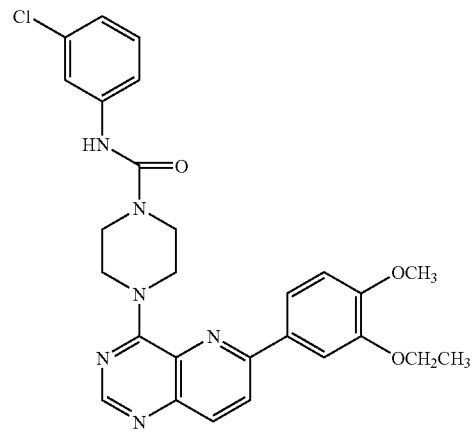

was obtained from ethyl iodide as starting material and was characterised as follows: MS (m/z): 534, 536 ([M+H]$^+$, 100).

Example 208

(4-[N-(3-chloro-phenylcarbamoyl)-piperazin-1-yl]-6-(3-isopropoxy-4-methoxy-phenyl)-pyrido[3,2-d] pyrimidine)

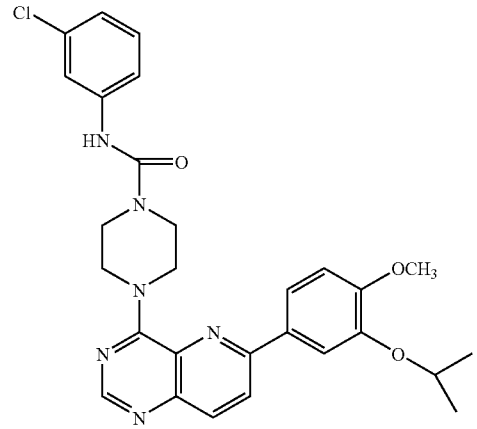

was obtained from isopropyl iodide as a starting material and was characterised as follows: MS (m/z): 548, 550 ([M+H]$^+$, 100).

Example 209

(4-[N-(3-chloro-phenylcarbamoyl)-piperazin-1-yl]-6-(3-cyclopropylmethoxy-4-methoxy-phenyl)-pyrido[3,2-d]pyrimidine)

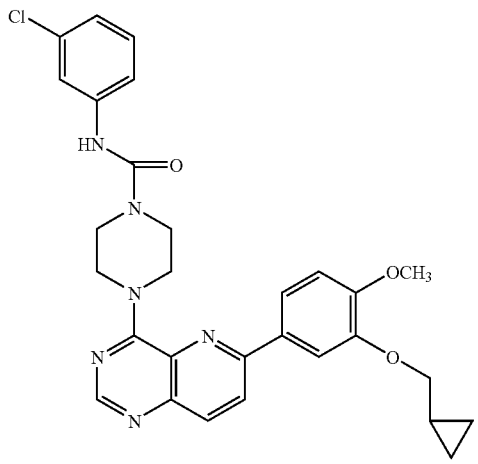

was obtained from cyclopropylmethyl bromide as a starting material and was characterised as follows: MS (m/z): 560, 562 ([M+H]+, 100).

Example 210

Synthesis of 2-acetamido-4,6-dichloro-pyrido[3,2-d]pyrimidine

A mixture of 2-acetamido-6-chloro-pyrido[3,2-d]pyrimidine (1.19 g, 5 mmol), N,N-diisopropylethylamine (2.6 ml, 15 mmol) and POCl₃ (0.7 ml, 7.5 mmol) in dioxane (50 ml), was stirred at room temperature for 1 hour. After concentration under reduced pressure, the residue was redissolved in dichloromethane (500 ml) and extracted with cold water (200 ml) till pH=6-7. The combined organic layers were dried over MgSO₄, filtered and concentrated under reduced pressure to yield the crude title compound which was characterised as follows: MS (m/z): 257, 259 ([M+H]+, 100). This compound was used for further reactions without any purification.

Example 211 & 212

Synthesis of 2-acetamido-4-[(S)-3-(Boc-amino)pyrrolidine]-6-chloro-pyrido[3,2-d]pyrimidine

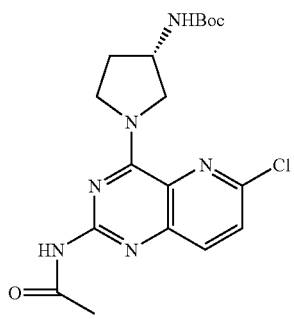

To a solution of 2-acetamido-4,6-dichloro-pyrido[3,2-d]pyrimidine (the crude residue obtained in the previous example 216a) in dioxane (20 ml) was added (S)-3-(Boc-amino)pyrrolidine (563 mg, 3.02 mmol). The reaction mixture was stirred at room temperature for 2 hours. The reaction was diluted with water and extracted with dichloromethane. The combined organic layers were evaporated in vacuo. The crude residue was purified by silica gel flash chromatography, the mobile phase being a MeOH/CH₂Cl₂ mixture in a ratio of 4:96, yielding two pure compounds, i.e.:

2-acetamido-4-[(S)-3-(Boc-amino)pyrrolidine]-6-chloro-pyrido[3,2-d]pyrimidine (example 211) (210 mg) which was characterised as follows: MS (m/z): 257, 259 ([M+H]+, 100); and 2-amino-4-[(S)-3-(Boc-amino)pyrrolidine]-6-chloro-pyrido[3,2-d]pyrimidine (example 212) (43 mg) which was characterised as follows: MS (m/z): 257, 259 ([M+H]+, 100).

Example 213

Synthesis of 2-amino-4-[(S)-3-(Boc-amino)pyrrolidine]-6-chloro-pyrido[3,2-d]pyrimidine

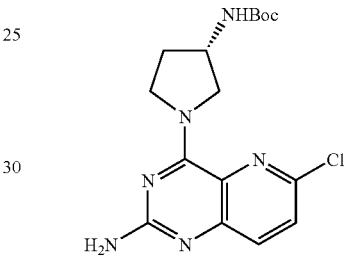

To a solution of 2-acetamido-4-[(S)-3-(Boc-amino)pyrrolidine]-6-chloro-pyrido[3,2-d]pyrimidine in methanol (10 ml) was added a solution of potassium carbonate (360 mg) in water (5 ml). The reaction was heated at 80° C. for 2 hours. The reaction was cooled down, diluted with water and extracted with dichloromethane. The combined organic layers were evaporated in vacuo and the crude residue was purified by flash chromatography on silica, the mobile phase being a mixture of acetone/CH₂Cl₂ (in a ratio of 40:60), followed by a mixture of CH₃OH/CH₂Cl₂ in a ratio of 4:96, yielding the title compound as a pure white solid (133 mg, yield: 71%) which was characterised as follows: MS (m/z): 365, 367 ([M+H]+, 100).

Example 214

Synthesis of 2-amino-4-[(S)-3-(Boc-amino)pyrrolidine]-6-(3,4-dimethoxyphenyl)-pyrido[3,2-d]pyrimidine

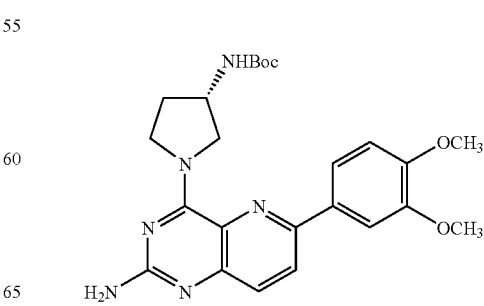

To a solution of 2-amino-4-[(S)-3-(Boc-amino)pyrrolidine]-6-chloro-pyrido[3,2-d]pyrimidine (100 mg, 0.27 mmol) in 1,4-dioxane (20 ml) and water (7 ml) was added 3,4-dimethoxyphenyl boronic acid (65 mg, 0.36 mmol), potassium carbonate (114 mg, 0.82 mmol) and tetrakis(triphenylphosphine)palladium(0) (16 mg, 0.014 mmol). The reaction mixture was refluxed for three hours, cooled down to room temperature and the solvents were evaporated in vacuo. The residue was purified by silica gel column chromatography, the mobile phase being a CH$_3$OH/dichloromethane mixture (in a ratio of 4:96), yielding the title compound as a pure white powder (79 mg, yield: 63%) which was characterised as follows: MS (m/z): 467 ([M+H]$^+$, 100).

Example 215

Synthesis of 2-amino-4-[(S)-3-(amino)pyrrolidine]-6-(3,4-dimethoxyphenyl)-pyrido[3,2-d]pyrimidine

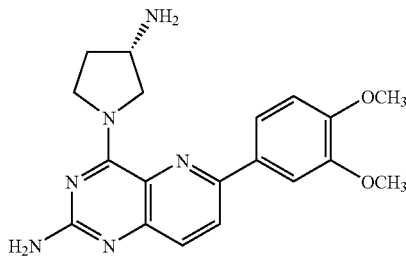

A solution of 2-amino-4-[(S)-3-(Boc-amino)pyrrolidine]-6-(3,4-dimethoxyphenyl)-pyrido[3,2-d]pyrimidine (113 mg, 0.24 mmol) in dichloromethane (10 ml) and trifluoroacetic acid (4 ml) was stirred at room temperature for 30 minutes. The solvents were evaporated. The salt was redissolved in water and the solution was made alkaline (pH=9) by the addition of a 33% aqueous ammonia solution. The solvents were evaporated in vacuo and the residue was purified by silica gel flash chromatography, the mobile phase being a mixture of CH$_3$OH/CH$_2$Cl$_2$ in a ratio of 4:96, containing 0.5% of an aqueous 33% ammonia solution, yielding the title compound as a pure white solid (76 mg, yield: 87%) which was characterised as follows: MS (m/z): 367 ([M+H]$^+$, 100).

Example 216

Synthesis of 2-amino-4-[3-(S)-4-chloro-phenoxy-acetyl-amino)pyrrolidin-1-yl]-6-(3,4-dimethoxyphenyl)-pyrido[3,2-d]pyrimidine

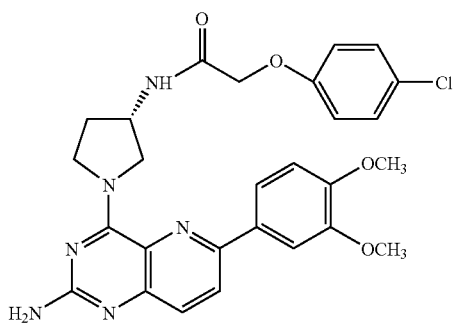

To a solution of 2-amino-4-[(S)-3-(amino)pyrrolidine]-6-(3,4-dimethoxyphenyl)-pyrido[3,2-d]pyrimidine (76 mg, 0.21 mmol) in DMF (10 ml) was added triethylamine (38 µl, 0.27 mmol) and p-chloro-phenoxy acetyl chloride (51 mg, 0.25 mmol). The reaction was stirred at 60° C. for 2 hours. The solvents were evaporated in vacuo and the crude residue was purified by silica gel flash chromatography, the mobile phase being a mixture of CH$_3$OH/CH$_2$Cl$_2$ in a ratio of 4:96, yielding the pure title compound (87 mg, yield: 78%) which was characterised as follows: MS (m/z): 535, 537 ([M+H]$^+$, 100).

Example 217

Synthesis of 2-amino-4-[3-(S)-3-methyl phenyl carbamoyl pyrrolidin-1-yl]-6-(3,4-dimethoxyphenyl)-pyrido[3,2-d]pyrimidine

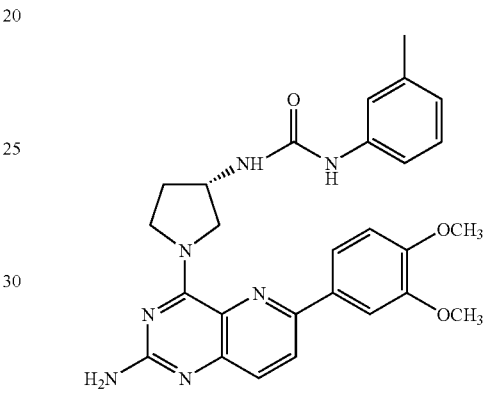

To a solution of 2-amino-4-[(S)-3-(amino)pyrrolidine]-6-(3,4-dimethoxyphenyl)-pyrido[3,2-d]pyrimidine (113 mg, 0.25 mmol) in dichloromethane (10 ml) was added m-tolyl isocyanate (0.28 mmol, 35 µl). The reaction was stirred at room temperature for 2 hours. The solvents were evaporated in vacuo and the crude residue was purified by silica gel flash chromatography, the mobile phase being a mixture of CH$_3$OH/CH$_2$Cl$_2$ in a ratio of 3:97, yielding the pure title compound (77 mg, yield: 62%) which was characterised as follows: MS (m/z): 500 ([M+H]$^+$, 100).

Example 218

Synthesis of 2-amino-6-(3,4-dimethoxyphenyl)-pyrido[3,2-d]pyrimidin-4(3H)thione

A suspension of 2-amino-6-(3,4-dimethoxyphenyl)-pyrido[3,2-d]pyrimidin-4(3H)one (100 mg, 0.34 mmol) and phosphorus pentasulfide (163 mg, 0.37 mmol) in pyridine (10 ml) was refluxed for 4 hours. The solvents were evaporated in vacuo. The residue was re-suspended in a small amount of water and filtered off, yielding the title compound which was used without any further purification and which was characterised as follows: MS (m/z): 315 ([M+H]$^+$, 100).

Example 219

Synthesis of 2-amino-4-thiomethyl-6-(3,4-dimethoxyphenyl)-pyrido[3,2-d]pyrimidine The crude compound obtained in example 218 was dissolved in NaOH 1 N. Then, methyl iodide (18 µl, 0.29 mmol)

was added and the reaction mixture was stirred at room temperature for 2 hours. Then, an additional amount of methyl iodide (9 µl) was added and the reaction was stirred for another hour at room temperature. A yellow precipitate was formed, which was filtered off. The precipitate was adsorbed on silica and purified by silica gel flash chromatography, the mobile phase being a methanol/dichloromethane mixture (in a ratio of 1:99), yielding the pure title compound (52 mg, yield: 47%) which was characterised as follows: MS (m/z): 329 ([M+H]$^+$, 100).

Example 220

Synthesis of
3-amino-6-chloro-pyridine-2-carbonitrile

To a suspension of 6-chloro-3-nitro-pyridine-2-carbonitrile (5.5 g, 30 mmol) in water (100 ml), was added acetic acid (5.4 ml, 90 mmol). The mixture was stirred at room temperature for 20 minutes. Then, $Na_2S_2O_4$ (20 g, 86%, 90 mmol) was added slowly. The reaction mixture was stirred at room temperature for another 2 hours. The precipitate was filtered off and washed with cold water (2×10 ml). The precipitate was dried over $P_2O_5$ yielding the title compound as a yellowish solid (3.7 g, yield: 80%) which was characterised as follows:
Rf=0.64 (EtOAc/$CH_2Cl_2$ 1:4); and
MS (m/z): 154, 156 ([M+H]$^+$, 100).

Example 221

Synthesis of
2,4-diamino-6-chloro-pyrido[3,2-d]pyrimidine

A mixture consisting of 3-amino-6-chloro-pyridine-2-carbonitrile (4.6 g, 30 mmol), chloroformamidine hydrochloride (6.9 g, 60 mmol) and dimethylsulfon (12 g) was heated at 165° C. for 30 minutes. After cooling to room temperature, water (500 ml) was added. The solution was neutralized with a 30% NaOH solution to pH 9-10. The precipitate was filtered off, washed with water, dried over $P_2O_5$, resulting in the pure title compound as a yellow solid (4.0 g, yield: 68%) which was characterised as follows:
Rf=0.40 (MeOH/$CH_2Cl_2$ 1:9); and
MS (m/z): 196, 198 ([M+H]$^+$, 100).

Example 222

Synthesis of
3-amino-6-chloro-pyridine-2-carboxamide

Either of the two following methods may be used:
Method A: to a suspension of 6-chloro-3-nitro-pyridine-2-carbonitrile (4 g, 22 mmol) in water (40 ml) was added a 33% aqueous solution of ammonia in water (8.8 ml). This suspension was stirred at room temperature for 30 minutes. Then, sodium dithionite (21.8 g, 124 mmol) was added portion wise. The resulting mixture was stirred for another 2 hours at room temperature. The precipitate was filtered off and washed with a small amount of water, yielding the title compound (2.7 g, yield: 72%). MS (m/z): 172, 174 ([M+H]$^+$, 100).
Method B: to a suspension of 6-chloro-3-nitro-pyridine-2-carbonitrile (11.01 g, 60 mmol) in methanol (120 ml), was added Raney-Nickel (3 g, washed with methanol to remove water) and the mixture was shaken under a $H_2$-atmosphere at room temperature for 4 hours. The catalyst was removed by filtration, washed with methanol (500 ml). Both filtrates were combined and then evaporated to dryness. The residue was dissolved in dichloromethane and the solution was filtered through a short and wide column with silica gel (100 g). The column was additionally washed with $CH_2Cl_2$/MeOH (200 ml, 4:1). The filtrate and washings were combined and evaporated to small volume. The formed precipitate was filtered off to give 3-amino-6-chloro-pyridine-2-carboxamide (8.1 g). The final filtrate was evaporated to dryness and the residue purified by column chromatography on silica gel (30 g). The compound was eluted with the following solvent systems: $CH_2Cl_2$ (200 ml), $CH_2Cl_2$/MeOH 100:1 (200 ml). The appropriate fractions were evaporated in vacuo yielding an additional 1.15 g of 3-amino-6-chloro-pyridine-2-carboxamide (total yield 9.25 g, i.e. 90%) which was characterised as follows:
M.p. 176-177° C.;
UV (MeOH): 212 (3.76), 256 (4.14), and 348 (3.76); and
elemental analysis: calculated for $C_6H_6ClN_3O$ (171.6): C, 42.00; H, 3.52; N, 24.49. Found: C, 42.42; H, 3.54; H, 24.11.

Example 223

Synthesis of 2-acetamido-4-morpholino-6-chloro-pyrido[3,2-d]pyrimidine

A mixture of 2-acetamido-6-chloro-pyrido[3,2-d]pyrimidin-4(3H)one (2.4 g, 10 mmol), N,N-diisopropylethylamine (5.4 ml, 30 mmol) and $POCl_3$ (2.8 ml, 30 mmol) in dioxane (100 ml), was stirred at room temperature for 2 hours. After concentration under reduced pressure, the residue was redissolved in dichloromethane (200 ml) and extracted with cold water till pH 6-7. The combined organic layers were dried over $MgSO_4$, filtered and concentrated under reduced pressure to yield crude 2-acetamido-4,6-dichloro-pyrido[3,2-d]pyrimidine. This crude residue was dissolved in 1,4-dioxane (100 ml) and morpholine (5 ml) was added. The resulting reaction mixture was stirred at 50° C. for 1 hour. After concentration under reduced pressure, the residue was purified by silica gel flash chromatography, the mobile phase being a mixture of MeOH/dichloromethane (in a ratio of 1:40), resulting in the pure title compound as a yellowish solid (1.6 g, yield: 68%) which was characterised as follows:
Rf=0.82 (MeOH/$CH_2Cl_2$ 1:19); and
MS (m/z): 308, 310 ([M+H]$^+$, 100).

Examples 224 to 237

Synthesis of 2-amino-4-morpholino-6-aryl-pyrido[3,2-d]pyrimidine analogues and 2-amino-4-morpholino-6-heteroaryl-pyrido[3,2-d]pyrimidine analogues To a solution of 2-amino-4-morpholino-6-chloro-pyrido[3,2-d]pyrimidine (53 mg, 0.2 mmol) in 1,4-dioxane (15 ml) and water (5 ml) was added an appropriate aryl or heteroaryl boronic acid (0.2 mmol), potassium carbonate (280 mg, 2 mmol) and tetrakis(triphenylphosphine)palladium(0) (30 mg, 0.026 mmol). The reaction mixture was refluxed for three hours, cooled down to room temperature and the solvents were evaporated in vacuo. The residue was purified by silica gel column chromatography, the mobile phase being a $CH_3OH$/dichloromethane mixture, thus resulting in the pure desired compounds in the following yields:

Example 224

(2-amino-4-morpholino-6-(2-furan)-pyrido[3,2-d]pyrimidine) was obtained from 2-furanboronic acid as a yellow solid (yield: 79%) and was characterised as follows:
Rf=0.36 (MeOH/CH$_2$Cl$_2$ 1:9);
UV (MeOH/H$_2$O, nm): 212.9, 290.9, 377.9; and
MS (m/z): 298 ([M+H]$^+$, 100).

Example 225

(2-amino-4-morpholino-6-(3-thiophene)-pyrido[3,2-d]pyrimidine) was obtained from 3-thiopheneboronic acid as a yellowish solid (yield: 73%) and was characterised as follows:
Rf=0.50 (MeOH/CH$_2$Cl$_2$ 1:9);
UV (MeOH/H$_2$O, nm): 215.3, 279.1, 362.5; and
MS (m/z): 314 ([M+H]$^+$, 100).

Example 226

(2-amino-4-morpholino-6-(4-pyridinyl)-pyrido[3,2-d]pyrimidine) was obtained from 4-pyridine boronic acid as a yellowish solid (yield: 90%) and was characterised as follows:
Rf=0.63 (MeOH/CH$_2$Cl$_2$ 1:9);
UV (MeOH/H$_2$O, nm): 214.1, 236.5, 280.3, 341, 356.6; and
MS (m/z): 309 ([M+H]$^+$, 100)

Example 227

(2-amino-4-morpholino-6-(5-methyl-2-thienyl)-pyrido[3,2-d]pyrimidine) was obtained from 5-methyl-2-thiophene boronic acid as a yellowish solid (yield: 69%) and was characterised as follows:
Rf=0.60 (MeOH/CH$_2$Cl$_2$ 1:9);
UV (MeOH/H$_2$O, nm): 214.1, 298.1, 380.3; and
MS (m/z): 328 ([M+H]$^+$, 100).

Example 228

(2-amino-4-morpholino-6-(6-methoxy-2-pyridinyl)-pyrido[3,2-d]pyrimidine) was obtained from 6-methoxy-2-pyridine boronic acid as a yellowish solid (yield: 75%) and was characterised as follows:
Rf=0.44 (MeOH/CH$_2$Cl$_2$ 1:9);
UV (MeOH/H$_2$O, nm): 214.1, 283.8, 359.5; and
MS (m/z): 339 ([M+H]$^+$, 100).

Example 229

(2-amino-4-morpholino-6-(5-indolyl)-pyrido[3,2-d]pyrimidine) was obtained from 5-indole boronic acid as a yellowish solid (90%) and was characterised as follows:
Rf=0.25 (MeOH/CH$_2$Cl$_2$ 1:9);
UV (MeOH/H$_2$O, nm): 216.5, 314.7, 422.5, 441.9; and
MS (m/z): 347 ([M+H]$^+$, 100).

Example 230

(2-amino-4-morpholino-6-(2-thienyl)-pyrido[3,2-d]pyrimidine) was obtained from 2-thiophene boronic acid as a yellowish solid (yield: 72%) and was characterised as follows:
Rf=0.70 (MeOH/CH$_2$Cl$_2$ 1:9);
UV (MeOH/H$_2$O, nm): 214.1, 293.3, 377.9; and
MS (m/z): 314 ([M+H]$^+$, 100).

Example 231

(2-amino-4-morpholino-6-(4-methyl-2-thienyl)-pyrido[3,2-d]pyrimidine) was obtained from 4-methyl-2-thiophene boronic acid as a yellowish solid (yield: 76%) and was characterised as follows:
Rf=0.45 (MeOH/CH$_2$Cl$_2$ 1:9);
UV (MeOH/H$_2$O, nm): 212.9, 298.1, 380.3;
MS (m/z): 328 ([M+H]$^+$, 100).

Example 232

(2-amino-4-morpholino-6-(3-pyridinyl)-pyrido[3,2-d]pyrimidine) was obtained from 3-pyridine boronic acid as a yellowish solid (yield: 90%) and was characterised as follows:
Rf=0.55 (MeOH/CH$_2$Cl$_2$ 1:9);
UV (MeOH/H$_2$O, nm): 214.1, 247.1, 285, 363.5; and
MS (m/z): 309 ([M+H]$^+$, 100).

Example 233

(2-amino-4-morpholino-6-(5-chloro-2-thienyl)-pyrido[3,2-d]pyrimidine) was obtained from 5-chloro-2-thiophene boronic acid as a yellowish solid (yield: 29%) and was characterised as follows:
Rf=0.65 (MeOH/CH$_2$Cl$_2$ 1:9);
UV (MeOH/H$_2$O, nm): 212.9, 298.1, 380.3; and
MS (m/z): 348 ([M+H]$^+$, 100).

Example 234

2-amino-4-morpholino-6-(3-chloro-4-fluorophenyl)-pyrido[3,2-d]pyrimidine was obtained from 3-chloro-4-fluorophenyl boronic acid as a yellowish solid (yield: 75%) and was characterised as follows:
Rf=0.55 (MeOH/CH$_2$Cl$_2$ 1:9);
UV (MeOH/H$_2$O, nm): 345, 480, 560; and
MS (m/z): 360 ([M+H]$^+$, 100).

Example 235

(2-amino-4-morpholino-6-(3,4-difluorophenyl)-pyrido[3,2-d]pyrimidine) was obtained from 3,4-difluorophenyl boronic acid as a yellowish solid (yield: 75%) and was characterised as follows:
Rf=0.64 (MeOH/CH$_2$Cl$_2$ 1:9);
UV (MeOH/H$_2$O, nm): 345, 465, 560; and
MS (m/z): 344 ([M+H]$^+$, 100).

Example 236

(2-amino-4-morpholino-6-(4-fluorophenyl)-pyrido[3,2-d]pyrimidine) was obtained from 4-fluorophenyl boronic acid as a white solid (yield: 85%) and was characterised as follows:
Rf=0.64 (MeOH/CH$_2$Cl$_2$ 1:9);
UV (MeOH/H$_2$O, nm): 250, 470, 560; and
MS (m/z): 326 ([M+H]$^+$, 100).

Example 237

(2-amino-4-morpholino-6-[4-(3,5-dimethylisoxazolyl)]-pyrido[3,2-d]pyrimidine) was obtained from 3,5-dimethylisoxazole-4-boronic acid as a yellowish solid (yield: 62%) and was characterised as follows:

Rf 0.60 (MeOH/CH$_2$Cl$_2$ 1:9);

UV (MeOH/H$_2$O, nm): 214.1, 269.6, 356.6; and

MS (m/z): 327 ([M+H]$^+$, 100).

Example 238

Synthesis of 2-acetamido-4-(N-homopiperazin-1-yl)-6-chloro-pyrido[3,2-d]pyrimidine

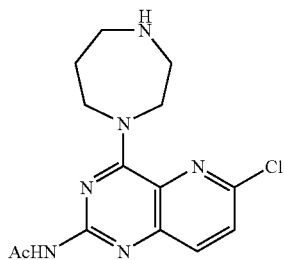

This compound was synthesized from homopiperazine according to the procedure of example 223, yielding the pure title compound as a yellowish solid (yield: 49%) which was characterised as follows:

Rf=0.17 (MeOH/CH$_2$Cl$_2$ 1:4); and

MS (m/z): 321, 323 ([M+H]$^+$, 100).

Example 239

Synthesis of 2-acetamido-4-[(N-3-methylphenylcarbamoyl)-homopiperazin-1-yl]-6-chloro-pyrido[3,2-d]pyrimidine

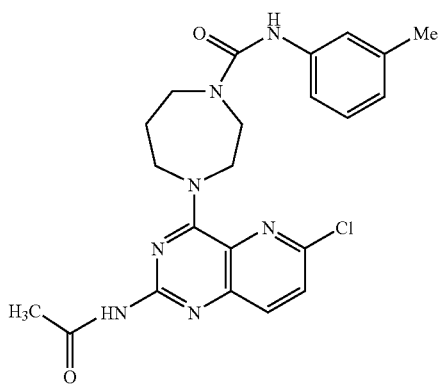

To a solution of 2-acetamido-6-chloro-4-(N-homopiperazin-1-yl)-pyrido[3,2-d]pyrimidine (95 mg, 0.3 mmol) in dichloromethane (10 ml) was added m-tolylisocyanate (40 mg, 0.3 mmol). The solution was stirred at room temperature for 1 hour. The solvents were evaporated in vacuo yielding the crude title compound, which was used for further reaction without any purification.

Example 240

Synthesis of 2-acetamido-4-[(N-3-methylphenylcarbamoyl)-homopiperazin-1-yl]-6-(3,4-dimethoxyphenyl)-pyrido[3,2-d]pyrimidine To a solution of crude 2-acetamido-6-chloro-4-[N-(3-methylphenylcarbamoyl)-homopiperazin-1-yl]-pyrido[3,2-d]pyrimidine (130 mg, 0.3 mmol) in dioxane (15 ml) and water (5 ml) was added 3,4-dimethoxyphenyl boronic acid (55 mg, 0.3 mmol), potassium carbonate (280 mg, 2 mmol) and tetrakis(triphenylphosphine)palladium(0) (30 mg, 0.026 mmol). The reaction mixture was refluxed for 30 minutes. The solvents were evaporated in vacuo. The crude residue was purified by silica gel flash chromatography, the mobile phase being a MeOH/CH$_2$Cl$_2$ mixture (in a ratio of 1:40), resulting in the pure title compound (126 mg, yield: 78%) which was characterised as follows: MS (m/z): 556 ([M+H]$^+$, 100).

Example 241

Synthesis of 2-amino-4-[(N-3-methylphenylcarbamoyl)-homopiperazin-1-yl]-6-(3,4-dimethoxyphenyl)-pyrido[3,2-d]pyrimidine

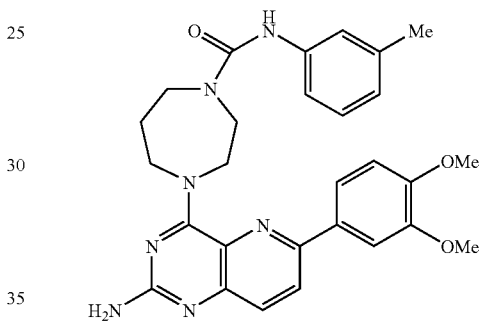

A solution of 2-acetamido-4-[(N-3-methylphenylcarbamoyl)-homopiperazin-1-yl]-6-(3,4-dimethoxyphenyl)-pyrido[3,2-d]pyrimidine (110 mg, 0.24 mmol) and potassium carbonate (83 mg, 0.6 mmol) in methanol (10 ml) and water (5 ml) was heated at 50° C. for 2 hours. The solvents were evaporated in vacuo and the crude residue was purified by silica gel flash chromatography, the mobile phase being a MeOH/CH$_2$Cl$_2$ mixture in a volume ratio of 1:30, resulting in the pure title compound (96 mg, yield: 93%) which was characterised as follows:

Rf=0.55 (MeOH/CH$_2$Cl$_2$ 1/9);

UV (MeOH/H$_2$O, nm): 245, 490, 565; and

MS (m/z): 514 ([M+H]$^+$, 100).

Example 242

Synthesis of 2-acetamido-4-[(R)-3-Boc-aminopyrrolidin-1-yl]-6-chloropyrido[3,2-d]pyrimidine

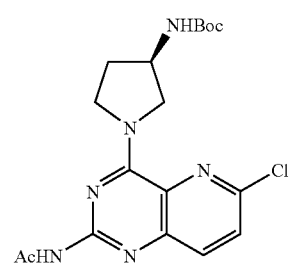

This compound was prepared from (R)-3-Boc-amino-pyrrolidine according to the procedure of example 223, resulting in the title compound as a yellowish solid (yield: 46%) which was characterised as follows:
Rf=0.55 (MeOH/CH$_2$Cl$_2$ 1:9); and
MS (m/z): 407, 409 ([M+H]$^+$, 100).

Example 243

Synthesis of 2-amino-4-[(R)-3-Boc-aminopyrrolidin-1-yl)]-6-(3,4-dimethoxyphenyl)-pyrido[3,2-d]pyrimidine

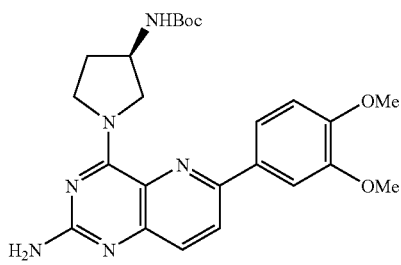

This compound was synthesized from the compound of example 242. In a first step, a Suzuki coupling with 3,4-dimethoxyphenyl boronic acid (general procedure as in examples 231 to 246) was performed. In a second step, alkaline hydrolysis of the acetyl group (using the procedure for the synthesis of example 230) yielded the pure title compound (yield: 81%) which characterised as follows:
Rf=0.54 (MeOH/CH$_2$Cl$_2$ 1:9);
UV (MeOH/H$_2$O, nm): 280, 470, 565; and
MS (m/z): 467 ([M+H]$^+$, 100).

Example 244 to 248

Synthesis of 2-amino-4-substituted-6-(3,4-dimethoxyphenyl)-pyrido[3,2-d]pyrimidines A suspension of 2-amino-6-(3,4-dimethoxyphenyl)-pyrido[3,2-d]pyrimidin-4(3H)one (298 mg, 1.0 mmol), 1,1,1,3,3,3-hexamethyldisilazane (1 ml, 4.7 mmol), an appropriate amine (4.0 mmol), p-toluenesulfonic acid (20 mg, 0.1 mmol) and ammonium sulfate (20 mg, 0.15 mmol) in pyridine (5 ml) was refluxed for 12 to 48 hours (depending upon the amine used; the reaction mixture became clear when reaction was completed). The solvents were evaporated in vacuo and the residue was purified by silica gel flash chromatography, the mobile phase being a MeOH/dichloromethane mixture (in a volume ratio of 1:20 to 1:30, depending upon the amine used), resulting into the pure title compounds as yellow solids as follows:
2-amino-4-(ethylenediamino-1-N-yl)-6-(3,4-dimethoxyphenyl)-pyrido[3,2-d]pyrimidine (example 244) was obtained from ethylene diamine (yield: 64%) and was characterised as follows:
Rf=0.25 (MeOH/CH$_2$Cl$_2$ 1:4); and
MS (m/z): 341 ([M+H]$^+$, 100).
2-amino-4-(1,3-diaminopropane-1-N-yl]-6-(3,4-dimethoxyphenyl)-pyrido[3,2-d]pyrimidine (example 245) was obtained from 1,3-diaminopropane (yield: 68%) and was characterised as follows:
Rf=0.28 (MeOH/CH$_2$Cl$_2$ 1:4); and
MS (m/z): 355 ([M+H]$^+$, 100).

Example 246

2-amino-4-[(1-Boc-piperidin-4-yl)amino]-6-(3,4-dimethoxyphenyl)-pyrido[3,2-d]pyrimidine

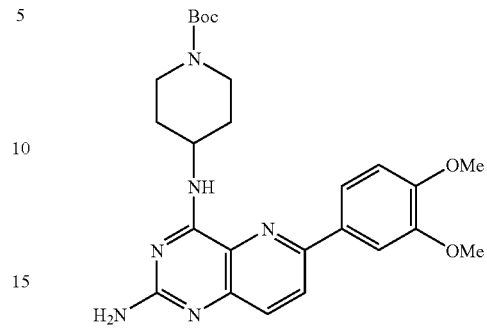

was obtained from 4-amino-N-Boc-piperidine (yield: 92%) and was characterised as follows:
Rf=0.58 (MeOH/CH$_2$Cl$_2$ 1:9);
UV (MeOH/H$_2$O, nm): 250, 480, 565; and
MS (m/z): 481 ([M+H]$^+$, 100).

Example 247

2-amino-4-[(1-Boc-piperidin-3-yl)amino]-6-(3,4-dimethoxyphenyl)-pyrido[3,2-d]pyrimidine

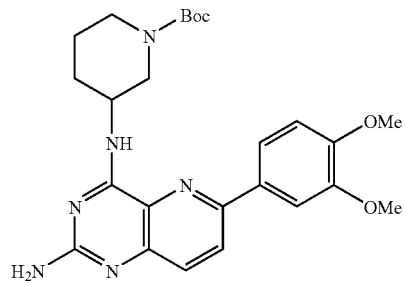

was obtained from 3-amino-N-Boc-piperidine (yield: 70%) and was characterised as follows:
Rf=0.60 (MeOH/CH$_2$Cl$_2$ 1:9);
UV (MeOH/H$_2$O, nm): 250, 490, 565; and
MS (m/z): 481 ([M+H]$^+$, 100).

Example 248

2-amino-4-[(1-Cbz-piperidin-3-yl)amino]-6-(3,4-dimethoxyphenyl)-pyrido[3,2-d]pyrimidine

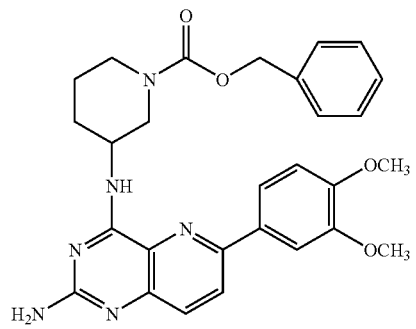

was synthesized from 3-amino-1-benzyloxycarbonyl-piperidine, resulting in the pure title compound (yield: 63%) which was characterised as follows: MS (m/z): 515 ([M+H]$^+$, 100).

Example 249

Synthesis of 2-amino-4-[(R)-3-aminopyrrolidin-1-yl]-6-(3,4-dimethoxyphenyl)-pyrido[3,2-d]pyrimidine

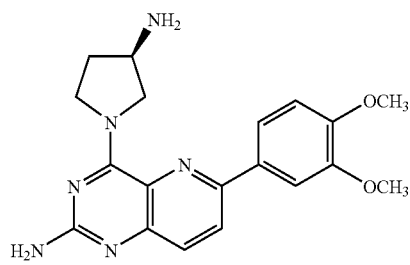

To a suspension of 2-amino-4-[(R)-3-Boc-aminopyrrolidin-1-yl]-6-(3,4-dimethoxyphenyl)pyrido[3,2-d]pyrimidine (94 mg, 0.2 mmol) in dichloromethane (5 ml) was added trifluoroacetic acid (2 ml). The resulting solution was stirred at room temperature for 30 minutes. The solvents were removed under reduced pressure. The residue was extracted with chloroform and washed with a 0.2 M $Na_2CO_3$ solution. The combined organic layers were evaporated in vacuo. The crude residue was purified by silica gel flash chromatography, the mobile phase being a MeOH/$CH_2Cl_2$ mixture in a volume ratio of 2:3, resulting in the pure title compound (70 mg, yield: 96%) which was characterised as follows: MS (m/z): 367 ([M+H]$^+$, 100).

Example 250

Synthesis of 2-amino-4-[3-(R)-(3-methylphenylcarbamoyl)-pyrrolidin-1-yl]-6-(3,4-dimethoxyphenyl)-pyrido[3,2-d]pyrimidine

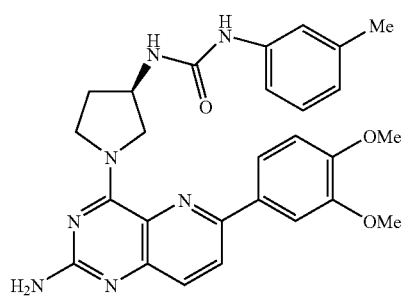

To a solution of 2-amino-4-[(R)-3-Boc-aminopyrrolidin-1-yl)]-6-(3,4-dimethoxyphenyl)-pyrido[3,2-d]pyrimidine (55 mg, 0.12 mmol) in dichloromethane (5 ml) was added trifluoroacetic acid (2 ml). The mixture was stirred at room temperature for 30 minutes. The solvents were evaporated in vacuo. To a suspension of this crude residue in dichloromethane (5 ml) was added N,N-diisopropylethylamine (0.5 ml) and m-tolyl isocyanate (16 µl). The reaction mixture was stirred at room temperature for 30 minutes. The solvents were evaporated in vacuo. The crude residue was purified by silica gel chromatography, the mobile phase being a MeOH/$CH_2Cl_2$ mixture (in a ratio of 1:20), resulting in the pure title compound (50 mg, yield: 85%) which was characterised as follows:

Rf=0.42 (MeOH/$CH_2Cl_2$ 1:9);
UV (MeOH/$H_2O$, nm): 240, 470, 560; and
MS (m/z): 500 ([M+H]$^+$, 100).

Example 251

Synthesis of 2-amino-4-[(3-methylphenylcarbamoyl)-ethylenediamine-1-N-yl]-6-(3,4-dimethoxyphenyl)-pyrido[3,2-d]pyrimidine

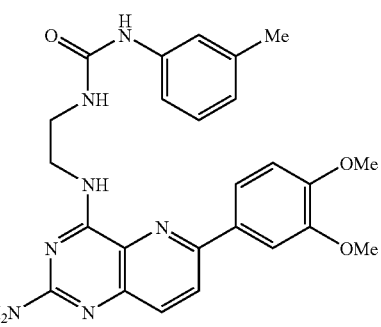

To a solution of 2-amino-4-(ethylenediamine-1-N-yl)-6-(3,4-dimethoxyphenyl)-pyrido[3,2-d]pyrimidine (70 mg, 0.2 mmol) in dichloromethane (10 ml) was added N,N-diisopropylethylamine (200 µl) and m-tolyl isocyanate (26 µl). The solution was stirred at room temperature for 1 hour. The solvents were evaporated in vacuo. The crude residue was purified by silica gel flash chromatography, the mobile phase being a MeOH/$CH_2Cl_2$ mixture, in a ratio of 1:15, yielding the pure title compound (72 mg, yield: 76%) which was characterised as follows:

Rf=0.32 (MeOH/$CH_2Cl_2$ 1:9);
UV (MeOH/$H_2O$, nm): 250, 560; and
MS (m/z): 474 ([M+H]$^+$, 100).

Example 252

Synthesis of 2-amino-4-[(3-methylphenylcarbamoyl)-3-aminopropane-amino-1-N-yl]-6-(3,4-dimethoxyphenyl)-pyrido[3,2-d]pyrimidine

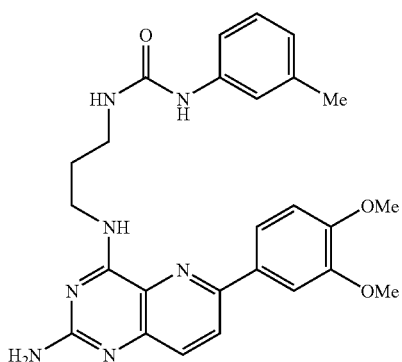

was obtained from 2-amino-4-(3-aminopropanamine-1-N-yl)-6-(3,4-dimethoxyphenyl)-pyrido[3,2-d]pyrimidine (using the procedure described for the synthesis of example 251) in 82% yield and was characterised as follows:

Rf=0.38 (MeOH/$CH_2Cl_2$ 1:9);
UV (MeOH/$H_2O$, nm): 250, 480, 560; and
MS (m/z): 488 ([M+H]$^+$, 100).

Example 253

Synthesis of 2-amino-4-[1-(3-methylphenylcarbamoyl)piperidin-4-yl)amino]-6-(3,4-dimethoxyphenyl)-pyrido[3,2-d]pyrimidine

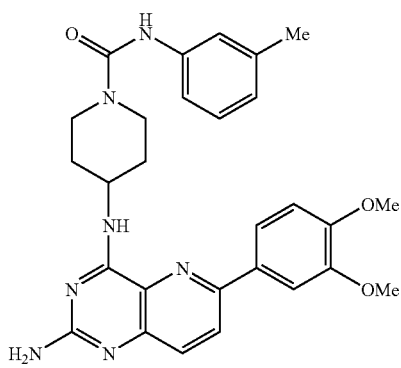

This compound was obtained from 2-amino-4-(1-Boc-piperidin-4-yl-amino)-6-(3,4-dimethoxyphenyl)-pyrido[3,2-d]pyrimidine as a yellowish solid (yield: 82%) which was characterised as follows:

Rf=0.40 (MeOH/CH$_2$Cl$_2$ 1:9);
UV (MeOH/H$_2$O, nm): 250, 470, 560; and
MS (m/z): 514 ([M+H]$^+$, 100).

Example 254

Synthesis of 2-amino-4-[(3-methylphenylcarbamoylpiperidin-3-yl)amino)-6-(3,4-dimethoxyphenyl]-pyrido[3,2-d]pyrimidine

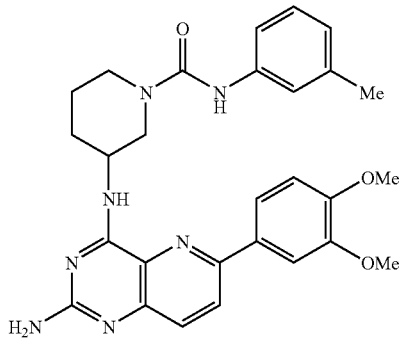

This compound was synthesized from 2-amino-4-(1-Boc-piperidin-3-ylamino)-6-(3,4-dimethoxyphenyl)-pyrido[3,2-d]pyrimidine by Boc-deprotection and coupling with m-tolyl isocyanate (using the procedure described for example 250), as a yellowish solid (yield: 88%) which was characterised as follows:

Rf=0.32 (MeOH/CH$_2$Cl$_2$ 1:9);
UV (MeOH/H$_2$O, nm): 250, 370, 560; and
MS (m/z): 514 ([M+H]$^+$, 100).

Example 255

Synthesis of 2-amino-4-[2-(4-chlorophenoxy-acetyl-ethylenediamine-1-N-yl]-6-(3,4-dimethoxyphenyl)-pyrido[3,2-d]pyrimidine

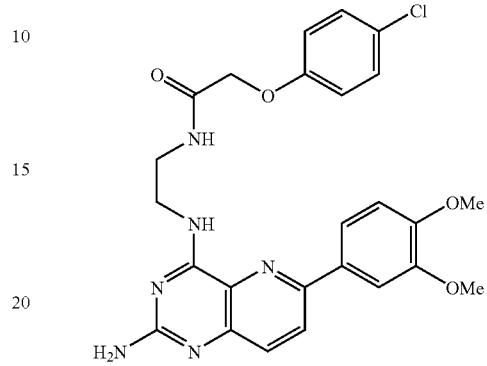

To a suspension of 2-amino-4-(ethylenediamine-1-N-yl)-6-(3,4-dimethoxyphenyl)-pyrido[3,2-d]pyrimidine (50 mg, 0.15 mmol) in dichloromethane (10 ml) was added diisopropylethylamine (200 µl) and 4-chloro-phenoxy acetyl chloride (30 mg, 0.15 mmol). The mixture was stirred at room temperature for 1 hour. The solvents were evaporated in vacuo. The crude residue was purified by flash chromatography, the mobile phase being a MeOH/CH$_2$Cl$_2$ mixture (in a volume ratio of 1:20), resulting in the pure title compound (40 mg, yield: 53%) which was characterised as follows:

Rf=0.35 (MeOH/CH$_2$Cl$_2$ 1:9);
UV (MeOH/H$_2$O, nm): 250, 480, 560; and
MS (m/z): 509, 511 ([M+H]$^+$, 100).

Example 256

Synthesis of 2-amino-4-[3-N-(4-chlorophenoxy-acetyl)-3-aminopropane-amine-1-N-yl]-6-(3,4-dimethoxyphenyl)-pyrido[3,2-d]pyrimidine

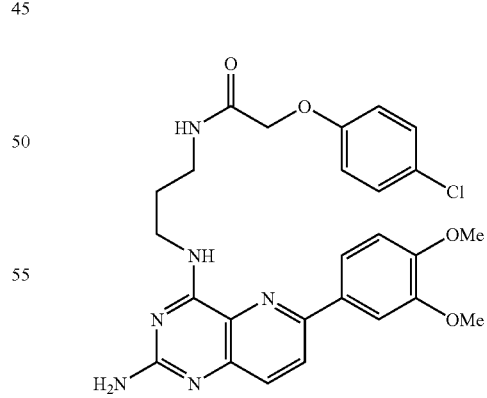

was synthesized from 2-amino-4-(3-aminopropanamine-1-N-yl)-6-(3,4-dimethoxyphenyl)-pyrido[3,2-d]pyrimidine and 4-chlorophenoxyacetyl chloride, using the procedure described for the synthesis of example 255, resulting in the pure title compound (yield: 56%) which was characterised as follows:

Rf=0.36 (MeOH/CH$_2$Cl$_2$ 1:9);
UV (MeOH/H$_2$O, nm): 250, 560; and
MS (m/z): 523, 525 ([M+H]$^+$, 100).

Example 257

Synthesis of 2-amino-4-[(3-(R)-(4-chlorophenoxy-acetyl-amino)-pyrrolidin-1-yl]-6-(3,4-dimethoxyphenyl)-pyrido[3,2-d]pyrimidine

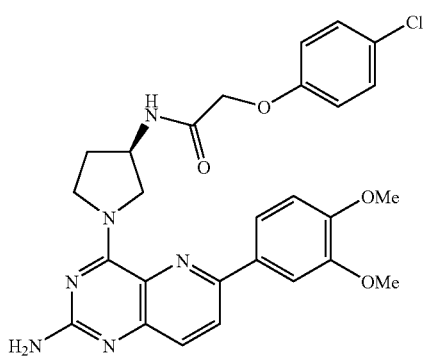

was synthesized from 2-amino-4-[(3-(R)-Boc-aminopyrrolidin-1-yl]-6-(3,4-dimethoxyphenyl)-pyrido[3,2-d]pyrimidine in two steps. The Boc group was deprotected (using the procedure described for example 249), then the free amino group was coupled with 4-chlorophenoxyacetyl chloride (using the procedure described for example 255), resulting in the pure title compound (yield: 68%) which was characterised as follows:

Rf=0.30 (MeOH/CH$_2$Cl$_2$ 1:9);
UV (MeOH/H$_2$O, nm): 280, 470, 560; and
MS (m/z): 535, 537 ([M+H]$^+$, 100).

Examples 258 to 266

Synthesis of 2-amino-4-substituted-6-(3,4-dimethoxyphenyl)pyrido[3,2-d]pyrimidines To a suspension of 2-acetamido-4-(1,2,4-triazolyl)-6-(3,4-dimethoxyphenyl)pyrido[3,2-d]pyrimidine (0.5 mmol) and N,N-diisopropylethylamine (3 mmol) in 1,4-dioxane (20 ml) was added an appropriate amine (1.5 mmol). The reaction mixture was refluxed for 2 hours. The solvents were evaporated in vacuo and the residue was redissolved in methanol (20 ml). A solution of K$_2$CO$_3$ (3 mmol) in water (5 ml) was added and the resulting reaction mixture was refluxed for 2 hours. After cooling to room temperature, the mixture was extracted with dichloromethane (100 ml). The organic phase was washed with a 0.5 M Na$_2$CO$_3$ solution and concentrated under reduced pressure. The residue was purified by silica gel flash chromatography, the mobile phase being a mixture of MeOH and dichloromethane, thus resulting into the pure title compounds in the following yields.

Example 258

2-amino-4-[(3-carboxylic acid isobutylamide)-piperidin-1-yl]-6-(3,4-dimethoxyphenyl)-pyrido[3,2-d]pyrimidine

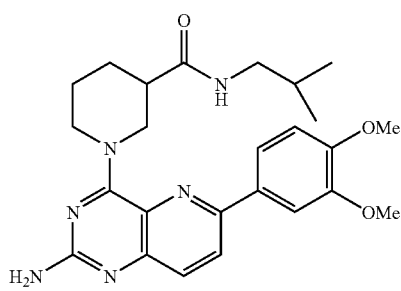

This compound was obtained from piperidine-3-carboxylic acid isobutyl amide, as a yellowish solid (yield: 60%) which was characterised as follows:

Rf=0.25 (MeOH/CH$_2$Cl$_2$ 1:9);
UV (MeOH/H$_2$O, nm): 245, 560; and
MS (m/z): 465 ([M+H]$^+$, 100).

Example 259

2-amino-4-(4-chlorophenyl-4-hydroxypiperidin-1-yl)-6-(3,4-dimethoxyphenyl)-pyrido[3,2-d]pyrimidine

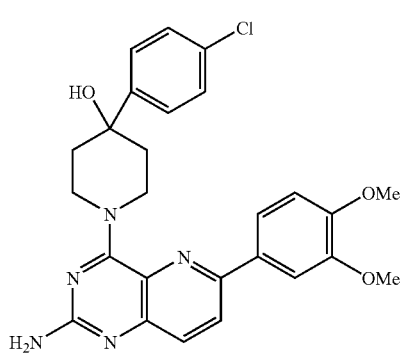

This compound was obtained from 4-(4-chlorophenyl)-4-hydroxy-piperidine, as a white solid (yield: 58%) which was characterised as follows:

Rf=0.42 (MeOH/CH$_2$Cl$_2$ 1:9);
UV (MeOH/H$_2$O, nm): 285, 365, 560; and
MS (m/z): 492, 494 ([M+H]$^+$, 100).

Example 260

2-amino-4-[4-(N-2-phenylethylacetamid-2-yl)piperazin-1-yl]-6-(3,4-dimethoxyphenyl)-pyrido[3,2-d]pyrimidine

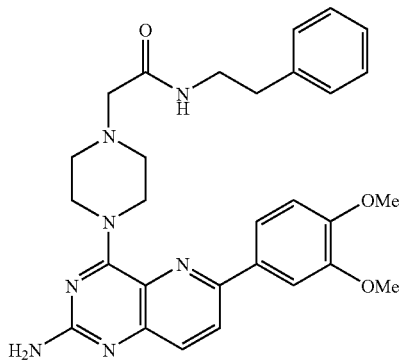

This compound was synthesized from N-(2-phenylethyl)-2-piperazin-1-ylacetamide as a yellowish solid (yield: 54%) which was characterised as follows:

Rf=0.38 (MeOH/CH$_2$Cl$_2$ 1:9);

UV (MeOH/H$_2$O, nm): 245, 560; and

MS (m/z): 528 ([M+H]$^+$, 100).

Example 261

2-amino-4-[2-(4-benzylpiperazin-1-yl)-2-oxo-ethane-amino]-6-(3,4-dimethoxyphenyl)-pyrido[3,2-d]pyrimidine

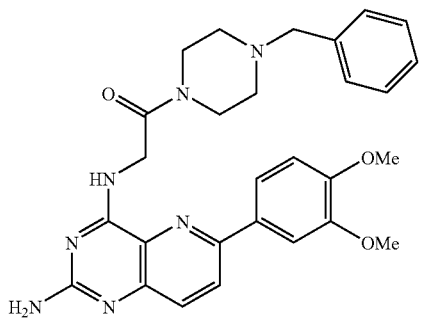

This compound was obtained from 2-amino-1-(4-benzylpiperazin-1-yl)ethanone as a yellowish solid (yield: 54%) which was characterised as follows:

Rf=0.32 (MeOH/CH$_2$Cl$_2$ 1:9);

UV (MeOH/H$_2$O, nm): 265, 585;

MS (m/z): 514 ([M+H]$^+$, 100)

Example 262

2-amino-4-[3-(4-acetylpiperazin-1-yl)-propan-3-one-1-yl-amino]-6-(3,4-dimethoxyphenyl)-pyrido[3,2-d]pyrimidine

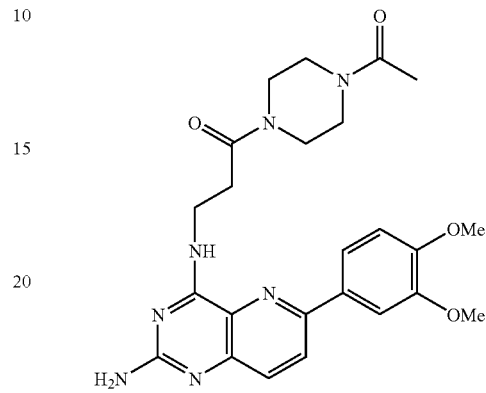

This compound was obtained from 1-(4-acetylpiperazin-1-yl)-3-aminopropan-1-one as a yellowish solid (yield: 60%) which was characterised as follows:

Rf=0.30 (MeOH/CH$_2$Cl$_2$ 1:9);

UV (MeOH/H$_2$O, nm): 250, 505, 580; and

MS (m/z): 480 ([M+H]$^+$, 100)

Example 263

2-amino-4-(N-pyrrolidinyl-acetamid-2-yl-piperazin-1-yl)-6-(3,4-dimethoxyphenyl)pyrido[3,2-d]pyrimidine

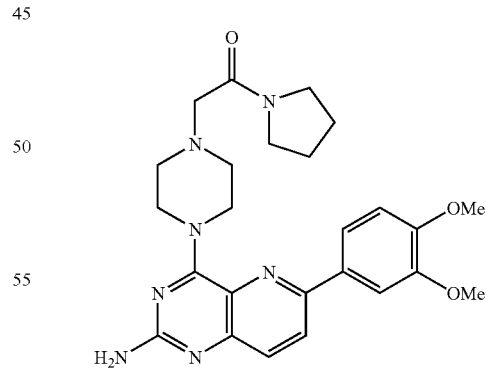

This compound was synthesized from 2-piperazine-1-yl-1-pyrrolidin-1-yl-ethanone (yield 59%) as a yellowish solid which was characterised as follows:

Rf=0.27 (MeOH/CH$_2$Cl$_2$ 1/9);

UV (MeOH/H$_2$O, nm): 245, 580; and

MS (m/z): 478 ([M+H]$^+$, 100)

Example 264
Synthesis of 2-amino-4-(N-pyridinylacetamid-2-yl-piperazin-1-yl)-6-(3,4-dimethoxyphenyl)-pyrido[3,2-d]pyrimidine

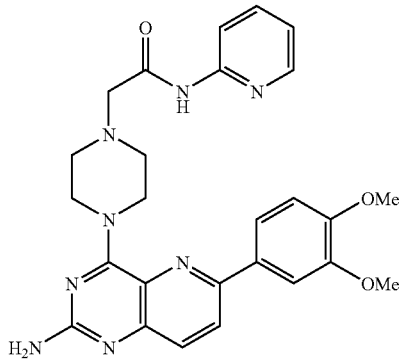

This compound was synthesized from 2-piperazin-1-yl-N-pyridin-2-ylacetamide as a yellowish solid (yield: 53%) which was characterised as follows:
Rf=0.33 (MeOH/CH$_2$Cl$_2$ 1:9);
UV (MeOH/H$_2$O, nm): 245, 365, 560; and
MS (m/z): 501 ([M+H]$^+$, 100)

Example 265
2-amino-4-[N-(piperazino)-acetyl-morpholino]-6-(3,4-dimethoxyphenyl)-pyrido[3,2-d]pyrimidine

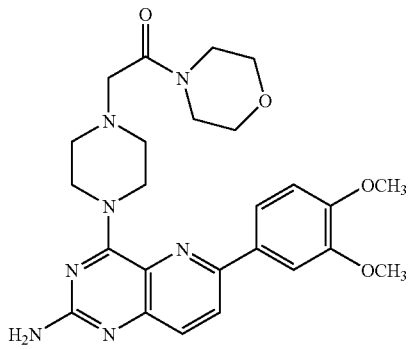

This compound was synthesized from N-[2-(1-piperazino)-acetyl]-morpholino as a yellowish solid (yield: 57%) which was characterised as follows:
Rf=0.45 (MeOH/CH$_2$Cl$_2$ 1:9);
UV (MeOH/H$_2$O, nm): 275, 365; and
MS (m/z): 494 ([M+H]$^+$, 100)

Example 266
Synthesis of 2-amino-4-[2-amino-1-(4-methyl-piperazin-1-yl)ethanone]-6-(3,4-dimethoxyphenyl)-pyrido[3,2-d]pyrimidine

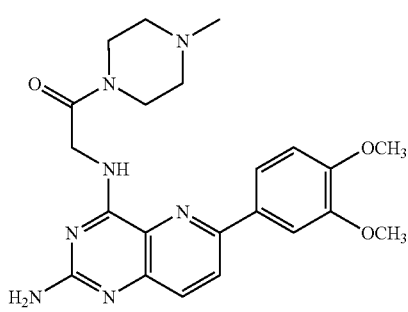

This compound was synthesized from 2-amino-1-(4-methylpiperazin-1-yl)ethanone as a yellowish solid (yield: 57%) which was characterised as follows:
Rf=0.20 (MeOH/CH$_2$Cl$_2$ 1:4);
UV (MeOH/H$_2$O, nm): 270, 355, 495;
MS (m/z): 438 ([M+H]$^+$, 100)

Examples 267 and 268
Synthesis of 2-acetamido-4-substituted-6-(3,4-dimethoxyphenyl)-pyrido[3,2-d]pyrimidine analogues To a suspension of 2-acetamido-4-(1,2,4-triazolyl)-6-(3,4-dimethoxyphenyl)pyrido[3,2-d]pyrimidine (0.5 mmol) and N,N-diisopropylethylamine (3 mmol) in 1,4-dioxane (20 ml) was added an appropriate amine (1.5 mmol). The reaction mixture was refluxed for 2 hours. The solvents were evaporated in vacuo and the residue was purified by silica gel chromatography, the mobile phase being a mixture of methanol and dichloromethane (in a ratio of 1:30) yielding the pure final compounds as follows:

Example 267
2-acetamido-4-[(N-pyridin-3-yl-acetamid)-2-yl-piperazin-1-yl]-6-(3,4-dimethoxyphenyl)-pyrido[3,2-d]pyrimidine

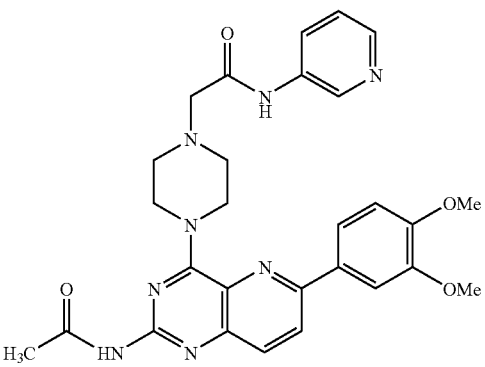

This compound was synthesized from 2-piperazin-1-yl-N-pyridin-3-ylacetamide as a yellowish solid (yield: 40%) and was characterised as follows:
Rf=0.40 (MeOH/CH$_2$Cl$_2$ 1:9);
UV (MeOH/H$_2$O, nm): 245, 370; and
MS (m/z): 543 ([M+H]$^+$, 100)

Example 268
2-acetamido-4-[(N-methyl-N-phenylacetamid)-2-yl-piperazin-1-yl]-6-(3,4-dimethoxyphenyl)-pyrido[3,2-d]pyrimidine

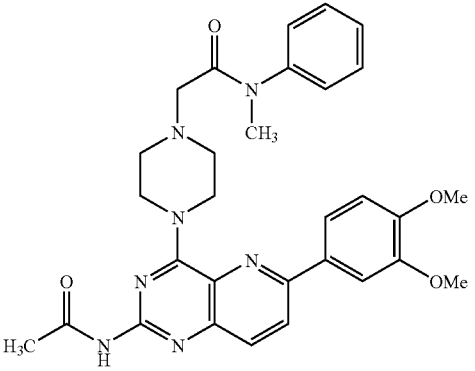

was synthesized from N-methyl-N-phenyl-2-piperazin-1-yl-acetamide as a yellowish solid (yield: 38%) and was characterised as follows:
Rf=0.45 (MeOH/CH$_2$Cl$_2$ 1:9);
UV (MeOH/H$_2$O, nm): 255, 360; and
MS (m/z): 556 ([M+H]$^+$, 100).

Examples 269 to 278

Synthesis of 2-acetamido-4-alkoxy-6-chloro-pyrido[3,2-d]pyrimidines

To a mixture of 2-acetamido-6-chloro-pyrido[3,2-d]pyrimidin-4(3H)-one (0.72 g, 3 mmol), triphenylphosphine (1.18 g, 4.5 mmol), and the appropriate alcohol (4.5 mmol) in dioxane (50 ml) was added di-isopropyl azodicarboxylate (0.91 g, 0.87 ml, 4.5 mmol). The mixture was stirred at room temperature for 24-36 hr and then evaporated in vacuo. The residue was purified by silica gel flash chromatography. The compound was eluted with the following solvent systems: CH$_2$Cl$_2$ (500 ml), CH$_2$Cl$_2$/AcOEt 5:1 (600 ml), CH$_2$Cl$_2$/AcOEt 4:1 (500 ml), CH$_2$Cl$_2$/AcOEt 1:1 (300 ml), CH$_2$Cl$_2$/MeOH 100:5 (500 ml). Evaporation of the product fractions gave the desired 4-alkyloxy-2-amino-6-chloropyrido[3,2-d]pyrimidine in yields of 45-60%, depending on the alcohol used. Analytical samples were obtained by crystallization of the 2-amino-4-alkoxy-6-chloro-pyrido[3,2-d]pyrimidine from ethyl acetate, diethyl ether or methanol. Unreacted 2-acetamido-6-chloro-pyrido[3,2-d]pyrimidin-4(3H)-one (40 to 20%) was also isolated during chromatography. The following compounds were synthesized according to this general procedure:

Example 269

2-acetamido-4-ethoxy-6-chloro-pyrido[3,2-d]pyrimidine

From ethanol (210 mg, 4.5 mmol) to give the pure title compound (0.48 g, yield: 60%) which was characterised as follows:
M.p. 233° C.;
UV (MeOH): 237 (4.58), 266 (4.15), 274 (4.14), 321 (3.73); and
Elemental analysis: Calc. for C$_{11}$H$_{11}$ClN$_4$O$_2$ (266.7): C, 49.54; H, 4.16; N, 21.01. Found: C, 49.01; H, 4.30; N, 20.70.

Example 270

2-acetamido-4-n-propoxy-6-chloro-pyrido[3,2-d]pyrimidine

From n-propanol (270 mg, 4.5 mmol) to give the pure title compound (0.42 g, yield: 50%) which was characterised as follows:
M.p. 191° C.;
UV (MeOH): 237 (4.58), 266 (4.15), 274 (4.14), 321 (3.73); and
Elemental analysis: Calc. for C$_{12}$H$_{13}$ClN$_4$O$_2$ (280.7): C, 51.35; H, 4.67; N, 19.96. Found: C, 51.16; H, 4.69; N, 19.94.

Example 271

2-acetamido-4-isopropoxy-6-chloro-pyrido[3,2-d]pyrimidine

From isopropanol (270 mg, 4.5 mmol) to give the pure title compound (0.479 g, yield: 57%) which was characterised as follows:
M.p. 244° C.;
UV (MeOH): 237 (4.59), 266 (4.15), 274 (4.15), 321 (3.73); and
Elemental analysis: Calc. for C$_{12}$H$_{13}$ClN$_4$O$_2$ (280.7): C, 51.35; H, 4.67; N, 19.96. Found: C, 51.30; H, 4.71; N, 20.05.

Example 272

2-acetamido-4-n-butoxy-6-chloro-pyrido[3,2-d]pyrimidine

From n-butanol (270 mg, 4.5 mmol) to give the pure title compound (0.504 g, 57%) which was characterised as follows:
M.p. 158-159° C.;
UV (MeOH): 237 (4.59), 266 (4.15), 274 (4.15), 321 (3.73); and
Elemental analysis: Calc. for C$_{13}$H$_{15}$ClN$_4$O$_2$ (294.7): C, 52.98; H, 5.13; N, 19.01. Found: C, 52.11; H, 5.16; N, 18.68.

Example 273

2-acetamido-4-isobutoxy-6-chloro-pyrido[3,2-d]pyrimidine

From isobutanol (333 mg, 4.5 mmol) to yield the pure title compound (0.46 g, 52%) which was characterised as follows:
M.p. 168° C.;
UV (MeOH): 237 (4.59), 266 (4.16), 274 (4.15), 321 (3.75); and
Elemental analysis: Calc. for C$_{13}$H$_{15}$ClN$_4$O$_2$ (294.7): C, 52.98; H, 5.13; N, 19.01. Found: C, 52.87; H, 5.16; N, 19.07.

Example 274

2-acetamido-4-sec.butoxy-6-chloro-pyrido[3,2-d]pyrimidine

From sec-butanol (400 mg, 4.5 mmol) to yield the pure title compound (0.442 g, 50%) which was characterised as follows:
M.p. 143-144° C.;
UV (MeOH): 237 (4.56), 266 (4.13), 274 (4.18), 321 (3.71); and
Elemental analysis: Calc. for C$_{13}$H$_{15}$ClN$_4$O$_2$ (294.7): C, 52.98; H, 5.13; N, 19.01. Found: C, 52.85; H, 5.13; N, 18.92.

Example 275

2-acetamido-4-n-pentoxy-6-chloro-pyrido[3,2-d]pyrimidine

From n-pentanol (333 mg, 4.5 mmol) to yield the pure title compound (0.37 g, 40%) which was characterised as follows:
M.p. 174° C.;
UV (MeOH): 238 (4.60), 266 (4.13), 275 (4.13), 322 (3.72); and
Elemental analysis: Calc. for C$_{14}$H$_{17}$ClN$_4$O$_2$ (308.8): C, 54.46; H, 5.55; N, 18.15. Found: C, 54.47; H, 5.66; N, 18.14.

Example 276

2-acetamido-4-benzyloxy-6-chloro-pyrido[3,2-d]pyrimidine

From benzylalcohol (486 mg, 4.5 mmol) and stirring for 72 hours to give the pure title compound as a yellowish powder (240 mg, 24%) which was characterised as follows:

M.p. 199-200° C.;

UV (MeOH): 207 (4.40), 237 (4.56), 265 (4.15), 274 (4.13), 322 (3.74); and

Elemental analysis: Calc. for $C_{16}H_{13}ClN_4O_2$ (328.8): C, 58.46; H, 3.99; N, 17.04. Found: C, 58.56; H, 4.04; N, 17.05.

Example 277

Synthesis of 2-acetamido-6-chloro-4-(2-ethoxyethoxy)-pyrido[3,2-d]pyrimidine 4 mmol 2-acetamido-6-chloro-pyrido[3,2-d]pyrimidin-4(3H)-one (0.954 g) was reacted with 6 mmol 2-ethoxyethanol (0.54 g) yielding the pure title compound (0.6 g, yield: 48%) which was characterised as follows:

M.p. 185° C.;

UV (MeOH): 208 (4.20), 237 (4.55), 266 (4.15), 274 (4.15), 321 (3.71); and

Elemental analysis: Calc. for C13H15ClN4O3 (310.7): C, 50.25; H, 4.87; N, 18.03. Found: C, 50.09; H, 4.98; N, 18.32

Example 278

Synthesis of 2-acetamido-6-chloro-4-(2-methoxyethoxy)-pyrido[3,2-d]pyrimidine 5 mmol 2-acetamido-6-chloro-pyrido[3,2-d]pyrimidin-4(3H)-one (1.2 g) was reacted with 7.5 mmol 2-methoxyethanol (0.54 g) to give the pure title compound (0.2 g, yield: 14%) which was characterised as follows:

M.p. 135° C.;

UV (MeOH): 208 (4.21), 236 (4.56), 266 (4.15), 274 (4.14), 321 (3.71); and

Elemental analysis: Calc. for C12H13ClN4O3×0.5H2O (305.7): C, 47.14; H, 4.62; N, 18.32. Found: C, 47.30; H, 4.49; N, 18.39.

Examples 279 to 305

Synthesis of 2-amino-4-alkoxy- and 2-amino-4-benzyloxy-6-(fluorophenyl)pyrido[3,2-d]pyrimidines To a degassed suspension of a 2-acetamido-4-alkoxy-6-chloro-pyrido[3,2-d]pyrimidine (0.5 mmol), 2-, 3-, or 4-fluorophenylboronic acid (80 mg, 0.57 mmol) and potassium carbonate (2-4 mmol) in a mixture of dioxane (7.3 ml) and water (1.6 ml) was added tetrakis(triphenylphosphine)palladium(0) (29 mg, 0.025 mmol). The mixture was refluxed (bath temperature 120° C.) for 24 hours. After cooling to room temperature dichloromethane (30 ml) was added and the mixture was washed with a brine solution. The organic layer was separated, dried over $Na_2SO_4$ and evaporated in vacuo. The resulting crude material was purified by silica gel flash chromatography. The compound was eluted with the following solvent systems: $CH_2Cl_2$ (100 ml), $CH_2Cl_2$/MeOH 100:1 (101 ml), 100:2 (102 ml), 100:3 (103 ml). Evaporation of the product fractions afforded the following 2-amino-4-O-substituted-6-(fluorophenyl)pyrido[3,2-d]pyrimidines as crystal solids in yields varying from 70-85%. In some cases the corresponding 2-acetamidoderivates were detected and also isolated as the faster-moving component. The analytical samples were prepared by recrystallization from ether or methanol.

Example 279

2-amino-4-ethoxy-6-(o-fluorophenyl)-pyrido[3,2-d]pyrimidine was prepared from 2-fluorophenylboronic acid (80 mg, 0.57 mmol) to yield the pure title compound (0.657 g, yield: 77%) which was characterised as follows:

M.p. 182° C.;

UV (MeOH): 231 (4.47), 284 (4.29), 348 (3.89); and

Elemental analysis: Calc. for $C_{15}H_{13}FN_4O$ (284.3): C, 63.37; H, 4.61; N, 19.41. Found: C, 62.70; H, 4.65; N, 19.41

Example 280

2-amino-4-ethoxy-6-(m-fluorophenyl)-pyrido[3,2-d]-pyrimidine from 3-fluorophenylboronic acid (80 mg, 0.57 mmol) to yield the pure title compound (0.69 g, yield: 81%) which was characterised as follows:

M.p. 174° C.;

UV (MeOH): 234 (4.43), 292 (4.31), 352 (3.92); and

Elemental analysis: Calc. for $C_{15}H_{13}FN_4O$ (284.3): C, 63.37; H, 4.61; N, 19.41. Found: C, 62.51; H, 4.72; N, 19.10

Example 281

2-amino-4-ethoxy-6-(p-fluorophenyl)pyrido[3,2-d]-pyrimidine from 4-fluorophenyl boronic acid (80 mg, 0.57 mmol) to give the pure title compound (0.657 g, yield: 77%) which was characterised as follows:

M.p. 188-189° C.;

UV (MeOH): 216 (4.48), 234 (4.44), 287 (4.34), 354 (3.89); and

Elemental analysis: Calc. for $C_{15}H_{13}FN_4O$ (284.3): C, 63.37; H, 4.61; N, 19.41. Found: C, 62.98; H, 4.63; N, 19.67

Example 282

2-amino-4-n-propoxy-6-(o-fluorophenyl)-pyrido[3,2-d]pyrimidine from 2-fluorophenyl boronic acid (80 mg, 0.57 mmol) to yield the pure title compound (0.698 g, yield: 78%) which was characterised as follows:

M.p. 191° C.;

UV (MeOH): 231 (4.49), 284 (4.30), 348 (3.90);

Elemental analysis: Calc. for $C_{15}H_{13}FN_4O$ (298.3): C, 64.42; H, 5.07; N, 18.78. Found: C, 64.15; H, 5.00; N, 18.76.

Example 283

2-amino-4-n-propoxy-6-(p-fluorophenyl)-pyrido[3,2-d]pyrimidine from 4-fluorophenyl boronic acid (80 mg, 0.57 mmol) to yield the pure title compound (0.698 g, yield: 78%) which was characterised as follows:

M.p. 185-186° C.;

UV (MeOH): 216 (4.50), 233 (4.46), 287 (4.35), 353 (3.90); and

Elemental analysis: Calc. for $C_{15}H_{13}FN_4O$ (298.3): C, 64.42; H, 5.07; N, 18.78. Found: C, 63.86; H, 5.37; N, 18.46.

Example 284

2-amino-4-isopropoxy-6-(m-fluorophenyl)-pyrido[3,2-d]pyrimidine from 3-fluoropheny boronic acid (80 mg, 0.57 mmol) to yield the pure title compound (0.698 g, yield: 78%) which was characterised as follows:

M.p. 200-201° C.;

UV (MeOH): 236 (4.38), 292 (4.29), 352 (3.91),

Elemental analysis: Calc. for $C_{16}H_{15}FN_4O$ (298.3): C, 64.42; H, 5.07; N, 18.78. Found: C, 63.07; H, 5.08; N, 18.06

Example 285

2-acetamido-4-isopropoxy-6-(p-fluorophenyl)-pyrido[3,2-d]pyrimidine from 4-fluorophenyl boronic acid (80 mg, 0.57 mmol) and isolated from the first fraction on column chromatography to give the pure title compound (0.694 g, yield: 68%) which was characterised as follows:

M.p. 196-197° C.;
UV (MeOH): 239 (4.39), 257 (4.24), 286 (4.30), 334 (3.99); and
Elemental analysis: Calc. for $C_{18}H_{17}FN_4O_2$ (340.4): C, 63.52; H, 5.03; N, 16.46. Found: C, 62.65; H, 4.73; N, 16.40

Example 286

2-amino-4-isopropoxy-6-(p-fluorophenyl)-pyrido[3,2-d]pyrimidine from 4-fluorophenylboronic acid (80 mg, 0.57 mmol) and isolated a the second fraction of column chromatography to give the pure title compound (0.143 g, yield: 16%) which was characterised as follows:

M.p. 191-192° C.;
UV (MeOH): 216 (4.50), 233 (4.46), 287 (4.35), 353 (3.90); and
Elemental analysis: Calc. for $C_{16}H_{15}FN_4O$ (298.3): C, 64.42; H, 5.07; N, 18.78. Found: C, 64.25; H, 5.16; N, 18.68

Example 287

2-amino-4-n-butoxy-6-(o-fluorophenyl)-pyrido[3,2-d]pyrimidine from 2-fluorophenyl boronic acid (80 mg, 0.57 mmol) to give the pure title compound (0.75 g, yield: 80%) which was characterised as follows:

M.p. 147-148° C.;
UV (MeOH): 232 (4.42), 284 (4.28), 348 (3.88); and
Elemental analysis: Calc. for $C_{17}H_{17}FN_4O$ (312.4): C, 65.37; H, 5.49; N, 17.94. Found: C, 64.55; H, 5.56; N, 17.62

Example 288

2-amino-4-n-butoxy-6-(m-fluorophenyl)-pyrido[3,2-d]pyrimidine from 3-fluorophenyl boronic acid (80 mg, 0.57 mmol) to give the pure title compound (0.61 g, yield: 65%) which was characterised as follows:

M.p. 160-161° C.;
UV (MeOH): 236 (4.38), 292 (4.29), 352 (3.91);
Elemental analysis: Calc. for $C_{17}H_{17}FN_4O$ (312.4): C, 65.37; H, 5.49; N, 17.94. Found: C, 64.84; H, 5.65; N, 18.03

Example 289

2-acetamido-4-n-butoxy-6-(p-fluorophenyl)-pyrido[3,2-d]pyrimidine from 4-fluorophenyl boronic acid (80 mg, 0.57 mmol) and isolated from the first fraction of column chromatography to give the pure title compound (0.16 g, yield: 15%) which was characterised as follows:

M.p. 170° C.;
UV (MeOH): 225 (4.32), 239 (4.39), 257 (4.22), 288 (4.32), 334 (4.00);
Elemental analysis: Calc. for $C_{19}H_{19}FN_4O_2$ (312.4): C, 64.40; H, 5.40; N, 15.81. Found: C, 63.73; H, 5.54; N, 15.50

Example 290

2-amino-4-n-butoxy-6-(p-fluorophenyl)-pyrido[3,2-d]pyrimidine from 4-fluorophenyl boronic acid (80 mg, 0.57 mmol) and isolated from the second fraction of column chromatography to give the pure title compound (0.73 g, yield: 78%) which was characterised as follows:

M.p. 172-173° C.;
UV (MeOH): 218 (4.50), 234 (4.39), 288 (4.35), 352 (3.89);
Elemental analysis: Calc. for $C_{17}H_{17}FN_4O$ (312.4): C, 65.37; H, 5.49; N, 17.94. Found: C, 64.84; H, 5.65; N, 18.03

Example 291

2-amino-4-isobutoxy-6-(o-fluorophenyl)-pyrido[3,2-d]pyrimidine from 2-fluorophenyl boronic acid (80 mg, 0.57 mmol) to give the pure title compound (0.75 g, yield: 78%) which was characterised as follows:

M.p. 165° C.;
UV (MeOH): 232 (4.46), 284 (4.32), 348 (3.93); and
Elemental analysis: Calc. for $C_{17}H_{17}FN_4O$ (312.4): C, 65.37; H, 5.49; N, 17.94. Found: C, 65.60; H, 5.75; N, 18.04

Example 292

2-amino-4-isobutoxy-6-(m-fluorophenyl)-pyrido[3,2-d]pyrimidine from 3-fluorophenyl boronic acid (80 mg, 0.57 mmol) to give the pure title compound (0.75 g, yield: 78%) which was characterised as follows:

M.p. 185° C.;
UV (MeOH): 236 (4.39), 292 (4.31), 352 (3.93);
Elemental analysis: Calc. for $C_{17}H_{17}FN_4O$ (312.4): C, 65.37; H, 5.49; N, 17.94. Found: C, 65.59; H, 5.55; N, 18.00

Example 293

2-amino-4-isobutoxy-6-(p-fluorophenyl)-pyrido[3,2-d]pyrimidine from 4-fluorophenylboronic acid (80 mg, 0.57 mmol) to give the pure title compound (0.806 g, yield: 86%) which was characterised as follows:

M.p. 196° C.;
UV (MeOH): 234 (4.40), 287 (4.34), 353 (3.89); and
Elemental analysis: Calc. for $C_{17}H_{17}FN_4O$ (312.4): C, 65.37; H, 5.49; N, 17.94. Found: C, 64.94; H, 5.42; N, 17.90

Example 294

2-amino-4-sec.butoxy-6-(o-fluorophenyl)-pyrido[3,2-d]pyrimidine from 2-fluorophenylboronic acid (80 mg, 0.57 mmol) to give the pure title compound (0.693 g, yield: 74%) which was characterised as follows:

M.p. 159° C.;
UV (MeOH): 233 (4.42), 284 (4.27), 348 (3.89); and
Elemental analysis: Calc. for $C_{17}H_{17}FN_4O$ (312.4): C, 65.37; H, 5.49; N, 17.94. Found: C, 65.60; H, 5.42; N, 17.70

Example 295

2-amino-4-sec.butoxy-6-(m-fluorophenyl)-pyrido[3,2-d]pyrimidine from 3-fluorophenyl boronic acid (80 mg, 0.57 mmol) to give the pure title compound (0.646 g, yield: 69%) which was characterised as follows:

M.p. 158-159° C.;
UV (MeOH): 237 (4.39), 292 (4.31), 352 (3.94); and
Elemental analysis: Calc. for $C_{17}H_{17}FN_4O$ (312.4): C, 65.37; H, 5.49; N, 17.94. Found: C, 64.58; H, 5.19; N, 18.04

Example 296

2-amino-4-sec. butoxy-6-(p-fluorophenyl)-pyrido[3,2-d]pyrimidine from 4-fluorophenyl boronic acid (80 mg, 0.57 mmol) to yield the pure title compound (0.645 g, yield: 69%) which was characterised as follows:

M.p. 148° C.;
UV (MeOH): 234 (4.37), 287 (4.31), 354 (3.87); and

Elemental analysis: Calc. for $C_{17}H_{17}FN_4O$ (312.4): C, 65.37; H, 5.49; N, 17.94. Found: C, 65.28; H, 5.34; N, 18.03

Example 297

2-amino-4-n-pentyloxy-6-(o-fluorophenyl)pyrido[3,2-d]pyrimidine from 2-fluorophenyl boronic acid (80 mg, 0.57 mmol) to give 0.803 g (yield: 82%) which was characterised as follows:
M.p. 136-137° C.;
UV (MeOH): 232 (4.43), 284 (4.28), 348 (3.89); and
Elemental analysis: Calc. for $C_{18}H_{19}FN_4O$ (326.4): C, 66.24; H, 5.87; N, 17.17. Found: C, 65.83; H, 5.62; N, 17.14

Example 298

2-amino-4-n-pentyloxy-6-(m-fluorophenyl)-pyrido[3,2-d]pyrimidine from 3-fluorophenyl boronic acid (80 mg, 0.57 mmol) to give the pure title compound (0.783 g, yield: 80%) which was characterised as follows:
M.p. 142-143° C.;
UV (MeOH): 236 (4.39), 292 (4.30), 351 (3.92); and
Elemental analysis: Calc. for $C_{18}H_{19}FN_4O$ (326.4): C, 66.24; H, 5.87; N, 17.17. Found: C, 65.36; H, 5.72; N, 16.52.

Example 299

2-amino-4-benzyloxy-6-(o-fluorophenyl)-pyrido[3,2-d]pyrimidine from 2-fluorophenyl boronic acid (80 mg, 0.57 mmol) to yield the pure title compound (0.748 g, yield: 72%) which was characterised as follows:
M.p. 200-202° C.;
UV (MeOH): 208 (4.45), 232 (4.43), 285 (4.28), 350 (3.90); and
Elemental analysis: Calc. for $C_{20}H_{15}FN_4O$ (346.4): C, 69.36; H, 4.37; N, 16.18. Found: C, 69.16; H, 4.59; N, 16.30.

Example 300

2-amino-4-benzyloxy-6-(m-fluorophenyl)-pyrido[3,2-d]pyrimidine from 3-fluorophenyl boronic acid (80 mg, 0.57 mmol) to give the pure title compound (0.717 g, yield: 69%) which was characterised as follows:
M.p. 199-200° C.;
UV (MeOH): 208 (4.43), 235 (4.39), 292 (4.30), 352 (3.92); and
Elemental analysis: Calc. for $C_{20}H_{15}FN_4O$ (346.4): C, 69.36; H, 4.37; N, 16.18. Found: C, 69.07; H, 4.44; N, 15.60.

Example 301

2-amino-4-benzyloxy-6-(p-fluorophenyl)-pyrido[3,2-d]pyrimidine from 4-fluorophenyl boronic acid (80 mg, 0.57 mmol) to give the pure title compound (0.81 g, yield: 78%) which was characterised as follows:
M.p. 225° C.;
UV (MeOH): 210 (4.46), 233 (4.43), 287 (4.35), 354 (3.92); and
Elemental analysis: Calc. for $C_{20}H_{15}FN_4O$ (346.4): C, 69.36; H, 4.37; N, 16.18. Found: C, 69.16; H, 4.59; N, 16.30.

Example 302

(2-amino-4-(2-ethoxyethoxy)-6-(2-fluorophenyl)-pyrido[3,2-d]pyrimidine) 0.39 mmol 2-acetamido-6-chloro-4-(2-ethoxyethoxy)-pyrido[3,2-d]-pyrimidine (0.12 g) was reacted with 2-fluorophenylboronic acid (60 mg, 0.43 mmol) to give the pure title compound (0.1 g, yield: 78%) which was characterised as follows:
M.p. 163° C.
UV (MeOH): 232 (4.43), 284 (4.29), 349 (3.92)
Elemental analysis: Calc. For C17H17FN4O2 (328.3): C, 62.19; H, 5.22; N, 17.06. Found: C, 61.66; H, 5.21; N, 17.18

Example 303

2-amino-4-(2-ethoxyethoxy)-6-(3-fluorophenyl)-pyrido[3,2-d]pyrimidine 0.39 mmol 2-acetamido-6-chloro-4-(2-ethoxyethoxy)-pyrido[3,2-d]-pyrimidine (0.12 g) was reacted with 3-fluorophenylboronic acid (60 mg, 0.43 mmol) to give the pure title compound (0.09 g, yield: 71%) which was characterised as follows:
M.p. 165° C.
UV (MeOH): 236 (4.41), 292 (4.33), 352 (3.94)
Elemental analysis: Calc. for: C17H17FN4O2 (328.3): C, 62.19; H, 5.22; N, 17.06. Found: C, 61.94; H, 5.25; N, 17.08.

Example 304

2-amino-4-(2-ethoxyethoxy)-6-(4-fluorophenyl)-pyrido[3,2-d]pyrimidine 0.39 mmol 2-acetamido-6-chloro-4-(2-ethoxyethoxy)-pyrido[3,2-d]-pyrimidine (0.12 g) was reacted with of 4-fluorophenylboronic acid (60 mg, 0.43 mmol) to give the pure title compound (0.10 g, 79%) which was characterised as follows:
M.p. 192° C.
UV (MeOH): 225 (4.37), 234 (4.42), 287 (4.36), 354 (3.91)
Elemental analysis: Calc. for C17H17FN4O2 (328.3): C, 62.19; H, 5.22; N, 17.06. Found: C, 62.13; H, 5.56; N, 17.44.

Example 305

(2-amino-4-(2-methoxyethoxy)-6-(4-fluorophenyl)-pyrido[3,2-d]pyrimidine): 0.32 mmol 2-acetamido-6-chloro-4-(2-methoxyethoxy)-pyrido[3,2-d]-pyrimidine (95 mg) was reacted with 4-fluorophenylboronic acid (50 mg, 0.36 mmol) to give the pure title compound (85 mg, yield: 85%) which was characterised as follows:
M.p. 204° C.
UV (MeOH): 224 (4.36), 234 (4.41), 287 (4.35), 354 (3.90)
Elemental analysis: Calc. for C16H15FN4O2 (314.3): C, 61.14; H, 4.81; N, 17.82. Found: C, 60.58; H, 4.86; N, 17.76.

Example 306 and 307

Synthesis of 2-acetamido-4-ethoxy-6-(3,4-dimethoxy)pyrido[3,2-d]pyrimidine (Example 306) and 2-amino-4-ethoxy-6-(3,4-dimethoxy)pyrido[3,2-d]pyrimidine (Example 307)

These compounds were synthesized from 2-acetamido-4-ethoxy-6-chloro-pyrido[3,2-d]pyrimidine, according to the general procedure mentioned for examples 279 to 305, using 3,4-dimethoxyphenyl boronic acid (instead of fluoro phenyl boronic acid) yielding a mixture of these two compounds which were separated by flash chromatography on silica and which were characterised as follows:
example 306: MS (m/z): 369 ([M+H]+, 100)
example 307: MS (m/z): 327 ([M+H]+, 100)

Example 308

Synthesis of 2-amino-4-(N-piperazin-1-yl)-6-(3,4-dimethoxyphenyl)pyrido[3,2-d]pyrimidine A mixture of 2-amino-6-(3,4-dimethoxy-phenyl)-pyrido[3,2-d]pyrimidin-4(3H)one (722 mg, 2.42 mmol), 1,1,1,3,3,3-hexamethyldisilazane (2.6 ml, 12 mmol), piperazine (840 mg, 9.75 mmol), p-toluenesulphonic acid (60 mg, 0.32 mmol) and ammonium sulphate (47 mg, 0.36 mmol) in pyridine (12 ml) is refluxed for 2 days. Upon cooling down to room temperature, the reaction mixture is evaporated with silica gel. The residue is purified by silica gel flash chromatography, the mobile phase being a mixture of methanol and dichloromethane (in a ratio of 15:85, with 1% triethylamine), affording the pure title compound (439 mg). An impure fraction is purified further by preparative TLC on silica eluting with 20% MeOH and 1% $Et_3N$ in $CH_2Cl_2$ to give another 140 mg of the title compound (combined yield: 579 mg, 65%) which was characterised as follows: MS (m/z): 367 ([M+H]$^+$, 100).

Examples 309 to 313

Synthesis of 2-amino-4-(N-acyl-piperazin-1-yl)-6-(3,4-dimethoxyphenyl)-pyrido[3,2-d]pyrimidines To a suspension of the compound of example 308 (36 mg, 98 µmol) in $CH_2Cl_2$ (2 ml) and triethylamine (15 µl) was added an appropriate acid chloride (105 µmol). The reaction mixture was stirred at room temperature for 45 minutes. The solvents were evaporated in vacuo and the residue was purified by preparative TLC on silica gel. Elution with 5% MeOH in $CH_2Cl_2$ afforded the pure title compounds in yields varying from 55 to 90%, depending on the acid chloride used. Details for each compound, including the starting acid chloride and the mass spectrum characterisation, are as follows:

Example 309

2-amino-4-[N-(cyclohexanoyl)-piperazin-1-yl]-6-(3,4-dimethoxyphenyl)-pyrido[3,2-d]pyrimidine was synthesized using cyclohexanecarbonyl chloride. MS (m/z): 477 ([M+H]$^+$, 100).

Example 310

2-amino-4-[N-(propionyl)-piperazin-1-yl]-6-(3,4-dimethoxy-phenyl)pyrido[3,2-d]pyrimidine

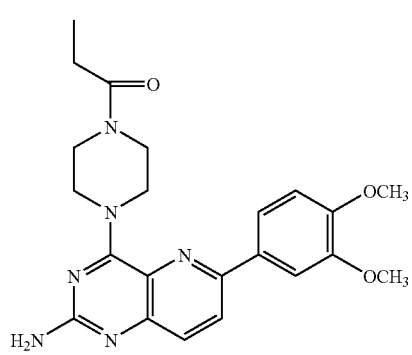

was synthesized using propionyl chloride. MS (m/z): 423 ([M+H]$^+$, 100).

Example 311

2-amino-4-[N-(hexanoyl)-piperazin-1-yl]-6-(3,4-dimethoxy-phenyl)pyrido[3,2-d]pyrimidine

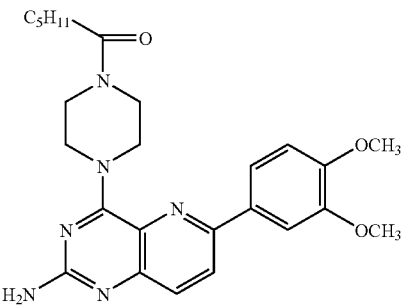

was synthesized using hexanoyl chloride. MS (m/z): 465 ([M+H]$^+$, 100).

Example 312

2-amino-4-[N-(methoxyacetyl)-piperazin-1-yl]-6-(3,4-dimethoxyphenyl)-pyrido[3,2-d]pyrimidine

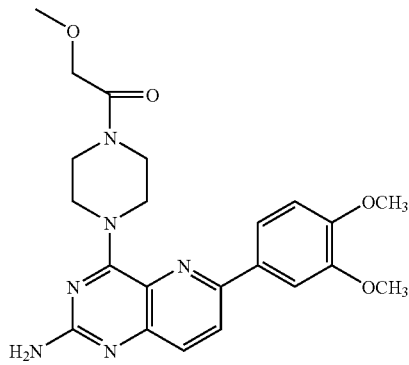

was synthesized using methoxyacetyl chloride. MS (m/z): 439 ([M+H]$^+$, 100).

Example 313

2-amino-4-[N-(methanesulfonyl)-piperazin-1-yl]-6-(3,4-dimethoxyphenyl)-pyrido[3,2-d]pyrimidine

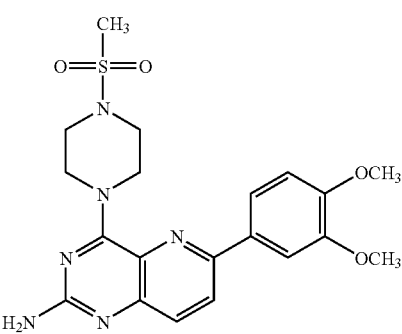

was synthesized using methanesulfonyl chloride. MS (m/z): 445 ([M+H]$^+$, 100).

Examples 314 to 319

Synthesis of 2-acetamido-4-cycloalkylamino-6-(4-fluorophenyl)-pyrido[3,2-d]pyrimidines and 2-acetamido-4-arylamino-6-(4-fluorophenyl)pyrido[3,2-d]pyrimidines To a suspension of 2-acetamido-4-(1,2,4-triazolyl)-6-(4-fluorophenyl)pyrido[3,2-d]pyrimidine (70 mg, 0.2 mmol) in dioxane (5 ml) was added a suitable amine (0.4 mmol). The reaction was stirred at room temperature for 48 hours. The solvents were evaporated in vacuo, yielding the crude title compounds which were purified by preparative TLC using a mixture of methanol and dichloromethane, in a ratio of 10:90, as mobile phase, yielding the title compounds in yields varying from 50 to 72%, depending on the amine used. Details for each compound, including the starting amine and the mass spectrum characterisation, are as follows:

2-acetamido-4-(N-acetylpiperazino)-6-(4-fluorophenyl)-pyrido[3,2-d]pyrimidine (example 314) was obtained from N-acetyl-piperazine. MS (m/z): 409 ([M+H]$^+$, 100). 2-acetamido-4-(N-methylpiperazino)-6-(4-fluorophenyl)-pyrido[3,2-d]pyrimidine (example 315) was obtained from N-methyl-piperazine. MS (m/z): 381 ([M+H]$^+$, 100). 2-acetamido-4-(N-piperidino)-6-(4-fluorophenyl)-pyrido[3,2-d]pyrimidine (example 316) was obtained from piperidine. MS (m/z): 366 ([M+H]$^+$, 100). 2-acetamido-4-(N-cyclohexylamino)-6-(4-fluorophenyl)-pyrido[3,2-d]pyrimidine (example 317) was obtained from cyclohexylamine. MS (m/z): 380 ([M+H]$^+$, 100). 2-acetamido-4-(N-(3-methylanilino))-6-(4-fluorophenyl)-pyrido[3,2-d]pyrimidine (example 318) was obtained from m-toluidine. MS (m/z): 388 ([M+H]$^+$, 100). 2-acetamido-4-(N-benzylamino)-6-(4-fluorophenyl)-pyrido[3,2-d]pyrimidine (example 319) was obtained from benzylamine. MS (m/z): 388 ([M+H]$^+$, 100).

Examples 320 to 325

Synthesis of 2-amino-4-cycloalkylamino-6-(4-fluorophenyl)-pyrido[3,2-d]pyrimidines and 2-amino-4-arylamino-6-(4-fluorophenyl)-pyrido[3,2-d]pyrimidines The appropriate 2-acetamido-4-cycloalkylamino-6-(4-fluorophenyl)-pyrido[3,2-d]pyrimidine or 2-acetamido-4-arylamino-6-(4-fluorophenyl)-pyrido[3,2-d]pyrimidine (0.5 mmol) was suspended in a mixture of dichloromethane (10 ml) and 0.3 N sodium ethoxide (10 ml). The reaction mixture was stirred overnight at room temperature. The solvents were evaporated in vacuo and the crude residue was purified by preparative TLC, using a mixture of methanol and dichloromethane (in a ratio of 10:90) as a mobile phase, yielding in yields from 45 to 65% the pure title compounds which were characterised by their mass spectrum as follows.

2-amino-4-(N-acetylpiperazino)-6-(4-fluorophenyl)-pyrido[3,2-d]pyrimidine (example 320) MS (m/z): 367 ([M+H]$^+$, 100).
2-amino-4-(N-methylpiperazino)-6-(4-fluorophenyl)-pyrido[3,2-d]pyrimidine (example 321) MS (m/z): 339 ([M+H]$^+$, 100). 2-amino-4-(N-piperidino)-6-(4-fluorophenyl)pyrido[3,2-d]pyrimidine (example 322) MS (m/z): 324 ([M+H]$^+$, 100). 2-amino-4-(N-cyclohexylamino)-6-(4-fluorophenyl)-pyrido[3,2-d]pyrimidine (example 323) MS (m/z): 338 ([M+H]$^+$, 100). 2-amino-4-(N-(3-methyl-anilino)-6-(4-fluorophenyl)pyrido[3,2-d]pyrimidine (example 324) MS (m/z): 346 ([M+H]$^+$, 100).
2-amino-4-N-(benzylamino)-6-(4-fluorophenyl)-pyrido[3,2-d]pyrimidine (example 325) MS (m/z): 346 ([M+H]$^+$, 100).

Example 326

Synthesis of 2-amino-4-(cyclopropylmethyloxy)-6-(4-fluorophenyl)pyrido[3,2-d]pyrimidine To a solution of 2-acetamido-4-(1,2,4-triazolyl)-6-(4-fluorophenyl)-pyrido[3,2-d]pyrimidine (52 mg, 0.15 mmol) in cyclopropylmethanol (1 ml) and dioxane (3 ml) was added NaH (60% dispersion in mineral oil, 0.25 mmol, 15 mg). The reaction mixture was stirred overnight at room temperature. The solvents were evaporated in vacuo, and the residue was purified by preparative TLC, the mobile phase being a methanol/dichloromethane mixture in a ratio of 10:90, yielding the pure title compound (22 mg, yield: 47%) which was characterised as follows: MS (m/z): 311 ([M+H]$^+$, 100).

Example 327

Synthesis of 2-amino-4-(4-morpholino-ethoxy)-6-(4-fluorophenyl)pyrido[3,2-d]pyrimidine To a solution of 2-acetamido-4-(1,2,4-triazolyl)-6-(4-fluorophenyl)-pyrido[3,2-d]pyrimidine (70 mg, 0.2 mmol) in N-(2-hydroxyethyl)morpholine (1 ml) and dioxane (4 ml) was added NaH (60% dispersion in mineral oil, 0.4 mmol, 8 mg). The reaction mixture was stirred at room temperature for 3 hours. The reaction mixture was diluted with dichloromethane and washed with brine and water. The combined organic layers were dried over Na$_2$SO$_4$. The residue was purified by preparative TLC, the mobile phase being a methanol/dichloromethane mixture in a ratio of 10:90, yielding the pure title compound (42 mg, yield: 57%) which was characterised as follows: MS (m/z): 370 ([M+H]$^+$, 100).

Examples 328 to 333

Synthesis of 2-acetamido-4-cycloalkylamino-6-chloro-pyrido[3,2-d]pyrimidines and 2-acetamido-4-arylamino-6-chloro-pyrido[3,2-d]pyrimidines To a solution of 2-acetamido-4,6-dichloro-pyrido[3,2-d]pyrimidine (0.83 mmol) in CH$_2$Cl$_2$ (10 ml) was added a suitable amine (3 equivalents). The reaction was stirred at room temperature for 1 hour. The solvents were evaporated in vacuo and the crude residue was purified by preparative TLC, the mobile phase being a methanol/dichloromethane mixture in a ratio of 10:90, yielding, in yields varying from 55% to 70% depending on the amine used, the pure title compounds which were characterised by their mass spectrum as follows:

2-acetamido-4-(N-acetylpiperazino)-6-chloro-pyrido[3,2-d]pyrimidine (example 328) MS (m/z): 349, 351 ([M+H]$^+$, 100). 2-acetamido-4-(N-methylpiperazino)-6-chloro-pyrido[3,2-d]pyrimidine (example 329) MS (m/z): 321, 323 ([M+H]$^+$, 100).
2-acetamido-4-(N-piperidino)-6-chloro-pyrido[3,2-d]pyrimidine (example 330) MS (m/z): 306, 308 ([M+H]$^+$, 100).
2-acetamido-4-(N-cyclohexylamino)-6-chloro-pyrido[3,2-d]pyrimidine (example 331) MS (m/z): 320, 322 ([M+H]$^+$, 100).
2-acetamido-4-[N-(3-methyl)-anilino]-6-chloro-pyrido[3,2-d]pyrimidine (example 332) MS (m/z): 328, 330 ([M+H]$^+$, 100).

2-acetamido-4-(N-morpholino)-6-chloro-pyrido[3,2-d]pyrimidine (example 333) MS (m/z): 308, 310 ([M+H]$^+$, 100).

Examples 334 to 339

Synthesis of 2-amino-4-cycloalkylamino-6-chloro-pyrido[3,2-d]pyrimidines and 2-amino-4-arylamino-6-chloro-pyrido[3,2-d]pyrimidines The appropriate 2-acetamido-4-cycloalkylamino-6-chloro-pyrido[3,2-d]pyrimidine or 2-acetamido-4-arylamino-6-chloro-pyrido[3,2-d]pyrimidine (0.5 mmol) was re-suspended in a mixture of dichloromethane (10 ml) and 0.3 N sodium ethoxide (10 ml). The reaction mixture was stirred overnight at room temperature. The solvents were evaporated in vacuo and the crude residue was purified by preparative TLC, using a mixture of methanol and dichloromethane (in a ratio of 10:90) as mobile phase, thus yielding in yields varying from 50% to 60% the pure title compounds which were characterised as follows.

2-amino-4-(N-acetylpiperazino)-6-chloro-pyrido[3,2-d]pyrimidine (example 334) MS (m/z): 307, 309 ([M+H]$^+$, 100.
2-amino-4-(N-methylpiperazino)-6-chloro-pyrido[3,2-d]pyrimidine (example 335) MS (m/z): 279, 281 ([M+H]$^+$, 100)
2-amino-4-(N-piperidino)-6-chloro-pyrido[3,2-d]pyrimidine (example 336). MS (m/z): 264, 266 ([M+H]$^+$, 100)
2-amino-4-(N-cyclohexylamino)-6-chloro-pyrido[3,2-d]pyrimidine (example 337) MS (m/z): 278, 280 ([M+H]$^+$, 100).
2-amino-4-[N-(3-methyl)-anilino]-6-chloro-pyrido[3,2-d]pyrimidine (example 338) MS (m/z): 286, 288 ([M+H]$^+$, 100).
2-amino-4-(N-morpholino)-6-chloro-pyrido[3,2-d]pyrimidine (example 339) MS (m/z): 266, 268 ([M+H]$^+$, 100).

Examples 340 to 353

Synthesis of 2-amino-4-cycloalkylamino-6-(p-acetamidophenyl)-pyrido(3,2-d)pyrimidines and 2-amino-4-arylamino-6-(p-acetamidophenyl)pyrido(3,2-d)pyrimidines To a solution of 2-amino-4-(alkylamino)-6-chloro-pyrido[3,2-d]pyrimidine (30 mg, 0.1 mmol) in dioxane (15 ml) was added 4-acetamidophenylboronic acid (27 mg, 0.15 mmol), tetrakis(triphenylphosphine)palladium(0) (20 mg, 0.017 mmol) and a solution of potassium carbonate (280 mg, 2.03 mmol) in water (5 ml). The reaction mixture was stirred at 80° C. for 30 minutes. The solvents were evaporated in vacuo, and the crude residue was purified by preparative TLC, using a mixture of methanol and dichloromethane (in a ratio of 10:90) as mobile phase, yielding in yields varying from 45 to 65% the pure title compounds which were characterised as follows:

2-amino-4-(N-acetylpiperazino)-6-(p-acetamidophenyl)-pyrido(3,2-d)pyrimidine (example 340) MS (m/z): 406 ([M+H]$^+$, 100).
2-amino-4-(N-piperidino)-6-(p-acetamidophenyl)-pyrido(3,2-d)pyrimidine (example 341) MS (m/z): 363 ([M+H]$^+$, 100).
2-amino-4-(N-methyl-piperazino)-6-(p-acetamidophenyl)-pyrido(3,2-d)pyrimidine (example 342) MS (m/z): 378 ([M+H]$^+$, 100)
2-amino-4-(N-cyclohexylamino)-6-(p-acetamidophenyl)-pyrido(3,2-d)pyrimidine (example 343) MS (m/z): 377 ([M+H]$^+$, 100).
2-amino-4-[N-(3-methyl)anilino]-6-(p-acetamidophenyl)-pyrido(3,2-d)pyrimidine (example 344) MS (m/z): 385 ([M+H]$^+$, 100).

Examples 345 to 350

Synthesis of 2-amino-4-alkoxy-6-chloro-pyrido(3,2-d)pyrimidines

A solution of 2-acetamido-4,6-dichloro-pyrido[3,2-d]pyrimidine (0.83 mmol) in CH$_2$Cl$_2$ (10 ml) was added to a solution of an appropriate alcohol (4 mmol) and NaH (0.4 mmol) in dichloromethane (1 ml). The reaction was stirred at room temperature for 1 hour. Then, an additional amount of NaH (0.1 mmol) is added and the reaction is further stirred at room temperature. The solvents were evaporated in vacuo and the crude residue was purified by preparative TLC, the mobile phase being a methanol/dichloromethane mixture in a ratio of 10:90.

2-amino-4-trifluoroethoxy-6-chloro-pyrido(3,2-d)pyrimidine (example 345) MS (m/z): 279, 281 ([M+H]$^+$, 100;
2-amino-4-ethoxy-6-chloro-pyrido(3,2-d)pyrimidine (example 346) MS (m/z): 225, 227 ([M+H]$^+$, 100)
2-amino-4-(methoxy-ethoxy)-6-chloro-pyrido(3,2-d)pyrimidine (example 347) MS (m/z): 255, 257 ([M+H]$^+$, 100)
2-amino-4-(isopropoxy)-6-chloro-pyrido(3,2-d)pyrimidine (example 348) MS (m/z): 239, 241 ([M+H]$^+$, 100)
2-amino-4-(cyclopropylmethyloxy)-6-chloro-pyrido(3,2-d)pyrimidine (example 349) MS (m/z): 251, 253 ([M+H]$^+$, 100). 2-amino-4-(4-morpholino-ethoxy)-6-chloropyrido(3,2-d)pyrimidine (example 350) MS (m/z): 310, 312 ([M+H]$^+$, 100)

Example 351

Synthesis of 2-amino-4-(trifluoroethoxy)-6-(4-fluorophenyl)-pyrido[3,2-d]pyrimidine To a degassed suspension of 2-amino-4-(trifluoroethoxy)-6-chloro-pyrido[3,2-d]pyrimidine (24 mg, 0.1 mmol), 4-fluorophenyl boronic acid (21 mg, 0.15 mmol), and potassium carbonate (280 mg, 2.03 mmol) in a mixture of dioxane (15 ml) and water (5 ml) was added a catalytic amount of tetrakis (triphenylphosphine)palladium(0) (20 mg, 0.017 mmol). The mixture was refluxed for 45 minutes. The solvents were evaporated in vacuo, and the crude residue was purified by preparative TLC, using a mixture of methanol and dichloromethane (in a ratio of 10:90) as mobile phase, yielding the pure title compound, which was characterised by its mass spectrum as follows: MS (m/z): 339 ([M+H]$^+$, 100).

Examples 352 to 357

Synthesis of 2-amino-4-alkoxy-6-(p-acetamidophenyl)-pyrido(3,2-d)pyrimidines

To a solution of 2-amino-4-alkoxy-6-chloro-pyrido[3,2-d] pyrimidine (0.1 mmol) in dioxane (15 ml) was added 4-acetamidophenylboronic acid (27 mg, 0.15 mmol), tetrakis (triphenylphosphine)palladium(0) (20 mg, 0.017 mmol) and a solution of potassium carbonate (280 mg, 2.03 mmol) in water (5 ml). The reaction mixture was stirred at 80° C. for 30 minutes. The solvents were evaporated in vacuo, and the crude residue was purified by preparative TLC, using a mixture of methanol and dichloromethane (in a ratio of 10:90) as mobile phase, yielding in yields varying from 40% to 60% the pure title compounds which were characterised as follows.

2-amino-4-trifluoro-ethoxy-6-(p-acetamidophenyl)-pyrido(3,2-d)pyrimidine (example 352) MS (m/z): 378 ([M+H]$^+$, 100) 2-amino-4-ethoxy-6-(p-acetamidophenyl)pyrido(3,2-d)pyrimidine (example 353) MS (m/z): 324 ([M+H]$^+$, 100)

2-amino-4-(methoxy-ethoxy)-6-(p-acetamidophenyl)-pyrido(3,2-d)pyrimidine (example 354) MS (m/z): 354 ([M+H]$^+$, 100)

2-amino-4-(isopropoxy)-6-(p-acetamidophenyl)-pyrido(3,2-d)pyrimidine (example 355) MS (m/z): 338 ([M+H]$^+$, 100)

2-amino-4-(cyclopropylmethyloxy)-6-(p-acetamidophenyl)-pyrido(3,2-d)pyrimidine (example 356) MS (m/z): 350 ([M+H]$^+$, 100)

2-amino-4-(4-morpholino-ethoxy)-6-(p-acetamidophenyl)-pyrido(3,2-d)pyrimidine (example 357) MS (m/z): 409 ([M+H]$^+$, 100).

Examples 358 to 364

Synthesis of 2-amino-4-(N-acyl-piperazin-1-yl]-6-(3,4-dimethoxyphenyl)-pyrido[3,2-d]pyrimidines To a solution of 2-amino-4-(N-piperazin-1-yl)-6-(3,4-dimethoxyphenyl)-pyrido[3,2-d]pyrimidine (35 mg, 96 μmol) in dichloromethane (2 ml) was added triethylamine (15 μl, 106 μmol), followed by an appropriate acyl chloride (105 μmol). After stirring for 30 minutes at room temperature, the reaction mixture was applied directly onto a plate of silica gel. Elution with mixtures of dichloromethane and methanol (6-10% MeOH in CH$_2$Cl$_2$) yielded the pure title compounds in yields ranging between 61% and 98% depending on the acyl chloride used. Details for each compound, including the starting acyl chloride and the mass spectrum characterisation, are as follows:

2-amino-4-[4-(N,N-dimethylcarbamoyl)piperazin-1-yl]-6-(3,4-dimethoxyphenyl)-pyrido[3,2-d]pyrimidine (example 358) was obtained from dimethylcarbamoyl chloride. MS (m/z): 438 ([M+H]$^+$, 100).

2-Amino-4-[N—(N,N-dimethylthiocarbamoyl)piperazin-1-yl]-6-(3,4-dimethoxy-phenyl)pyrido[3,2-d]pyrimidine (example 359) was obtained from N,N-dithiocarbamoyl chloride. MS (m/z): 454 [M+H]$^+$, 100).

2-amino-4-[N-(trimethylacetyl)piperazin-1-yl]-6-(3,4-dimethoxyphenyl)-pyrido[3,2-d]pyrimidine (example 360) was obtained from pivaloyl chloride; MS (m/z): 451 [M+H]$^+$, 100).

2-amino-4-[N-(4-pentenoyl)piperazin-1-yl]-6-(3,4-dimethoxyphenyl)-pyrido[3,2-d]pyrimidine (example 361) was obtained from 4-pentenoyl chloride; MS (m/z): 449 ([M+H]$^+$, 100).

2-amino-4-[4-(2-methylpropionyl)piperazin-1-yl]-6-(3,4-dimethoxyphenyl)-pyrido[3,2-d]pyrimidine (example 362) was obtained from isobutyryl chloride; MS (m/z): 437 [M+H]$^+$, 100).

2-amino-4-[4-(3,3-dimethylbutyryl)piperazin-1-yl]-6-(3,4-dimethoxyphenyl)-pyrido[3,2-d]pyrimidine (example 363) was obtained from 3,3-dimethyl butyryl chloride. MS (m/z): 465 ([M+H]$^+$, 100).

2-amino-4-[4-(2-propenoyl)piperazin-1-yl]-6-(3,4-dimethoxyphenyl)-pyrido[3,2-d]pyrimidine (example 364) was obtained from acryloyl chloride; MS (m/z): 421 ([M+H]$^+$, 100).

Examples 365 and 366

Synthesis of 2-amino-4-(N-(thio)-carbamoylpiperazin-1-yl]-6-(3,4-dimethoxyphenyl)-pyrido[3,2-d]pyrimidines To a solution of 2-amino-4-(N-piperazin-1-yl)-6-(3,4-dimethoxyphenyl)-pyrido[3,2-d]pyrimidine (35 mg, 96 μmol) in of dichloromethane (2 ml) was added an appropriate alkyl (thio)isocyanate (0.11 mmol). After stirring for 45 minutes at room temperature, the reaction mixture was applied directly onto a plate of silica gel. Elution with 10% MeOH in CH$_2$Cl$_2$ yielded the final compounds in yields varying from 97 to 100%, depending on the isocyanate used.

Example 365

(2-amino-4-[4-(N-butylcarbamoyl)piperazin-1-yl]-6-(3,4-dimethoxyphenyl)-pyrido[3,2-d]pyrimidine was obtained from n-butyl isocyanate; MS (m/z): 466 ([M+H]$^+$, 100).

Example 366

(2-amino-4-[4-(N-hexylcarbamoyl)piperazin-1-yl]-6-(3,4-dimethoxyphenyl)-pyrido[3,2-d]pyrimidine) was obtained from n-hexyl isocyanate; MS (m/z): 494 ([M+H]$^+$, 100).

Example 367

Synthesis of 2-amino-4-{4-[N-(tert-butoxycarbonyl)glycyl]piperazin-1-yl}-6-(3,4-di-methoxyphenyl)-pyrido[3,2-d]pyrimidine A solution of 2-amino-4-(N-piperazin-1-yl)-6-(3,4-dimethoxyphenyl)pyrido[3,2-d]pyrimidine (100 mg, 0.27 mmol), N-(tert-butoxycarbonyl)glycine (54 mg, 0.31 mmol), of N,N-diisopropylethylamine (DIPEA, 115 μl, 0.70 mmol)) and of obenzotriazol-1-yl-N,N,N',N'-tetramethyluronium tetrafluoroborate (140 mg, 0.44 mmol, TBTU) in dry N,N-dimethylformamide (3 ml) was stirred under an N$_2$ atmosphere for 4 h at room temperature. The reaction mixture was applied directly onto a plate of silica gel and purified twice by preparative thin layer chromatography (PTLC; 8 and 6% MeOH in CH$_2$Cl$_2$, respectively) yielding the pure title compound (27 mg, 52 μmol, yield: 19%) which was characterised by its mass spectrum as follows: MS (m/z): 524 ([M+H]$^+$, 100).

Example 368

Synthesis of 2-amino-4-(N-piperazin-1-yl)-6-(4-fluorophenyl)-pyrido-[3,2-d]pyrimidine A suspension of 2-amino-4-oxo-6-(4-fluorophenyl)-pyrido-[3,2-d]pyrimidine (1.97 g, 7.69 mmol), piperazine (2.69 g, 31.2 mmol), p-toluenesulfonic acid monohydrate (195 mg, 1.0 mmol), ammonium sulfate (156 mg, 1.2 mmol), 1,1,1,3,3,3-hexamethyldisilazane (8.5 ml, 40.3 mmol) in pyridine (40 ml) was heated at reflux for 4 days. Another aliquot of piperazine was added and the reaction mixture was heated at reflux for one more day. Upon cooling, the reaction mixture was evaporated with silica gel and purified twice on a silica gel column (15-20% methanol 1% triethylamine in dichloromethane) to afford the pure title compound (1.82 g, yield: 73%) which was characterised by its mass spectrum as follows: MS (m/z): 325 ([M+H]$^+$, 100).

Examples 369 to 374

Synthesis of 2-amino-4-(N-phenoxyacetyl-piperazin-1-yl)-6-(4-fluorophenyl)pteridines To a solution of 2-amino-4-(N-piperazin-1-yl)-6-(4-fluorophenyl)-pyrido[3,2-d]pyrimidine (40 mg, 0.12 mmol) in dry DMF (2 ml) was added an appropriate phenoxyacetic acid derivative (0.14 mmol), DIPEA (54 μl, 0.33 mmol) and TBTU (66 mg, 0.21 mmol) was stirred under an $N_2$ atmosphere for 3 h at room temperature. The reaction mixture was applied directly onto a plate of silica gel. PTLC in 8% MeOH in $CH_2Cl_2$ afforded the desired product in yields ranging from 9 to 54%, depending on the phenoxy acetic acid used.

2-amino-4-[4-(2-naphthoxy-acetyl)piperazin-1-yl]-6-(4-fluorophenyl)-pyrido[3,2-d]pyrimidine (example 369) was obtained from 2-naphthoxyacetic acid and was characterised by its mass spectrum as follows: MS (m/z): 509 ([M+H]$^+$, 100).

2-amino-4-[4-(3-methylphenoxy-acetyl)piperazin-1-yl]-6-(4-fluorophenyl)-pyrido[3,2-d]pyrimidine (example 370) was obtained from 3-methyl phenoxyacetic acid and was characterised by its mass spectrum as follows: MS (m/z): 473 ([M+H]$^+$, 100).

2-amino-4-[4-(3-chlorophenoxy-acetyl)piperazin-1-yl]-6-(4-fluorophenyl)-pyrido[3,2-d]pyrimidine (example 371) was obtained from 3-chloro-phenoxyacetic acid and was characterised by its mass spectrum as follows: MS (m/z): 493 ([M+H]$^+$, 100).

2-amino-4-[4-(2,4-dichlorophenoxy-acetyl)piperazin-1-yl]-6-(4-fluorophenyl)-pyrido[3,2-d]pyrimidine (example 372) was obtained from 2,4-di-chloro-phenoxyacetic acid and was characterised by its mass spectrum as follows: MS (m/z): 527 ([M+H]$^+$, 100).

2-amino-4-[4-(4-fluorophenoxy-acetyl)piperazin-1-yl]-6-(4-fluorophenyl)-pyrido[3,2-d]pyrimidine (example 373) was obtained from 4-fluoro-phenoxyacetic acid and was characterised by its mass spectrum as follows: MS (m/z): 477 ([M+H]$^+$, 100).

2-amino-4-[4-(4-bromophenoxy-acetyl)piperazin-1-yl]-6-(4-fluorophenyl)-pyrido[3,2-d]pyrimidine (example 374) was obtained from 4-bromo-phenoxyacetic acid and was characterised by its mass spectrum as follows: MS (m/z): 537 ([M+H]$^+$, 100).

Example 375

Synthesis of 2-acetylamino-4-(N-piperazin-1-yl)-6-chloro-pyrido[3,2-d]pyrimidine To a solution of crude 2-acetylamino-4,6-dichloropyrido[3,2-d]pyrimidine (1 g, 3.9 mmol) in $CH_2Cl_2$ (600 ml) was added piperazine (4.77 g, 55.4 mmol). The reaction mixture was stirred at room temperature for 45 minutes. Upon concentration under reduced pressure to 100 ml, the mixture is applied onto a column of silica gel. The mobile phase being a mixture of 10% methanol, 1% triethylamine in $CH_2Cl_2$, yielding the pure title compound (800 mg, yield: 67%) which was characterised by its mass spectrum as follows: MS (m/z): 307 ([M+H]$^+$, 100).

Example 376

Synthesis of 2-amino-4-(N-piperazin-1-yl)-6-chloro-pyrido[3,2-d]pyrimidine

To a solution of 2-acetylamino-4-(N-piperazin-1-yl)-6-chloro-pyrido[3,2-d]pyrimidine (800 mg, 2.61 mmol) in methanol (40 ml) and water (20 ml) was added potassium carbonate (1.14 g, 8.2 mmol). The reaction mixture was heated at reflux for 45 minutes and, upon cooling, extracted with of $CH_2Cl_2$ (500 ml). The layers were separated and the aqueous phase was extracted 5 times with a small amount of $CH_2Cl_2$. The combined organic phases were dried over $MgSO_4$, filtered and evaporated under reduced pressure to yield the crude title compound (630 mg, yield: 91%), which was used as such in the following reaction step and was characterised by its mass spectrum as follows: MS (m/z): 265 ([M+H]$^+$, 100).

Example 377

Synthesis of 2-amino-4-[4-(4-chlorophenoxy-acetyl)piperazin-1-yl]-6-chloro-pyrido[3,2-d]pyrimidine To a suspension of 2-amino-4-(N-piperazin-1-yl)-6-chloro-pyrido[3,2-d]pyrimidine (630 mg, 2.38 mmol) in dichloromethane (100 ml) was added triethylamine (405 μl, 2.85 mmol) followed by of 4-chlorophenoxyacetyl chloride (560 mg, 2.73 mmol). After stirring for 1 hour at room temperature (the reaction mixture clarifies immediately), the reaction was quenched with water. The layers were separated and the aqueous phase was extracted 2 times with a small amount of $CH_2Cl_2$. The combined organic phases were dried over $MgSO_4$, filtered and evaporated with silica gel. The crude residue was purified by silica gel flash chromatography, the mobile phase being a mixture of methanol and dichloromethane (in a ratio of 5:95), yielding the pure title compound (566 mg, yield: 55%) which was characterised by its mass spectrum as follows: MS (m/z): 433 ([M+H]$^+$, 100).

Examples 378 to 388

Synthesis of 2-amino-4-[N-(4-chlorophenoxy-acetyl)piperazin-1-yl]-6-aryl-pyrido-[3,2-d]pyrimidines and 2-amino-4-[N-(4-chlorophenoxy-acetyl)piperazin-1-yl]-6-heteroaryl-pyrido-[3,2-d]pyrimidines A suspension of 2-amino-4-[4-(4-chlorophenoxyacetyl)piperazin-1-yl]-6-chloropyrido[3,2-d]pyrimidine (40 mg, 92 μmol), potassium fluoride (22 mg, 0.37 mmol) and an appropriate (hetero)aryl boronic acid (0.11 mmol) in dioxane (2 ml) and of water (0.5 ml) was purged with nitrogen for 15 minutes. Then, tetrakis(triphenylphosphine)palladium(0), (6-10 mg, 5-9 μmol) was added and the reaction mixture was heated at reflux for 1 hour under a nitrogen atmosphere. Upon cooling, the mixture was applied directly onto a plate of silica gel. PTLC in 5% MeOH in $CH_2Cl_2$ afforded the final product in yields varying from 18 to 98%, depending on the aryl or heteroaryl boronic acid used.

2-amino-4-[N-(4-chlorophenoxyacetyl)piperazin-1-yl]-6-(4-cyanophenyl)pyrido-[3,2-d]pyrimidine (example 378) was obtained from 4-cyano-phenyl boronic acid and was characterised by its mass spectrum as follows: MS (m/z): 500 ([M+H]$^+$, 100).

2-amino-4-[N-(4-chlorophenoxyacetyl)piperazin-1-yl]-6-(4-trifluoromethylphenyl)-pyrido-[3,2-d]pyrimidine (example 379) was obtained from 4-trifluoromethyl-phenyl boronic acid and was characterised by its mass spectrum as follows: MS (m/z): 543 [M+H]$^+$, 100).

2-amino-4-[N-(4-chlorophenoxyacetyl)piperazin-1-yl]-6-(3-fluorophenyl)pyrido-[3,2-d]pyrimidine (example 380) was obtained from 3-fluoro-phenyl boronic acid and was characterised by its mass spectrum as follows: MS (m/z): 493 [M+H]$^+$, 100).

2-amino-4-[N-(4-chlorophenoxyacetyl)piperazin-1-yl]-6-(furan-3-yl)pyrido-[3,2-d]pyrimidine (example 381) was obtained from 3-furanyl boronic acid and was characterised by its mass spectrum as follows: MS (m/z): 465 [M+H]$^+$, 100).

2-amino-4-[N-(4-chlorophenoxyacetyl)piperazin-1-yl]-6-(thiophen-3-yl)pyrido-[3,2-d]pyrimidine (example 382)

was obtained from 3-thienyl boronic acid and was characterised by its mass spectrum as follows: MS (m/z): 481 [M+H]$^+$, 100). 2-amino-4-[N-(4-chlorophenoxyacetyl) piperazin-1-yl]-6-(3,4-difluorophenyl)pyrido-[3,2-d]pyrimidine (example 383) was obtained from 3,4-difluorophenyl boronic acid and was characterised by its mass spectrum as follows: MS (m/z): 511 [M+H]$^+$, 100).

2-amino-4-[N-(4-chlorophenoxyacetyl)piperazin-1-yl]-6-(4-chlorophenyl)pyrido-[3,2-d]pyrimidine (example 384) was obtained from 4-chloro-phenyl boronic acid and was characterised by its mass spectrum as follows: MS (m/z): 509 [M+H]$^+$, 100). 2-amino-4-[N-(4-chlorophenoxyacetyl)piperazin-1-yl]-6-(3-chlorophenyl)pyrido-[3,2-d]pyrimidine (example 385) was obtained from 3-chlorophenyl boronic acid and was characterised by its mass spectrum as follows: MS (m/z): 509 ([M+H]$^+$, 100).

2-amino-4-[N-(4-chlorophenoxyacetyl)piperazin-1-yl]-6-(pyridin-4-yl)pyrido-[3,2-d]pyrimidine (example 386) was obtained from 4-pyridinyl boronic acid and was characterised by its mass spectrum as follows: MS (m/z): 476 ([M+H]$^+$, 100).

2-amino-4-[N-(4-chlorophenoxyacetyl)piperazin-1-yl]-6-(3-chloro-4-fluorophenyl)-pyrido-[3,2-d]pyrimidine (example 387) was obtained from 3-chloro-4-fluoro-phenyl boronic acid and was characterised by its mass spectrum as follows: MS (m/z): 527 ([M+H]$^+$, 100).

2-amino-4-[N-(4-chlorophenoxyacetyl)piperazin-1-yl]-6-(propen-1-yl)pyrido-[3,2-d]pyrimidine (example 388) was obtained from trans-1-propen-1-yl boronic acid and was characterised by its mass spectrum as follows: MS (m/z): 439 ([M+H]$^+$, 100.

Examples 389 and 390

Synthesis of 2-amino-4-[N-(3-methyl-phenyl-carbamoyl)piperazin-1-yl]-6-aryl-pyrido[3,2-d]pyrimidine The following compounds were synthesized according to the general procedure of examples 156-162, using 3-methylphenyl isocyanate (instead of 3-chlorophenyl isocyanate), and were characterised by their mass spectrum as follows: 2-amino-4-[N-(3-methyl-phenyl-carbamoyl)-piperazin-1-yl]-6-phenyl-pyrido[3,2-d]pyrimidine (example 389): MS (m/z): 440 ([M+H]$^+$, 100). 2-amino-4-[N-(3-methylphenyl-carbamoyl)-piperazin-1-yl]-6-(4-fluorophenyl)-pyrido[3,2-d]pyrimidine (example 390): MS (m/z): 458 ([M+H]$^+$, 100).

Example 391

Synthesis of 2-amino-6-(4-fluorophenyl)-pyrido(3,2-d)pyrimidin-4(3H)thione

A suspension of 2-amino-6-(4-fluorophenyl)-pyrido(3,2-d)pyrimidin-4(3H)one (2.56 g, 10 mmol) and phosphorus pentasulfide (2.5 g, 11 mmol) in pyridine (200 ml) was refluxed for 4 hours. The reaction mixture was cooled down and the precipitate was filtered off, yielding the pure title compound, which was used without any further purification (2 g, yield: 73%) and was characterised by its mass spectrum as follows: MS (m/z): 273 ([M+H]$^+$, 100)

Example 392

Synthesis of 2-amino-4-thiomethyl-6-(4-fluorophenyl)-pyrido(3,2-d)pyrimidine

To a solution of 2-amino-6-(4-fluorophenyl)-pyrido(3,2-d) pyrimidin-4(3H)thione (55 mg, 0.2 mmol) in a 1 N NaOH solution (10 ml) was added methyliodide (0.2 mmol, 12 µl). The reaction was stirred at room temperature for 12 hours. The reaction mixture was diluted with diethylether and the organic layer was extracted with water. The combined organic layers were evaporated in vacuo and the crude residue was purified by preparative thin layer chromatography on silica, the mobile phase being a mixture of methanol and dichloromethane, in a ratio of 5:95, yielding the pure title compound (41 mg, yield: 72%) which was characterised by its mass spectrum as follows: MS (m/z): 287 ([M+H]$^+$, 100).

Examples 393 to 395

Synthesis of 2-amino-4-thioalkyl-6-(4-fluorophenyl) pyrido(3,2-d)pyrimidines

The same procedure as for the synthesis of 2-amino-4-thiomethyl-6-(4-fluorophenyl)-pyrido(3,2-d)pyrimidine was used, using an appropriate alkyl halide.

2-amino-4-thioethyl-6-(4-fluorophenyl)pyrido(3,2-d)pyrimidine (example 393) was obtained from iodoethane and was characterised by its mass spectrum as follows: MS (m/z): 301 ([M+H]$^+$, 100).

2-amino-4-thioisopropyl-6-(4-fluorophenyl)pyrido(3,2-d) pyrimidine (example 394) was obtained from 2-iodopropane and was characterised by its mass spectrum as follows: MS (m/z): 315. ([M+H]$^+$, 100).

2-amino-4-(2-methoxy-thioethyl)-6-(4-fluorophenyl)pyrido (3,2-d)pyrimidine (example 395) was obtained from 2-bromoethyl methyl ether and was characterised by its mass spectrum as follows: MS (m/z): 330 ([M+H]$^+$, 100).

Examples 396 to 401

Synthesis of 2-acetamido-4-alkylamino-6-(4-fluorophenyl)pyrido[3,2-d]pyrimidines To a suspension of 2-acetamido-4-(1,2,4-triazolyl)-6-(4-fluorophenyl)pyrido[3,2-d]pyrimidine (70 mg, 0.2 mmol) in dioxane (5 ml) was added a suitable amine (0.4 mmol). The reaction was stirred at room temperature for 24 hours. The solvents were evaporated in vacuo yielding the crude title compounds which were purified by preparative TLC on silica, using a mixture of methanol and dichloromethane, in a ratio of 10:90 as mobile phase, yielding the title compounds in yields varying from 58% to 78%, depending on the amine used.

2-acetamido-4-ethylamino-6-(4-fluorophenyl)pyrido[3,2-d] pyrimidine (example 396) was obtained from a solution of ethylamine in dioxane and was characterised by its mass spectrum as follows: MS (m/z): 326 ([M+H]$^+$, 100).

2-acetamido-4-isopropylamino-6-(4-fluorophenyl)pyrido[3,2-d]pyrimidine (example 397) was obtained from isopropylamine and was characterised by its mass spectrum as follows: MS (m/z): 340 ([M+H]$^+$, 100). 2-acetamido-4-(2-methoxy-ethylamino)-6-(4-fluorophenyl)pyrido[3,2-d] pyrimidine (example 398) was obtained from 2-methoxyethylamine and was characterised by its mass spectrum as follows: MS (m/z): 356 ([M+H]$^+$, 100).

2-acetamido-4-[3,4-(methylenedioxy)anilino]-6-(4-fluorophenyl)pyrido[3,2-d]pyrimidine (example 399) was obtained from 3,4-(methylenedioxy)aniline and was characterised by its mass spectrum as follows: MS (m/z): 418 ([M+H]$^+$, 100).

2-acetamido-4-(thiomorpholino-1,1-dioxide)-6-(4-fluorophenyl)pyrido[3,2-d]pyrimidine (example 400) was obtained from thiomorpholine-1,1-dioxide and was characterised by its mass spectrum as follows: MS (m/z): 316 ([M+H]⁺, 100).

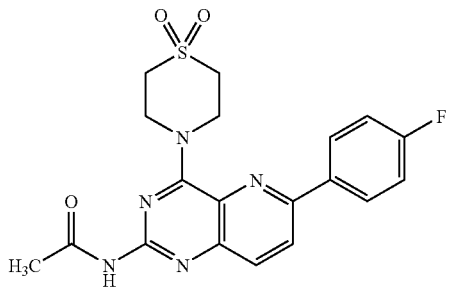

2-acetamido-4-(tetrahydro-3-thiophen-amino-1,1-dioxide)-6-(4-fluorophenyl)pyrido[3,2-d]pyrimidine (example 401)

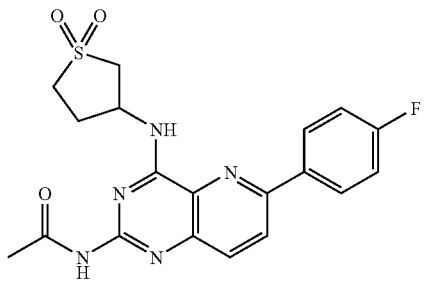

was obtained from tetrahydro-3-thiophen-amine-1,1-dioxide and was characterised by its mass spectrum as follows: MS (m/z): 316 ([M+H]⁺, 100).

Examples 402 to 407

Synthesis of 2-amino-4-alkylamino-6-(4-fluorophenyl)pyrido[3,2-d]pyrimidines

The crude 2-acetamido-4-alkylamino-6-(4-fluorophenyl)pyrido[3,2-d]pyrimidine (0.5 mmol) was suspended in a mixture of dichloromethane (10 ml) and 0.5 N sodium ethoxide (10 ml). The reaction mixture was stirred overnight at room temperature. The solvents were evaporated in vacuo and the crude residue was purified by preparative thin layer chromatography on silica, using a mixture of methanol and dichloromethane (in a volume ratio of 10:90) as a mobile phase providing, in yields varying from 45% to 65%, the pure title compounds which were characterised by their mass spectra as follows:

2-amino-4-ethylamino-6-(4-fluorophenyl)pyrido[3,2-d]pyrimidine (example 402): MS (m/z): 284 ([M+H]⁺, 100);

2-amino-4-isopropylamino-6-(4-fluorophenyl)pyrido[3,2-d]pyrimidine (example 403): MS (m/z): 298 ([M+H]⁺, 100);

2-amino-4-(2-methoxyethylamino)-6-(4-fluorophenyl)pyrido[3,2-d]pyrimidine (example 404): MS (m/z): 314 ([M+H]⁺, 100);

2-amino-4-[3,4-(methylenedioxy)anilino]-6-(4-fluorophenyl)pyrido[3,2-d]pyrimidine (example 405): MS (m/z): 376 ([M+H]⁺, 100);

2-amino-4-(thiomorpholino-1,1-dioxide)-6-(4-fluorophenyl)pyrido[3,2-d]pyrimidine (example 406): MS (m/z): 374 ([M+H]⁺, 100); and 2-amino-4-(tetrahydro-3-thiophen-amine-1,1-dioxide)-6-(4-fluorophenyl)pyrido[3,2-d]pyrimidine (example 407): MS (m/z): 374 ([M+H]⁺, 100).

Examples 408 to 411

Synthesis of 2-acetamido-4-(alkylamino)-6-(4-fluorophenyl)pyrido[3,2-d]pyrimidines To a suspension of 2-acetamido-4-(1,2,4-triazolyl)-6-(4-fluorophenyl)pyrido[3,2-d]pyrimidine (70 mg, 0.2 mmol) in dioxane (5 ml) was added a suitable amine hydrochloride (0.4 mmol) and triethylamine (0.6 mmol, 10 μl). The reaction was stirred at room temperature for 24 hours. The solvents were evaporated in vacuo yielding the crude title compounds which were purified by preparative thin layer chromatography on silica, using a mixture of methanol and dichloromethane, in a volume ratio of 10:90 as mobile phase, providing the title compounds in yields varying from 42% to 68%, depending on the amine hydrochloride used. The following indicates, for each compound, the starting amine hydrochloride and the mass spectrum characterising data.

2-acetamido-4-[1-(4-acetyl-piperazin-1-yl)-3-amino-propan-1-one]-6-(4-fluorophenyl)pyrido[3,2-d]pyrimidine (example 408)

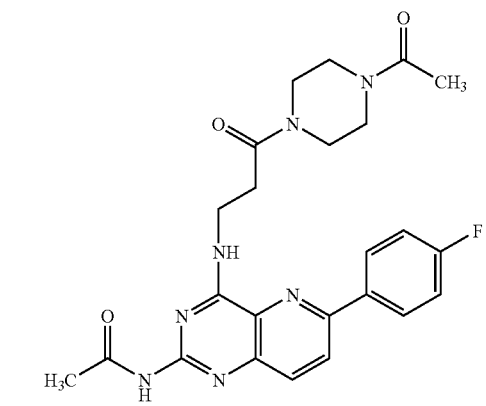

was obtained from 1-(4-acetyl-piperazin-1-yl)-3-amino-propan-1-one hydrochloride; MS (m/z): 480 ([M+H]⁺, 100).

2-acetamido-4-[2-amino-1-(4-methylpiperazin-1-yl)ethanone]-6-(4-fluorophenyl)pyrido[3,2-d]pyrimidine (example 409)

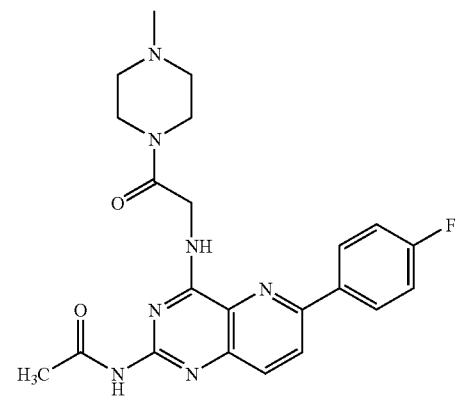

was obtained from 2-amino-1-(4-methylpiperazin-1-yl)etha-none dihydrochloride; MS (m/z): 438 ([M+H]+, 100).
2-acetamido-4-(3-methanesulfonyl-propylamino)-6-(4-fluo-rophenyl)pyrido[3,2-d]pyrimidine (example 410)

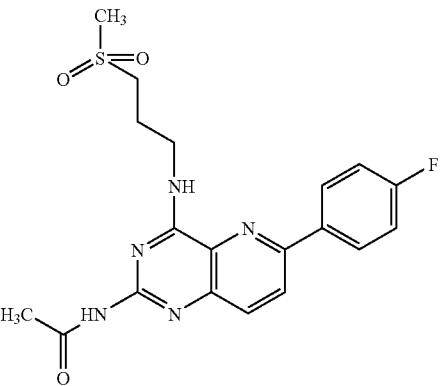

was obtained from 3-methanesulfonyl-propylamine hydro-chloride; MS (m/z): 418 ([M+H]+, 100).
2-acetamido-4-(2-amino-ethylmethylsulfone)-6-(4-fluo-rophenyl)pyrido[3,2-d]pyrimidine (example 411)

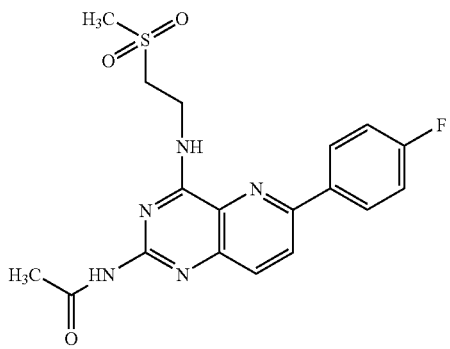

was obtained from 2-amino-ethyl methylsulfone hydrochlo-ride; MS (m/z): 404 ([M+H]+, 100).

Examples 412 to 415

Synthesis of 2-amino-4-(alkylamino)-6-(4-fluo-rophenyl)pyrido[3,2-d]pyrimidines

A suitable 2-acetamido-4-alkylamino-6-(4-fluorophenyl) pyrido[3,2-d]pyrimidine (0.5 mmol) was suspended in a mixture of dichloromethane (10 ml) and 0.5 N sodium ethoxide (10 ml). The reaction mixture was stirred overnight at room temperature. The solvents were evaporated in vacuo and the crude residue was purified by preparative thin layer chromatography on silica, using a mixture of methanol and dichloromethane (in a volume ratio of 10:90) as a mobile phase, providing in yields varying from 35% to 60% the pure title compounds which were characterised by their mass spectra.
2-amino-4-[1-(4-acetyl-piperazin-1-yl)-3-amino-propan-1-one]-6-(4-fluorophenyl)pyrido[3,2-d]pyrimidine (example 412): MS (m/z): 438 ([M+H]+, 100). 2-amino-4-[2-amino-1-(4-methylpiperazin-1-yl)ethanone]-6-(4-fluorophenyl)pyrido[3,2-d]pyrimidine (example 413); MS (m/z): 397 ([M+H]+, 100).

2-amino-4-[(3-methanesulfonyl)-propylamino]-6-(4-fluoro-phenyl)pyrido[3,2-d]pyrimidine (example 414); MS (m/z): 376 ([M+H]+, 100). 2-amino-4-[(2-aminoethyl)me-thylsulfone]-6-(4-fluorophenyl)pyrido[3,2-d]pyrimidine (example 415); MS (m/z): 362 ([M+H]+, 100).

Examples 416 to 418

Synthesis of 2-amino-4-alkoxy-6-(4-fluorophenyl) pyrido[3,2-d]pyrimidines

To a solution of 2-amino-4-thiomethyl-6-(4-fluorophe-nyl)-pyrido(3,2-d)pyrimidine (28 mg, 0.1 mmol) in an appropriate alcohol (5 ml) was added a lithium diisoproylamide solution in tetrahydrofurane (0.5 ml of a 2 M solution). This solution was stirred at 50° C. for 6 hours. The excess alcohol was evaporated in vacuo and the crude residue was further purified by preparative thin layer chromatography on silica, using a mixture of methanol and dichloromethane (in a volume ratio of 10:90) as a mobile phase, providing the pure title compounds in yields varying from 35 to 65%. The following indicates for each compound the starting alcohol and the mass spectrum characterising data:
2-amino-4-(2-butoxy-ethoxy)-6-(4-fluorophenyl)pyrido[3,2-d]pyrimidine (example 416) was obtained from 2-bu-toxyethanol; MS (m/z): 357 ([M+H]+, 100).
2-amino-4-(2-fluoro-ethoxy)-6-(4-fluorophenyl)pyrido[3,2-d]pyrimidine (example 417) was obtained from 2-fluoro-ethanol; MS (m/z): 303 ([M+H]+, 100); and
2-amino-4-[2-(methoxyethoxy)ethoxy]-6-(4-fluorophenyl) pyrido[3,2-d]pyrimidine (example 418) was obtained from 2-(2-methoxyethoxy)ethanol; MS (m/z): 359 ([M+H]+, 100).

Examples 419 to 423

Synthesis of 2-amino-4-benzyloxy-6-(4-fluoro)phenyl pyrido[3,2-d]pyrimidines

To a suspension of 2-acetamido-4-(1,2,4-triazolyl)-6-(4-fluorophenyl)pyrido[3,2-d]pyrimidine (70 mg, 0.2 mmol) in dichloromethane (10 ml) was added an appropriate benzyla-lcohol (0.6 mmol) and NaH (24 mg of a 60% dispersion, 0.6 mmol). The reaction was stirred at 30° C. for 24 hours. The solvents were evaporated in vacuo yielding the crude title compounds which were purified by preparative thin layer chromatography, using a mixture of methanol and dichloromethane, in a volume ratio of 10:90 as mobile phase, providing the pure title compounds in yields varying from 58% to 78%, depending on the benzylalcohol used. The following indicates for each compound the starting benzylalcohol and mass spectrum characterising data:
2-amino-4-(2-chloro-benzyloxy)-6-(4-fluorophenyl)pyrido [3,2-d]pyrimidine (example 419) was obtained from 2-chloro-benzylalcohol; MS (m/z): 381 ([M+H]+, 100). 2-amino-4-(4-fluoro-benzyloxy)-6-(4-fluorophenyl)py-rido[3,2-d]pyrimidine (example 420) was obtained from 4-fluoro-benzylalcohol; MS (m/z): 365 ([M+H]+, 100).
2-amino-4-(3-methyl-benzyloxy)-6-(4-fluorophenyl)pyrido [3,2-d]pyrimidine (example 421) was obtained from 3-me-thyl-benzylalcohol; MS (m/z): 361 ([M+H]+, 100).
2-amino-4-(4-trifluoromethyl-benzyloxy)-6-(4-fluorophe-nyl)pyrido[3,2-d]pyrimidine (example 422) was obtained from 4-trifluoromethyl-benzyl-alcohol; MS (m/z): 415 ([M+H]+, 100); and 2-amino-4-(4-cyano-benzyloxy)-6-(4-fluorophenyl)pyrido[3,2-d]pyrimidine (example 423) was obtained from 4-cyano-benzyl-alcohol; MS (m/z): 372 ([M+H]⁺, 100).

Example 424

Synthesis of 6-(4-fluorophenyl)-pyrido[3,2-d]pyrimidin-4(3H)one

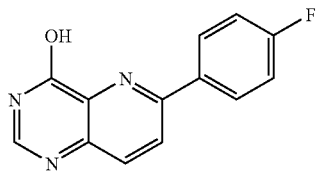

To a solution of 6-chloro-pyrido[3,2-d]pyrimidin-4(3H)one (1.0 g, 5.5 mmol) in dioxane (80 ml) and water (20 ml) was added 4-fluorophenylboronic acid (770 mg, 5.5 mmol), K$_2$CO$_3$ (2.28 g, 16.5 mmol), and tetrakis(triphenylphosphine)palladium(0) (290 mg, 0.25 mmol). The mixture was heated at reflux for 20 hours. After cooling to room temperature, the reaction mixture was neutralized to pH 5-6 with acetic acid, concentrated to a small volume, filtered and washed with water to yield a crude product. The crude residue was purified by silica gel flash chromatography, the mobile phase being a mixture of methanol and dichloromethane, in a volume ratio of 1:30, yielding the title compound as a white solid (1.2 g, yield: 90%) which was characterised by its mass spectrum as follows: MS (m/z): 242 ([M+H]⁺, 100).

Example 425

Synthesis of 4-chloro-6-(4-fluorophenyl)-pyrido[3,2-d]pyrimidine

To a mixture of 6-(4-fluorophenyl)-pyrido[3,2-d]-pyrimidin-4(3H)one (482 mg, 2 mmol) in toluene (20 ml), was added diisopropylethylamine (1.0 ml, 6 mmol) and phosphorus oxychloride (0.56 ml, 6 mmol). The reaction mixture was refluxed for 1 hour. After concentration under reduced pressure, the residue was extracted with dichloromethane (100 ml), and washed with ice water till pH 6-7. The combined organic layers were dried over MgSO$_4$, filtered and concentrated under reduced pressure yielding the title compound as a yellowish solid (0.50 g, yield 96%) which was characterised as follows: Rf=0.90 (MeOH/CH$_2$Cl$_2$=1/9).

Example 426

Synthesis of 4-amino-6-(4-fluorophenyl)-pyrido[3,2-d]pyrimidine)

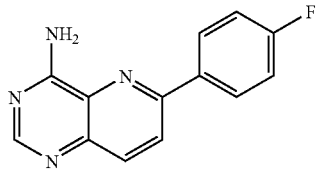

To an ammonia solution in methanol (5 ml of a 6 M solution) was added 4-chloro-6-(4-fluorophenyl)-pyrido[3,2-d]pyrimidine (26 mg, 0.1 mmol). The mixture was stirred at room temperature for 12 hours. After concentration under reduced pressure, the residue was purified by silica gel flash chromatography, the mobile phase being a mixture of methanol and dichloromethane, in a volume ratio of 1:30, yielding the title compound (20 mg, yield 83%) as a white solid which was characterised by its mass spectrum as follows: MS (m/z): 241 ([M+H]⁺, 100).

Example 427

Synthesis of 4-morpholino-6-(4-fluorophenyl)-pyrido[3,2-d]pyrimidine

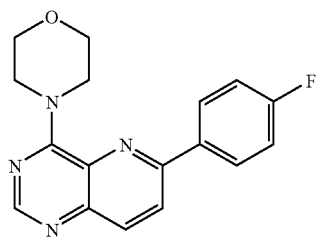

A mixture of 4-chloro-6-(4-fluorophenyl)-pyrido[3,2-d]pyrimidine (56 mg, 0.2 mmol) and morpholine (200 µl) in dioxane (5 ml) was refluxed for 1 hour. After concentration under reduced pressure, the residue was purified by silica gel flash chromatography, the mobile phase being a mixture of methanol and dichloromethane, in a volume ratio of 1:60, yielding the title compound (60 mg, yield 97%) as a white solid which was characterised by its mass spectrum as follows: MS (m/z): 311 ([M+H]⁺, 100).

Example 428

Synthesis of 4-phenoxy-6-(4-fluorophenyl)-pyrido[3,2-d]pyrimidine

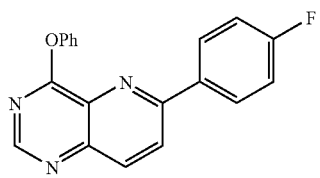

To a solution of phenol (94 mg, 1 mmol) in dioxane (5 ml) was added sodium hydride (40 mg of a 60% dispersion in mineral oil, 1.0 mmol). The mixture was stirred at room temperature for 10 minutes. Then, 4-chloro-6-(4-fluorophenyl)-pyrido[3,2-d]pyrimidine (52 mg, 0.2 mmol) was added to this solution. The resulting mixture was stirred at room temperature for another 30 minutes. After concentration under reduced pressure, the residue was purified by silica gel flash chromatography, the mobile phase being a mixture of methanol and dichloromethane, in a volume ratio of 1:60, yielding the title compound (60 mg, yield 95%) as a white

Example 429

Synthesis of 4-ethoxy-6-(4-fluorophenyl)-pyrido[3,2-d]pyrimidine

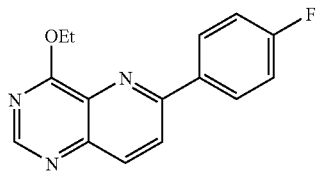

This compound was synthesized from 4-chloro-6-(4-fluorophenyl)-pyrido[3,2-d]pyrimidine and ethanol in 87% yield, using the procedure described for the synthesis of 4-phenoxy-6-(4-fluorophenyl)-pyrido[3,2-d]pyrimidine. The mass spectrum characterising data was as follows: MS (m/z): 270 ([M+H]$^+$, 100).

Example 430

Synthesis of 4-[3,4-(methylenedioxy)anilino]-6-(4-fluorophenyl)pyrido[3,2-d]pyrimidine

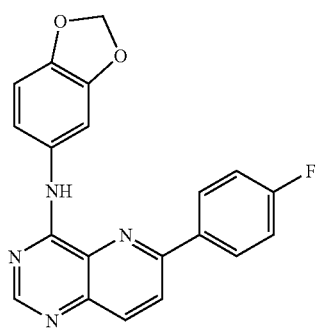

was synthesized from 4-chloro-6-(4-fluorophenyl)-pyrido[3,2-d]pyrimidine and 3,4-(methylendioxy)aniline in 94% yield, using the procedure described for the synthesis of 4-morpholino-6-(4-fluorophenyl)-pyrido[3,2-d]pyrimidine. The mass spectrum characterising data was as follows: MS (m/z): 361 ([M+H]$^+$, 100).

Example 431

Synthesis of 4-[2-(N,N-dimethylamino)ethoxy]-6-(4-fluorophenyl)-pyrido[3,2-d]pyrimidine

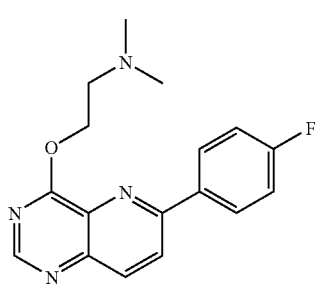

was synthesized from 4-chloro-6-(4-fluorophenyl)-pyrido[3,2-d]pyrimidine and 2-(N,N-dimethylamino)ethanol/NaH, in 20% yield, using the procedure described for the synthesis of 4-phenoxy-6-(4-fluorophenyl)-pyrido[3,2-d]pyrimidine. The mass spectrum characterising data was as follows: MS (m/z): 313 ([M+H]$^+$, 100).

Example 432

Synthesis of 4-(2-methoxyethoxy)-6-(4-fluorophenyl)-pyrido[3,2-d]pyrimidine

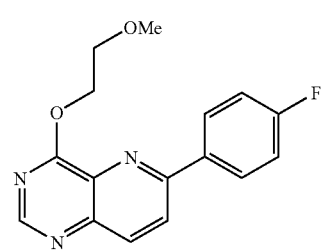

was synthesized from 4-chloro-6-(4-fluorophenyl)-pyrido[3,2-d]pyrimidine and 2-methoxyethanol in 78% yield, using the procedure described for the synthesis of 4-phenoxy-6-(4-fluorophenyl)-pyrido[3,2-d]pyrimidine The mass spectrum characterising data is as follows: MS (m/z): 300 ([M+H]$^+$, 100).

Example 433

Synthesis of 3-amino-6-(4-fluorophenyl)-pyridine-2-carboxylic acid amide

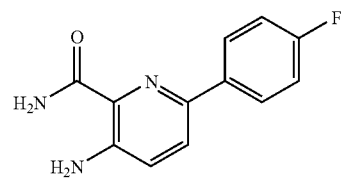

To a solution of 3-amino-6-chloropyridine-2-carboxylic acid amide (2.57 g, 15 mmol) in dioxane (200 ml) and water (50 ml) was added 4-fluorophenylboronic acid (2.1 g, 15 mmol), K$_2$CO$_3$ (6.2 g, 45 mmol), and tetrakis(triphenylphosphine) palladium(0) (860 mg, 0.75 mmol). The mixture was heated at reflux for 3 hours. After cooling to room temperature, the reaction mixture was concentrated to a small volume, filtrated and washed with water to yield a crude product. The residue was purified by silica gel flash chromatography, the mobile phase being a mixture of methanol and dichloromethane, in a volume ratio of 1:80, yielding the title compound (2.9 g, yield 85%) as a white solid. The mass spectrum characterising data was as follows: MS (m/z): 232 ([M+H]+, 100).

Example 434

Synthesis of 2-methyl-6-(4-fluorophenyl)-pyrido[3,2-d]pyrimidin-4(3H)one

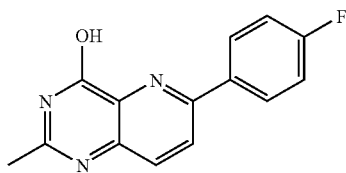

A suspension of 3-amino-6-(4-fluorophenyl)-pyridine-2-carboxylic acid amide (0.46 g, 2.0 mmol) in triethyl orthoacetate (10 ml) was heated under reflux for 3 hours. After cooling to room temperature, the precipitate was collected by filtration and washed with diethyl ether, yielded the title compound as a white solid (360 mg, yield 70%) which was characterised as follows: MS (m/z): 256 ([M+H]+, 100).

Example 435

Synthesis of 2-ethyl-6-(4-fluorophenyl)-pyrido[3,2-d]pyrimidin-4(3H)one

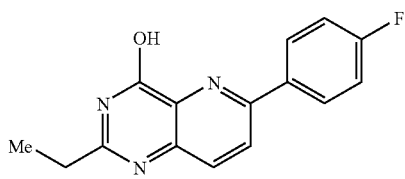

was synthesized from 3-amino-6-(4-fluorophenyl)-pyridine-2-carboxylic acid amide and triethyl orthopropioanate in 93% yield, using the procedure of example 434 and was characterised as follows: MS (m/z): 270 ([M+H]+, 100).

Example 436

Synthesis of 2-chloromethyl-6-(4-fluorophenyl)-pyrido[3,2-d]pyrimidin-4(3H)one

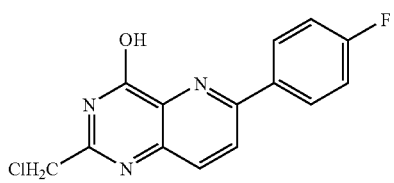

was synthesized from 3-amino-6-(4-fluorophenyl)-pyridine-2-carboxylic acid amide and trietyl orthochloroacetate in 93% yield, using the procedure of example 434 and was characterised as follows: MS (m/z): 290 ([M+H]+, 100).

Examples 437 and 438

Synthesis of 2-methyl-4-chloro-6-(4-fluorophenyl)-pyrido[3,2-d]pyrimidine and 2-methyl-4-(N,N-diethylamino)-6-(4-fluorophenyl)-pyrido[3,2-d]pyrimidine

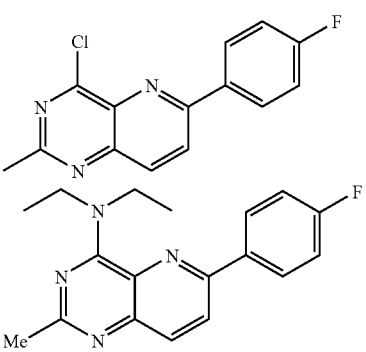

To a suspension of 2-methyl-6-(4-fluorophenyl)-pyrido[3,2-d]pyrimidin-4(3H)one (0.255 g, 1.0 mmol) in dioxane (10 ml) was added triethylamine (0.41 ml, 3 mmol) and POCl$_3$ (0.28 ml, 3 mmol). The mixture was refluxed for 1 hour. After concentration under reduced pressure, the residue was extracted with dichloromethane (100 ml) and washed with ice water till pH=6-7. The combined organic layers were dried over MgSO$_4$, filtrated and concentrated under reduced pressure. The crude residue was purified by silica gel flash chromatography, the mobile phase being a mixture of methanol and dichloromethane in a volume ratio gradually ranging from 1:50 to 1:10, yielding two compounds which were characterised as follows:

2-methyl-4-chloro-6-(4-fluorophenyl)-pyrido[3,2-d]pyrimidine (example 437) as a white solid (yield 28%): MS (m/z): 274 ([M+H]+, 100); and 2-methyl-4-(N,N-diethylamino)-6-(4-fluorophenyl)-pyrido[3,2-d]pyrimidine (example 438) as a yellowish solid (yield 48%); MS (m/z): 311 ([M+H]+, 100).

Example 439

Synthesis of 3-amino-6-(3-fluorophenyl)-pyridine-2-carboxylic acid amide

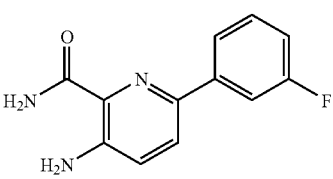

was synthesized from 3-amino-6-chloropyridine-2-carboxylic acid amide and 3-fluorophenylboronic acid in 92% yield as a white solid, using the procedure described for the synthesis of 3-amino-6-(4-fluorophenyl)-pyridine-2-carboxylic acid amide. The mass spectrum was as follows: MS (m/z): 232 ([M+H]+, 100).

Example 440

Synthesis of 2,4-dihydroxy-6-(3-fluorophenyl)-pyrido[3,2-d]pyrimidine

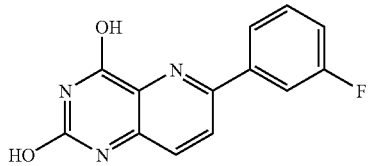

A mixture of 3-amino-6-(3-fluorophenyl)-pyridine-2-carboxylic acid amide (0.46 g, 2.0 mmol) and triphosgene (0.30 g, 1.0 mmol) in dioxane (10 ml) was heated under reflux for 2 hours. After cooling to room temperature, the precipitate was collected by filtration and washed with diethyl ether. The title compound was obtained as a yellowish solid (410 mg, yield 80%) which was characterised as follows: MS (m/z): 258 ([M+H]+, 100).

Example 441

Synthesis of 2,4-dihydroxy-6-(4-fluorophenyl)-pyrido[3,2-d]pyrimidine

This compound was synthesized in 90% yield according to the procedure of example 440, using 3-amino-6-(4-fluorophenyl)-pyridine-2-carboxylic acid amide as starting material. The mass spectrum was as follows: MS (m/z): 258 ([M+H]+, 100).

Example 442

Synthesis of 2,4-dichloro-6-(4-fluorophenyl)-pyrido[3,2-d]pyrimidine

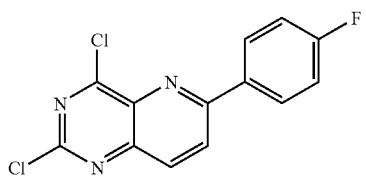

A suspension of 2,4-dihydroxy-6-(4-fluorophenyl)-pyrido[3,2-d]pyrimidine (0.52 g, 2.0 mmol) in phosphorus oxychloride (10 ml) and diisopropylethylamine (1 ml) was refluxed for 6 hours. After concentration under reduced pressure, the residue was extracted with dichloromethane (100 ml) and washed with ice water till pH=6-7. The combined organic layers were dried over MgSO4, filtered and concentrated under reduced pressure. The crude residue was purified by silica gel flash chromatography, the mobile phase being a mixture of methanol and dichloromethane, in a volume ratio of 1:50, yielding the title compound as a white solid (400 mg, yield 68%) which was characterised as follows: MS (m/z): 295 ([M+H]+, 100).

Example 443

Synthesis of 2-methyl-4-amino-6-(4-fluorophenyl)-pyrido[3,2-d]pyrimidine

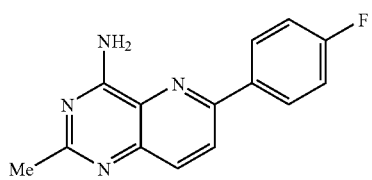

This compound was synthesized from 2-methyl-4-chloro-6-(4-fluorophenyl)pyrido[3,2-d]pyrimidine and a ammonia solution in methanol in 99% yield, using the procedure described for the synthesis of 4-amino-6-(4-fluorophenyl)-pyrido[3,2-d]pyrimidine. The mass spectrum was as follows: MS (m/z): 255 ([M+H]+, 100).

Example 444

Synthesis of 2,4-diethoxy-6-(4-fluorophenyl)-pyrido[3,2-d]pyrimidine

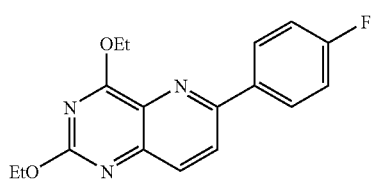

Sodium hydride (80 mg of a 60% dispersion in mineral oil, 2.0 mmol) was added to absolute ethanol (10 ml). The mixture was stirred at room temperature for 10 minutes. Then, 2,4-dichloro-6-(4-fluorophenyl)-pyrido[3,2-d]pyrimidine (60 mg, 0.2 mmol) was added to this solution. The resulting mixture was stirred at room temperature for another 40 minutes. After concentration under reduced pressure, the residue was purified by silica gel flash chromatography, the mobile phase being a mixture of ethanol and dichloromethane, in a volume ratio of 1:200, yielding the pure title compound (48 mg, yield 77%) as a white solid which was characterised as follows: MS (m/z): 314 ([M+H]+, 100).

Example 445

Synthesis of 2,4-diisopropoxy-6-(4-fluorophenyl)-pyrido[3,2-d]pyrimidine

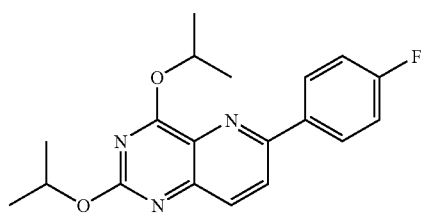

was synthesized from isopropanol in 65% yield, using the procedure described in example 444. The mass spectrum was as follows: MS (m/z): 342 ([M+H]+, 100).

Example 446

Synthesis of 2,4-di-(2-methoxy-ethoxy)-6-(4-fluorophenyl)-pyrido[3,2-d]pyrimidine

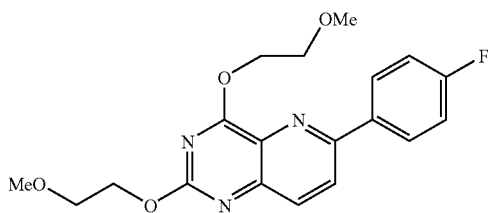

was synthesized from 2-methoxyethanol in 80% yield, using the procedure described described in example 444. The mass spectrum was as follows: MS (m/z): 374.1 ([M+H]+, 100).

Example 447

Synthesis of 2-methyl-4-(2-methoxyethoxy)-6-(4-fluorophenyl)-pyrido[3,2-d]pyrimidine

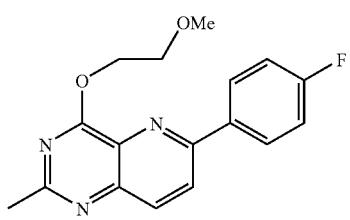

Sodium hydride (80 mg of a 60% dispersion in mineral oil, 2.0 mmol) was added to 2-methoxyethanol (10 ml). The mixture was stirred at room temperature for 10 minutes. Then, 2-methyl-4-chloro-6-(4-fluorophenyl)-pyrido[3,2-d]pyrimidine (110 mg, 0.4 mmol) was added to this solution. The resulting mixture was stirred at room temperature for another 40 minutes. After concentration under reduced pressure, the residue was purified by silica gel flash chromatography, the mobile phase being a mixture of ethanol and dichloromethane, in a volume ratio of 1:100, affording the pure title compound (110 mg, yield 88%) as a white solid which was characterised as follows: MS (m/z): 314 ([M+H]+, 100).

Example 448

Synthesis of 2-chloro-4-(3-methoxypropylamino)-6-(4-fluorophenyl)pyrido[3,2-d]pyrimidine

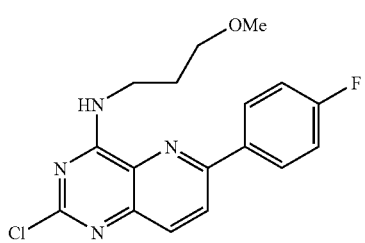

A mixture of 2,4-dichloro-6-(4-fluorophenyl)-pyrido[3,2-d]pyrimidine (60 mg, 0.2 mmol) and 3-methoxypropylamine (89 mg, 1.0 mmol) in dioxane (5 ml) was stirred at room temperature for 1 hour. After concentration under reduced pressure, the residue was purified by silica gel flash chromatography, the mobile phase being a mixture of methanol/dichloromethane in a volume ratio of 1:80, affording the pure title compound (69 mg, yield 99%) as a white solid which was characterised as follows: MS (m/z): 347 ([M+H]+, 100).

Example 449

Synthesis of 2-chloro-4-ethylamino-6-(4-fluorophenyl)-pyrido[3,2-d]pyrimidine

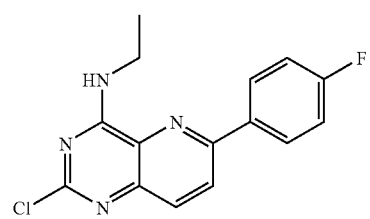

was synthesized from 2,4-dichloro-6-(4-fluorophenyl)-pyrido[3,2-d]pyrimidine and ethylamine in 99% yield, as a white solid which was characterised as follows: MS (m/z): 303 ([M+H]+, 100).

Example 450

Synthesis of 2-ethyl-4-(2-methoxyethoxy)-6-(4-fluorophenyl)-pyrido[3,2-d]pyrimidine

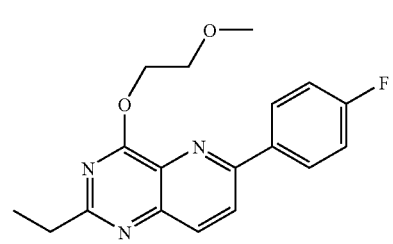

was synthesized from 2-ethyl-6-(4-fluorophenyl)-4-hydroxyl pyrido[3,2-d]pyrimidine and 2-methoxyethanol in 46% yield, using the procedure described for the synthesis of 2-methyl-4-(2-methoxyethoxy)-6-(4-fluorophenyl)-pyrido[3,2-d]pyrimidine. The mass spectrum was as follows: MS (m/z): 328 ([M+H]+, 100).

Example 451

Synthesis of 2-chloro-4-isopropoxy-6-(4-fluorophenyl)-pyrido[3,2-d]pyrimidine

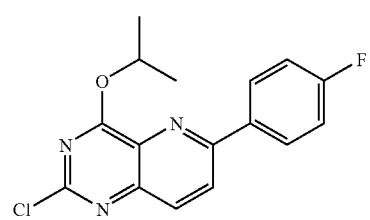

Sodium hydride (12 mg of a 60% of a dispersion in mineral oil, 0.3 mmol) was added to isopropanol (5 ml). The mixture was stirred at room temperature for 10 minutes. Then, 2,4-dichloro-6-(4-fluorophenyl)-pyrido[3,2-d]pyrimidine (60 mg, 0.2 mmol) was added to this solution. The resulting mixture was stirred at room temperature for another 40 minutes. After concentration under reduced pressure, the residue was purified by silica gel flash chromatography, the mobile phase being a mixture of isopropanol and dichloromethane in a volume ratio of 1:200, yielding the pure title compound (21 mg, yield 30%) as a white solid which was characterised as follows: MS (m/z): 318 ([M+H]+, 100).

Example 452

Synthesis of 2-methyl-4-ethoxy-6-(4-fluorophenyl)-pyrido[3,2-d]pyrimidine

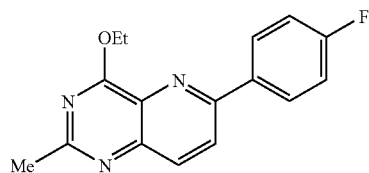

was synthesized from 2-methyl-4-chloro-6-(4-fluorophenyl)-pyrido[3,2-d]pyrimidine and ethanol in 99% yield, using the procedure described in example 447. The mass spectrum was as follows: MS (m/z): 284 ([M+H]+, 100).

Examples 453 to 468

The synthetic procedure is shown in scheme I below, including illustrative but non-limiting solvents, reaction temperature and reagents.

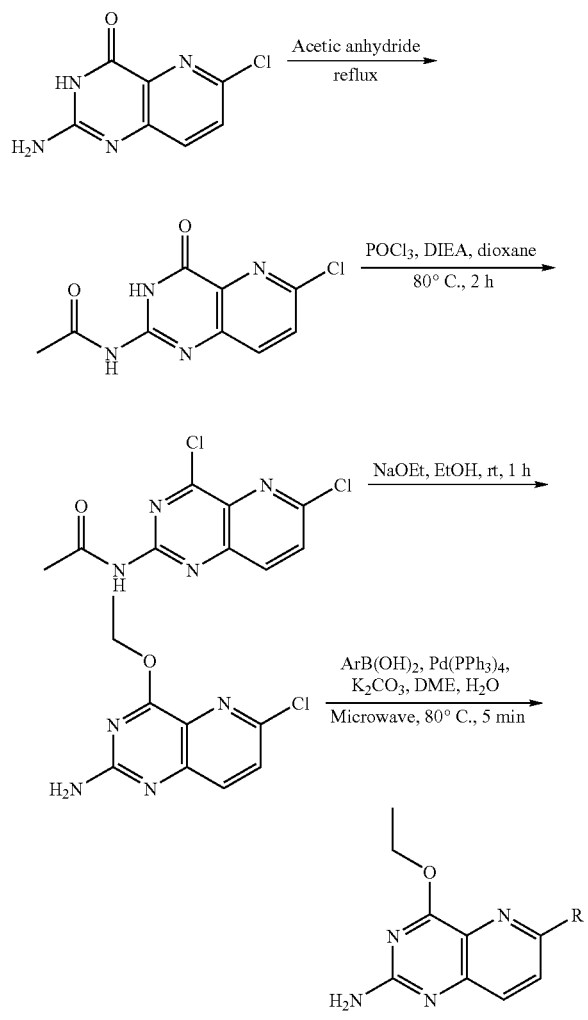

Example 453

Synthesis of N-(4,6-dichloro-pyrido[3,2-d]pyrimidin-2-yl)-acetamide

To a suspension of 2-acetamido-6-chloro-3H-pyrido[3,2-d]pyrimidin-4-one (2.38 g, 10 mmol) and DIEA (5.2 mL, 30 mmol) in dioxane (120 mL) was added POCl$_3$ (2.8 mL, 30 mmol). The mixture was heated to 80° C. for 2 hours. After removal of solvent, the residue was stirred with crashed ice for 10 minutes, then extracted with ethyl acetate. The organic layer was washed with brine, dried over sodium sulfate and concentrated to dryness providing the pure title compound as a brown solid (2.01 g, yield 78%) which was characterised as follows: MS (m/z) 256.9 [M+H]+.

Example 454

Synthesis of 6-chloro-4-ethoxy-pyrido[3,2-d]pyrimidin-2-ylamine

To a suspension of N-(4,6-dichloro-pyrido[3,2-d]pyrimidin-2-yl)-acetamide (0.98 g, 3.8 mmol) in ethanol (35 mL) was added a solution of 21% Na ethanolate in ethanol (2.8 mL, 7.6 mmol). After stirring at room temperature for one hour, the solution was diluted with ethyl acetate then washed with brine. The aqueous layer was extracted with dichloromethane. The combined organic layers were dried over Na$_2$SO$_4$ and concentrated to yield the pure title compound as a beige solid (0.6 g, yield 70%) which was characterised as follows: MS (m/z) 225.6 [M+H]+.

Examples 455 to 467

Synthesis of 6-aryl-4-ethoxy-pyrido[3,2-d]pyrimidin-2-ylamines and 6-heteroaryl-4-ethoxy-pyrido[3,2-d]pyrimidin-2-ylamines A mixture of 6-chloro-4-ethoxy-pyrido[3,2-d]pyrimidin-2-ylamine (23 mg, 0.1 mmol), potassium carbonate (27 mg, 0.2 mmol), tetrakis(triphenylphosphine) palladium (8 mg, 0.007 mmol) and the corresponding boronic acid or pinacol ester (0.12 mmol) in DME (1.5 mL) and water (1 mL) was heated to 100° C. for 10 minutes under microwave irradiation. Solvents were concentrated in vacuo and the residue was purified by RP HPLC using a C18 column with a gradient of H$_2$O, 0.1% TFA-acetonitrile, to provide the desired product. This procedure provided, with yields ranging from 5% to 65% depending upon the aryl or heteroaryl group introduced at the 6-position of the pyrido[3,2-d]pyrimidine ring system, the following pure title compounds represented by the structural formula below, which were characterized by their mass spectra as indicated in Table 1.

TABLE 1

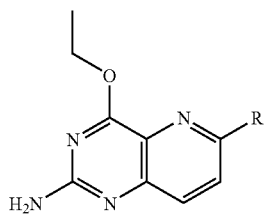

| Example | R | Name | M + H |
|---|---|---|---|
| 455 | phenyl | 4-ethoxy-6-phenyl-pyrido[3,2-d]pyrimidin-2-ylamine | 267.7 |
| 456 | pyridin-4-yl | 4-ethoxy-6-pyridin-4-yl-pyrido[3,2-d]pyrimidin-2-ylamine | 268.5 |
| 457 | 4-methylphenyl | 4-ethoxy-6-p-tolyl-pyrido[3,2-d]pyrimidin-2-ylamine | 281.7 |
| 458 | 4-CF$_3$-phenyl | 4-ethoxy-6-(4-trifluoromethyl-phenyl)-pyrido[3,2-d]pyrimidin-2-ylamine | 335.9 |
| 459 | 4-OMe-3-F-phenyl | 4-ethoxy-6-(3-fluoro-4-methoxy-phenyl)-pyrido[3,2-d]pyrimidin-2-ylamine | 315.9 |
| 460 | 3,4-difluorophenyl | 6-(3,4-difluoro-phenyl)-4-ethoxy-pyrido[3,2-d]pyrimidin-2-ylamine | 303.8 |
| 461 | 4-OMe-phenyl | 4-ethoxy-6-(4-methoxy-phenyl)-pyrido[3,2-d]pyrimidin-2-ylamine | 297.8 |
| 462 | 4-F-3-Cl-phenyl | 6-(3-chloro-4-fluoro-phenyl)-4-ethoxy-pyrido[3,2-d]pyrimidin-2-ylamine | 319.8 |
| 463 | 4-Cl-phenyl | 6-(4-chloro-phenyl)-4-ethoxy-pyrido[3,2-d]pyrimidin-2-ylamine | 301.0 |
| 464 | 4-Cl-3-F-phenyl | 6-(4-chloro-3-fluoro-phenyl)-4-ethoxy-pyrido[3,2-d]pyrimidin-2-ylamine | 319.0 |
| 465 | 4-NH$_2$-phenyl | 6-(4-amino-phenyl)-4-ethoxy-pyrido[3,2-d]pyrimidin-2-ylamine | 282.0 |

TABLE 1-continued

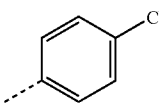

| Example | R | Name | M + H |
|---|---|---|---|
| 466 | (4-CN-phenyl) | 4-(2-amino-4-ethoxy-pyrido[3,2-d]pyrimidin-6-yl)-benzonitrile | 292.1 |
| 467 | (thiophen-2-yl) | 4-Ethoxy-6-thiophen-2-yl-pyrido[3,2-d]pyrimidin-2-ylamine | 273.0 |

Examples 468 to 498

The synthetic procedure is shown in scheme II below including non-limiting solvents and reaction temperature and reagents.

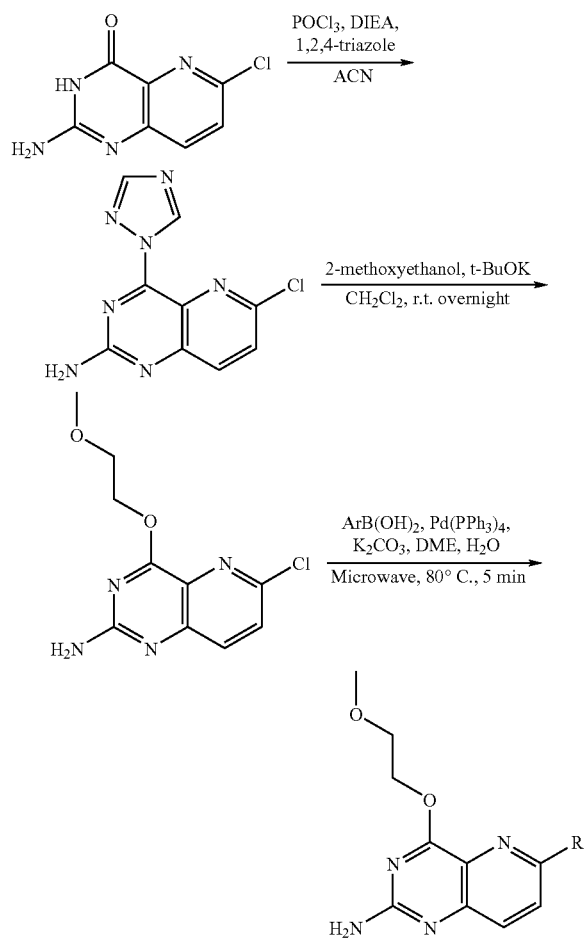

Example 468

Synthesis of 6-chloro-4-[1,2,4]triazol-1-yl-pyrido[3,2-d]pyrimidin-2-ylamine

A solution of 1,2,4-triazole (1.4 g, 20 mmol) and phosphorus oxychloride (1.4 mL, 15 mmol) in dry acetonitrile (40 mL) was adder to a stirred suspension of 2-amino-6-chloro-3H-pyrido[3,2-d]pyrimidin-4-one (1 g, 5 mmol) and DIEA (4.4 mL, 25 mmol) in dry acetonitrile (30 mL). The mixture was stirred at room temperature for 24 hours. 2 molar equivalents of 1,2,4-triazole (0.7 g, 10 mmol), 1.5 equivalent of phosphorus oxychloride (0.7 mL, 7.5 mmol) and 2.5 equivalents of DIEA (2.2 mL, 12.5 mmol) were added to the mixture. After stirring at room temperature for 48 hours, the same amount of the above reagents was added again. The reaction mixture was stirred for 7 full days and the yellow precipitate was filtered off, washed successively with acetonitrile, DCM and ether. The solid was dried under vacuum, providing the pure title compound as a yellow solid (667 mg, yield 53%) which was characterised as follows: MS (m/z) 248.8 [M+H]$^+$.

Example 469

Synthesis of 6-chloro-4-(2-methoxy-ethoxy)-pyrido[3,2-d]pyrimidin-2-ylamine

Potassium t-butoxide (4 mL, 4 mmol; 1 M in THF) was added to a suspension mixture of 6-chloro-4-[1,2,4]triazol-1-yl-pyrido[3,2-d]pyrimidin-2-ylamine (1 g, 4 mmol) and 2-methoxyethanol (0.32 mL, 4 mmol) in DCM (50 mL). After stirring at room temperature for 10 minutes, the mixture was diluted with DCM (100 mL) and washed with brine. The organic layer was dried over Na$_2$SO$_4$ and concentrated to afford the pure title compound as a beige solid (0.91 g, yield 90%) which was characterised as follows: MS (m/z) 225.0 [M+H]$^+$.

Examples 470 to 498

Synthesis of 6-aryl-4-(2-methoxy-ethoxy)-pyrido[3,2-d]pyrimidin-2-ylamines and 6-heteroaryl-4-(2-methoxy-ethoxy)-pyrido[3,2-d]pyrimidin-2-ylamines A mixture of 6-chloro-4-(2-methoxy-ethoxy)-pyrido[3,2-d]pyrimidin-2-ylamine (15 mg, 0.06 mmol), potassium carbonate (16 mg, 0.12 mmol), tetrakis(triphenylphosphine) palladium (10 mg) and a suitable boronic acid or pinacol ester (0.08 mmol) in DME (1 mL) and water (0.5 mL) was heated to 80° C. for 5 minutes by microwave. Solvents were concentrated in vacuo and the residue was purified by RP HPLC using a C18 column with a gradient of $H_2O$, 0.1% TFA-acetonitrile, to provide the desired product. This procedure provided, with yields ranging from 30% to 70% depending upon the aryl or heteroaryl group introduced at the 6-position of the pyrido[3,2-d]pyrimidine ring, the pure title compounds represented by the following structural formula, which were characterized by their mass spectrum MS as indicated in Table 2.

TABLE 2

| Example | R | Name | M + H |
|---|---|---|---|
| 470 | (2-methoxy-ethoxy) | 4,6-bis-(2-methoxy-ethoxy)-pyrido[3,2-d]pyrimidin-2-ylamine | 295.1 |
| 471 | 3,4-dimethoxy-phenyl | 6-(3,4-dimethoxy-phenyl)-4-(2-methoxy-ethoxy)-pyrido[3,2-d]pyrimidin-2-ylamine | 357.1 |
| 472 | phenyl | 4-(2-methoxy-ethoxy)-6-phenyl-pyrido[3,2-d]pyrimidin-2-ylamine | 297.1 |
| 473 | pyridin-4-yl | 4-(2-methoxy-ethoxy)-6-pyridin-4-yl-pyrido[3,2-d]pyrimidin-2-ylamine | 298.1 |
| 474 | p-tolyl | 4-(2-methoxy-ethoxy)-6-p-tolyl-pyrido[3,2-d]pyrimidin-2-ylamine | 311.1 |
| 475 | 4-trifluoromethyl-phenyl | 4-(2-methoxy-ethoxy)-6-(4-trifluoromethyl-phenyl)-pyrido[3,2-d]pyrimidin-2-ylamine | 365.1 |
| 476 | 3-fluoro-4-methoxy-phenyl | 6-(3-fluoro-4-methoxy-phenyl)-4-(2-methoxy-ethoxy)-pyrido[3,2-d]pyrimidin-2-ylamine | 345.1 |
| 477 | 3,4-difluoro-phenyl | 6-(3,4-difluoro-phenyl)-4-(2-methoxy-ethoxy)-pyrido[3,2-d]pyrimidin-2-ylamine | 333.1 |
| 478 | 4-methoxy-phenyl | 4-ethoxy-6-(4-methoxy-phenyl)-pyrido[3,2-d]pyrimidin-2-ylamine | 327.1 |
| 479 | 3-chloro-4-fluoro-phenyl | 6-(3-chloro-4-fluoro-phenyl)-4-(2-methoxy-ethoxy)-pyrido[3,2-d]pyrimidin-2-ylamine | 349.0 |

TABLE 2-continued

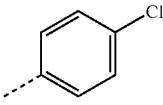

| Example | R | Name | M + H |
|---|---|---|---|
| 480 | 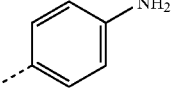 4-Cl-phenyl | 6-(4-chloro-phenyl)-4-(2-methoxy-ethoxy)-pyrido[3,2-d]pyrimidin-2-ylamine | 331.0 |
| 481 | 4-NH₂-phenyl | 6-(4-amino-phenyl)-4-(2-methoxy-ethoxy)-pyrido[3,2-d]pyrimidin-2-ylamine | 312.1 |
| 482 | thiophen-2-yl | 4-(2-methoxy-ethoxy)-6-thiophen-2-yl-pyrido[3,2-d]pyrimidin-2-ylamine | 303.5 |
| 483 | 4-Cl-3-F-phenyl | 6-(4-chloro-3-fluoro-phenyl)-4-(2-methoxy-ethoxy)-pyrido[3,2-d]pyrimidin-2-ylamine | 349.3 |
| 484 | 4-OH-phenyl | 4-[2-amino-4-(2-methoxy-ethoxy)-pyrido[3,2-d]pyrimidin-6-yl]-phenol | 313.3 |
| 485 | 2-OH-phenyl | 2-[2-amino-4-(2-methoxy-ethoxy)-pyrido[3,2-d]pyrimidin-6-yl]-phenol | 313.3 |
| 486 | 2,4-diF-phenyl | 6-(2,4-difluoro-phenyl)-4-(2-methoxy-ethoxy)-pyrido[3,2-d]pyrimidin-2-ylamine | 333.3 |
| 487 | 4-(tBuC(O)NH)-phenyl | N-{4-[2-amino-4-(2-methoxy-ethoxy)-pyrido[3,2-d]pyrimidin-6-yl]-phenyl}-2,2-dimethyl-propionamide | 396.5 |
| 488 | 4-SO₂Me-phenyl | 6-(4-methanesulfonyl-phenyl)-4-(2-methoxy-ethoxy)-pyrido[3,2-d]pyrimidin-2-ylamine | 375.5 |
| 489 | 4-(iPrC(O)NH)-phenyl | N-{4-[2-amino-4-(2-methoxy-ethoxy)-pyrido[3,2-d]pyrimidin-6-yl]-phenyl}-isobutyramide | 382.5 |

TABLE 2-continued

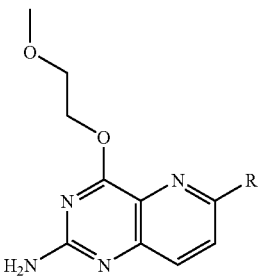

| Example | R | Name | M + H |
|---|---|---|---|
| 490 | | 6-(2,4-dimethyl-thiazol-5-yl)-4-(2-methoxy-ethoxy)-pyrido[3,2-d]pyrimidin-2-ylamine | 332.1 |
| 491 | | 6-(5,6-dihydro-4H-[1,3]oxazin-2-yl)-4-(2-methoxy-ethoxy)-pyrido[3,2-d]pyrimidin-2-ylamine | 380.1 |
| 492 | | 6-(4-isopropoxy-phenyl)-4-(2-methoxy-ethoxy)-pyrido[3,2-d]pyrimidin-2-ylamine | 355.1 |
| 493 | | 4-(2-methoxy-ethoxy)-6-(morpholine-4-sulfonyl)-pyrido[3,2-d]pyrimidin-2-ylamine | 446.5 |
| 494 | | {4-[2-amino-4-(2-methoxy-ethoxy)-pyrido[3,2-d]pyrimidin-6-yl]-phenyl}-methanol | 327.5 |
| 495 | | {4-[2-amino-4-(2-methoxy-ethoxy)-pyrido[3,2-d]pyrimidin-6-yl]-phenyl}-acetonitrile | 336.5 |
| 496 | | N-{4-[2-amino-4-(2-methoxy-ethoxy)-pyrido[3,2-d]pyrimidin-6-yl]-phenyl}-methanesulfonamide | 390.0 |
| 497 | | N-{4-[2-Amino-4-(2-methoxy-ethoxy)-pyrido[3,2-d]pyrimidin-6-yl]-benzyl}-acetamide | 368.3 |
| 498 | | N-{4-[2-Amino-4-(2-methoxy-ethoxy)-pyrido[3,2-d]pyrimidin-6-yl]-benzyl}-methanesulfonamide | 404.5 |

Examples 499 to 502

The synthetic procedure is shown in scheme III below including non-limiting solvents, reaction temperature and reagents.

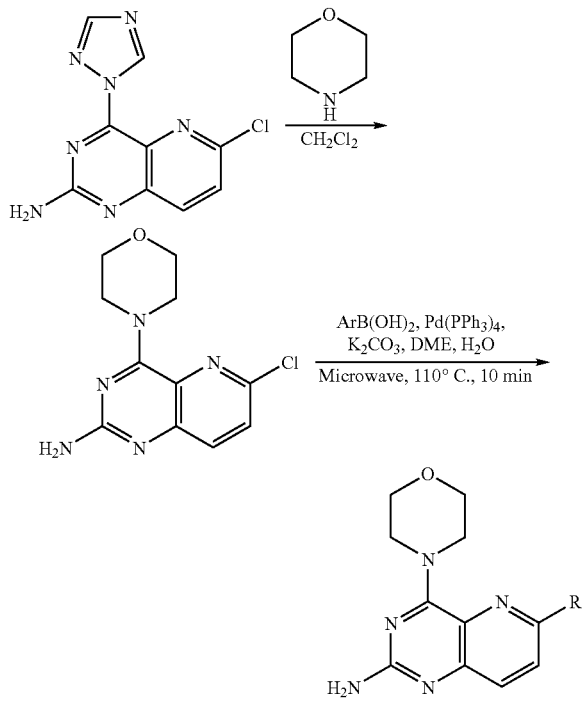

Example 499

Synthesis of 6-chloro-4-morpholin-4-yl-pyrido[3,2-d]pyrimidin-2-ylamine

A suspension of 6-chloro-4-[1,2,4]triazol-1-yl-pyrido[3,2-d]pyrimidin-2-ylamine (0.1 g, 0.4 mmol) and morpholine (0.07 mL, 0.8 mmol) in DCM (10 mL) was stirred at room temperature for 48 hours. After the removal of solvent, the residue was purified by flash chromatography (using 5% i-PrOH/DCM as the eluent), providing the title compound (0.26 g, 99% yield) as a yellow solid which was characterised as follows: MS (m/z) 266.0 [M+H]$^+$.

Examples 500 to 502

Synthesis of 6-aryl-4 morpholin-4-yl-pyrido[3,2-d]pyrimidin-2-ylamines

A mixture of 6-chloro-4-morpholin-4-yl-pyrido[3,2-d]pyrimidin-2-ylamine (20 mg, 0.075 mmol), potassium carbonate (21 mg, 0.15 mmol), tetrakis(triphenylphosphine) palladium (10 mg) and a suitable boronic acid or pinacol ester (0.082 mmol) in DME (1 mL) and water (0.5 mL) was heated to 110° C. for 10 minutes by microwave. Solvents were concentrated in vacuo and the residue was purified by RP HPLC using a C18 column with a gradient of H$_2$O, 0.1% TFA-acetonitrile, to provide, with yields ranging from 20% to 50% depending upon the aryl group introduced at the 6-position of the pyrido[3,2-d]pyrimidine ring, the pure title compounds represented by the following structural formula, which were characterized by their mass spectrum MS as indicated in Table 3 below.

TABLE 3

| Example | R | Name | M + H |
|---------|---|------|-------|
| 500 | ⌬–NHCOMe | N-[4-(2-amino-4-morpholin-4-yl-pyrido[3,2-d]pyrimidin-6-yl)-phenyl]-acetamide | 365.1 |
| 501 | ⌬–NHCOCH(CH₃)₂ | N-[4-(2-amino-4-morpholin-4-yl-pyrido[3,2-d]pyrimidin-6-yl)-phenyl]-isobutyramide | 393.2 |
| 502 | ⌬–NH₂ | 6-(4-amino-phenyl)-4-morpholin-4-yl-pyrido[3,2-d]pyrimidin-2-ylamine | 323.1 |

Examples 503 to 506

The synthetic procedure is shown in scheme IV below including non-limiting solvents, reaction temperature and reagents.

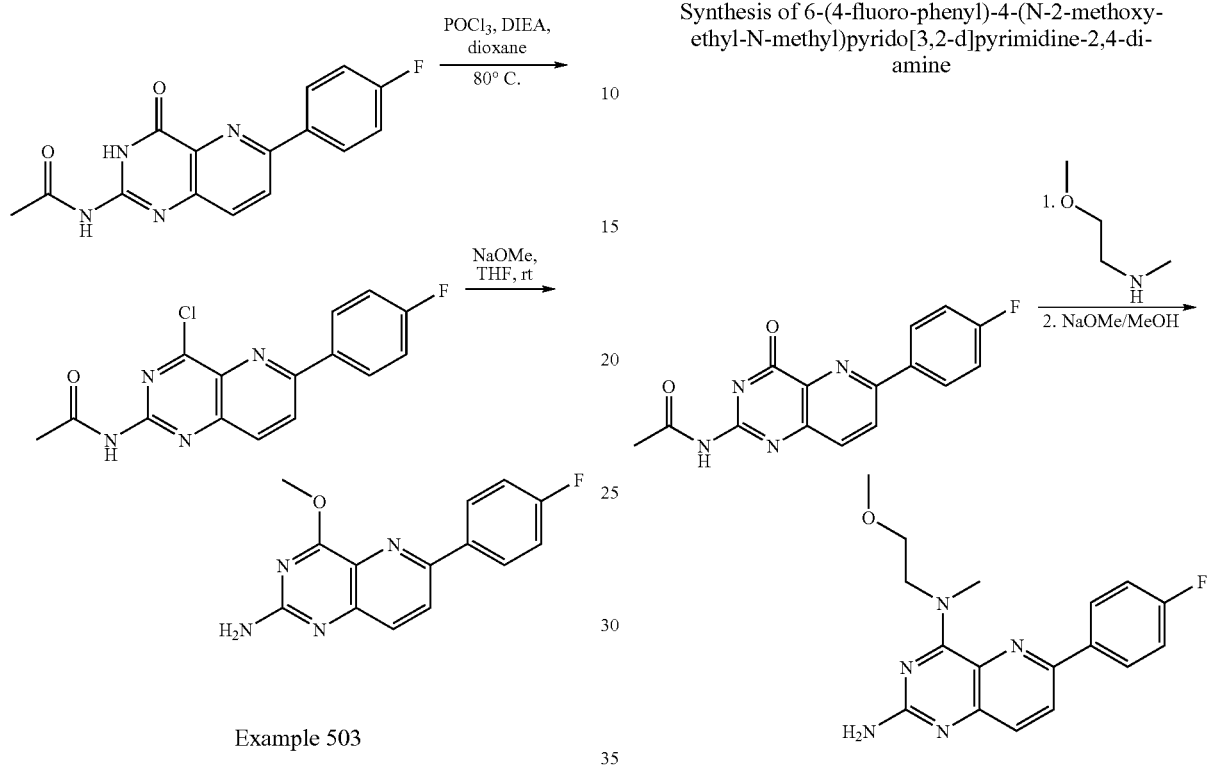

Example 503

Synthesis of N-[4-chloro-6-(4-fluoro-phenyl)-pyrido [3,2-d]pyrimidin-2-yl]-acetamide To a suspension of N-[6-(4-fluoro-phenyl)-4-oxo-3,4-dihydro-pyrido[3,2-d]pyrimidin-2-yl]-acetamide (0.77 g, 2.58 mmol) and DIEA (1.34 mL, 7.74 mmol) in dioxane (25 mL) was added POCl$_3$ (0.73 mL, 7.74 mmol). The mixture was heated to 80° C. for 30 minutes. After the removal of solvent, the residue was dissolved in ethyl acetate (200 mL) and the solution was filtered through a short column with silica gel. The column was additionally washed with ethyl acetate. The filtrate and washings were combined and concentrated. The precipitate formed was isolated by filtration to give the pure title compound as a brown solid (0.43 g, yield 43%) which was characterised as follows: MS (m/z) 317.0 [M+H]$^+$.

Example 504

Synthesis of 6-(4-fluoro-phenyl)-4-methoxy-pyrido [3,2-d]pyrimidin-2-ylamine Sodium methoxide (0.32 mL, 0.158 mmol; 0.5 N in MeOH) was added to a solution of N-[4-chloro-6-(4-fluoro-phenyl)-pyrido[3,2-d]pyrimidin-2-yl]-acetamide (20 mg, 0.063 mmol) in THF (1.5 mL). After stirring at room temperature for 20 minutes, solvents were concentrated in vacuo and the residue was purified by RP HPLC using a C18 column with a gradient of H$_2$O and 0.1% TFA-acetonitrile, to provide the pure title compound as a white solid (14 mg, yield 50%) which was characterised as follows: MS (m/z) 271.0 [M+H]$^+$.

Example 505

Synthesis of 6-(4-fluoro-phenyl)-4-(N-2-methoxyethyl-N-methyl)pyrido[3,2-d]pyrimidine-2,4-diamine

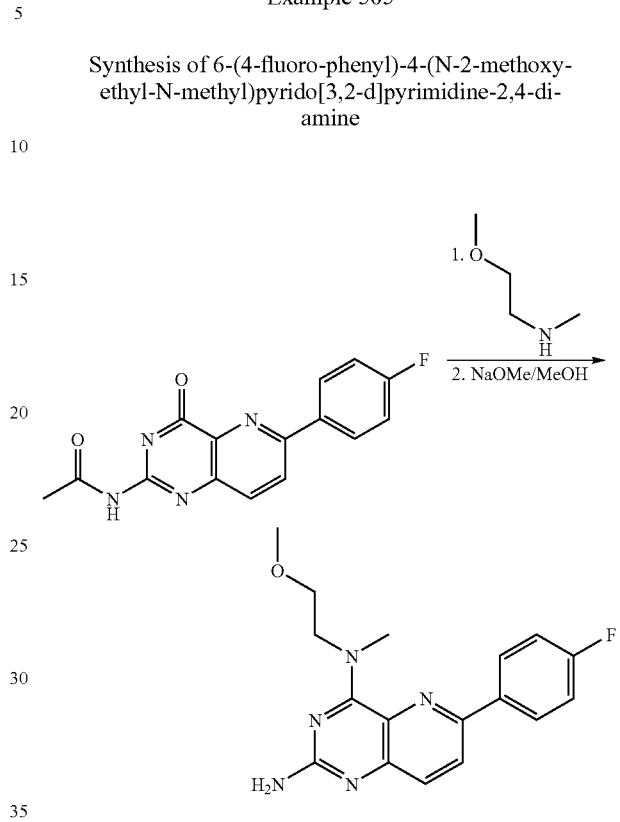

A mixture of N-[4-chloro-6-(4-fluorophenyl)-pyrido[3,2-d]pyrimidin-2-yl]-acetamide (25 mg, 0.08 mmol) and N-(2-methoxyethyl)methylamine (0.2 mL) in dioxane (1.5 mL) was heated to 80° C. for 5 minutes under microwave irradiation. Then, NaOMe (0.5 mL; 0.5 N in MeOH) was added and the mixture was heated to 70° C. for 5 minutes under microwave irradiation. Solvents were removed in vacuo and the residue was purified by RP HPLC, using a C18 column with a gradient of H$_2$O and 0.1% TFA-acetonitrile, to provide the pure title compound as a white solid (13.5 mg, yield 38%) which was characterised as follows: MS (m/z) 328.0 [M+H]$^+$.

Example 506

Synthesis of N-[2-amino-6-(4-fluoro-phenyl)-pyrido [3,2-d]pyrimidin-4-yl]-O-ethyl-hydroxylamine

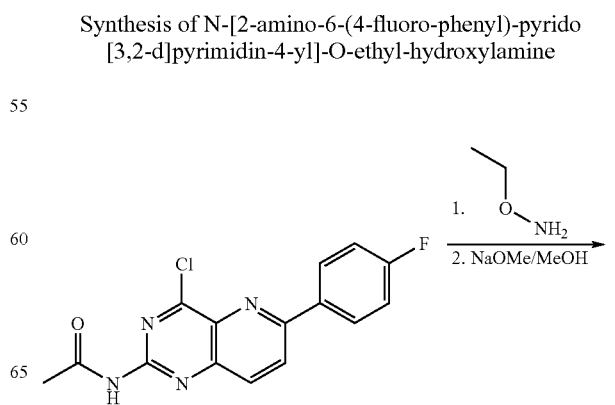

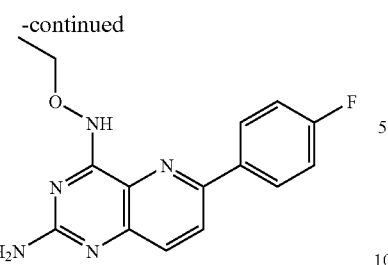

The procedure for the preparation of example 505 was repeated, except for the use of O-ethylhydroxylamine instead of N-(2-methoxyethyl)methylamine. The mass spectrum of the pure title compound was: MS (m/z) 300.1 [M+H]⁺.

Examples 507 to 538

Compounds were made by Suzuki Cross-coupling using synthesis method A (Table 6) or method B (Table 5) respectively, each shown below with non-limiting solvents, reaction temperature and reagents, and using analytical methods A or B respectively.

Synthesis Method A (Details Shown in Table 4)

Synthesis Method B: the procedure was the same as Method A, except the reaction mixtures were heated at 80° C. for 30 minutes in an oil bath.

Analytical Method A: Gradient—2-98% B/3 minutes (A=0.1% Trifluoroacetic acid/Water, B=0.1% Trifluoroacetic acid/Acetonitrile) flow rate 3 ml/minute. Column: 50×4.6 mm Synergi Polar RP 4 µm 80 A. UV monitored at 254 nm, mass spec scan range 200-900 m/z.

Analytical Method B: Gradient—0-100% B/2 minutes then hold 1 minute at 100% B (A=1% acetic acid/water, B=1% acetic acid/MeOH) flow rate 1.5 ml/minute. Column: 30×2 mm Synergi Polar RP 4 µm 80 A. UV monitored at 254 nm, mass spec scan range 100-1000 m/z.

| Compound | MW | amount | mmoles | equivalents |
|---|---|---|---|---|
| 6-chloro-4-ethoxy-pyrido[3,2-d]pyrimidin-2-ylamine | 224.65 | 15 mg | 0.067 | 1 |
| boronic acid | | | 0.073 | 1.1 |
| Pd(PPh₃)₄ | 1155.6 | 5-10 mg | 0.0043-0.0087 | 6-12 mol % |
| 0.27 M aqu. K₂CO₃ | 138.21 | 500 µL | 0.135 | 2 |
| dimethoxyethane (DME) | | 1 mL | | |

For the array, the heteroaryl chloride (300 mg) was dissolved in DME (20 ml) and 1 ml was distributed to each of twenty 2-5 ml microwave vials. To each vial was added the respective boronic acid and 500 µL of a 0.27M aqueous solution of K₂CO₃ with stirring. A spatula tip (5-10 mg) of Pd(PPh₃)₄ was added to each vessel and the vials top were crimped. Each vial was then heated at 80° C. for 5 minutes under microwave irradiation. The reaction mixtures were cooled to room temperature, de-crimped and aliquots were removed for LC/MS analysis. The reaction mixtures were concentrated to dryness in vacuo. The residues were dissolved in 1 ml of DMF and 20 µL TFA and filtered into a 96 well deepwell plate. The title compounds obtained, represented by the structural formula shown below, were purified by preparative LC/MS. The purified fractions were analyzed by LC/MS for purity and identity.

TABLE 5

(synthesis method B)

| Example | R (* = point of attachment) | observed Mass ([M + H]⁺) | amount (mg) | analytical Method |
|---|---|---|---|---|
| 507 | *-OCH₃ (phenyl) | 297 | 11.5 | B |

TABLE 5-continued
(synthesis method B)
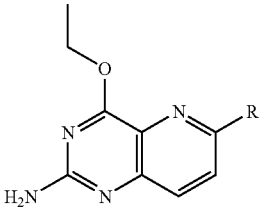
| Example | R (* = point of attachment) | observed Mass ([M + H]+) | amount (mg) | analytical Method |
|---|---|---|---|---|
| 508 | 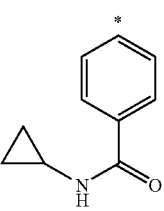 | 324 | 10.2 | B |
| 509 | 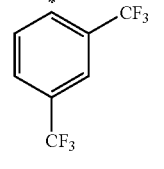 | 350 | 12.8 | B |
| 510 | 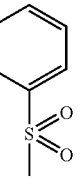 | 403 | 14.6 | B |
| 511 | 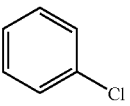 | 345 | 17.6 | B |
| 512 |  | 301 | 18 | A |
| 513 |  | 257 | 15.9 | A |
| 514 | 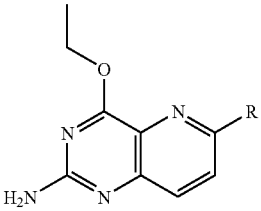 | 273 | 15.7 | A |
TABLE 5-continued
(synthesis method B)
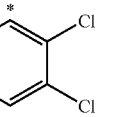
| Example | R (* = point of attachment) | observed Mass ([M + H]+) | amount (mg) | analytical Method |
|---|---|---|---|---|
| 515 | 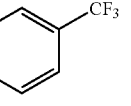 | 366 | 25.7 | A |
| 516 | 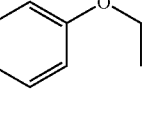 | 335 | 17.5 | A |
| 517 | 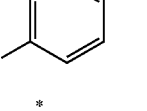 | 335 | 19.2 | A |
| 518 | 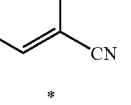 | 311 | 23 | A |
| 519 | 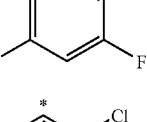 | 303 | 18.5 | A |
| 520 | 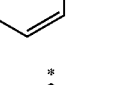 | 292 | 18.2 | A |
| 521 | 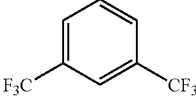 | 303 | 18.7 | A |
| 522 | | 301 | 17 | A |
| 523 | | 403 | 18.2 | B |

TABLE 5-continued
(synthesis method B)
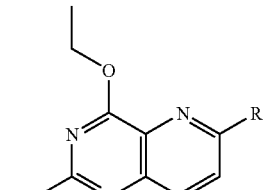
| Example | R (* = point of attachment) | observed Mass ([M + H]+) | amount (mg) | analytical Method |
|---|---|---|---|---|
| 524 | 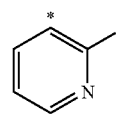 | 257 | 15.9 | A |
| 525 | 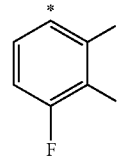 | 286 | 8.5 | A |
| 526 | 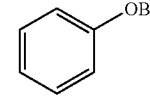 | 321 | 15 | A |
| 527 | 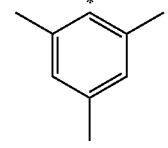 | 373 | 22.1 | A |
| 528 | 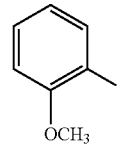 | 309 | 8.9 | A |
| 529 | 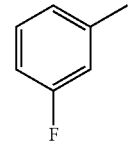 | 315 | 15.2 | A |
| 530 | 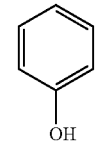 | 299 | 22.2 | A |
| 531 | 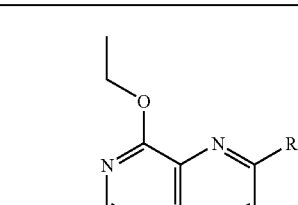 | 283 | 12.7 | A |
| 532 | 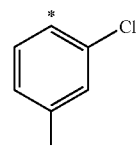 | 310 | 21.9 | A |
| 533 | 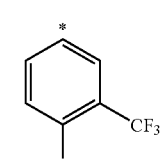 | 369 | 15.4 | B |
| 534 | 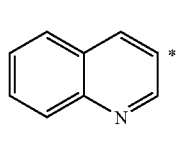 | 369 | 21.8 | A |
| 535 | 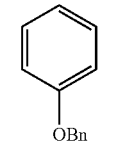 | 318 | 5.8 | A |
| 536 | 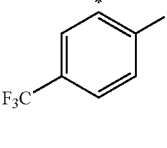 | 373 | 17.3 | B |
| 537 | 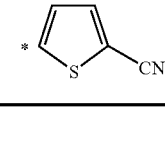 | 369 | 14.8 | A |
| 538 | | 298 | 3.3 | B |

TABLE 6

| | (synthesis method A) | | | |
|---|---|---|---|---|
| Example | Structure | amount (g) | observed mass (M + H) | analytical Method |
| 539 | | 0.0271 | 303 | A |
| 540 | | 0.0164 | 281 | A |
| 541 | | 0.0177 | 335 | A |
| 542 | | 0.0158 | 335, 337 | A |
| 543 | | 0.0168 | 295 | A |
| 544 | | 0.0169 | 321 | A |

TABLE 6-continued (synthesis method A)

| Example | Structure | amount (g) | observed mass (M + H) | analytical Method |
|---------|-----------|------------|------------------------|-------------------|
| 545 | 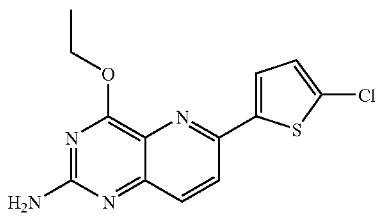 | 0.0129 | 307, 309 | A |
| 546 | 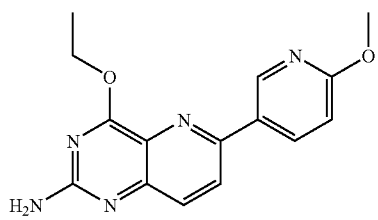 | 0.0207 | 298 | A |
| 547 | 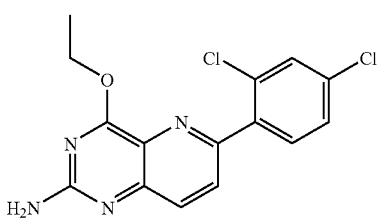 | 0.0155 | 335, 337 | A |
| 548 | 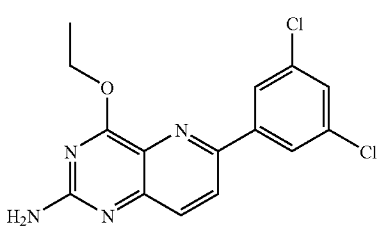 | 0.0175 | 335, 337 | A |
| 549 | 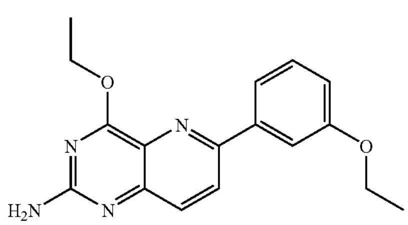 | 0.0176 | 311 | A |
| 550 | 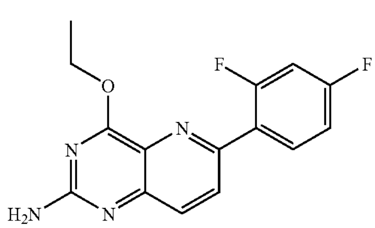 | 0.0162 | 303 | A |

TABLE 6-continued (synthesis method A)

| Example | Structure | amount (g) | observed mass (M + H) | analytical Method |
|---------|-----------|------------|----------------------|-------------------|
| 551 | 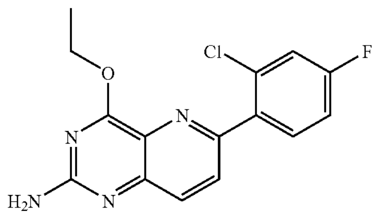 | 0.0144 | 319 | A |
| 552 | 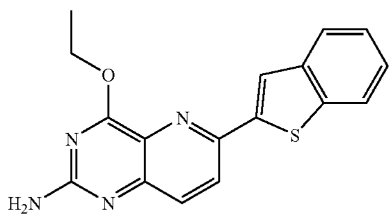 | 0.0132 | 323 | A |
| 553 | 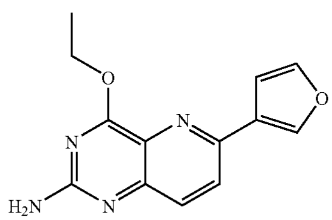 | 0.0145 | 257 | A |
| 554 | 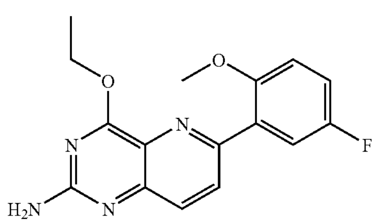 | 0.0166 | 315 | A |
| 555 | 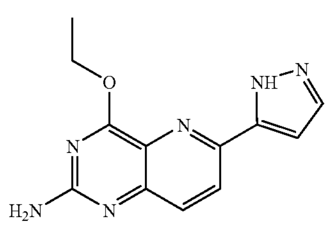 | 0.0137 | 257 | A |
| 556 | 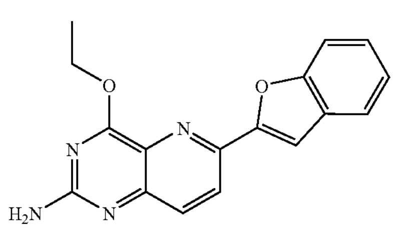 | 0.0168 | 307 | A |

Example 557

Anti-HCV Assay/Replicon Assay

The anti-HCV activity of the pyrido[3,2-d]pyrimidine derivatives of this invention was tested in a human hepatoma Huh-7 cell line harbouring a HCV replicon. The assay comprised the following steps:

Step 1: Compound Preparation and Serial Dilution 1. for water soluble pyrido[3,2-d]pyrimidine derivatives, a volume of 500 μL of solution in cell media (DMEM, 10% FBS, P/S, L-Glutamine) was prepared with a concentration being twice the concentration of the starting final serial dilution concentration. A volume of 150 μL of the solution was added to the pre-specified wells in column 1 of a 96-well cell culture plate (PerkinElmer, white plate, cat. #6005181, for EC50 assay; black plate, cat. #6005182 for CC50 assay). The rest of the plate, columns 2-12, was filled with 100 μL of cell media. The plate was then placed on a Precision 2000 Workstation to start the serial dilution. Compounds were diluted three times each step from column 1 to column 10. Column 11 was used as a blank control (no compound added).

2. for pyrido[3,2-d]pyrimidine derivatives requiring DMSO to dissolve, serial dilution is performed in 50% DMSO in a 384-well plate. A solution containing a compound at 100-fold concentration of the starting final serial dilution concentration was prepared in 50% DMSO and added to the pre-specified wells in column 1 of a polypropylene 384-well plate. The plate was then placed on a Precision 2000 Workstation to start the serial dilution. After the serial dilution, a volume of 2 μL of the solution was transferred from the 384-well plate to a 96-well cell culture plate containing 100 μL of cell media on a Biomek FX Workstation. The DMSO concentration in the final assay condition was 0.5% after cells are added to the plate and the total volume in each well is brought to 200 μL.

Step 2: to each well of the serial dilution plate prepared above, 100 μL of cell media containing 6000 suspended Huh-7 HCV replicon cells was added with a Multidrop workstation. The plates were incubated for 3 days at 37° C. with 5% $CO_2$.

Step 3: Detection:

a) for the $EC_{50}$ assay, the media in a 96-well cell culture plate was aspirated with a Biotek EL405 plate-washer. A volume of 200 μL of a solution containing a 1:1 mixture of cell-lysis buffer (Promega, Luciferase Cell Culture Lysis 5× Reagent, cat. #E1531) and luciferase substrate solution (Promega, Luciferase Assay, cat. #E4550) was added to each well of the plate with Multidrop. The plate was incubated for 30 minutes at room temperature before the luminescence signal was measured with a TopCount plate-reader.

b) for the $CC_{50}$ assay, a volume of 100 μL of pre-mixed CellTiter-Glo (Promega, cat. #G7572) solution is added directly to the cell culture in each well of the plate and the luminescence signal is measured with a TopCount plate-reader after 10 minutes of incubation at room temperature.

Table 7 below shows $EC_{50}$ and $CC_{50}$ values (expressed in nM and μM respectively, i.e. nmol/l and μmol/l), as well as the $CC_{50}/EC_{50}$ ratio (selectivity index) of a few derivatives tested in this assay. Results in table 7 are expressed by the following data:

the 50% effective concentration ($EC_{50}$), i.e. the concentration that protects 50% of the cell monolayer from virus-induced cythopathic effect, and the 50% cytostatic concentration ($CC_{50}$), i.e. the concentration that results in 50% inhibition of cell growth.

Table 7 further indicates the nature of substituents being present in positions 2, 4 and 6 of the pyrido[3,2-d]pyrimidine derivatives of the invention.

TABLE 7

| Example | position 2 | position 4 | position 6 | $EC_{50}$ (nM) | $CC_{50}$ (μM) | $CC_{50}/EC_{50}$ |
|---|---|---|---|---|---|---|
| 11 | Me | (4-CONH(3-Me)Ph)piperazinyl | (3,4-diOMe)Ph | 75 | 7.3 | 98 |
| 14 | Cl | (4-CONH(3-Me)Ph)piperazinyl | (3,4-diOMe)Ph | 150 | 25.1 | 167 |
| 19 | OCH2CH2OPh | (4-CONH(3-Me)Ph)piperazinyl | (3,4-diOMe)Ph | 480 | 25.1 | 52 |
| 32 | NH2 | NH(3-Me)Ph | (3,4-diOMe)Ph | 258 | 50.1 | 195 |
| 33 | NH2 | NH(3,4-OCH2O-)Ph | (3,4-diOMe)Ph | 8 | 4.8 | 636 |
| 34 | NH2 | NH(3-Br)Ph | (3,4-diOMe)Ph | 51 | 7.7 | 151 |
| 38 | NH2 | NHCH2CH2morpholinyl | (3,4-diOMe)Ph | 47 | 7.1 | 151 |
| 50 | NH2 | (4-CH2CH2OPh)piperazinyl | (3,4-diOMe)Ph | 58 | 18.0 | 310 |
| 52 | NH2 | (4-2-pyridyl)piperazinyl | (3,4-diOMe)Ph | 42 | 3.0 | 72 |
| 55 | NH2 | (4-CH2(2,3-OCH2O-)Ph)piperazinyl | (3,4-diOMe)Ph | 340 | 25.1 | 74 |
| 57 | NH2 | (4-CH2Ph)piperazinyl | (3,4-diOMe)Ph | 45 | 24.6 | 546 |
| 63 | NH2 | (4-CONH(3-Cl)Ph)piperazinyl | (3,4-diOMe)Ph | 7 | 0.70 | 106 |
| 65 | NH2 | (4-COCH2OPh)piperazinyl | (3,4-diOMe)Ph | 280 | 25.1 | 90 |
| 84 | CH | (4-CONH(3-Cl)Ph)piperazinyl | (3,4-diMe)Ph | 130 | 21.8 | 167 |
| 85 | CH | (4-CONH(3-Cl)Ph)piperazinyl | (3,4-OCH2O-)Ph | 19 | 1.2 | 64 |
| 86 | CH | (4-CONH(3-Cl)Ph)piperazinyl | (3-Cl-4-OEt)Ph | 250 | 25.1 | 100 |
| 94 | NH(4-Me)Ph | (4-CONH(3-Me)Ph)piperazinyl | (3,4-diOMe)Ph | 74 | 25.1 | 339 |
| 106 | NH2 | (4-CONH(4-F)Ph)piperazinyl | (3-OMe-4-OiPr)Ph | 35 | 3.6 | 102 |
| 121 | CH | (4-CONH(4-Cl)Ph)piperazinyl | (3-Me-4-OMe)Ph | 120 | 19.4 | 162 |
| 124 | CH | (4-CONH(3-Cl)Ph)piperazinyl | (3-OMe-4-OiPr)Ph | 35 | 2.5 | 71 |
| 168 | NH2 | (4-CONH(3-Cl)Ph)piperazinyl | (3-Me-4-OMe)Ph | 27 | 2.6 | 97 |
| 171 | NH2 | (4-CONH(3-Cl)Ph)piperazinyl | (3-F-4-OEt)Ph | 15 | 1.5 | 101 |
| 173 | NH2 | (4-CONH(3-Cl)Ph)piperazinyl | (3,4-OCH2O-)Ph | 24 | 3.4 | 143 |
| 180 | NH2 | morpholinyl | (3,4-OCH2O-)Ph | 150 | 25.1 | 167 |
| 184 | NH2 | (4-COMe)piperazinyl | (3,4-OCH2O-)Ph | 170 | 21.8 | 128 |
| 187 | NH2 | (4-COCH2O(4-Cl)Ph)piperazinyl | (3,4-OCH2O-)Ph | 19 | 1.2 | 64 |
| 188 | NH2 | (4-COCH2O(4-Cl)Ph)piperazinyl | (3,4-diCl)Ph | 58 | 12.3 | 211 |
| 189 | NH2 | (4-COCH2O(4-Cl)Ph)piperazinyl | (3,4-OCH2CH2O-)Ph | 9 | 0.43 | 50 |
| 190 | NH2 | (4-CONH(3-Me)Ph)piperazinyl | (3,4-OCH2O-)Ph | 12 | 0.61 | 51 |
| 191 | NH2 | (4-CONH(3-Me)Ph)piperazinyl | (3,4-diCl)Ph | 9 | 1.2 | 132 |
| 192 | NH2 | (4-CONH(3-Me)Ph)piperazinyl | (3,4-OCH2CH2O-)Ph | 5 | 0.69 | 147 |
| 201 | NH2 | (4-COCH2O(4-Cl)Ph)piperazinyl | (4-F)Ph | 45 | 25.1 | 558 |

TABLE 7-continued

| Example | position 2 | position 4 | position 6 | EC$_{50}$ (nM) | CC$_{50}$ (μM) | CC$_{50}$/EC$_{50}$ |
|---|---|---|---|---|---|---|
| 210 | NH2 | OCH2Ph | (3-F)Ph | 220 | 18.8 | 85 |
| 211 | NH2 | OCH2Ph | (4-F)Ph | 210 | 37.5 | 179 |
| 241 | NH2 | (4-CONH(3-Cl)Ph)-1-diazacycloheptanyl | (3,4-diOMe)Ph | 11 | 2.4 | 218 |
| 246 | NH2 | NH-4-(1-CO2tBu)piperidinyl | (3,4-diOMe)Ph | 22 | 1.5 | 70 |
| 247 | NH2 | NH-3-(1-CO2tBu)piperidinyl | (3,4-diOMe)Ph | 22 | 5.2 | 238 |
| 254 | NH2 | NH-3-(1-CONH(3-Me)Ph)piperidinyl | (3,4-diOMe)Ph | 50 | 7.3 | 147 |
| 258 | NH2 | 3-(1-CONHCH2CHMe2)piperidinyl | (3,4-diOMe)Ph | 74 | 4.2 | 56 |
| 260 | NH2 | (4-CH2CONHCH2CH2Ph)piperazinyl | (3,4-diOMe)Ph | 36 | 2.6 | 73 |
| 262 | NH2 | NHCH2CH2CO(4-COMe)piperazinyl | (3,4-diOMe)Ph | 96 | 25.1 | 261 |
| 263 | NH2 | (4-CH2CO-1-pyrrolidinyl)piperazinyl | (3,4-diOMe)Ph | 28 | 2.9 | 102 |
| 265 | NH2 | (4-CH2CO-4-morpholinyl)piperazinyl | (3,4-diOMe)Ph | 31 | 2.6 | 84 |
| 279 | NH2 | OEt | (2-F)Ph | 690 | 37.5 | 54 |
| 280 | NH2 | OEt | (3-F)Ph | 300 | 37.5 | 125 |
| 281 | NH2 | OEt | (4-F)Ph | 59 | 50.1 | 856 |
| 282 | NH2 | OnPr | (2-F)Ph | 560 | 50.1 | 89 |
| 283 | NH2 | OnPr | (4-F)Ph | 95 | 21.0 | 221 |
| 285 | NHCOMe | OiPr | (4-F)Ph | 51 | 25.1 | 492 |
| 286 | NH2 | OiPr | (4-F)Ph | 45 | 50.1 | 1113 |
| 290 | NH2 | OnBu | (4-F)Ph | 340 | 21.3 | 63 |
| 293 | NH2 | OiBu | (4-F)Ph | 370 | 25.1 | 68 |
| 296 | NH2 | OsBu | (4-F)Ph | 560 | 37.5 | 67 |
| 297 | NH2 | OnPentyl | (2-F)Ph | 760 | 50.1 | 66 |
| 298 | NH2 | OnPentyl | (3-F)Ph | 365 | 28.0 | 77 |
| 303 | NH2 | OCH2CH2OEt | (3-F)Ph | 560 | 50.1 | 89 |
| 304 | NH2 | OCH2CH2OEt | (4-F)Ph | 44 | 37.5 | 852 |
| 305 | NH2 | OCH2CH2OMe | (4-F)Ph | 18 | 50.1 | 2863 |
| 307 | NH2 | OEt | (3,4-diOMe)Ph | 190 | 50.1 | 264 |
| 320 | NH2 | (4-COMe)piperazinyl | (4-F)Ph | 230 | 19.9 | 87 |
| 326 | NH2 | OCH2cPr | (4-F)Ph | 99 | 25.1 | 254 |
| 351 | NH2 | OCH2CF3 | (4-F)Ph | 190 | 25.1 | 132 |
| 353 | NH2 | OEt | (4-NHCOMe)Ph | 450 | 25.1 | 56 |
| 355 | NH2 | OiPr | (4-NHCOMe)Ph | 210 | 25.1 | 120 |
| 356 | NH2 | OCH2cPr | (4-NHCOMe)Ph | 290 | 25.1 | 87 |
| 370 | NH2 | (4-COCH2O(3-Me)Ph)piperazinyl | (4-F)Ph | 52 | 3.4 | 65 |
| 371 | NH2 | (4-COCH2O(3-Cl)Ph)piperazinyl | (4-F)Ph | 30 | 25.1 | 837 |
| 372 | NH2 | (4-COCH2O(2,4-diCl)Ph)piperazinyl | (4-F)Ph | 320 | 25.1 | 78 |
| 373 | NH2 | (4-COCH2O(4-F)Ph)piperazinyl | (4-F)Ph | 130 | 19.2 | 148 |
| 378 | NH2 | (4-COCH2O(4-Cl)Ph)piperazinyl | (4-CN)Ph | 8 | 4.3 | 571 |
| 379 | NH2 | (4-COCH2O(4-Cl)Ph)piperazinyl | (4-CF3)Ph | 75 | 21.6 | 287 |
| 381 | NH2 | (4-COCH2O(4-Cl)Ph)piperazinyl | 3-furyl | 61 | 9.1 | 149 |
| 382 | NH2 | (4-COCH2O(4-Cl)Ph)piperazinyl | 3-thiophenyl | 9 | 13.1 | 1523 |
| 384 | NH2 | (4-COCH2O(4-Cl)Ph)piperazinyl | (3,4-diF)Ph | 53 | 12.2 | 231 |
| 384 | NH2 | (4-COCH2O(4-Cl)Ph)piperazinyl | (4-Cl)Ph | 53 | 7.9 | 148 |
| 385 | NH2 | (4-COCH2O(4-Cl)Ph)piperazinyl | (3-Cl)Ph | 61 | 7.4 | 122 |
| 386 | NH2 | (4-COCH2O(4-Cl)Ph)piperazinyl | 4-pyridyl | 1 | 6.0 | 4585 |
| 387 | NH2 | (4-COCH2O(4-Cl)Ph)piperazinyl | (3-Cl-4-F)Ph | 21 | 5.9 | 280 |
| 389 | NH2 | (4-CONH(3-Me)Ph)piperazinyl | Ph | 21 | 4.2 | 200 |
| 390 | NH2 | (4-CONH(3-Me)Ph)piperazinyl | (4-F)Ph | 6 | 3.5 | 575 |
| 392 | NH2 | SMe | (4-F)Ph | 49 | 25.1 | 512 |
| 393 | NH2 | SEt | (4-F)Ph | 234 | 36.0 | 154 |
| 394 | NH2 | SiPr | (4-F)Ph | 187 | 50.1 | 268 |
| 395 | NH2 | SCH2CH2OMe | (4-F)Ph | 49 | 13.6 | 278 |
| 398 | NHCOMe | NHCH2CH2OMe | (4-F)Ph | 410 | 25.1 | 61 |
| 402 | NH2 | NHEt | (4-F)Ph | 376 | 30.0 | 80 |
| 406 | NH2 | 4-thioxomorpholinyl | (4-F)Ph | 13 | 25.1 | 1931 |
| 415 | NH2 | NHCH2CH2SO2Me | (4-F)Ph | 99 | 11.7 | 118 |
| 417 | NH2 | OCH2CH2F | (4-F)Ph | 11 | 25.1 | 2282 |
| 459 | NH2 | OEt | (3-F-4-OMe)Ph | 320 | 25.1 | 78 |
| 460 | NH2 | OEt | (3,4-diF)Ph | 113 | 16.3 | 145 |
| 461 | NH2 | OEt | (4-OMe)Ph | 270 | 25.1 | 93 |
| 462 | NH2 | OEt | (3-Cl-4-F)Ph | 428 | 50.1 | 117 |
| 463 | NH2 | OEt | (4-Cl)Ph | 511 | 50.1 | 98 |
| 465 | NH2 | OEt | (4-NH2)Ph | 346 | 50.1 | 145 |
| 467 | NH2 | OEt | 2-thiophenyl | 443 | 50.1 | 113 |
| 471 | NH2 | OCH2CH2OMe | (3,4-diOMe)Ph | 380 | 25.1 | 66 |
| 500 | NH2 | morpholinyl | (4-NHCOMe)Ph | 49 | 36.0 | 735 |
| 501 | NH2 | morpholinyl | (4-NHCOCHMe2)Ph | 49 | 7.3 | 149 |
| 502 | NH2 | morpholinyl | (4-NH2)Ph | 99 | 8.1 | 82 |
| 504 | NH2 | OMe | (4-F)Ph | 33 | 14.3 | 434 |
| 546 | NH2 | OEt | 5-(2-OMe)pyridyl | 370 | 25.1 | 68 |
| 549 | NH2 | OEt | (3-OEt)Ph | 470 | 25.1 | 53 |
|  | NHCOMe | OEt | (4-F)Ph | 148 | 25.1 | 170 |

(Table 7-end)

Example 558

HIV-1 Assay

This assay is based on the quantification of the HIV-induced cytopathic effect by a calorimetric detection of the viability of virus-infected cells in the presence or absence of tested inhibitors. The HIV-induced cell death was determined by using as a metabolic substrate 2,3-bis(2-methoxy-4-nitro-5-sulfophenyl)-2H-tetrazolium-5-carboxanilide (hereinafter referred as XTT) which was converted only by live cells into a product with specific absorption characteristics, as described by Weislow et al., *J. Natl. Cancer Inst.* (1989) 81:577.

The assay protocol for the determination of $EC_{50}$ includes the following steps:
1. MT-2 cells were maintained in RPMI-1640 medium supplemented with 10% fetal bovine serum, glutamine and antibiotics.
2. Cells were infected by the wild-type HIV-1 strain $III_B$ (ABI, Columbia, Md.) for 3 hours at 37° C. using a multiplicity of infection (MOI) of 0.01.
3. Prepare a set of solutions containing various concentrations of the tested inhibitor by making 5-fold serial dilutions in 96-well plate (100 µl/well). Alternatively, test single drug concentration (100 µl/well). Distribute the infected cells into the 96-well plate containing the inhibitors (20,000 cells in 100 µl/well). Include the following control samples, untreated infected cells (100% cell death) and control drug-treated infected cells (full protection).
4. Incubate the cells for 5 days at 37° C.
5. Prepare XTT solution (6 mL per assay plate) at a concentration of 2 mg/mL in a phosphate-buffered saline at pH 7.4. Heat the solution in water-bath for 10 minutes at 56° C. Add 50 µl of N-methylphenazonium methasulfate (5 µg/mL) per 6 mL of XTT solution.
6. Remove 100 µl media from each well on the assay plate.
7. Add 100 µl of the XTT substrate solution per well and incubate at 37° C. for 45 to 60 minutes in a $CO_2$ incubator.
8. Add 20 µl of 2% Triton X-100 per well to inactivate the virus.
9. Read the absorbance at 450 nm with subtracting off the background absorbance at 650 nm.
10. Plot the percentage absorbance relative to untreated control and estimate the $EC_{50}$ value as drug concentration resulting in a 50% protection of the infected cells. Alternatively, calculate the percentage of inhibition for a fixed concentration, relative to the full protection with the control drug.

This assay has been performed on a set of compounds of the invention, and results are reported in table 8 below, also indicating the nature of substituents being present in positions 4 and 6 of the pyrido[3,2-d]pyrimidine derivatives of the invention (all being amino-substituted in position 2).

TABLE 8

| Example | 4-substituent | 6-substituent | MT2 HIV % inhib. @ 5 µM |
|---|---|---|---|
| 36 | (4-Me)piperazinyl | (3,4-diOMe)Ph | 3 |
| 226 | morpholinyl | 4-pyridyl | 9 |
| 281 | OEt | (4-F)Ph | 17 |
| 286 | OiPr | (4-F)Ph | 11 |
| 210 | OCH2Ph | (3-F)Ph | 5 |
| 211 | OCH2Ph | (4-F)Ph | 17 |
| 303 | OCH2CH2OEt | (3-F)Ph | 8 |
| 304 | OCH2CH2OEt | (4-F)Ph | 9 |

TABLE 8-continued

| Example | 4-substituent | 6-substituent | MT2 HIV % inhib. @ 5 µM |
|---|---|---|---|
| 320 | (4-COMe)piperazinyl | (4-F)Ph | 12 |
| 340 | (4-COMe)piperazinyl | (4-NHCOMe)Ph | 4 |
| 353 | OEt | (4-NHCOMe)Ph | 4 |
| 460 | OEt | (3,4-diF)Ph | 11 |

The invention claimed is:
1. A compound having the structural formula:

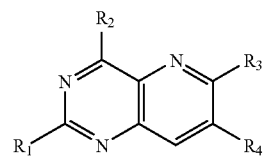

wherein:
$R_1$ is selected from the group consisting of hydrogen, halogen, cyano, carboxylic acid, acyl, thioacyl, $C_{1-7}$ alkoxycarbonyl, acyloxy, carbonate, carbamate, $C_{1-7}$ alkyl, $C_{6-30}$ aryl, amino, acetamido, N-protected amino, (mono- or di) $C_{1-7}$ alkylamino, (mono- or di) $C_{6-30}$ arylamino, (mono- or di) $C_{3-10}$ cycloalkylamino, (mono- or di) hydroxy $C_{1-7}$ alkylamino, (mono- or di) $C_{1-4}$ alkyl-$C_{6-30}$ arylamino, mercapto $C_{1-7}$ alkyl, $C_{1-7}$ alkyloxy, and groups of the formula $R_6$—$NR_7R_{12}$, wherein $R_6$ is a bond or $C_{1-3}$ alkylene, wherein $R_7$ and $R_{12}$ are independently selected from the group consisting of hydrogen, $C_{1-7}$ alkyl, $C_{2-7}$ alkenyl, $C_{2-7}$ alkynyl, $C_{6-30}$ aryl, $C_{6-30}$ aryl-$C_{1-7}$ alkyl, $C_{3-10}$ cycloalkyl and $C_{2-15}$ heteroaryl having one or more heteroatoms in one or more rings, wherein each heteroatom is independently selected from the group consisting of nitrogen, oxygen, sulfur, selenium, and phosphorus and wherein each ring has from 3 to 10 atoms, or wherein $R_7$ and $R_{12}$ together form a $C_{2-15}$ heterocycle having one or more heteroatoms in one or more rings, wherein each heteroatom is independently selected from the group consisting of nitrogen, oxygen, sulfur, selenium, and phosphorus and wherein each ring has from 3 to 10 atoms, $R_2$ is selected from the group consisting of N-containing $C_{2-15}$ having one or more heteroatoms in one or more rings, wherein each heteroatom is independently selected from the group consisting of nitrogen, oxygen, sulfur, selenium, and phosphorus and wherein each ring has from 3 to 10 atoms; $C_{1-7}$ alkoxy-$C_{1-7}$ alkoxy; $C_{2-15}$ heterocyclic-substituted $C_{1-7}$ alkoxy, wherein said heterocyclic has one or more heteroatoms in one or more rings, wherein each heteroatom is independently selected from the group consisting of nitrogen, oxygen, sulfur, selenium, and phosphorus, and wherein each ring has from 3 to 10 atoms; $C_{3-10}$ cycloalkoxy; $C_{3-10}$ cycloalkyl-$C_{1-7}$ alkoxy; halo $C_{1-7}$ alkyloxy; $C_{6-30}$ aryloxy; $C_{6-30}$ aryl-$C_{1-7}$ alkyloxy; oxy $C_{2-15}$ heterocyclic having one or more heteroatoms in one or more rings, wherein each heteroatom is independently selected from the group consisting of nitrogen, oxygen, sulfur, selenium, and phosphorus and wherein each ring has from 3 to 10 atoms; thio $C_{1-7}$ alkyl-thio $C_{1-7}$ alkyl; $C_{2-15}$ heterocyclic-substituted thio $C_{1-7}$ alkyl, wherein said heterocyclic has one or more heteroatoms in one or more rings, wherein each heteroatom is independently selected from the group consisting of nitrogen, oxygen, sulfur, selenium, and phosphorus, and wherein each ring has from 3 to 10 atoms; thio $C_{3-10}$ cycloalkyl; thio $C_{3-10}$ cycloalkyl-$C_{1-7}$ alkyl; halo thio-$C_{1-7}$ alkyl; $C_{6-30}$ arylthio; $C_{6-30}$ aryl-$C_{1-7}$ alkylthio; thio $C_{2-15}$ heterocyclic having one or more heteroatoms in one or more rings, wherein each heteroatom is independently selected from the group consisting of nitrogen, oxygen, sulfur, selenium, and phosphorus and wherein each ring has from 3 to 10 atoms; and $C_{2-15}$ heterocyclic-substituted thio $C_{1-7}$ alkyl, wherein said heterocyclic has one or more heteroatoms in one or more rings, wherein each heteroatom is independently selected from the group consisting of nitrogen, oxygen, sulfur, selenium, and phosphorus, and wherein each ring has from 3 to 10 atoms;

$R_3$ and $R_4$ are independently selected from the group consisting of hydrogen, halogen, $C_{2-15}$ heteroaryl having one or more heteroatoms in one or more rings, wherein each heteroatom is independently selected from the group consisting of nitrogen, oxygen, sulfur, selenium, and phosphorus and wherein each ring has from 3 to 10 atoms, and $C_{6-30}$ aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, $C_{6-30}$ aryloxy, $C_{6-30}$ aryl-$C_{1-7}$ alkyloxy, oxy $C_{2-15}$ heterocyclic having one or more heteroatoms in one or more rings, wherein each heteroatom is independently selected from the group consisting of nitrogen, oxygen, sulfur, selenium, and phosphorus and wherein each ring has from 3 to 10 atoms, $C_{2-15}$ heterocyclic-substituted $C_{1-7}$ alkyloxy, wherein said heterocyclic has one or more heteroatoms in one or more rings, wherein each heteroatom is independently selected from the group consisting of nitrogen, oxygen, sulfur, selenium, and phosphorus, and wherein each ring has from 3 to 10 atoms, thio $C_{1-7}$ alkyl, thio $C_{3-10}$ cycloalkyl, thio $C_{6-30}$ aryl, thio-$C_{2-15}$ heterocyclic, wherein said heterocyclic has one or more heteroatoms in one or more rings, wherein each heteroatom is independently selected from the group consisting of nitrogen, oxygen, sulfur, selenium, and phosphorus and wherein each ring has from 3 to 10 atoms, $C_{6-30}$ aryl-$C_{1-7}$ alkylthio, $C_{2-15}$ heterocyclic-substituted $C_{1-7}$ alkylthio, wherein said heterocyclic has one or more heteroatoms in one or more rings, wherein each heteroatom is independently selected from the group consisting of nitrogen, oxygen, sulfur, selenium, and phosphorus and wherein each ring has from 3 to 10 atoms, formyl, carbamoyl, thiocarbamoyl, ureido, thioureido, sulfonamido, hydroxylamino, $C_{1-7}$ alkoxyamino, mercaptoamino, thio $C_{1-7}$ alkylamino, acylamino, thioacylamino, cyano, carboxylic acid or esters or thioesters or halides or anhydrides or amides thereof, thiocarboxylic acid or esters or thioesters or halides or anhydrides or amides thereof, $C_{1-7}$ alkylamino, $C_{3-10}$ cycloalkylamino, $C_{2-7}$ alkenylamino, $C_{3-10}$ cyclo-alkenylamino, $C_{2-7}$ alkynylamino, $C_{6-30}$ arylamino, $C_{6-30}$ aryl-$C_{1-7}$ alkylamino, hydroxy $C_{1-7}$ alkylamino, mercapto $C_{1-7}$ alkylamino, $C_{2-15}$ heterocyclic amino, wherein said heterocyclic has one or more heteroatoms in one or more rings, wherein each heteroatom is independently selected from the group consisting of nitrogen, oxygen, sulfur, selenium, and phosphorus and wherein each ring has from 3 to 10 atoms, hydrazino, $C_{1-7}$ alkylhydrazino and phenylhydrazino, provided that $R_3$ and $R_4$ are not both hydrogen, or a pharmaceutically acceptable addition salt or a stereochemical isomeric form thereof or a N-oxide thereof.

2. A compound according to claim 1, wherein $R_1$ is not hydrogen.

3. A compound according to claim 1, wherein $R_1$ is amino or acetamido.

4. A compound according to claim 1, wherein $R_1$ is amino or acetamido, and further wherein $R_3$ is a substituted $C_{6-30}$ aryl group.

5. A compound according to claim 1, wherein $R_1$ is amino or acetamido, wherein $R_3$ is a substituted $C_{6-30}$ aryl group and wherein $R_4$ is hydrogen.

6. A compound according to claim 1, wherein the N-containing $C_{2-15}$ heterocyclic of $R_2$ is selected from the group consisting of N-thiomorpholinyl, N-piperidinyl, N-homopiperidinyl and N-pyrrolidinyl.

7. A compound selected from the group consisting of:
2-acetamido-4-[(N-3-methyl-phenylcarbamoyl)-piperazin-1-yl]-6-(3,4-dimethoxyphenyl)-pyrido[3,2-d]pyrimidine,
2-amino-4-[(N-3-methyl-phenylcarbamoyl)-piperazin-1-yl]-6-(3,4-dimethoxyphenyl)-pyrido[3,2-d]pyrimidine,
2-amino-7-chloro-pyrido[3,2-d]pyrimidin-4(3H)one,
2-amino-7-(3,4-dimethoxyphenyl)-pyrido[3,2-d]pyrimidin-4(3H)one,
2-acetamido-7-(3,4-dimethoxyphenyl)-pyrido[3,2-d]pyrimidin-4(3H)one,
2-acetamido-4-(1,2,4-triazolyl)-7-(3,4-dimethoxyphenyl)-pyrido[3,2-d]pyrimidine,
2-amino-4-(N-3-methyl-phenyl-carbamoyl)-piperazin-1-yl])-7-(3,4-dimethoxyphenyl)-pyrido[3,2-d]pyrimidine,
2-amino-6-phenyl-pyrido[3,2-d]pyrimidin-4(3H)one,
2-acetamido-6-phenyl-pyrido[3,2-d]pyrimidin-4(3H)one,
2-acetamido-4-(1,2,4-triazolyl)-6-phenyl-pyrido[3,2-d]pyrimidine,
2-acetamido-4-(N-piperazin-1-yl)-6-phenyl-pyrido[3,2-d]pyrimidine,
2-acetamido-4-(N-morpholino)-6-(3,4-dimethoxyphenyl)-pyrido[3,2-d]pyrimidine,
2-acetamido-6-chloro-4-(2-ethoxyethoxy)-pyrido[3,2-d]pyrimidine,
2-acetamido-6-chloro-4-(2-methoxyethoxy)-pyrido[3,2-d]pyrimidine,
2-amino-4-(2-ethoxyethoxy)-6-(2-fluorophenyl)-pyrido[3,2-d]pyrimidine,
2-amino-4-(2-ethoxyethoxy)-6-(3-fluorophenyl)-pyrido[3,2-d]pyrimidine,
2-amino-4-(2-ethoxyethoxy)-6-(4-fluorophenyl)-pyrido[3,2-d]pyrimidine,
2-amino-4-(2-methoxyethoxy)-6-(4-fluorophenyl)-pyrido[3,2-d]pyrimidine,
2-acetamido-4-ethoxy-6-(3,4-dimethoxy)-pyrido[3,2-d]pyrimidine,
2-amino-4-trifluoroethoxy-6-chloro-pyrido(3,2-d)pyrimidine,
2-amino-4-ethoxy-6-chloro-pyrido(3,2-d)pyrimidine,
2-amino-4-(methoxy-ethoxy)-6-chloro-pyrido(3,2-d)pyrimidine,
2-amino-4-(isopropoxy)-6-chloro-pyrido(3,2-d)pyrimidine,
2-amino-4-(cyclopropylmethyloxy)-6-chloro-pyrido(3,2-d)pyrimidine, 2-amino-4-(4-morpholino-ethoxy)-6-chloro-pyrido(3,2-d)pyrimidine,
2-amino-4-(methoxy-ethoxy)-6-(p-acetamidophenyl)-pyrido(3,2-d)pyrimidine,
2-amino-4-(isopropoxy)-6-(p-acetamidophenyl)-pyrido(3,2-d)pyrimidine,
2-amino-4-(4-morpholino-ethoxy)-6-(p-acetamidophenyl)-pyrido(3,2-d)pyrimidine,
2-amino-4-[N-(4-pentenoyl)piperazin-1-yl]-6-(3,4-dimethoxyphenyl)-pyrido[3,2-d]pyrimidine,
2-amino-4-[4-(2-methylpropionyl)piperazin-1-yl]-6-(3,4-dimethoxyphenyl)-pyrido[3,2-d]pyrimidine,
2-amino-4-[4-(3,3-dimethylbutyryl)piperazin-1-yl]-6-(3,4-dimethoxyphenyl)-pyrido[3,2-d]pyrimidine,
2-amino-4-[4-(N-butylcarbamoyl)piperazin-1-yl]-6-(3,4-dimethoxy-phenyl)-pyrido[3,2-d]pyrimidine,
2-amino-4-{4-[N-(tert-butoxycarbonyl)glycyl]piperazin-1-yl}-6-(3,4-di-methoxyphenyl)-pyrido[3,2-d]pyrimidine,
2-amino-4-(N-piperazin-1-yl)-6-(4-fluorophenyl)-pyrido-[3,2-d]pyrimidine,
2-amino-4-[4-(2-naphthoxy-acetyl)piperazin-1-yl]-6-(4-fluorophenyl)-pyrido[3,2-d]pyrimidine,
2-amino-4-[4-(3-methylphenoxy-acetyl)piperazin-1-yl]-6-(4-fluorophenyl)-pyrido[3,2-d]pyrimidine,
2-amino-4-[4-(3-chlorophenoxy-acetyl)piperazin-1-yl]-6-(4-fluorophenyl)-pyrido[3,2-d]pyrimidine,
2-amino-4-[4-(2,4-dichlorophenoxy-acetyl)piperazin-1-yl]-6-(4-fluorophenyl)-pyrido[3,2-d]pyrimidine,
2-amino-4-[4-(4-fluorophenoxy-acetyl)piperazin-1-yl]-6-(4-fluorophenyl)-pyrido[3,2-d]pyrimidine,
2-amino-4-[4-(4-bromophenoxy-acetyl)piperazin-1-yl]-6-(4-fluorophenyl)-pyrido[3,2-d]pyrimidine,
2-acetylamino-4-(N-piperazin-1-yl)-6-chloro-pyrido[3,2-d]pyrimidine,
2-amino-4-(N-piperazin-1-yl)-6-chloro-pyrido[3,2-d]pyrimidine,
2-amino-4-[4-(4-chlorophenoxy-acetyl)piperazin-1-yl]-6-chloro-pyrido[3,2-d]pyrimidine,
2-amino-4-[N-(4-chlorophenoxyacetyl)piperazin-1-yl]-6-(4-cyanophenyl)pyrido-[3,2-d]pyrimidine,
2-amino-4-[N-(4-chlorophenoxyacetyl)piperazin-1-yl]-6-(4-trifluoromethylphenyl)-pyri-do-[3,2-d]pyrimidine,
2-amino-4-[N-(4-chlorophenoxyacetyl)piperazin-1-yl]-6-(3-fluorophenyl)pyrido-[3,2-d]pyrimidine,
2-amino-4-[N-(4-chlorophenoxyacetyl)piperazin-1-yl]-6-(furan-3-yl)pyrido-[3,2-d]pyrimidine,
2-amino-4-[N-(4-chlorophenoxyacetyl)piperazin-1-yl]-6-(thiophen-3-yl)pyrido-[3,2-d]pyrimidine,
2-amino-4-[N-(4-chlorophenoxyacetyl)piperazin-1-yl]-6-(3,4-difluorophenyl)pyrido-[3,2-d]pyrimidine,
2-amino-4-[N-(4-chlorophenoxyacetyl)piperazin-1-yl]-6-(4-chlorophenyl)pyrido-[3,2-d]pyrimidine,
2-amino-4-[N-(4-chlorophenoxyacetyl)piperazin-1-yl]-6-(3-chlorophenyl)pyrido-[3,2-d]pyrimidine,
2-amino-4-[N-(4-chlorophenoxyacetyl)piperazin-1-yl]-6-(pyridin-4-yl)pyrido-[3,2-d]pyrimidine,
2-amino-4-[N-(4-chlorophenoxyacetyl)piperazin-1-yl]-6-(3-chloro-4-fluorophenyl)-pyri-do-[3,2-d]pyrimidine,
2-amino-4-[N-(4-chlorophenoxyacetyl)piperazin-1-yl]-6-(propen-1-yl)pyrido-[3,2-d]pyrimidine,
2-amino-6-(4-fluorophenyl)-pyrido(3,2-d)pyrimidin-4(3H)thione,
2-amino-4-thiomethyl-6-(4-fluorophenyl)-pyrido(3,2-d)pyri-midine,
2-amino-4-thioethyl-6-(4-fluorophenyl)pyrido(3,2-d)pyrimidine,
2-amino-4-thioisopropyl-6-(4-fluorophenyl)pyrido(3,2-d)pyrimidine,
2-amino-4-(2-methoxy-thioethyl)-6-(4-fluorophenyl)pyrido(3,2-d)pyrimidine,
2-acetamido-4-ethylamino-6-(4-fluorophenyl)pyrido[3,2-d]pyrimidine,
2-acetamido-4-isopropylamino-6-(4-fluorophenyl)pyrido[3,2-d]pyrimidine,
2-acetamido-4-(2-methoxy-ethylamino)-6-(4-fluorophenyl)pyrido[3,2-d]pyrimidine,
2-acetamido-4-[3,4-(methylenedioxy)anilino]-6-(4-fluorophenyl)pyrido[3,2-d]pyrimidine,
2-acetamido-4-(thiomorpholino-1,1-dioxide)-6-(4-fluorophenyl)pyrido[3,2-d]pyrimidine,
2-acetamido-4-(tetrahydro-3-thiophen-amino-1,1-dioxide)-6-(4-fluorophenyl)pyrido[3,2-d]pyrimidine,
2-amino-4-ethylamino-6-(4-fluorophenyl)pyrido[3,2-d]pyrimidine,
2-amino-4-isopropylamino-6-(4-fluorophenyl)pyrido[3,2-d]pyrimidine,
2-amino-4-(2-methoxyethylamino)-6-(4-fluorophenyl)pyrido[3,2-d]pyrimidine,
2-amino-4-[3,4-(methylenedioxy)anilino]-6-(4-fluorophenyl)pyrido[3,2-d]pyrimidine,
2-amino-4-(thiomorpholino-1,1-dioxide)-6-(4-fluorophenyl)pyrido[3,2-d]pyrimidine,
2-amino-4-(tetrahydro-3-thiophen-amine-1,1-dioxide)-6-(4-fluorophenyl)pyrido[3,2-d]pyrimidine,
2-acetamido-4-[1-(4-acetyl-piperazin-1-yl)-3-amino-propan-1-one)]-6-(4-fluorophenyl)pyrido[3,2-d]pyrimidine,
2-acetamido-4-[2-amino-1-(4-methylpiperazin-1-yl)ethanone]-6-(4-fluorophenyl)pyrido[3,2-d]pyrimidine,
2-acetamido-4-(3-methanesulfonyl-propylamino)-6-(4-fluorophenyl)pyrido[3,2-d]pyrimidine,
2-acetamido-4-(2-amino-ethylmethylsulfone)-6-(4-fluorophenyl)pyrido[3,2-d]pyri-midine,
2-amino-4-[1-(4-acetyl-piperazin-1-yl)-3-amino-propan-1-one]-6-(4-fluorophenyl)pyrido[3,2-d]pyrimidine,
2-amino-4-[2-amino-1-(4-methylpiperazin-1-yl)ethanone]-6-(4-fluorophenyl)pyrido[3,2-d]pyrimidine,
2-amino-4-[(3-methanesulfonyl)-propylamino]-6-(4-fluorophenyl)pyrido[3,2-d]pyrimidine,
2-amino-4-[(2-amino-ethyl)methylsulfone]-6-(4-fluorophenyl)pyrido[3,2-d]pyrimidine,
2-amino-4-(2-butoxy-ethoxy)-6-(4-fluorophenyl)pyrido[3,2-d]pyrimidine,
2-amino-4-(2-fluoro-ethoxy)-6-(4-fluorophenyl)pyrido[3,2-d]pyrimidine,
2-amino-4-[2-(methoxyethoxy)ethoxy]-6-(4-fluorophenyl)pyrido[3,2-d]pyrimidine,
2-amino-4-(2-chloro-benzyloxy)-6-(4-fluorophenyl)pyrido[3,2-d]pyrimidine,
2-amino-4-(4-fluoro-benzyloxy)-6-(4-fluorophenyl)pyrido[3,2-d]pyrimidine,
2-amino-4-(3-methyl-benzyloxy)-6-(4-fluorophenyl)pyrido[3,2-d]pyrimidine,
2-amino-4-(4-trifluoromethyl-benzyloxy)-6-(4-fluorophenyl)pyrido[3,2-d]pyrimidine,
2-amino-4-(4-cyano-benzyloxy)-6-(4-fluorophenyl)pyrido[3,2-d]pyrimidine,
6-(4-fluorophenyl)-pyrido[3,2-d]pyrimidin-4(3H)one,
4-chloro-6-(4-fluorophenyl)-pyrido[3,2-d]pyrimidine,
4-amino-6-(4-fluorophenyl)-pyrido[3,2-d]pyrimidine),
4-morpholino-6-(4-fluorophenyl)-pyrido[3,2-d]pyrimidine,
4-phenoxy-6-(4-fluorophenyl)-pyrido[3,2-d]pyrimidine, 4-ethoxy-6-(4-fluorophenyl)-pyrido[3,2-d]pyrimidine,
4-[3,4-(methylenedioxy)anilino]-6-(4-fluorophenyl)-pyrido[3,2-d]pyrimidine,
4-[2-(N,N-dimethylamino)ethoxy]-6-(4-fluorophenyl)-pyrido[3,2-d]pyrimidine,
4-(2-methoxyethoxy)-6-(4-fluorophenyl)-pyrido[3,2-d]pyrimidine,
3-amino-6-(4-fluorophenyl)-pyridine-2-carboxylic acid amide,
2-methyl-6-(4-fluorophenyl)-pyrido[3,2-d]pyrimidin-4(3H)one,
2-ethyl-6-(4-fluorophenyl)-pyrido[3,2-d]pyrimidin-4(3H)one,
2-chloromethyl-6-(4-fluorophenyl)-pyrido[3,2-d]pyrimidin-4(3H)one,
2-methyl-4-chloro-6-(4-fluorophenyl)-pyrido[3,2-d]pyrimidine,
2-methyl-4-(N,N-diethylamino)-6-(4-fluorophenyl)-pyrido[3,2-d]pyrimidine,
3-amino-6-(3-fluorophenyl)-pyridine-2-carboxylic acid amide,
2,4-dihydroxy-6-(3-fluorophenyl)-pyrido[3,2-d]pyrimidine,
2,4-dihydroxy-6-(4-fluorophenyl)-pyrido[3,2-d]pyrimidine,
2,4-dichloro-6-(4-fluorophenyl)-pyrido[3,2-d]pyrimidine,
2-methyl-4-amino-6-(4-fluorophenyl)-pyrido[3,2-d]pyrimi-dine,
2,4-diethoxy-6-(4-fluorophenyl)-pyrido[3,2-d]pyrimidine,
2,4-diisopropoxy-6-(4-fluorophenyl)-pyrido[3,2-d]pyrimi-dine,
2,4-di-(2-methoxy-ethoxy)-6-(4-fluorophenyl)-pyrido[3,2-d]pyrimidine,
2-methyl-4-(2-methoxyethoxy)-6-(4-fluorophenyl)-pyrido[3,2-d]pyrimidine,
2-chloro-4-(3-methoxypropylamino)-6-(4-fluorophenyl)pyrido[3,2-d]pyrimidine,
2-chloro-4-ethylamino-6-(4-fluorophenyl)-pyrido[3,2-d]pyrimidine,
2-ethyl-4-(2-methoxyethoxy)-6-(4-fluorophenyl)-pyrido[3,2-d]pyrimidine,
2-chloro-4-isopropoxy-6-(4-fluorophenyl)-pyrido[3,2-d]pyrimidine,
2-methyl-4-ethoxy-6-(4-fluorophenyl)-pyrido[3,2-d]pyrimi-dine,
N-(4,6-dichloro-pyrido[3,2-d]pyrimidin-2-yl)-acetamide,
6-chloro-4-ethoxy-pyrido[3,2-d]pyrimidin-2-ylamine,
4-ethoxy-6-phenyl-pyrido[3,2-d]pyrimidin-2-ylamine,
4-ethoxy-6-pyridin-4-yl-pyrido[3,2-d]pyrimidin-2-ylamine,
4-ethoxy-6-p-tolyl-pyrido[3,2-d]pyrimidin-2-ylamine,
4-ethoxy-6-(4-trifluoromethyl-phenyl)-pyrido[3,2-d]pyrimidin-2-ylamine,
4-ethoxy-6-(3-fluoro-4-methoxy-phenyl)-pyrido[3,2-d]pyrimidin-2-ylamine,
6-(3,4-difluoro-phenyl)-4-ethoxy-pyrido[3,2-d]pyrimidin-2-ylamine,
4-ethoxy-6-(4-methoxy-phenyl)-pyrido[3,2-d]pyrimidin-2-ylamine,
6-(3-chloro-4-fluoro-phenyl)-4-ethoxy-pyrido[3,2-d]pyrimidin-2-ylamine,
6-(4-chloro-phenyl)-4-ethoxy-pyrido[3,2-d]pyrimidin-2-ylamine,
6-(4-chloro-3-fluoro-phenyl)-4-ethoxy-pyrido[3,2-d]pyrimidin-2-ylamine,
6-(4-amino-phenyl)-4-ethoxy-pyrido[3,2-d]pyrimidin-2-ylamine,
4-(2-amino-4-ethoxy-pyrido[3,2-d]pyrimidin-6-yl)-benzonitrile,
4-Ethoxy-6-thiophen-2-yl-pyrido[3,2-d]pyrimidin-2-ylamine,
6-chloro-4-[1,2,4]triazol-1-yl-pyrido[3,2-d]pyrimidin-2-ylamine,
6-chloro-4-(2-methoxy-ethoxy)-pyrido[3,2-d]pyrimidin-2-ylamine,
4,6-bis-(2-methoxy-ethoxy)-pyrido[3,2-d]pyrimidin-2-ylamine,
6-(3,4-dimethoxy-phenyl)-4-(2-methoxy-ethoxy)-pyrido[3,2-d]pyrimidin-2-ylamine,
4-(2-methoxy-ethoxy)-6-phenyl-pyrido[3,2-d]pyrimidin-2-ylamine,
4-(2-methoxy-ethoxy)-6-pyridin-4-yl-pyrido[3,2-d]pyrimidin-2-ylamine,
4-(2-methoxy-ethoxy)-6-p-tolyl-pyrido[3,2-d]pyrimidin-2-ylamine,
4-(2-methoxy-ethoxy)-6-(4-trifluoromethyl-phenyl)-pyrido[3,2-d]pyrimidin-2-ylamine,
6-(3-fluoro-4-methoxy-phenyl)-4-(2-methoxy-ethoxy)-pyrido[3,2-d]pyrimidin-2-ylamine,
6-(3,4-difluoro-phenyl)-4-(2-methoxy-ethoxy)-pyrido[3,2-d]pyrimidin-2-ylamine,
4-ethoxy-6-(4-methoxy-phenyl)-pyrido[3,2-d]pyrimidin-2-ylamine,
6-(3-chloro-4-fluoro-phenyl)-4-(2-methoxy-ethoxy)-pyrido[3,2-d]pyrimidin-2-ylamine,
6-(4-chloro-phenyl)-4-(2-methoxy-ethoxy)-pyrido[3,2-d]pyrimidin-2-ylamine,
6-(4-amino-phenyl)-4-(2-methoxy-ethoxy)-pyrido[3,2-d]pyrimidin-2-ylamine,
4-(2-methoxy-ethoxy)-6-thiophen-2-yl-pyrido[3,2-d]pyrimidin-2-ylamine,
6-(4-chloro-3-fluoro-phenyl)-4-(2-methoxy-ethoxy)-pyrido[3,2-d]pyrimidin-2-ylamine,
4-[2-amino-4-(2-methoxy-ethoxy)-pyrido[3,2-d]pyrimidin-6-yl]-phenol,
2-[2-amino-4-(2-methoxy-ethoxy)-pyrido[3,2-d]pyrimidin-6-yl]-phenol,
6-(2,4-difluoro-phenyl)-4-(2-methoxy-ethoxy)-pyrido[3,2-d]pyrimidin-2-ylamine,
N-{4-[2-amino-4-(2-methoxy-ethoxy)-pyrido[3,2-d]pyrimidin-6-yl]-phenyl}-2,2-dimethyl-propionamide,
6-(4-methanesulfonyl-phenyl)-4-(2-methoxy-ethoxy)-pyrido[3,2-d]pyrimidin-2-ylamine,
N-{4-[2-amino-4-(2-methoxy-ethoxy)-pyrido[3,2-d]pyrimidin-6-yl]-phenyl}-isobutyramide,
6-(2,4-dimethyl-thiazol-5-yl)-4-(2-methoxy-ethoxy)-pyrido[3,2-d]pyrimidin-2-ylamine,
6-(5,6-dihydro-4H-[1,3]oxazin-2-yl)-4-(2-methoxy-ethoxy)-pyrido[3,2-d]pyrimidin-2-ylamine,
6-(4-isopropoxy-phenyl)-4-(2-methoxy-ethoxy)-pyrido[3,2-d]pyrimidin-2-ylamine,
4-(2-methoxy-ethoxy)-6-(morpholine-4-sulfonyl)-pyrido[3,2-d]pyrimidin-2-ylamine,
{4-[2-amino-4-(2-methoxy-ethoxy)-pyrido[3,2-d]pyrimidin-6-yl]-phenyl}-methanol,
{4-[2-amino-4-(2-methoxy-ethoxy)-pyrido[3,2-d]pyrimidin-6-yl]-phenyl}-acetonitrile,
N-{4-[2-amino-4-(2-methoxy-ethoxy)-pyrido[3,2-d]pyrimidin-6-yl]-phenyl}-methanesulfonamide,
N-{4-[2-Amino-4-(2-methoxy-ethoxy)-pyrido[3,2-d]pyrimidin-6-yl]-benzyl}-acetamide, N-{4-[2-Amino-4-(2-methoxy-ethoxy)-pyrido[3,2-d]pyrimidin-6-yl]-benzyl}-methanesulfonamide,
6-chloro-4-morpholin-4-yl-pyrido[3,2-d]pyrimidin-2-ylamine,
N-[4-(2-amino-4-morpholin-4-yl-pyrido[3,2-d]pyrimidin-6-yl)-phenyl]-acetamide,
N-[4-(2-amino-4-morpholin-4-yl-pyrido[3,2-d]pyrimidin-6-yl)-phenyl]-isobutyramide,
6-(4-amino-phenyl)-4-morpholin-4-yl-pyrido[3,2-d]pyrimidin-2-ylamine,
N-[4-chloro-6-(4-fluoro-phenyl)-pyrido[3,2-d]pyrimidin-2-yl]-acetamide,
6-(4-fluoro-phenyl)-4-methoxy-pyrido[3,2-d]pyrimidin-2-ylamine,
6-(4-fluoro-phenyl)-4-(N-2-methoxyethyl-N-methyl)-pyrido[3,2-d]pyrimidine-2,4-diamine,
N-[2-amino-6-(4-fluoro-phenyl)-pyrido[3,2-d]pyrimidin-4-yl]-O-ethyl-hydroxylamine,
6-(2-methoxyphenyl)-4-ethoxy-pyrido[3,2-d]pyrimidin-2-ylamine,
6-[4-(N-methylamido)-phenyl]-4-ethoxy-pyrido[3,2-d]pyrimidin-2-ylamine,
6-[4-(N-cyclopropylamido)-phenyl]-4-ethoxy-pyrido[3,2-d]pyrimidin-2-ylamine,
6-(2,4-bis(trifluoromethyl)phenyl]-4-ethoxy-pyrido[3,2-d]pyrimidin-2-ylamine,
6-(4-methylsulphonylphenyl)-4-ethoxy-pyrido[3,2-d]pyrimidin-2-ylamine,
6-(3-chlorophenyl)-4-ethoxy-pyrido[3,2-d]pyrimidin-2-ylamine,
6-(furan-2-yl)-4-ethoxy-pyrido[3,2-d]pyrimidin-2-ylamine,
6-(thiophen-3-yl)-4-ethoxy-pyrido[3,2-d]pyrimidin-2-ylamine,
6-(4-(morpholinomethyl)phenyl)-4-ethoxy-pyrido[3,2-d]pyrimidin-2-ylamine,
6-(2,3-dichlorophenyl)-4-ethoxy-pyrido[3,2-d]pyrimidin-2-ylamine,
6-(2-(trifluoromethyl)phenyl)-4-ethoxy-pyrido[3,2-d]pyrimidin-2-ylamine,
6-(2-ethoxyphenyl)-4-ethoxy-pyrido[3,2-d]pyrimidin-2-ylamine,
6-(2,5-difluorophenyl)-4-ethoxy-pyrido[3,2-d]pyrimidin-2-ylamine,
6-(3-cyanophenyl)-4-ethoxy-pyrido[3,2-d]pyrimidin-2-ylamine,
6-(3,5-difluorophenyl)-4-ethoxy-pyrido[3,2-d]pyrimidin-2-ylamine,
6-(2-chlorophenyl)-4-ethoxy-pyrido[3,2-d]pyrimidin-2-ylamine,
6-(3,5-di(trifluoromethyl)phenyl)-4-ethoxy-pyrido[3,2-d]pyrimidin-2-ylamine,
6-(pyrazol-4-yl)-4-ethoxy-pyrido[3,2-d]pyrimidin-2-ylamine,
6-(2-fluoro-pyridin-3-yl)-4-ethoxy-pyrido[3,2-d]pyrimidin-2-ylamine,
6-(2,3,4-trifluorophenyl)-4-ethoxy-pyrido[3,2-d]pyrimidin-2-ylamine,
6-(2-benzyloxyphenyl)-4-ethoxy-pyrido[3,2-d]pyrimidin-2-ylamine,
6-(2,4,6-trimethylphenyl)-4-ethoxy-pyrido[3,2-d]pyrimidin-2-ylamine,
6-(3-fluoro,4-methoxyphenyl)-4-ethoxy-pyrido[3,2-d]pyrimidin-2-ylamine,
6-(2-methyl,4-fluorophenyl)-4-ethoxy-pyrido[3,2-d]pyrimidin-2-ylamine,
6-(4-hydroxyphenyl)-4-ethoxy-pyrido[3,2-d]pyrimidin-2-ylamine,
6-(4-dimethylaminophenyl)-4-ethoxy-pyrido[3,2-d]pyrimidin-2-ylamine,
6-(2-chloro-4-trifluoromethyl-phenyl)-4-ethoxy-pyrido[3,2-d]pyrimidin-2-ylamine,
6-(4-chloro-3-trifluoromethylphenyl)-4-ethoxy-pyrido[3,2-d]pyrimidin-2-ylamine,
6-(quinolin-3-yl)-4-ethoxy-pyrido[3,2-d]pyrimidin-2-ylamine,
6-(4-benzyloxyphenyl)-4-ethoxy-pyrido[3,2-d]pyrimidin-2-ylamine,
6-(2-chloro-5-trifluoromethylphenyl)-4-ethoxy-pyrido[3,2-d]pyrimidin-2-ylamine,
6-(2-cyanothiophen-5-yl)-4-ethoxy-pyrido[3,2-d]pyrimidin-2-ylamine,
6-(2,3-difluorophenyl)-4-ethoxy-pyrido[3,2-d]pyrimidin-2-ylamine,
6-(2-methylphenyl)-4-ethoxy-pyrido[3,2-d]pyrimidin-2-ylamine,
6-(3-trifluoromethylphenyl)-4-ethoxy-pyrido[3,2-d]pyrimidin-2-ylamine,
6-(2,4-dichlorophenyl)-4-ethoxy-pyrido[3,2-d]pyrimidin-2-ylamine,
6-(3,5-dimethylphenyl)-4-ethoxy-pyrido[3,2-d]pyrimidin-2-ylamine,
6-(3,4,5-trifluorophenyl)-4-ethoxy-pyrido[3,2-d]pyrimidin-2-ylamine,
6-(5-chlorothiophen-2-yl)-4-ethoxy-pyrido[3,2-d]pyrimidin-2-ylamine,
6-(2-methoxypyridin-5-yl)-4-ethoxy-pyrido[3,2-d]pyrimidin-2-ylamine,
6-(2,4-dichlorophenyl)-4-ethoxy-pyrido[3,2-d]pyrimidin-2-ylamine,
6-(3,5-dichlorophenyl)-4-ethoxy-pyrido[3,2-d]pyrimidin-2-ylamine,
6-(3-ethoxyphenyl)-4-ethoxy-pyrido[3,2-d]pyrimidin-2-ylamine,
6-(2,4-difluorophenyl)-4-ethoxy-pyrido[3,2-d]pyrimidin-2-ylamine,
6-(2-chloro-4-fluorophenyl)-4-ethoxy-pyrido[3,2-d]pyrimidin-2-ylamine,
6-(1-benzothiophen-2-yl)-4-ethoxy-pyrido[3,2-d]pyrimidin-2-ylamine,
6-(furan-3-yl)-4-ethoxy-pyrido[3,2-d]pyrimidin-2-ylamine,
6-(2-methoxy-5-fluorophenyl)-4-ethoxy-pyrido[3,2-d]pyrimidin-2-ylamine,
6-(pyrazol-3-yl)-4-ethoxy-pyrido[3,2-d]pyrimidin-2-ylamine, and
6-(1-benzofuran-2-yl)-4-ethoxy-pyrido[3,2-d]pyrimidin-2-ylamine, or a pharmaceutically acceptable addition salt or a stereochemical isomeric form thereof or a N-oxide thereof.

8. A pharmaceutical composition comprising one or more pharmaceutically acceptable carriers and a compound according to claim 1 or 7.

9. A pharmaceutical composition according to claim 8, further comprising one or more antiviral agents.

10. A pharmaceutical composition according to claim 9, wherein said one or more antiviral agents are selected from the group consisting of retroviral enzyme inhibitors, nucleoside reverse transcriptase inhibitors, non-nucleoside reverse transcriptase inhibitors, reverse transcriptase inhibitors and HIV-1 protease inhibitors.

11. A pharmaceutical composition according to claim 9, wherein said one or more antiviral agents are selected from the group consisting of zidovudine, lamivudine, didanosine, stavudine, zalcitabine, nevirapine, delavirdine, foscamet sodium, saquinavir, ritonavir, indinavir, nelfinavir, acemannan, acyclovir, adefovir, alovudine, alvircept, amantadine, aranotin, arildone, atevirdine, pyridine, cidofovir, cipamfylline, cytarabine, desciclovir, disoxaril, edoxudine, enviradene, enviroxime, famciclovir, famotine, fiacitabine, fialuridine, floxuridine, fosarilate, fosfonet, ganciclovir, idoxuridine, kethoxal, lobucavir, memotine, methisazone, penciclovir, pirodavir, somantadine, sorivudine, tilorone, trifluridine, valaciclovir, vidarabine, viroxime, zinviroxime, moroxydine, podophyllotoxin, ribavirine, rimantadine, stallimycine, statolon, tromantadine, xenazoic acid, and their pharmaceutically acceptable salts.

12. A pharmaceutical composition according to claim 8, wherein said one or more pharmaceutically acceptable carriers are selected from the group consisting of wetting agents, dispersing agents, stickers, adhesives, surface-active agents, thickening agents, complexing agents, gelling agents, solvents, coatings, antibacterial, antifungal agents and isotonic agents.

13. A pharmaceutical composition according to claim 8, being for oral, rectal, intramuscular or intraperitoneous administration.

14. A method of treatment of an infection due to a virus from the Flaviridae family comprising the step of administering a patient in need thereof of a therapeutic amount of a compound having the structural formula:

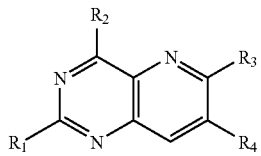

wherein:
$R_1$ is selected from the group consisting of hydrogen, halogen, cyano, carboxylic acid, acyl, thioacyl, $C_{1-7}$ alkoxycarbonyl, acyloxy, carbonate, carbamate, $C_{1-7}$ alkyl, $C_{6-30}$ aryl, amino, acetamido, N-protected amino, (mono- or di) $C_{1-7}$ alkylamino, (mono- or di) $C_{6-30}$ arylamino, (mono- or di) $C_{3-10}$ cycloalkylamino, (mono- or di) hydroxy $C_{1-7}$ alkylamino, (mono- or di) $C_{1-4}$ alkyl-$C_{6-30}$ arylamino, mercapto $C_{1-7}$ alkyl, $C_{1-7}$ alkyloxy, and groups of the formula $R_6$—$NR_7R_{12}$, wherein $R_6$ is a bond or $C_{1-3}$ alkylene, wherein $R_7$ and $R_{12}$ are independently selected from the group consisting of hydrogen, $C_{1-7}$ alkyl, $C_{2-7}$ alkenyl, $C_{2-7}$ alkynyl, $C_{6-30}$ aryl, $C_{6-30}$ aryl-$C_{1-7}$ alkyl, $C_{3-10}$ cycloalkyl and $C_{2-15}$ heteroaryl having one or more heteroatoms in one or more rings, wherein each heteroatom is independently selected from the group consisting of nitrogen, oxygen, sulfur, selenium, and phosphorus and wherein each ring has from 3 to 10 atoms, or wherein $R_7$ and $R_{12}$ together form a $C_{2-15}$ heterocycle having one or more heteroatoms in one or more rings, wherein each heteroatom is independently selected from the group consisting of nitrogen, oxygen, sulfur, selenium, and phosphorus and wherein each ring has from 3 to 10 atoms;
$R_2$ is selected from the group consisting of (mono- or di-) $C_{1-12}$ alkylamino; mono-$C_{6-30}$ arylamino; di-$C_{6-30}$ arylamino; (mono- or di-) $C_{3-10}$ cycloalkylamino; (mono- or di-) hydroxy$C_{1-7}$ alkylamino; (mono- or di-) $C_{1-4}$ alkyl-$C_{6-30}$ arylamino; (mono- or di-) $C_{6-30}$ aryl-$C_{1-4}$ alkylamino; morpholinyl; mercapto $C_{1-7}$ alkyl; $C_{1-7}$ alkoxy; N-containing $C_{2-15}$ heterocyclic having one or more heteroatoms in one or more rings, wherein each heteroatom is independently selected from the group consisting of nitrogen, oxygen, sulfur, selenium, and phosphorus and wherein each ring has from 3 to 10 atoms; $C_{1-7}$ alkoxy-$C_{1-7}$ alkoxy; $C_{2-15}$ heterocyclic-substituted $C_{1-7}$ alkoxy, wherein said heterocyclic has one or more heteroatoms in one or more rings, wherein each heteroatom is independently selected from the group consisting of nitrogen, oxygen, sulfur, selenium, and phosphorus, and wherein each ring has from 3 to 10 atoms; $C_{3-10}$ cycloalkoxy; $C_{3-10}$ cycloalkyl-$C_{1-7}$ alkoxy; halo $C_{1-7}$ alkyloxy; $C_{6-30}$ aryloxy; $C_{6-30}$ aryl-$C_{1-7}$ alkyloxy; oxy $C_{2-15}$ heterocyclic having one or more heteroatoms in one or more rings, wherein each heteroatom is independently selected from the group consisting of nitrogen, oxygen, sulfur, selenium, and phosphorus and wherein each ring has from 3 to 10 atoms; thio $C_{1-7}$ alkyl-thio $C_{1-7}$ alkyl; $C_{2-15}$ heterocyclic-substituted thio $C_{1-7}$ alkyl, wherein said heterocyclic has one or more heteroatoms in one or more rings, wherein each heteroatom is independently selected from the group consisting of nitrogen, oxygen, sulfur, selenium, and phosphorus, and wherein each ring has from 3 to 10 atoms; thio $C_{3-10}$ cycloalkyl; thio $C_{3-10}$ cycloalkyl-$C_{1-7}$ alkyl; halo thio-$C_{1-7}$ alkyl; $C_{6-30}$ arylthio; $C_{6-30}$ aryl-$C_{1-7}$ alkylthio; thio $C_{2-15}$ heterocyclic having one or more heteroatoms in one or more rings, wherein each heteroatom is independently selected from the group consisting of nitrogen, oxygen, sulfur, selenium, and phosphorus and wherein each ring has from 3 to 10 atoms; $C_{2-15}$ heterocyclic-substituted thio $C_{1-7}$ alkyl, wherein said heterocyclic has one or more heteroatoms in one or more rings, wherein each heteroatom is independently selected from the group consisting of nitrogen, oxygen, sulfur, selenium, and phosphorus, and wherein each ring has from 3 to 10 atoms; homopiperazinyl and piperazinyl, wherein said homopiperazinyl or piperazinyl is optionally N-substituted with a substituent $R_5$ selected from the group consisting of formyl, acyl, thioacyl, amide, thioamide, sulfonyl, sulfinyl, carboxylate, thiocarboxylate, amino-substituted acyl, $C_{1-7}$ alkoxy-$C_{1-7}$ alkyl, $C_{1-7}$ alkyl, $C_{3-10}$ cycloalkyl-$C_{1-7}$ alkyl, $C_{3-10}$ cycloalkyl, di $C_{1-7}$ alkylamino-$C_{1-7}$ alkyl, $C_{2-15}$ heterocyclic-substituted $C_{1-7}$ alkyl, wherein said heterocyclic has one or more heteroatoms in one or more rings, wherein each heteroatom is independently selected from the group consisting of nitrogen, oxygen, sulfur, selenium, and phosphorus, and wherein each ring has from 3 to 10 atoms, acyl-substituted $C_{1-7}$ alkyl, thioacyl-substituted $C_{1-7}$ alkyl, amido-substituted $C_{1-7}$ alkyl, thioamido-substituted $C_{1-7}$ alkyl, carboxylato-substituted $C_{1-7}$ alkyl, thiocarboxylato-substituted $C_{1-7}$ alkyl, (amino-substituted acyl) $C_{1-7}$ alkyl, $C_{2-15}$ heterocyclic having one or more heteroatoms in one or more rings, wherein each heteroatom is independently selected from the group consisting of nitrogen, oxygen, sulfur, selenium, and phosphorus and wherein each ring has from 3 to 10 atoms, carboxylic acid ester, ω-cyano-$C_{1-7}$ alkyl, ω-carboxylic ester-$C_{1-7}$ alkyl, halo $C_{1-7}$ alkyl, $C_{2-7}$ alkenyl, $C_{2-7}$ alkynyl, $C_{6-30}$ aryl-$C_{2-7}$ alkenyl, $C_{6-30}$ aryloxy-$C_{1-7}$ alkyl, $C_{6-30}$ aryl-$C_{1-7}$ alkyl and $C_{6-30}$ aryl, wherein the aryl moiety of each of said $C_{6-30}$ aryl-$C_{2-7}$ alkenyl, $C_{6-30}$ aryloxy-$C_{1-7}$ alkyl, $C_{6-30}$ aryl-$C_{1-7}$ alkyl and $C_{6-30}$ aryl radicals is optionally substituted with one or more substituents independently selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, $C_{6-30}$ aryloxy, $C_{6-30}$ aryl-$C_{1-7}$ alkyloxy, oxy $C_{2-15}$ heterocyclic having one or more heteroatoms in one or more rings, wherein each heteroatom is independently selected from the group consisting of nitrogen, oxygen, sulfur, selenium, and phosphorus and wherein each ring has from 3 to 10 atoms, $C_{2-15}$ heterocyclic-substituted $C_{1-7}$ alkyloxy, wherein said heterocyclic has one or more heteroatoms in one or more rings, wherein each heteroatom is independently selected from the group consisting of nitrogen, oxygen, sulfur, selenium, and phosphorus and wherein each ring has from 3 to 10 atoms, thio $C_{1-7}$ alkyl, thio $C_{3-10}$ cycloalkyl, thio $C_{6-30}$ aryl, thio-$C_{2-15}$ heterocyclic having one or more heteroatoms in one or more rings, wherein each heteroatom is independently selected from the group consisting of nitrogen, oxygen, sulfur, selenium, and phosphorus and wherein each ring has from 3 to 10 atoms, $C_{6-30}$ aryl-$C_{1-7}$ alkylthio, $C_{2-15}$ heterocyclic-substituted $C_{1-7}$ alkylthio, wherein said heterocyclic has one or more heteroatoms in one or more rings, wherein each heteroatom is independently selected from the group consisting of nitrogen, oxygen, sulfur, selenium, and phosphorus, and wherein each ring has from 3 to 10 atoms, formyl, carbamoyl, thiocarbamoyl, ureido, thioureido, sulfonamido, hydroxylamino, $C_{1-7}$ alkoxy-amino, mercaptoamino, thio $C_{1-7}$ alkylamino, acylamino, thioacylamino, cyano, carboxylic acid or esters or thioesters or halides or anhydrides or amides thereof, thiocarboxylic acid or esters or thioesters or halides or anhydrides or amides thereof, $C_{1-7}$ alkylamino, $C_{3-10}$ cycloalkylamino, $C_{2-7}$ alkenylamino, $C_{3-10}$ cyclo-alkenylamino, $C_{2-7}$ alkynylamino, $C_{6-30}$ aryl amino, $C_{6-30}$ aryl-$C_{1-7}$ alkylamino, hydroxy $C_{1-7}$ alkylamino, mercapto $C_{1-7}$ alkylamino, $C_{2-15}$ heterocyclic amino, wherein said heterocyclic has one or more heteroatoms in one or more rings, wherein each heteroatom is independently selected from the group consisting of nitrogen, oxygen, sulfur, selenium, and phosphorus, and wherein each ring has from 3 to 10 atoms, hydrazino, $C_{1-7}$ alkylhydrazino and phenylhydrazino;

$R_3$ and $R_4$ are independently selected from the group consisting of hydrogen halogen, $C_{2-15}$ heteroaryl having one or more heteroatoms in one or more rings, wherein each heteroatom is independently selected from the group consisting of nitrogen, oxygen, sulfur, selenium, and phosphorus and wherein each ring has from 3 to 10 atoms, and $C_{6-30}$ aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, $C_{6-30}$ aryloxy, $C_{6-30}$ aryl-$C_{1-7}$ alkyloxy, oxy $C_{2-15}$ heterocyclic having one or more heteroatoms in one or more rings, wherein each heteroatom is independently selected from the group consisting of nitrogen, oxygen, sulfur, selenium, and phosphorus and wherein each ring has from 3 to 10 atoms, $C_{2-15}$ heterocyclic-substituted $C_{1-7}$ alkyloxy, wherein said heterocyclic has one or more heteroatoms in one or more rings, wherein each heteroatom is independently selected from the group consisting of nitrogen, oxygen, sulfur, selenium, and phosphorus, and wherein each ring has from 3 to 10 atoms, thio $C_{1-7}$ alkyl, thio $C_{3-10}$ cycloalkyl, thio $C_{6-30}$ aryl, thio-$C_{2-15}$ heterocyclic having one or more heteroatoms in one or more rings, wherein each heteroatom is independently selected from the group consisting of nitrogen, oxygen, sulfur, selenium, and phosphorus and wherein each ring has from 3 to 10 atoms, $C_{6-30}$ aryl-$C_{1-7}$ alkylthio, $C_{2-15}$ heterocyclic-substituted $C_{1-7}$ alkylthio, wherein said heterocyclic has one or more heteroatoms in one or more rings, wherein each heteroatom is independently selected from the group consisting of nitrogen, oxygen, sulfur, selenium, and phosphorus, and wherein each ring has from 3 to 10 atoms, formyl, carbamoyl, thiocarbamoyl, ureido, thioureido, sulfonamido, hydroxylamino, $C_{1-7}$ alkoxy-amino, mercaptoamino, thio $C_{1-7}$ alkylamino, acylamino, thioacylamino, cyano, carboxylic acid or esters or thioesters or halides or anhydrides or amides thereof, thiocarboxylic acid or esters or thioesters or halides or anhydrides or amides thereof, $C_{1-7}$ alkylamino, $C_{3-10}$ cycloalkylamino, $C_{2-7}$ alkenylamino, $C_{3-10}$ cyclo-alkenylamino, $C_{2-7}$ alkynylamino, $C_{6-30}$ arylamino, $C_{6-30}$ aryl-$C_{1-7}$ alkylamino, hydroxy $C_{1-7}$ alkylamino, mercapto $C_{1-7}$ alkylamino, $C_{2-15}$ heterocyclic amino, wherein said heterocyclic has one or more heteroatoms in one or more rings, wherein each heteroatom is independently selected from the group consisting of nitrogen, oxygen, sulfur, selenium, and phosphorus, and wherein each ring has from 3 to 10 atoms, hydrazino, $C_{1-7}$ alkylhydrazino and phenylhydrazino, provided that $R_3$ and $R_4$ are not both hydrogen, and further provided that $R_4$ is hydrogen when $R_2$ is mono $C_{6-30}$ arylamino, or a pharmaceutically acceptable addition salt or a stereochemical isomeric form thereof or a N-oxide thereof.

15. The method according to claim 14, wherein said virus belongs to a genus selected from the group consisting of Genus *Flavivirus*, Genus *Hepacivirus* and Genus *Pestivirus*.

16. The method according to claim 14, wherein said infection is hepatitis C.

17. A method of treatment of an infection due to a virus from the Flaviridae family comprising the step of administering a patient in need thereof of a therapeutic amount of a compound according to claim 1 or 7.

* * * * *